US010544183B2

(12) United States Patent
Haydon et al.

(10) Patent No.: US 10,544,183 B2
(45) Date of Patent: *Jan. 28, 2020

(54) URIDINE NUCLEOSIDE DERIVATIVES, COMPOSITIONS AND METHODS OF USE

(71) Applicants: TUFTS UNIVERSITY, Boston, MA (US); Philip G. Haydon, Boston, MA (US); Jinbo Lee, Andover, MA (US)

(72) Inventors: Philip G. Haydon, Boston, MA (US); Jinbo Lee, Andover, MA (US)

(73) Assignee: TUFTS UNIVERSITY, Boston, MA (US)

(*) Notice: Subject to any disclaimer, the term of this patent is extended or adjusted under 35 U.S.C. 154(b) by 341 days.

This patent is subject to a terminal disclaimer.

(21) Appl. No.: 14/775,426

(22) PCT Filed: Mar. 13, 2014

(86) PCT No.: PCT/US2014/026865
§ 371 (c)(1),
(2) Date: Sep. 11, 2015

(87) PCT Pub. No.: WO2014/160502
PCT Pub. Date: Oct. 2, 2014

(65) Prior Publication Data
US 2016/0075731 A1 Mar. 17, 2016

Related U.S. Application Data

(60) Provisional application No. 61/780,219, filed on Mar. 13, 2013, provisional application No. 61/883,604, filed on Sep. 27, 2013.

(51) Int. Cl.
A61K 31/7064 (2006.01)
A61K 31/7068 (2006.01)
A61K 31/7072 (2006.01)
C07H 19/06 (2006.01)

(52) U.S. Cl.
CPC ......... C07H 19/06 (2013.01); A61K 31/7064 (2013.01); A61K 31/7068 (2013.01); A61K 31/7072 (2013.01)

(58) Field of Classification Search
None
See application file for complete search history.

(56) References Cited

U.S. PATENT DOCUMENTS

| 5,962,459 | A | 10/1999 | Piazza et al. |
| 6,875,751 | B2 | 4/2005 | Imbach et al. |
| 6,989,376 | B2 | 1/2006 | Watkins et al. |
| 7,585,851 | B2 | 9/2009 | Bryant et al. |
| 7,737,128 | B2 | 6/2010 | Renshaw |
| 7,851,456 | B2 | 12/2010 | Boyer et al. |
| 7,964,580 | B2 | 6/2011 | Sofia et al. |
| 8,143,234 | B2 | 3/2012 | Wurtman et al. |
| 8,158,776 | B2 | 4/2012 | Boyer et al. |
| 8,314,064 | B2 | 11/2012 | Watkins et al. |
| 8,518,882 | B2 | 8/2013 | Wurtman et al. |
| 8,598,141 | B2 | 12/2013 | Haydon et al. |
| 8,785,620 | B2 * | 7/2014 | Haydon ............... C07D 405/14 536/28.53 |
| 9,163,055 | B2 | 10/2015 | Haydon et al. |
| 9,227,993 | B2 | 1/2016 | Haydon et al. |
| 9,750,760 | B2 | 9/2017 | Haydon |
| 9,913,855 | B2 | 3/2018 | Haydon |
| 10,138,265 | B2 * | 11/2018 | Haydon ............. A61K 31/7064 |
| 2005/0074819 | A1 | 4/2005 | Inoue et al. |
| 2005/0203053 | A1 | 9/2005 | Wurtman et al. |
| 2006/0069061 | A1 | 3/2006 | Wurtman et al. |
| 2007/0004670 | A1 | 1/2007 | Wurtman et al. |
| 2009/0105189 | A1 | 4/2009 | Wurtman et al. |
| 2012/0035115 | A1 | 2/2012 | Manoharan et al. |
| 2013/0324495 | A1 | 12/2013 | Fischer et al. |
| 2014/0162972 | A1 | 6/2014 | Haydon et al. |
| 2014/0371167 | A1 | 12/2014 | Haydon et al. |
| 2015/0045319 | A1 | 2/2015 | Haydon et al. |
| 2015/0265647 | A1 | 9/2015 | Haydon et al. |
| 2016/0243148 | A1 * | 8/2016 | Haydon ............... C07D 405/14 |
| 2016/0318968 | A1 * | 11/2016 | Haydon ............... C07D 405/14 |

FOREIGN PATENT DOCUMENTS

| JP | S62207218 | | 9/1987 |
| JP | H0559087 | | 3/1993 |
| WO | WO 1999/009998 A1 | | 3/1999 |
| WO | WO2001062726 | | 8/2001 |
| WO | WO2007002945 | | 1/2007 |
| WO | WO2008115499 | | 9/2008 |
| WO | WO 2012/073237 A1 | | 6/2012 |
| WO | WO2013049686 | | 4/2013 |
| WO | WO13/049686 | * | 4/2014 |
| WO | WO2014052896 | | 4/2014 |
| WO | WO2014160502 | | 10/2014 |

OTHER PUBLICATIONS

Mizuno et al., Journal of Organic Chemistry, 1974, 39(9), 1250-1255.*
Akiyama, "A Synthesis of 5'-O-Acryloyl-5-fluorouridine by Use of p-Methoxybenzyl Group as an N3-Imide Protecting Group of 5-Fluorouridinel)," Bull. Chem. Soc. Jpn. vol. 64, No. 7, 2266-2269 (1991).
Akiyama, "Inflammatory response in Alzheimer's disease," Tohoku J.Exp.Med. 174, 295-303 (1994).
Asquith et al., "Autoimmune disease: Rheumatoid arthritis," European Journal of Immunology, 2009, 39: 1991-2058.
Bacskai et al., "Imaging of amyloid-beta deposits in brains of living mice permits direct observation of clearance of plaques with immunotherapy," Nat. Med. 7, 369-372 (2001).

(Continued)

Primary Examiner — Traviss C McIntosh, III
(74) Attorney, Agent, or Firm — Lisa M. Warren; Morse, Barnes-Brown & Pendleton, P.C.

(57) ABSTRACT

This disclosure relates to uridine nucleoside derivatives, compositions comprising therapeutically effective amounts of those nucleoside derivatives and methods of using those nucleoside derivatives or compositions in treating disorders that are responsive to ligands, such as agonists, of $P_2Y_6$ receptor, e.g., neuronal disorders, including neurodegenerative disorders (e.g., Alzheimer's disease, Parkinson's disease) and traumatic CNS injury, pain, Down Syndrome (DS), glaucoma and inflammatory conditions.

36 Claims, 29 Drawing Sheets

(56) References Cited

OTHER PUBLICATIONS

Figure 1:
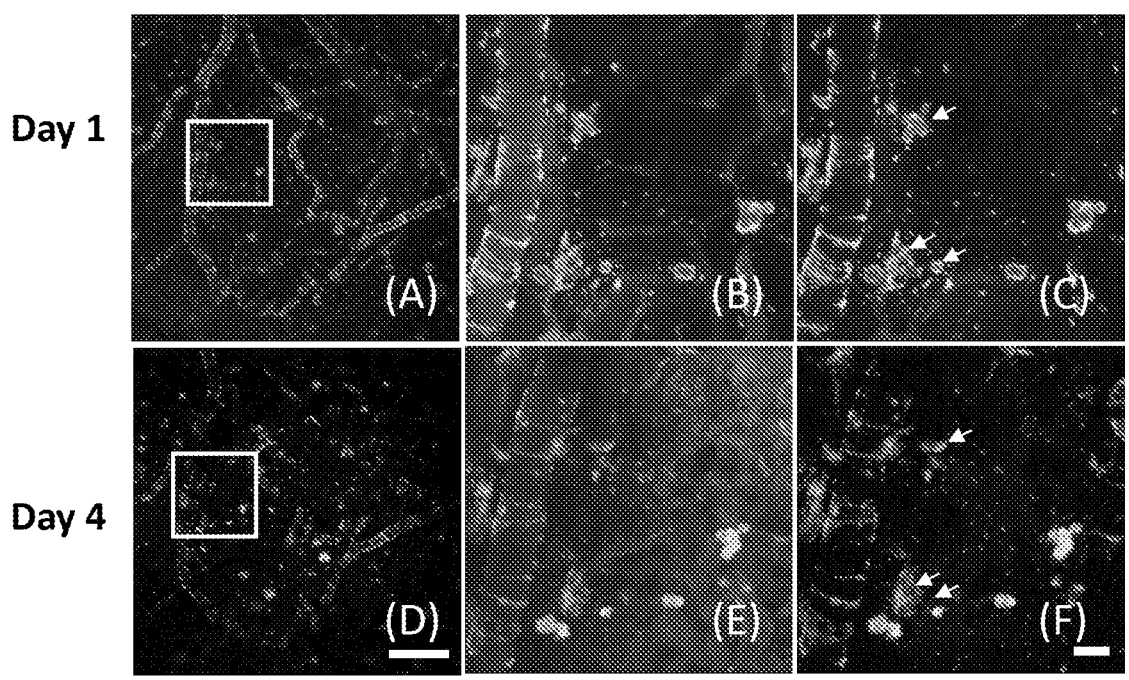

Bacskai et al., "Non-Fc-mediated mechanisms are involved in clearance of amyloid-β in vivo by immunotherapy," J. Neurosci. 22, 7873-7878 (2002).
Balasubramanian et al., "Activation of distinct P2Y receptor subtypes stimulates insulin secretion in MIN6 mouse pancreatic β cells," Biochem. Pharmacol. 79, 1317-1326 (2010).
Banerjee et al. "Efficient and Convenient Palladium-Catalyzed Amination of Allylic Alcohols with N-Heterocycles", Angewandte Chemie International Edition (2012), vol. 51, No. 46, pp. 11556 to 11560.
Bouhenni et al., "Animal Models of Glaucoma,," Journal of Biomedicine and Biotechnology, Volumne 2012, Article ID 692609, 11 pages, doi: 10.1155/2012/692609.
Brunschweiger et al., "P2 Receptors Activated by Uracil Nucleotides—an Update," Current Medicinal Chemistry, 2006, 13, 289-312.
Burnstock et al., "Adenosine and ATP receptors in the brain," Curr.Top.Med.Chem. 11, 973-1011 (2011).
Burnstock et al., "P2 Purinergic Receptors: Modulation of Cell Function and Therapeutic Potential," Perspectives in Pharmacology 2000, 295(3), 862.
CAS RN 106362-71-4, STN Entry Date Jan. 31, 1987.
CAS RN 110104-24-0, STN Entry Date Sep. 5, 1987.
CAS RN 114766-52-8, STN Entry Date Jun. 11, 1988.
CAS RN 129141-73-7, STN Entry Date Aug. 31, 1990.
CAS RN 166190-76-7, STN Entry Date Aug. 11, 1995.
CAS RN 50908-28-6, STN Entry Date Nov. 16, 1984.
CAS RN 51172-66-8, STN Entry Date Nov. 16, 1984.
Casaschi et al., "Palladium Catalysed Tandem Cyclisation-Anion Capture. Part 6: Synthesis of Sugar, Nucleoside, Purine, Benzodiazepinone and β-lactam Analogues via Capture of in situ Generated Vinylstannanes," Tetrahedron 2000, 56, 7553-7560.
Cleary et al., "Natural oligomers of the amyloid-β protein specifically disrupt cognitive function," Nat. Neurosci. 8, 79-84 (2005).
Conrad et al., "Animal Models of Psoriasis and Psoriatic Arthritis: An Update," Current Rheumatology Reports 2006, 8:342-347.
Costanzi et al., "Human P2Y$_6$ Receptor: Molecular Modeling Leads to the Rational Design of a Novel Agonist Based on a Unique Conformational Preference," J. Med. Chem., 2005, 48, 8108.
Cross et al. , "Rules for the Nomenclature of Organic Chemistry—Section E: Stereochemistry (Recommendations 1974)," Pure Appl. Chem. 45,11-30 (1976).
Cusack et al., "Purines, Pyrimidines, and Imidazoles. Part XL.1 A New Synthesis of a D-Ribofuranosylamine Derivative and its Use in the Synthesis of Pyrimidine and Imidazole Nucleosides," J. Chem. Soc. Perkin Trans. 1: Organic Bio-Organic Chem. 1973, 16, 1720-1731.
Dineley et al., "Accelerated plaque accumulation, associative learning deficits, and up-regulation of alpha 7 nicotinic receptor protein in transgenic mice co-expressing mutant human presenilin 1 and amyloid precursor proteins," J. Biol. Chem. 277, 22768-22780 (2002).
El-Khoury et al., "Microglia, scavenger receptors, and the pathogenesis of Alzheimer's disease," Neurobiol.Aging 19, S81-S84 (1998).
El-Tayeb et al., "Structural modifications of UMP, UDP, and UTP leading to subtype-selective agonists for P2Y$_2$, P2Y$_4$, and P2Y$_6$ receptors," J. Med. Chem. 54, 2878-2890 (2011).
El-Tayeb et al., "Synthesis and structure-activity relationships of uracil nucleotide derivatives and analogues as agonists at human P2Y$_2$, P2Y$_4$, and P2Y$_6$ receptors," J. Med. Chem., 49 (24), 7076-7087 (2006).
Endo et al., "1-Oxidopyridin-2-yldiazomethane: a Water-soluble Alkylating Agent for Nucleosides and Nucleotides," J.C.S. Chem. Comm. 1973, 673-674.
Fiala et al., "Ineffective phagocytosis of amyloid-beta by macrophages of Alzheimer's disease patients," J. Alzheimers. Dis. 7, 221-232 (2005).

Freir et al. "Aβ oligomers inhibit synapse remodelling necessary for memory consolidation," Neurobiol. Aging A5632, 2211-2218 (2011).
Gaikwad et al., "Signal regulatory protein-β1: a microglial modulator of phagocytosis in Alzheimer's disease," Am. J. Pathol. 175, 2528-2539 (2009).
Getz et al., "Atherosclerosis, Thrombosis, and Vascular Biology: Animal Models of Atherosclerosis," Arterioscler Thromb Vasc Biol. 2012;32:1104-1115, Mar. 1, 2012.
Ghosh et al., "beta-Secretase as a therapeutic target for Alzheimer's disease," Neurotherapeutics. 5, 399-408 (2008).
Grbic et al., "Intestinal Inflammation Increases the Expression of the P2Y6 Receptor on Epithelial Cells and the Release of CXC Chemokine Ligand 8 by UDP," J. Immunol. 2008, 180:2659-2668.
Guidance for Industry and Reviewers Estimating the Safe Starting Dose in Clinical Trials for Therapeutics in Adult Healthy Volunteers, Center for Biologics Evaluation and Research, Dec. (2002).
Hardy et al., "The amyloid hypothesis of Alzheimer's disease: progress and problems on the road to therapeutics," Science, 297, 353-356 (2002).
Hickman et al., "Microglial dysfunction and defective β-amyloid clearance pathways in aging Alzheimer's disease mice," J. Neurosci. 28(33): 8354-8360 (2008).
Jacobson et al., "P2Y nucleotide receptors: promise of therapeutic applications," Drug Discovery Today, 2010, 15, 570.
Jessen et al., "Bioreversible protection of Nucleoside Diphosphates," Angewandte Chemie International Edition, 2008, vol. 47, pp. 8719-8722.
Kamenetz et al., "APP processing and synaptic function," Neuron 37, 925-937 (2003).
Kellner et al.,"A multifunctional bioconjugate module for versatile photoaffinity labeling and click chemistry of RNA," Nucleic Acids Research, 2011, 39 (16): 7348-7360.
Kim et al., "P2Y$_6$ Nucleotide Receptor Activates PKC to Protect 1321N1 Astrocytoma Cells Against Tumor Necrosis Factor-Induced Apoptosis," Cell. Mol. Neurobiol. 23, 401-418 (2003).
Kimura et al. "Metabolism of a novel hypnotic, N3-phenacyluridine, and hypnotic and sedative activities of its enantiomer metabolites in mouse", Xenobiotica (2000), vol. 30, No. 6, pp. 643 to 653.
Kimura et al., "Sleep promoting effects of N3-benzyluridine in unrestrained rats," Research Communications in Psychology, Psychiatry and Behavior, 1993, vol. 18 (3 & 4), pp. 111-119, CAPLUS Accession No. 1995:344707.
Klunk et al., "Imaging Aβ plaques in living transgenic mice with multiphoton microscopy and methoxy-X04, a systemically administered Congo red derivative," J. Neuropathol. Exp. Neurol. 61, 797-805 (2002).
Koenigsknecht-Talboo et al., "Microglial phagocytosis induced by fibrillar β-amyloid and IgGs are differentially regulated by proinflammatory cytokines," J. Neurosci. 25, 8240-8249 (2005).
Koizumi et al., "UDP acting at P2Y$_6$ receptors is a mediator of microglial phagocytosis," Nature, 446, 1091-1095 (2007).
Korcok et al., "Mechanisms of Signal Transduction: P2Y6 Nucleotide Receptors Activate NF-kB and Increase Survival of Osteoclasts," J. Biol. Chem. 280, 16909-16915 (2005).
Lee et al., "The role of microglia in amyloid clearance from the AD brain," J.Neural Transm. 117, 949-960 (2010).
Li et al., "Soluble Aβ oligomers inhibit long-term potentiation through a mechanism involving excessive activation of extrasynaptic NR2B-containing NMDA receptors," J. Neurosci. 31, 6627-6638 (2011).
Liu et al., "CX3CR1 in microglia regulates brain amyloid deposition through selective protofibrillar amyloid-beta phagocytosis," J. Neurosci. 30, 17091-17101 (2010).
Malmsjo et al. , "Potent P2Y$_6$receptor mediated contractions in human cerebral arteries," BMC Pharmacol. 3, 4 (2003).
Mamedova et al., "Attenuation of apoptosis in vitro and ischemia/reperfusion injury in vivo in mouse skeletal muscle by P2Y$_6$ receptor activation," Pharmacol. Res. 58, 232-239 (2008).
Mandrekar et al., "Microglia mediate the clearance of soluble Aβ through fluid phase macropinocytosis," J. Neurosci. 29, 4252-4262 (2009).

(56) References Cited

OTHER PUBLICATIONS

Maruoka et al., "Pyrimidine Ribonucleotides with Enhanced Selectivity as P2Y$_6$Receptor Agonists: Novel 4-Alkyloxyimino, (S)-Methanocarba, and 5'-Triphosphate y-Ester Modifications," J. Med. Chem., 53 (11), 4488-4501 (2010).

Maruyama et al., "A New Method for the Synthesis of N-phenyl-uracil and -pyrimidine Nucleosides," J. Chem. Soc. Perkin Trans. 1: Organic Bio-Organic Chem. 1995, 7, 733-734.

Meyer-Luehmann et al., "Rapid appearance and local toxicity of amyloid-β plaques in a mouse model of Alzheimer's disease," Nature 451, 720-724 (2008).

Mizoguchi et al., Animal Models of Inflammatory Bowel Disease, Progress in Molecular Biology and Translational Science, vol. 105, 263-320, Copyright 2012, Elsevier Inc.

Mizuno et al., "Nucleotide. II. Syntheses and Deblocking of 1-Oxido-2-pyridylmethyl Protected Nucleosides and Nucleotides," J. Org. Chem. 1974, 39(9), 1250-1255.

Ojika et al., "PTAQUILOSIDE, A Potent Carcinogen Isolated from Bracken Fern *Pteridium aquilinum* Var. *latiusculum*: Structure Elucidation Based on Chemical and Spectral Evidence, and Reactions with Amino Acids, Nucleosides, and Nucleotides," Tetrahedron 1987, 43(22), 5261-5274.

Okada et al., "Analgesic Effects of Intrathecal Administration of P2Y Nucleotide Receptor Agonists UTP and UDP in Normal and Neuropathic Pain Model Rats," J. Pharmacol. & Exp. Therapeutics, 303(1), 66-73 (2002).

Ralevic et al., "Involvement of Purinergic Signaling in Cardiovascular Diseases," Drug News Perspect 2003, 16(3), 133.

Sajiki et al., "Development of Diversified Methods for Chemical Modification of the 5,6-Double Bond of Uracil Derivatives Depending on Active Methylene Compounds," Molecules 2012, 17, 6519-6546.

Selkoe et al., "Alzheimer's disease: molecular understanding predicts amyloid-based therapeutics," Annu.Rev.Pharmacol.Toxicol. 43, 545-584 (2003).

Selkoe, "Alzheimer's disease," Cold Spring Harb.Perspect.Biol. 3 (2011).

Sperling et al. "Amyloid deposition is associated with impaired default network function in older persons without dementia," Neuron 63, 178-188 (2009).

Tozaki-Saitoh et al., "P2Y12 receptors in spinal microglia are required for neuropathic pain after peripheral nerve injury," J. of Neurosci., 28, 4949-4956 (2008).

Walsh et al., "Naturally secreted oligomers of amyloid β protein potently inhibit hippocampal long-term potentiation in vivo," Nature 416, 535-539 (2002).

Wilcock et al., "Anti-amyloid-beta immunotherapy in Alzheimer's disease: relevance of transgenic mouse studies to clinical trials," J. Alzheimers. Dis. 15, 555-569 (2008).

Yoshida et al., "Use of 4-Bromomethyl-7-Methoxycoumarin for Derivatization of Pyrimidine Compounds in Serum Analysed by High-Performance Liquid Chromatography with Fluorimetric Detection," J. Chromatography, Biomedical Applications 1986, 383(1), 61-68.

Cox et al., "The pyrimidinergic P2Y$_6$ receptor mediates a novel release of proinflammatory cytokines and chemokines in monocytic cells stimulated with UDP," *Biochemical and Biophysical Research Communications*, vol. 330, No. 2, (2005), pp. 467-473.

Garcia et al., "P2Y$_6$ Receptor Potentiates Pro-Inflammatory Responses in Macrophages and Exhibits Differential Roles in Atherosclerotic Lesion Development," *PLOS ONE*, vol. 9, No. 10, Oct. 2014, p. e111385 (13 pages).

Grbic et al., "P2Y$_6$ Receptor Contributes to Neutrophil Recruitment to Inflamed Intestinal Mucosa by Increasing CXC Chemokine Ligand 8 Expression in an AP-1-dependent Manner in Epithelial Cells," *Inflammatory Bowel Diseases*, vol. 18, No. 8, Aug. 2012, pp. 1456-1469.

Rogers et al., "Inflammation and Alzheimer's Disease Pathogenesis," *Neurobiology of Aging* (1996), vol. 17, No. 5, pp. 681-686.

CAS RN 166190-75-6, STN Entry Date Aug. 11, 1995.

Non-Final Office Action issued in U.S. Appl. No. 14/987,554, dated Aug. 24, 2017.

Notice of Allowance issued in U.S. Appl. No. 14/432,104, dated Oct. 23, 2017.

Final Office Action issued in U.S. Appl. No. 14/987,554, dated Jun. 1, 2018.

Notice of Allowance issued in U.S. Appl. No. 14/210,333, dated Jul. 6, 2018.

\* cited by examiner (C)

(D)

(E)

(F)

(C)

(A)

(B)

(A)　　　　　　　　　　　(B)

* p<0.05,  p<0.02, *p<0.002

URIDINE NUCLEOSIDE DERIVATIVES, COMPOSITIONS AND METHODS OF USE

RELATED APPLICATIONS

This application is a national stage application under 35 U.S.C. § 371 of International Patent Application No. PCT/US2014/026865, filed on Mar. 13, 2014, which claims the benefit of and priority from U.S. Provisional Patent Application 61/780,219, filed Mar. 13, 2013 and 61/883,604, filed Sep. 27, 2013. Each of the foregoing applications is incorporated herein by reference in its entirety.

FIELD OF THE INVENTION

This disclosure relates to compounds, compositions and methods for treating neuronal disorders, including neurodegenerative disorders (e.g., Alzheimer's disease, Parkinson's disease) and traumatic CNS injury, pain, Down Syndrome (DS), glaucoma and inflammatory conditions.

BACKGROUND OF THE INVENTION $P_2Y$ receptors are G-protein-coupled receptors (GPCRs) that are selectively activated by naturally occurring extracellular nucleotides, including, for example, adenine and pyrimidine nucleotides. There are two clusters of $P_2Y$ receptors: the $G_q$-coupled $P_2Y_1$-like receptors, including $P_2Y_{1,2,4,6,11}$ subtypes; and the $G_i$-coupled $P_2Y_{12}$-like receptors, including $P_2Y_{12,13,14}$ subtypes. Of the four $P_2Y$ receptors, i.e., $P_2Y_{2,4,6,14}$ subtypes, which can be activated by pyrimidine nucleotides, the $P_2Y_2$ and $P_2Y_4$ subtypes are activated by uridine triphosphate (UTP), $P_2Y_6$ receptor is activated by uridine diphosphate (UDP), and $P_2Y_{14}$ is activated by UDP or UDP-glucose.

The $P_2Y_6$ receptor has been implicated in a number of disorders, including, for example, neurodegeneration, osteoporosis, ischemic effect in skeletal muscle, and diabetes. It has been reported that agonists of $P_2Y_6$ receptor counteract apoptosis induced by tumor necrosis factor α in astrocytoma cells and induce protection in a model of ischemic hindleg skeletal muscle. $P_2Y_6$ receptor was also reported to play a role in phagocytosis in microglial cells when activated by its endogenous agonist UDP. See, e.g., Malmsjo et al. *BMC Pharmacol.* 2003, 3, 4; Balasubramanian et al. *Biochem. Pharmacol.* 2010, 79, 1317-1332; Kim et al. *Cell. Mol. Neurobiol.* 2003, 23, 401-418; Mamedova et al. *Pharmacol. Res.* 2008, 58, 232-239; Korcok et al. *J. Biol. Chem.* 2005, 58, 232-239; and Koizumi et al. *Nature,* 2007, 446, 1091-1095. These reports suggest that ligands of the $P_2Y_6$ receptor are of interest in the search for new treatments for $P_2Y_6$ receptor-related conditions.

Therefore, there is a need for new ligands, such as agonists, of $P_2Y_6$ receptor activity that are useful in therapeutic preparations for the treatment of disorders mediated by the receptor, including neurodegeneration, traumatic brain injury and pain.

SUMMARY OF THE INVENTION

The present disclosure addresses the aforementioned need by providing compounds of formulae I and II:

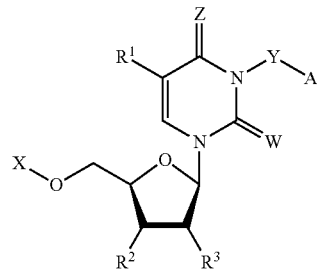

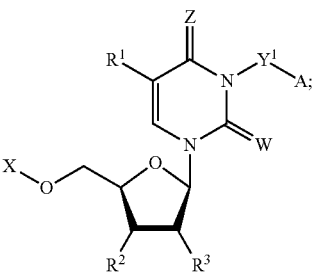

wherein the variables are as defined herein, along with pharmaceutically acceptable salts thereof. In certain embodiments, these compounds are capable of modulating $P_2Y_6$ receptor activity, either directly or indirectly, i.e., these compounds are $P_2Y_6$ receptor-modulating compounds. In certain embodiments, the compounds as described herein are agonists of the $P_2Y_6$ receptor, which, directly or indirectly, activate the $P_2Y_6$ receptor. Compounds of formulae I (including formula I-A and formula I-B) and II can be used to treat the conditions as described herein.

The present disclosure also provides compositions that comprise the compounds described herein. The disclosure also includes the use of the compounds disclosed herein in the manufacture of a medicament for the treatment of one or more of the conditions described herein In another aspect of the disclosure, there is provided methods for studying $P_2Y_6$ receptor activity using the agonists of the disclosure, which include the compounds of all formulae disclosed herein, all of the individual compounds disclosed herein, and all of their prodrugs and salts. For example, cells in culture may be contacted with one or more of the compounds provided herein and their impact on $P_2Y_6$ receptor activity, as well as cellular function, can be evaluated. Such studies are useful for evaluating the use of agonists of the disclosure as in vitro research tools for evaluating $P_2Y_6$ receptor activity and its cellular and biochemical impact on different cell types.

In another aspect of the disclosure, there is provided a method of modulating $P_2Y_6$ receptor activity by using one or more of the compounds described herein, or their prodrugs and/or salts. For example, the invention provides a method of modulating $P_2Y_6$ receptor activity in a patient in need thereof by administering to the patient a therapeutically effective amount of one or more of the compounds described herein, or their prodrugs and/or salts Similarly, the invention provides a method of modulating $P_2Y_6$ receptor activity in a patient in need thereof by administering to the patient a therapeutically effective amount of one or more of the compounds described herein, or their prodrugs and/or salt in a pharmaceutical composition.

In another aspect of the disclosure, there is provided a method for treating neuronal disorders, including neurodegenerative disorders (e.g., Alzheimer's disease, Parkinson's disease) and traumatic CNS injury, pain, Down Syndrome (DS), glaucoma and inflammatory conditions in a subject in need or at risk thereof using a compound described herein.

In another aspect, the disclosure provides methods for decreasing plaque burden, improving cognitive function, decreasing or delaying cognitive impairment, improving or restoring memory, enhancing synaptic plasticity, or improving hippocampal long term potentiation by administering to a subject in need or at risk thereof a $P_2Y_6$ receptor agonist. Also provided are methods of enhancing beta amyloid clearance. Subjects in need include subjects having Alzheimer's disease (including subjects suspected of having Alzheimer's disease). Additional subjects in need thereof are subjects having Down Syndrome, and administration of a $P_2Y_6$ receptor agonist or a $P_2Y_6$ receptor-modulating compound is used to treat Down Syndrome by, for example, improving cognitive function, decreasing cognitive impairment, improving or restoring memory, improving hippocampal long term potentiation, enhancing synaptic plasticity, or enhancing clearance of beta amyloid. Further subjects in need thereof are subjects having Parkinson's disease. Exemplary $P_2Y_6$ receptor agonists are disclosed herein.

In another aspect, the disclosure provides methods for clearing or otherwise decreasing extracellular alpha-synuclein, decreasing intracellular accumulation of alpha-synuclein, and/or decreasing or preventing the formation of Lewy bodies in a subject in need thereof by administrating a $P_2Y_6$ receptor agonist to the subject. In certain embodiments, the subject in need thereof is a subject having Parkinson's disease, and administration of a compound of the disclosure provides a method of treating Parkinson's disease by, for example, improving or preventing further motor impairment associated with Parkinson's disease and/or improving or preventing memory impairment and other symptoms of neurodegeneration. Without being bound by theory, phagocytosis of extracellular alpha-synuclein, which may be promoted by the $P_2Y_6$ receptor agonists, decreases extracellular and intracellular accumulation of alpha-synuclein, as well as Lewy body formation and the resulting neurodegeneration.

In another aspect, the disclosure provides methods for treating glaucoma by administering to a subject in need thereof an effective amount of one or more of the compounds, salts, or prodrugs disclosed herein. In certain embodiments, administration of an effective amount of one or more of the compounds, salts, or prodrugs can decrease intraocular pressure in the subject in need thereof.

In another aspect, the disclosure provides methods for treating an inflammatory condition in a subject in need thereof comprising administering to the subject an effective amount of one or more of the compounds, salts, or prodrugs according to the present disclosure. In certain embodiments, the disclosure provides a method for reducing the plasma concentration of one or more cytokines in plasma of a subject, such as a subject with an inflammatory condition. Suitable cytokines are described herein. In either case, the disclosure provides numerous examples of inflammatory conditions which may be treated (e.g., the subject in need thereof has an inflammatory condition described herein). In certain embodiments, the subject is administered an effective amount of a compound, salt or prodrug of the disclosure. In certain embodiments, the inflammatory condition is not Alzheimer's disease and/or the subject being treated does not have, and/or has not been diagnosed with, and/or is not suspected of having Alzheimer's disease.

In certain embodiments, the disclosure provides a method of treating an inflammatory condition characterized, in whole or in part, by elevated IL-12 and/or increased IL-12 activity by administering a compound, salt or prodrug of the disclosure. Exemplary conditions are described herein. Similarly the disclosure provides a method of treating an inflammatory condition characterized, in whole or in part, by elevated levels of one or more of IL-4, IL-10, or IL-12. Methods of reducing the plasma concentration of one or more of any of these cytokines in plasma are also provided.

In certain embodiments, the disclosure provides methods for treating one or more of: rheumatoid arthritis, psoriasis, psoriatic arthritis, atherosclerosis, Crohn's disease, ulcerative colitis, irritable bowel syndrome, or multiple sclerosis.

In certain embodiments, the disclosure provides methods for treating any of the conditions described herein, such as in a subject at risk for developing the condition, by initiating treatment prior to onset of one or more symptoms and/or prior to achieving a level of decline at which standard of care treatment is typically initiated. In such prophylactic embodiments, the disclosure contemplates, in certain embodiments, that treatment delays onset of symptoms and/or delays further decline and/or reduces severity of symptoms.

The disclosure contemplates combinations of any of the aspects and/or embodiments described herein. For example, any of the compounds described herein, such as any of the $P_2Y_6$ modulating compounds (e.g., compounds that modulate $P_2Y_6$ receptor activity) described herein, may be used in the treatment of any of the conditions described herein, such as by administering an effective amount to a subject in need thereof. Similarly, any of the compounds described herein may be provided as compositions, such as pharmaceutical compositions, and any such pharmaceutical compositions may be used in the treatment of any of the conditions described herein.

DETAILED DESCRIPTION OF THE FIGURES

FIG. 1 shows two-photon microscopy images of the amyloid plaques labeled with methoxyX04 in the barrel cortex in living PSAPP mice: (A) image on day 1; (B) magnified view of the portion of the image in the white box in FIG. 1A, in which the blood plasma was labeled with Rhodamine dextran; (C) magnified view of the portion of the image in the white box in FIG. 1A, where the arrows indicate dense core plaques; (D) image of the same imaging area on day 4, after the injection of UDP; (E) magnified view of the portion of the image in the white box in FIG. 1D, in which the blood plasma was labeled with Rhodamine dextran; and (F) magnified view of the portion of the image in the white box in FIG. 1D, where the arrows indicate dense core plaques.

Figure 2:
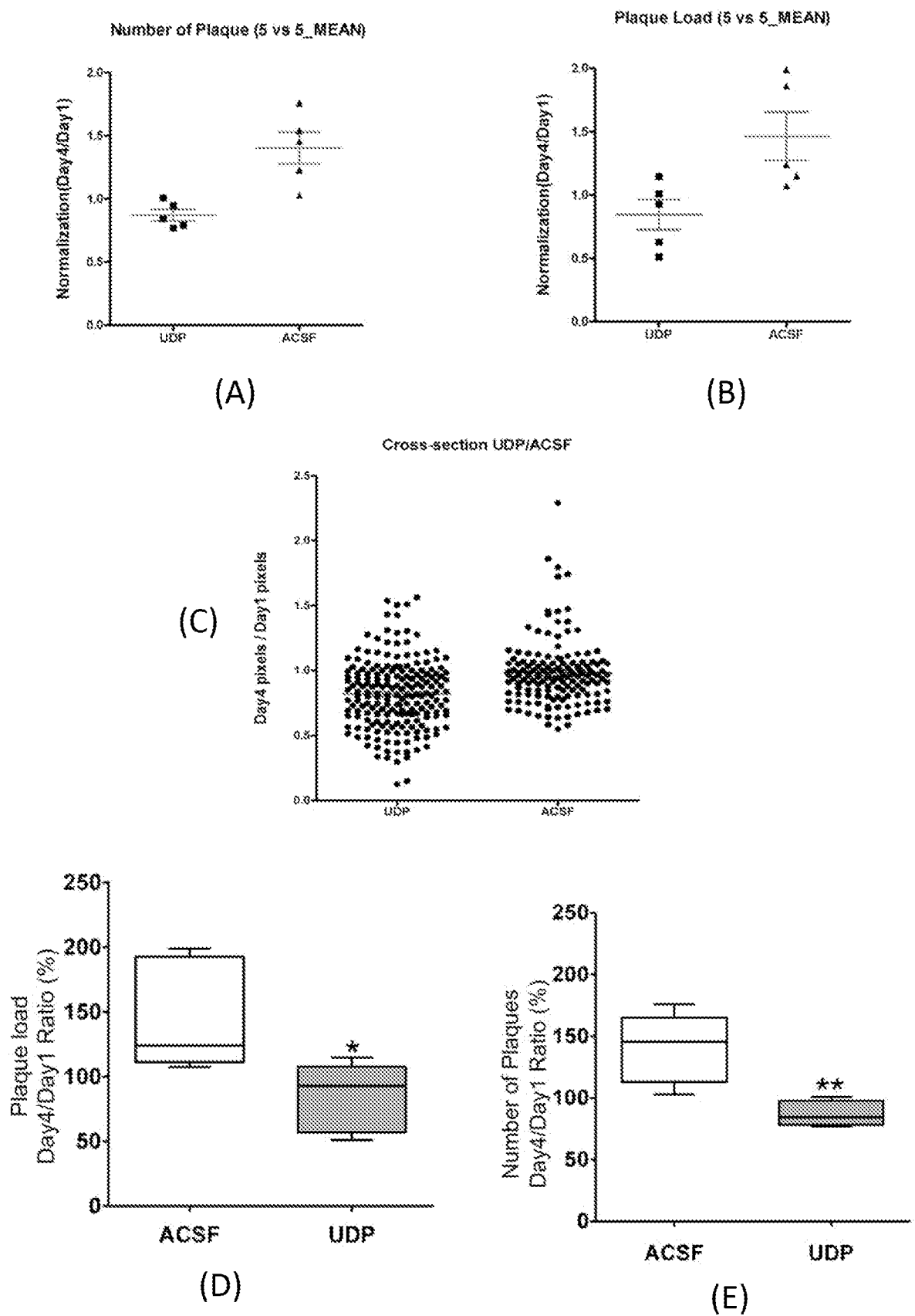

FIG. 2 shows a quantitative analysis of the number of plaques, plaque load and size of cross-section of individual plaques in the barrel cortex in PSAPP mice after treatment with UDP or artificial cerebral spinal fluid (ACSF): (A) quantitative analysis of the number of plaques; (B) quantitative analysis of the plaque load; (C) quantitative analysis of the size of cross-section of plaques; (D) UDP treatment reduces plaque load as shown by significant reductions in day 4/day 1 ratios of plaque load; and (E) UDP treatment reduces number of plaques as shown by significant reductions in day 4/day 1 ratios of plaque load.

Figure 3:
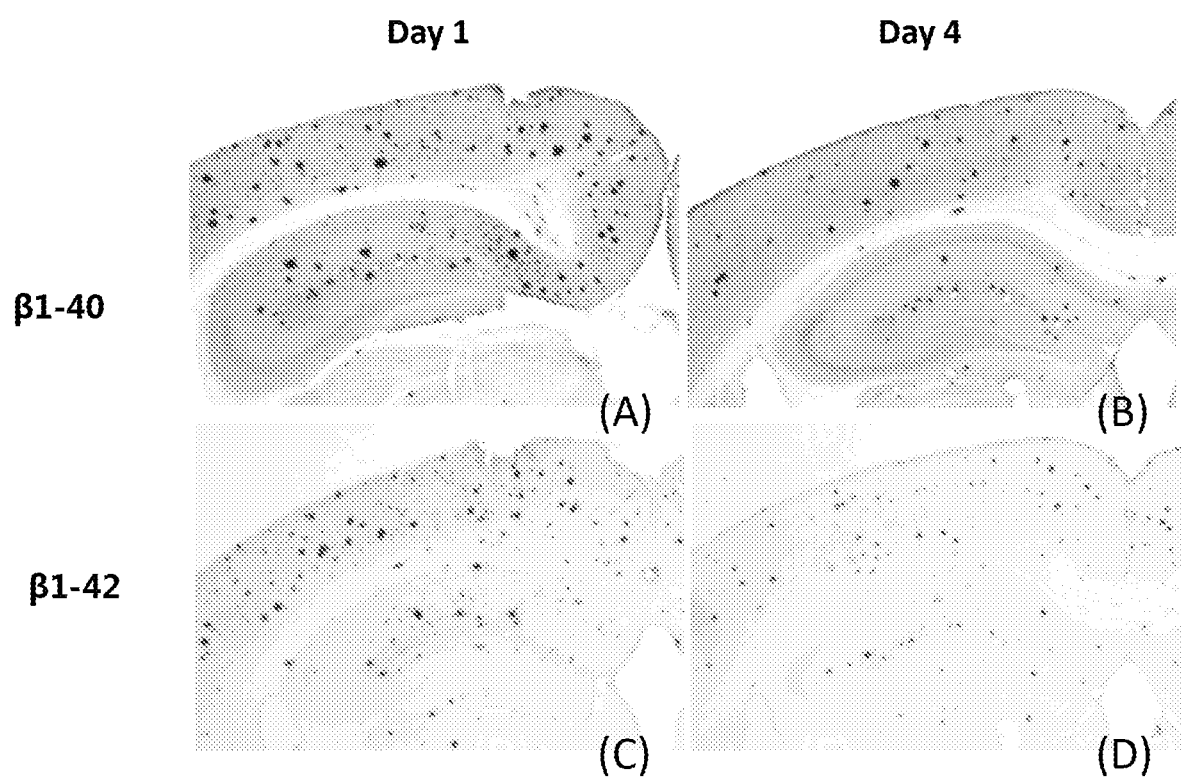

FIG. 3 shows postmortem immunohistochemistry analysis of the plaque load in cortex and hippocampus of PSAPP mice after treatment with UDP. Amyloid beta peptide specific antibodies β1-40 and β 1-42 were used in the immunohistochemistry analysis: (A) immunohistochemistry analysis using β1-40 on day 1; (B) immunohistochemistry analysis using β1-40 on day 4, after treatment with UDP; (C) immunohistochemistry analysis using β1-42 on day 1; and (D) immunohistochemistry analysis using β1-42 on day 4, after treatment with UDP.

Figure 4:
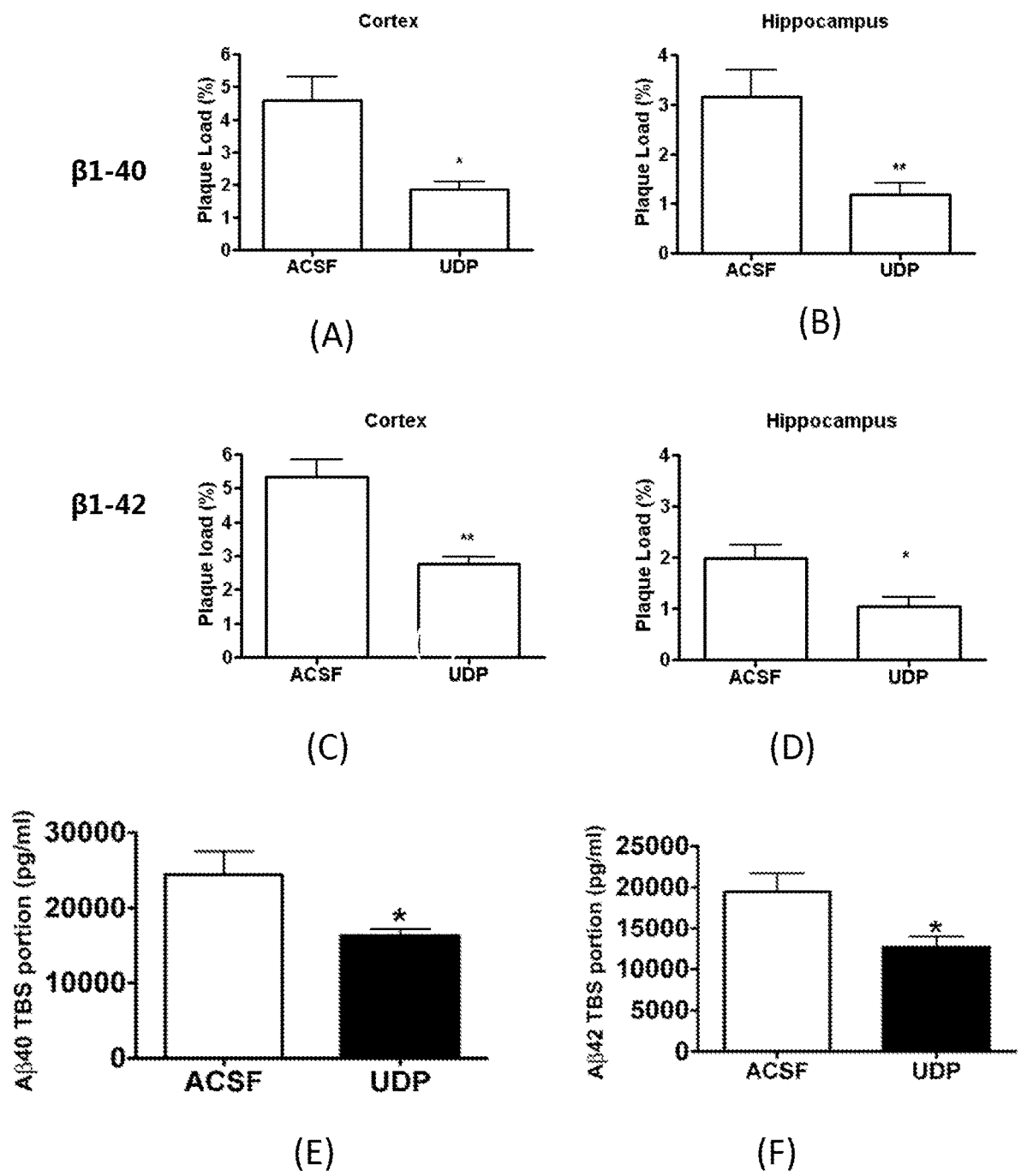

FIG. 4 shows quantification of plaque load (%) in the cortex and hippocampus of the PSAPP mice after treatment with UDP or ACSF. Amyloid beta peptide specific antibodies β1-40 and β1-42 were used in the quantification. (A) plaque load (%) in cortex using β1-40 staining; (B) plaque load (%) in hippocampus using β1-40 staining; (C) plaque load (%) in cortex using β1-42 staining; (D) plaque load (%) in hippocampus using β1-42 staining; (E) UDP treatment decreased soluble Aβ40 level detected with ELISA; and (F) UDP treatment decreased soluble Aβ42 level detected with ELISA.

Figure 5:
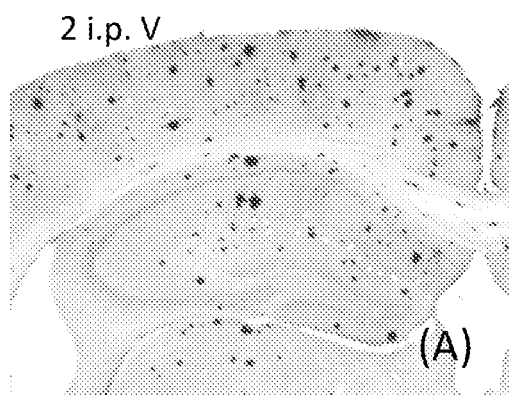
Figure 5:
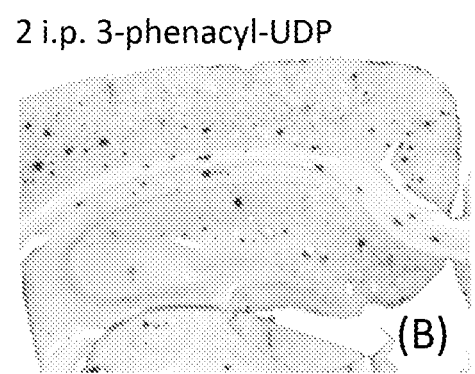
Figure 5:
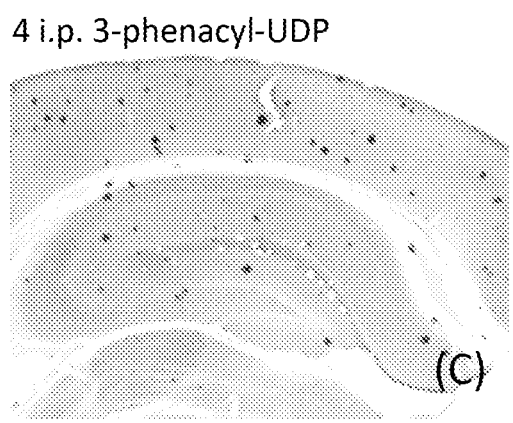
Figure 5:
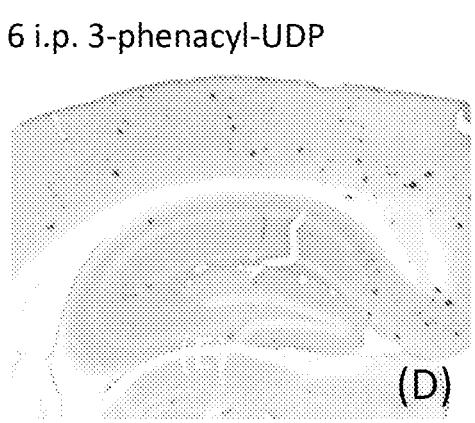

FIG. 5 shows a postmortem immunohistochemistry analysis of the plaque load in cortex and hippocampus of PSAPP mice after intraperitoneal (i.p.) injection of 3-phenacyl-UDP for 2, 4 and 6 consecutive days. Amyloid beta specific antibody β1-40 was used in the analysis. (A) immunohistochemistry analysis using β1-40 without 3-phenacyl-UDP treatment; (B) immunohistochemistry analysis using β1-40 after intraperitoneal injection of 3-phenacyl-UDP for 2 consecutive days; (C) immunohistochemistry analysis using β1-40 after intraperitoneal injection of 3-phenacyl-UDP for 4 consecutive days; and (D) immunohistochemistry analysis using β1-40 after intraperitoneal injection of 3-phenacyl-UDP for 6 consecutive days.

Figure 6:
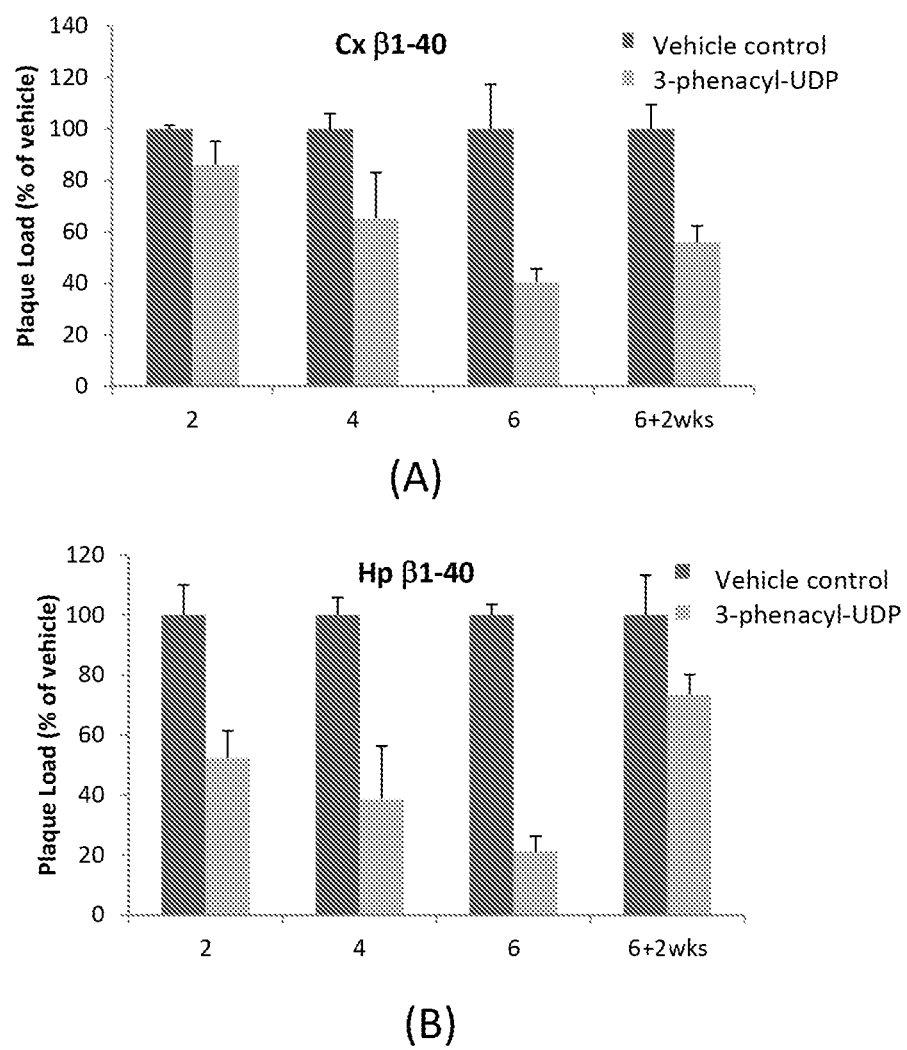
Figure 6:
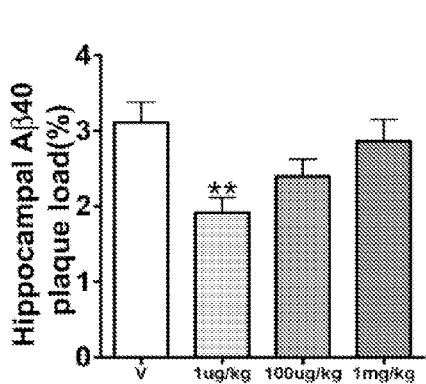
Figure 6:
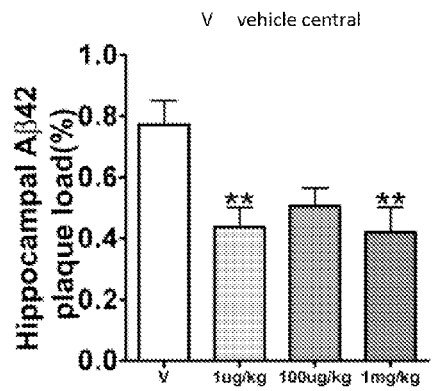
Figure 6:
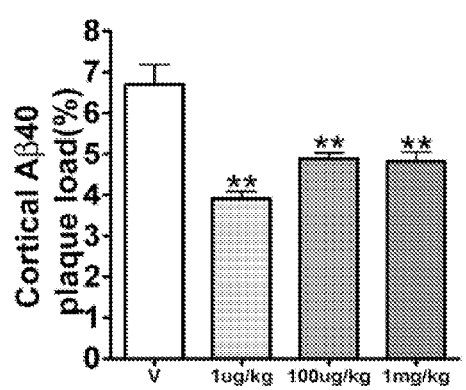
Figure 6:
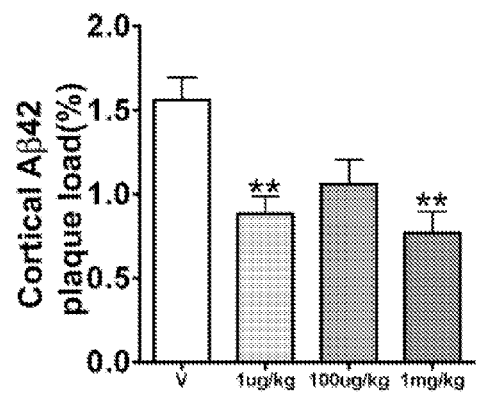

FIG. 6 shows quantification of plaque load (%) in cortex (Cx) and hippocampus (Hp) of the PSAPP mice after treatment with 3-phenacyl-UDP or vehicle control for 2, 4, 6 consecutive days and for 6 days+2 weeks. The vehicle controls used for intracerebroventricular (icy) and Intraperitoneal (ip) administration of compounds were ACSF and saline, respectively. Amyloid beta peptide specific antibody β1-40 was used in quantification. (A) Plaque load (%) in cortex using β1-40 staining; (B) plaque load (%) in hippocampus using β1-40 staining; (C) Aβ40 plaque load (%) in hippocampus after one week of daily treatment with 3-phenacyl-UDP (PSB0474) at three doses; (D) Aβ42 plaque load (%) in hippocampus after one week of daily treatment with 3-phenacyl-UDP (PSB0474) at three doses; (E) Aβ40 plaque load (%) in cortex after one week of daily treatment with 3-phenacyl-UDP (PSB0474) at three doses; and (F) Aβ42 plaque load (%) in cortex after one week of daily treatment with 3-phenacyl-UDP (PSB0474) at three doses.

Figure 7:
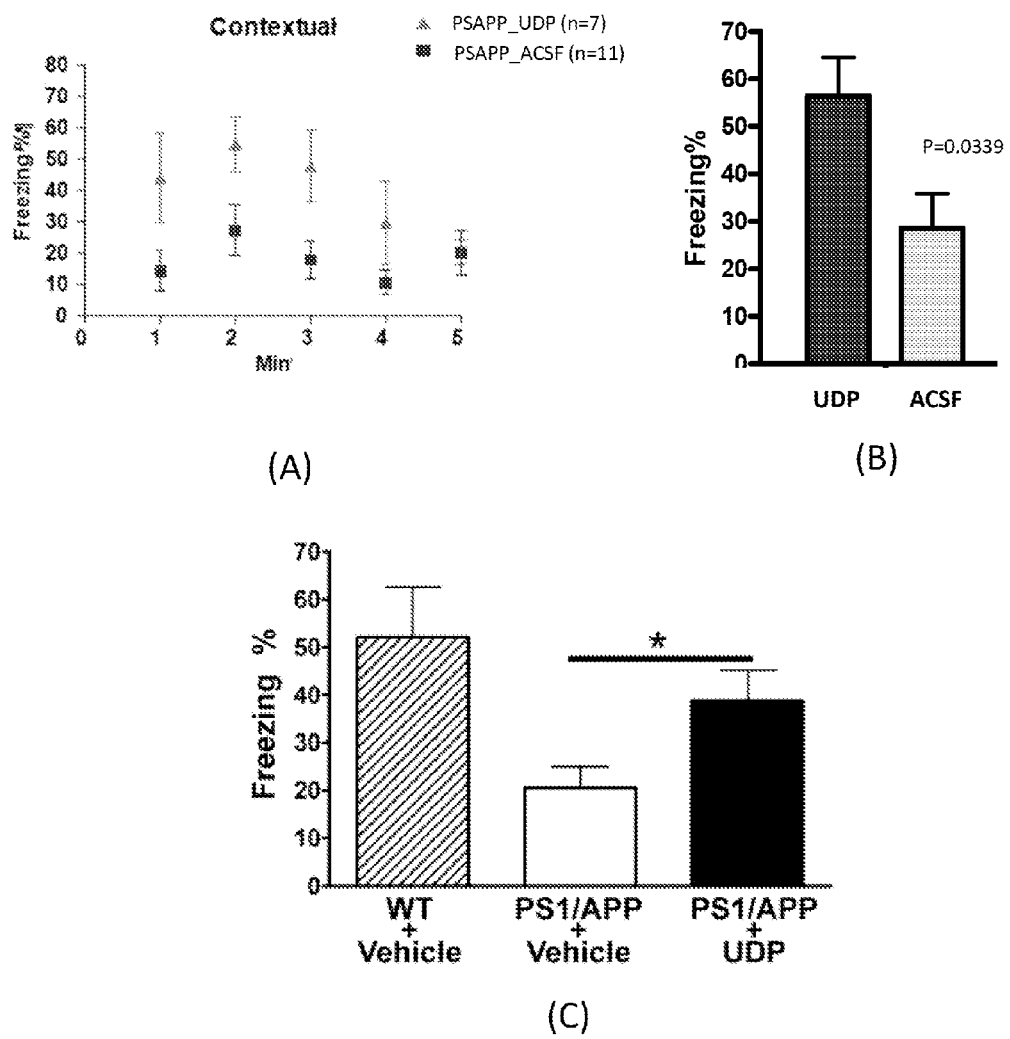

FIG. 7 shows freezing behavior (freezing %) of PASPP mice in fear conditioning studies after treatment with ACSF or UDP: (A) freezing behavior (freezing %) of PASPP mice 5 minutes following treatment with ACSF and UDP; (B) analysis of total freezing percentage of PSAPP mice treated with ACSF or UDP; and (C) using the contextual fear conditioning test PSAPP mice treated with ACSF (white bar) showed significantly less freezing time compared to the age-matched wildtype (line bar), suggesting the memory deficits in PS1/APP; UDP-treatment 3 days prior to the test significantly improved the freezing behavior (black bar) compared to ACSF treatment.

Figure 8:
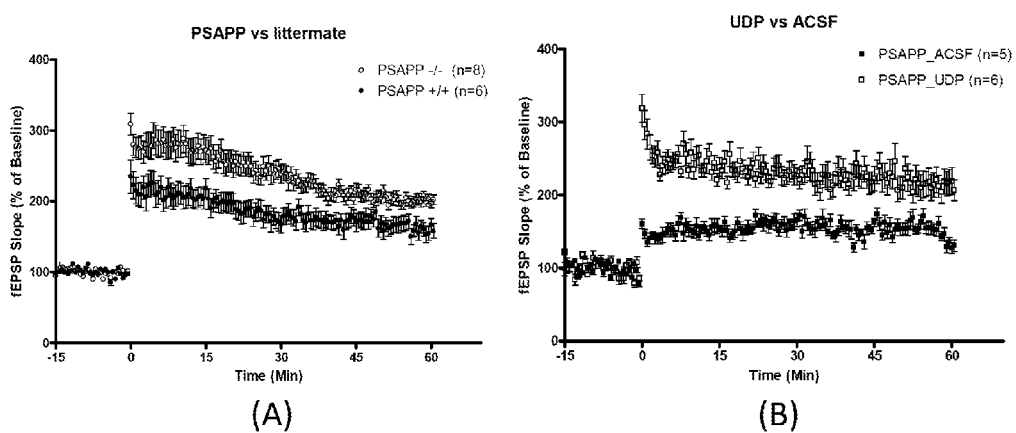
Figure 8:
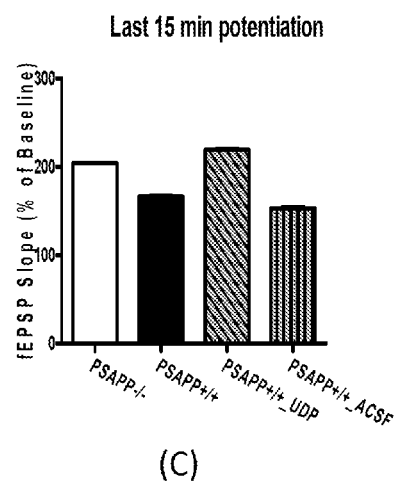

FIG. 8 shows hippocampal long-term potentiation (LTP) recorded as field excitatory postsynaptic potential (fEPSP) % in PSAPP mice, with high-frequency stimulation (HFS), 100 pulses at 100 Hz, four times in 20-second intervals: (A) depressed LTP (fEPSP %) at the schaffer collateral synapse within the CA1 area of the hippocampus in aged PSAPP mice (PSAPP+/+), as compared to littermates (PSAPP−/−); (B) increased LTP (fEPSP %) in PSAPP mice after treatment with UDP or ACSF; (C) analysis of the last 15 min potentiation, as fEPSP slope (%), in PSAPP mice.

Figure 9:
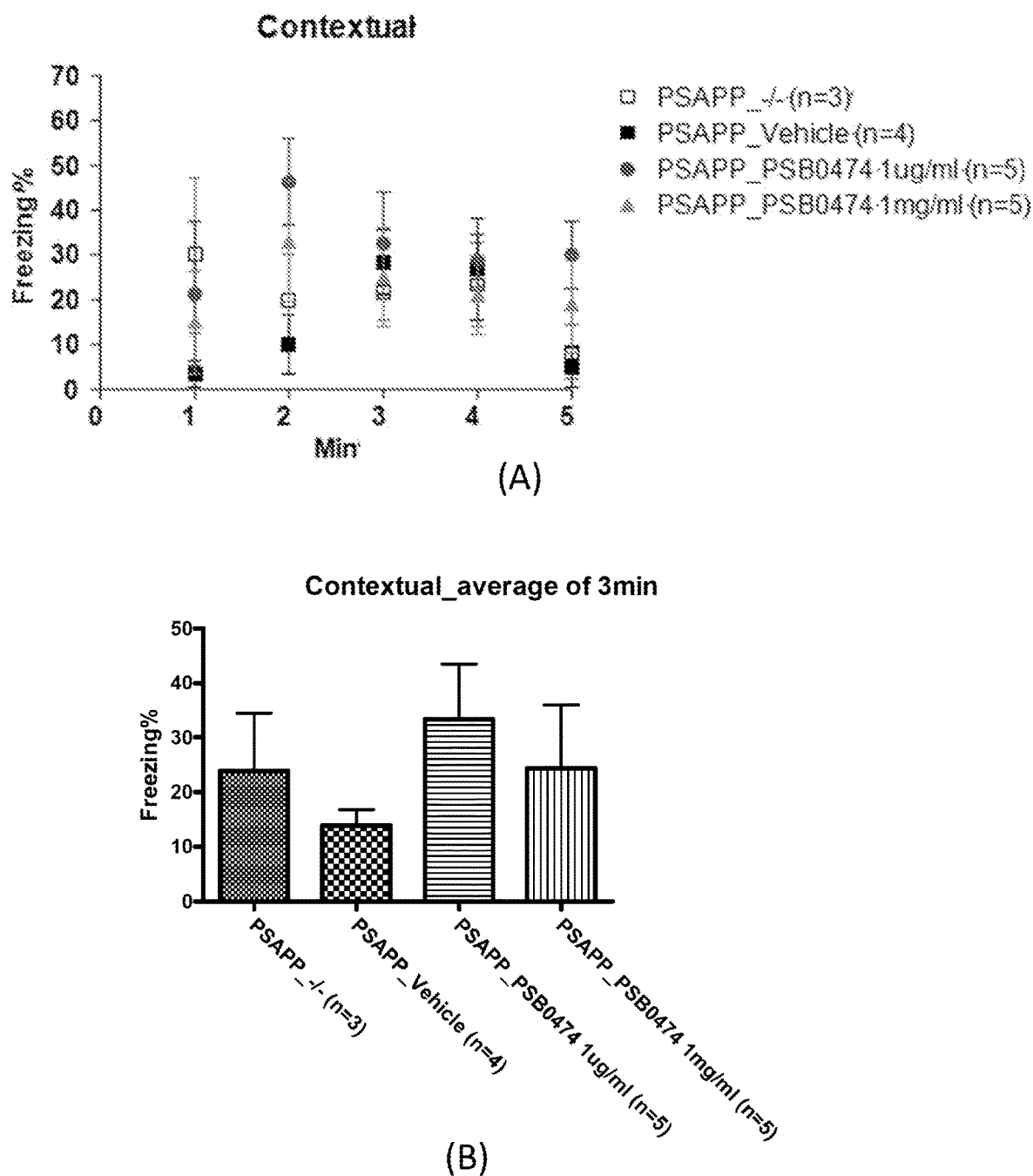
Figure 9:
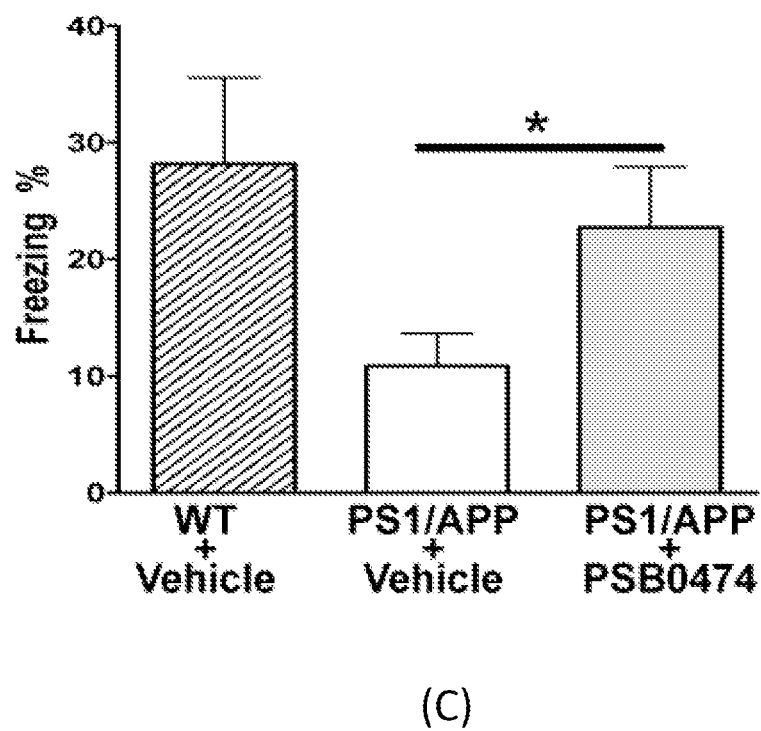

FIG. 9 shows freezing behavior (as freezing %) of PASPP mice in fear conditioning studies after treatment with 3-phenacyl-UDP (PSB0474). (A) freezing behavior (freezing %) of control littermates (PSAPP−/−), and PASPP mice 5 minutes following treatment with saline vehicle control or with 3-phenacyl-UDP (PSB0474) at two different dosages, i.e. 1 µg/ml and 1 mg/ml; (B) analysis of total freezing percentage of PSAPP mice; and (C) using the contextual fear conditioning test PSAPP mice treated with ACSF (white bar) showed significantly less freezing time compared to the age-matched wildtype (line bar), demonstrating the memory deficits in PS1/APP; one week treatment with 1 µg/kg 3-phenacyl-UDP (PSB0474) (grey bar) rescued the memory deficit as compared to the vehicle treatment (white bar).

Figure 10:
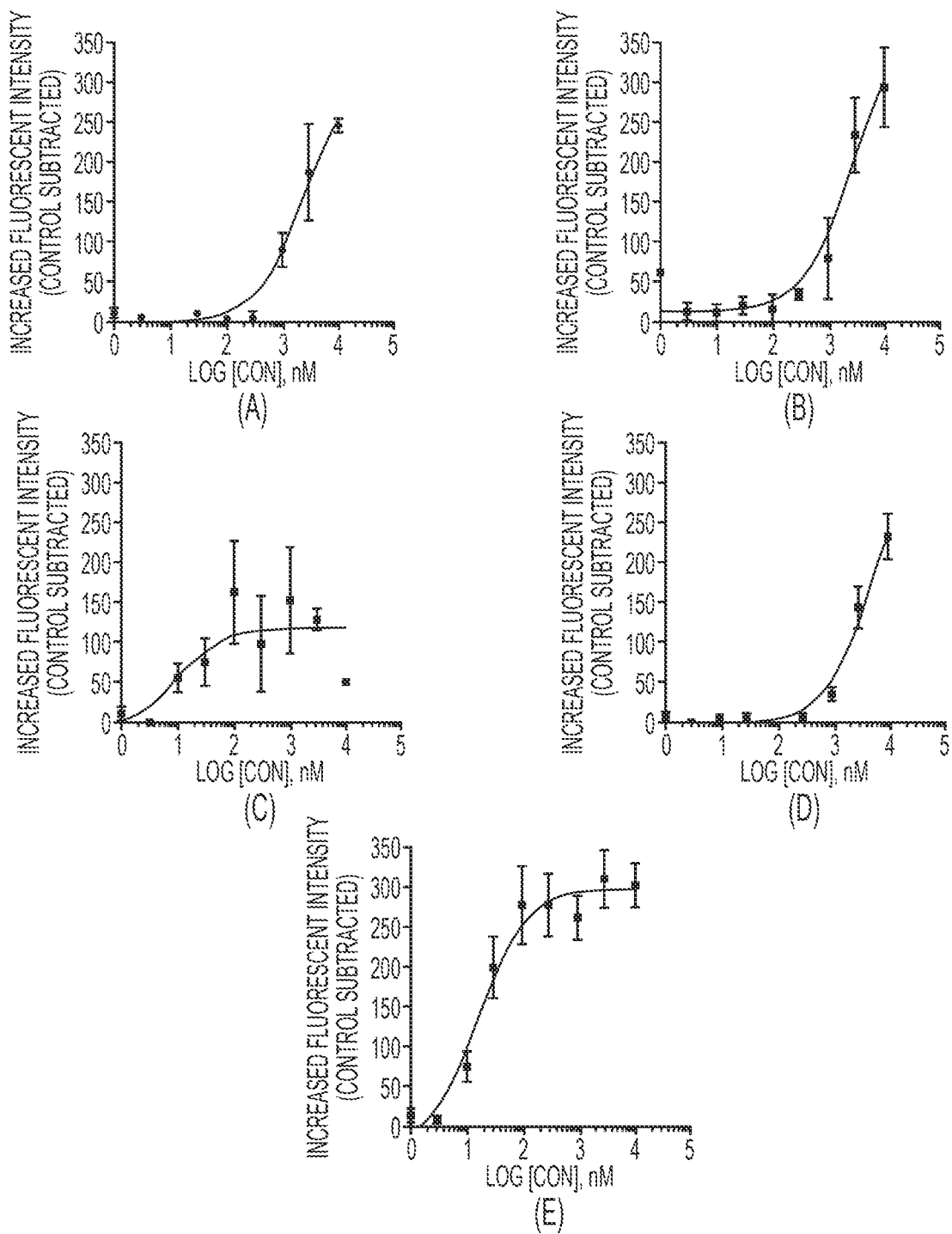
Figure 10:
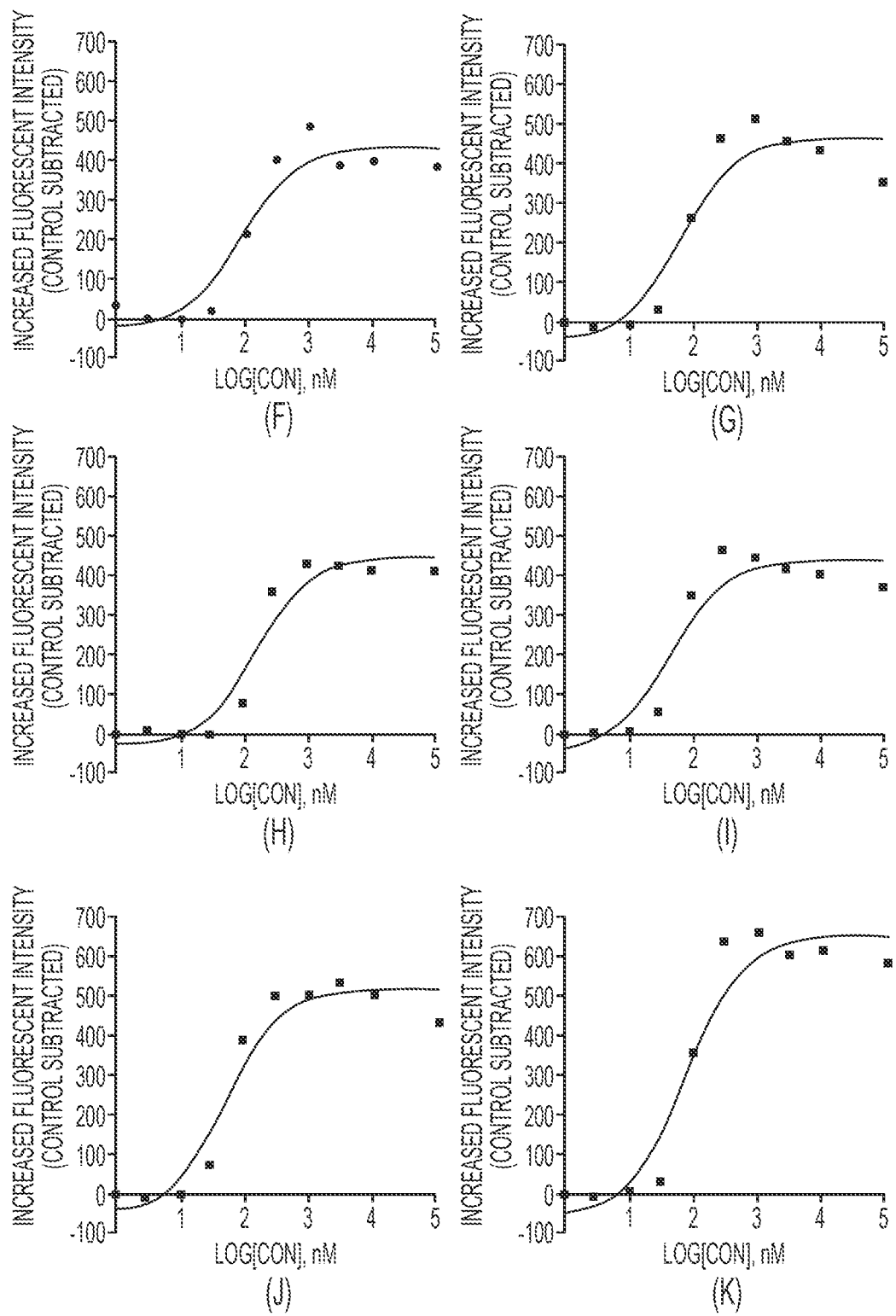

FIG. 10 shows dose-response activation of the $P_2Y_6$ receptor using compounds of the present disclosure, where compounds were tested for activation of $P_2Y_6$ receptor by measuring receptor induced $Ca^{2+}$ changes with the fluorescent $Ca^{2+}$ indicator fluo-4: (A) dose-response activation of the $P_2Y_6$ receptor using the sodium salt of the diphosphate derivative of compound 6; (B) dose-response activation of the $P_2Y_6$ receptor using the sodium salt of the diphosphate derivative of compound 3; (C) dose-response activation of the $P_2Y_6$ receptor using the sodium salt of the diphosphate derivative of compound 4; (D) dose-response activation of the using the sodium salt of the diphosphate derivative of compound 1; (E) dose-response activation of the $P_2Y_6$ receptor using the sodium salt of the diphosphate derivative of compound 5; (F) dose-response activation of the $P_2Y_6$ receptor using the sodium salt of the diphosphate derivative of compound 32; (G) dose-response activation of the $P_2Y_6$ receptor using the sodium salt of the diphosphate derivative of compound 33; (H) dose-response activation of the $P_2Y_6$ receptor using the sodium salt of the diphosphate derivative of compound 34; (I) dose-response activation of the $P_2Y_6$ receptor using the sodium salt of the diphosphate derivative of compound 35; (J) dose-response activation of the $P_2Y_6$ receptor using the sodium salt of the diphosphate derivative of compound 36; and (K) dose-response activation of the $P_2Y_6$ receptor using the sodium salt of the diphosphate derivative of compound 37.

Figure 11:
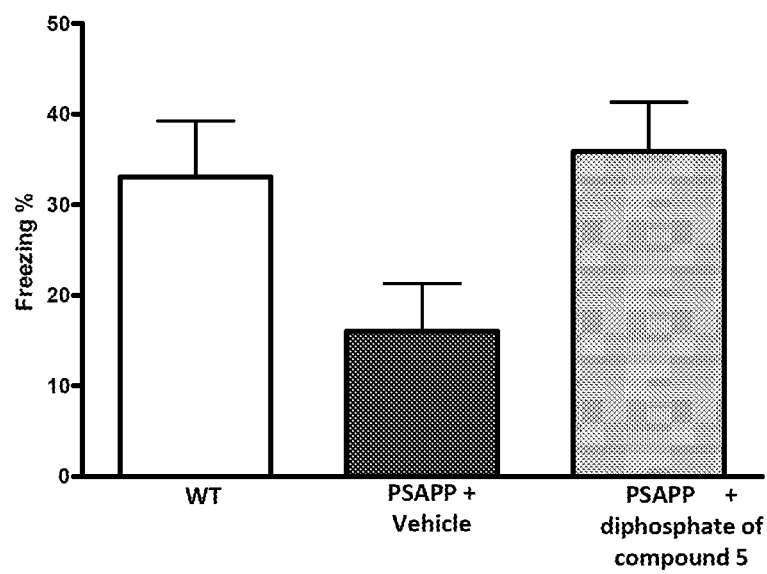

FIG. 11 shows freezing behavior (freezing %) of PASPP mice in fear conditioning studies after treatment with vehicle control or the diphosphate derivative of compound 5: using the contextual fear conditioning test PSAPP mice treated with vehicle control (black bar) showed significantly less freezing time compared to the age-matched wildtype (white bar), suggesting the memory deficits in PSAPP; administration of the diphosphate derivative of compound 5 prior to the test significantly improved the freezing behavior (line bar) compared to the control treatment indicating that the diphosphate derivative of compound 5 restores memory.

Figure 12:
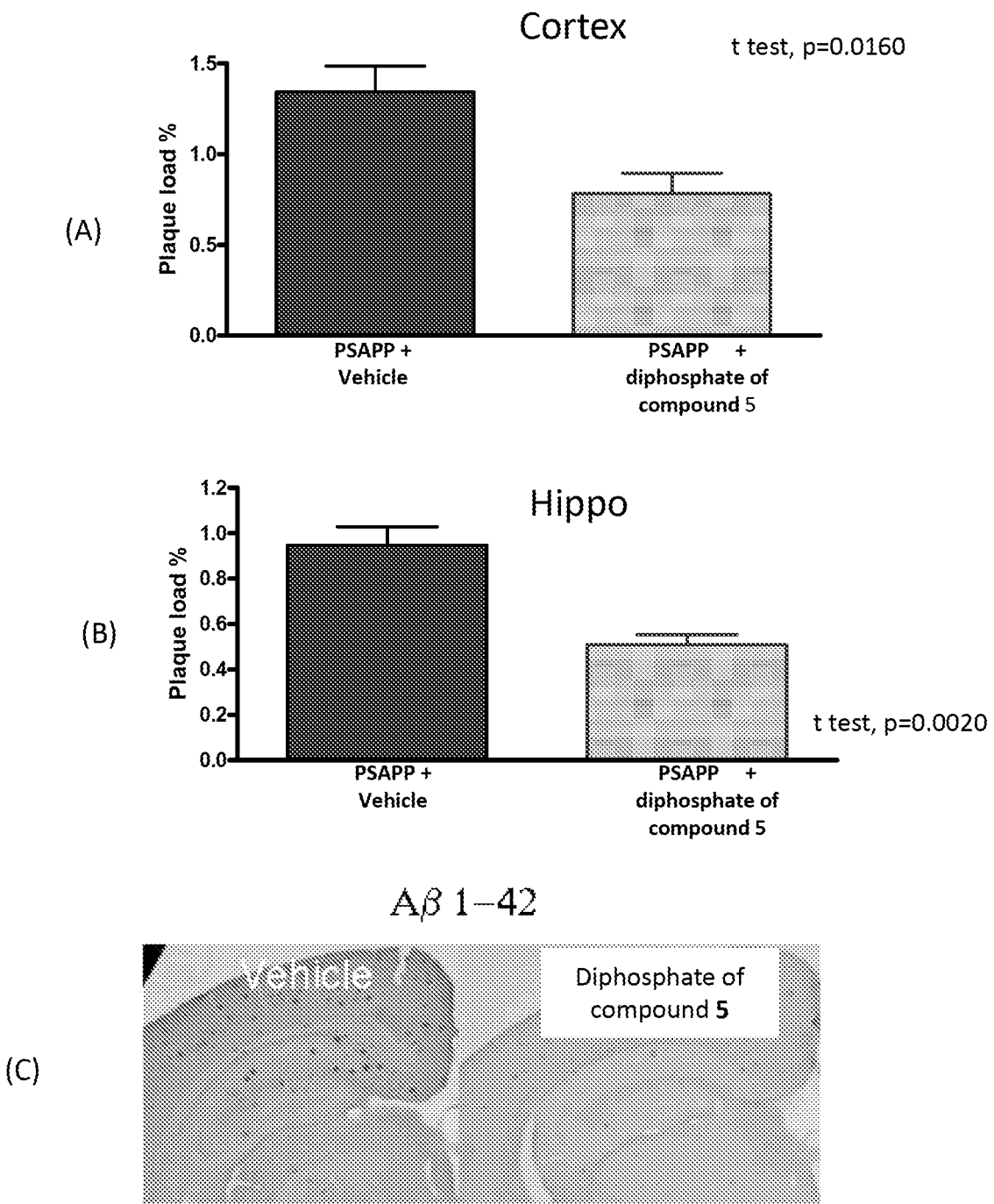

FIG. 12 shows plaque load in cortex (Cx) and hippocampus (Hp) of the PSAPP mice after treatment with the diphosphate derivative of compound 5 or vehicle control. (A) Aβ plaque load (%) in cortex after treatment with the diphosphate derivative of compound 5 or vehicle control; (B) Aβ plaque load (%) in hippocampus after treatment with the diphosphate derivative of compound 5 or vehicle control; and (C) postmortem immunohistochemistry analysis of the Aβ42 plaque load in cortex and hippocampus of PSAPP mice after treatment with the diphosphate derivative of compound 5 or vehicle control. Amyloid beta specific antibody β1-42 was used in the analysis.

Figure 13:
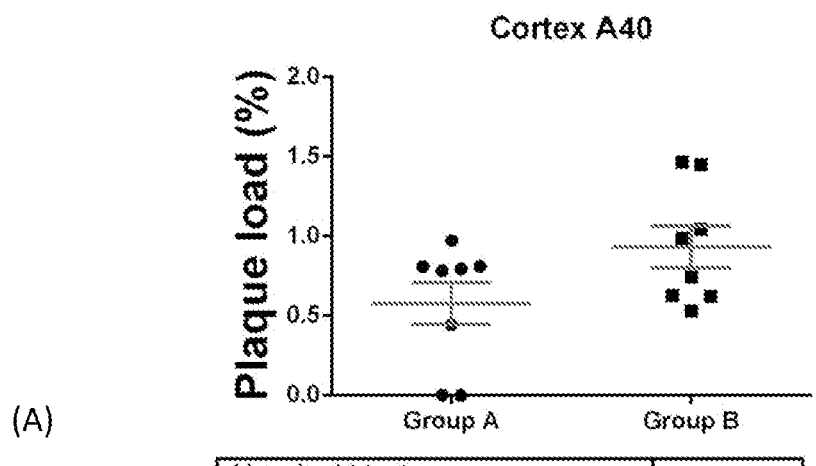
Figure 13:
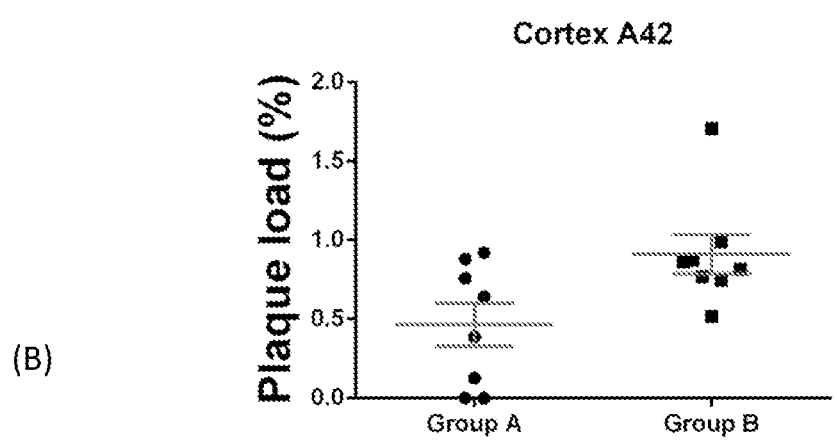

FIG. 13 shows quantification of plaque load (%) in the cortex of the PSAPP mice after treatment with nucleoside compound 5. Amyloid beta peptide specific antibodies β1-40 and β1-42 were used in the quantification. (A) plaque load (%) in cortex using β1-40 staining; (B) plaque load (%) in cortex using β1-42 staining.

Figure 14:
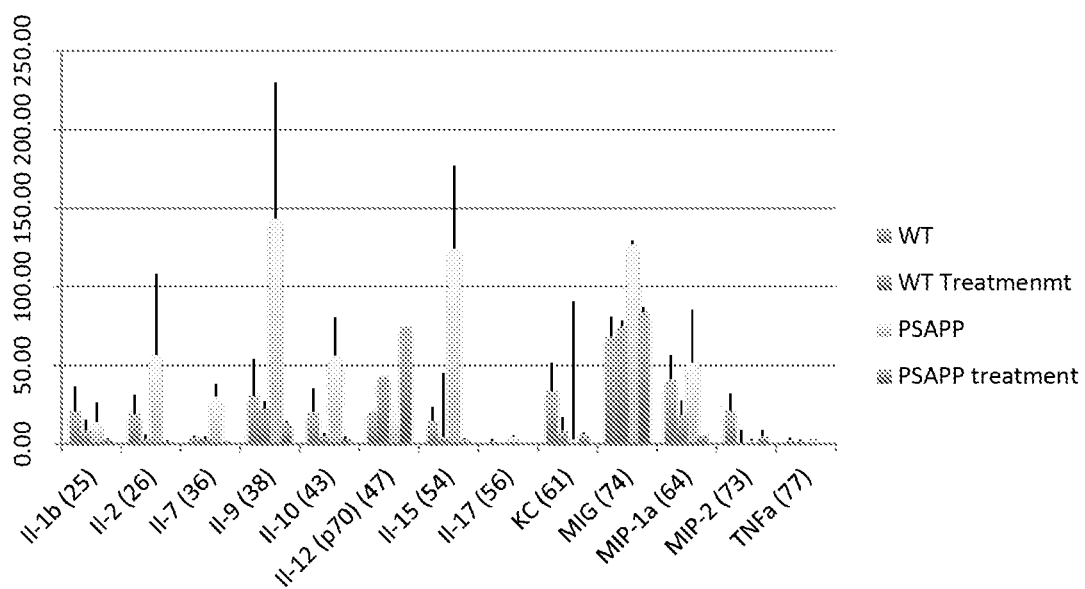

FIG. 14 summarizes plasma cytokine levels (pg/ml) in wildtype and PSAPP mice treated for 7 days (i.p.) with vehicle or the diphosphate derivative of compound 5 (1 µg/kg). Plasma cytokine levels are measured in pg/ml. The x-axis of the graph shows the various cytokines examined and the y-axis represents concentration. For each cytokine shown along the x-axis, the graph provides four bars indicative of the results for the various treatment groups which are, from left to right: untreated wildtype animals, wildtype animals treated with the diphosphate derivative compound 5, untreated PSAPP animals, and PSAPP animals treated with the diphosphate derivative compound 5.

Figure 15:
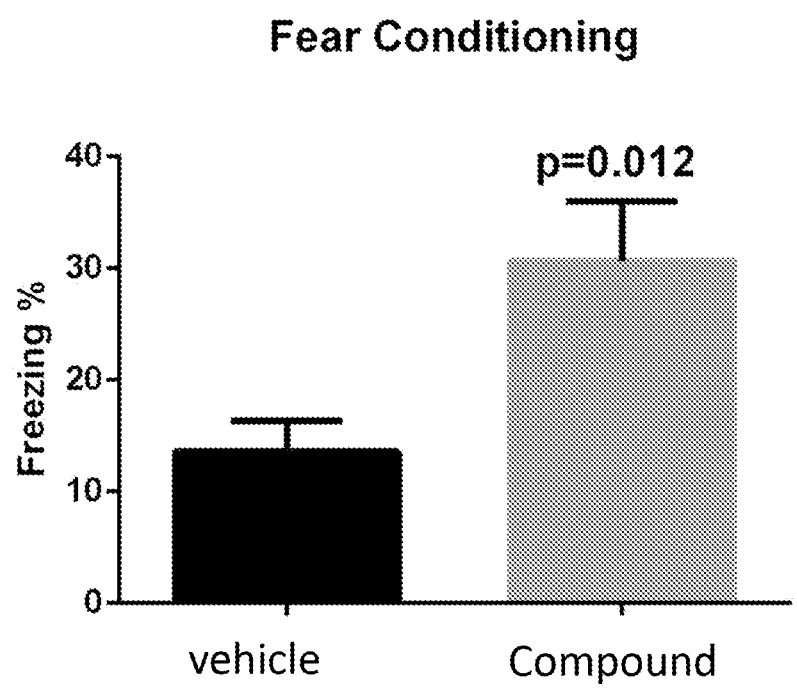

FIG. 15 summarizes results of a fear conditioning assay. PSAPP mice were treated daily for 100 days with vehicle or compound 5 (10 µg/kg; denoted on the figure as "compound"). Compound or vehicle was administered intraperitoneally (i.p.). The mice were then assessed in a fear conditioning task for memory formation.

Figure 16:
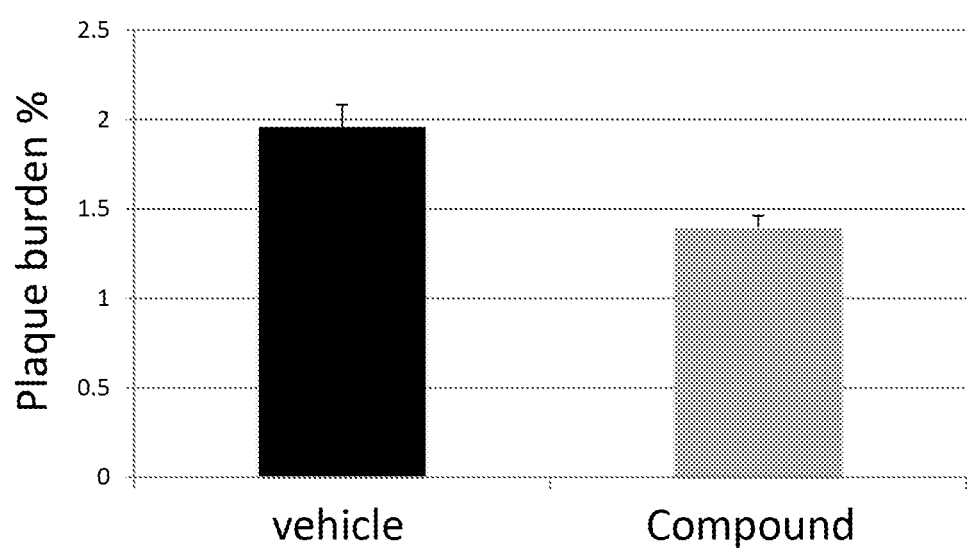

FIG. 16 summarizes results illustrating decrease in plaque burden following 100 days of treatment with compound 5.

Figure 17:
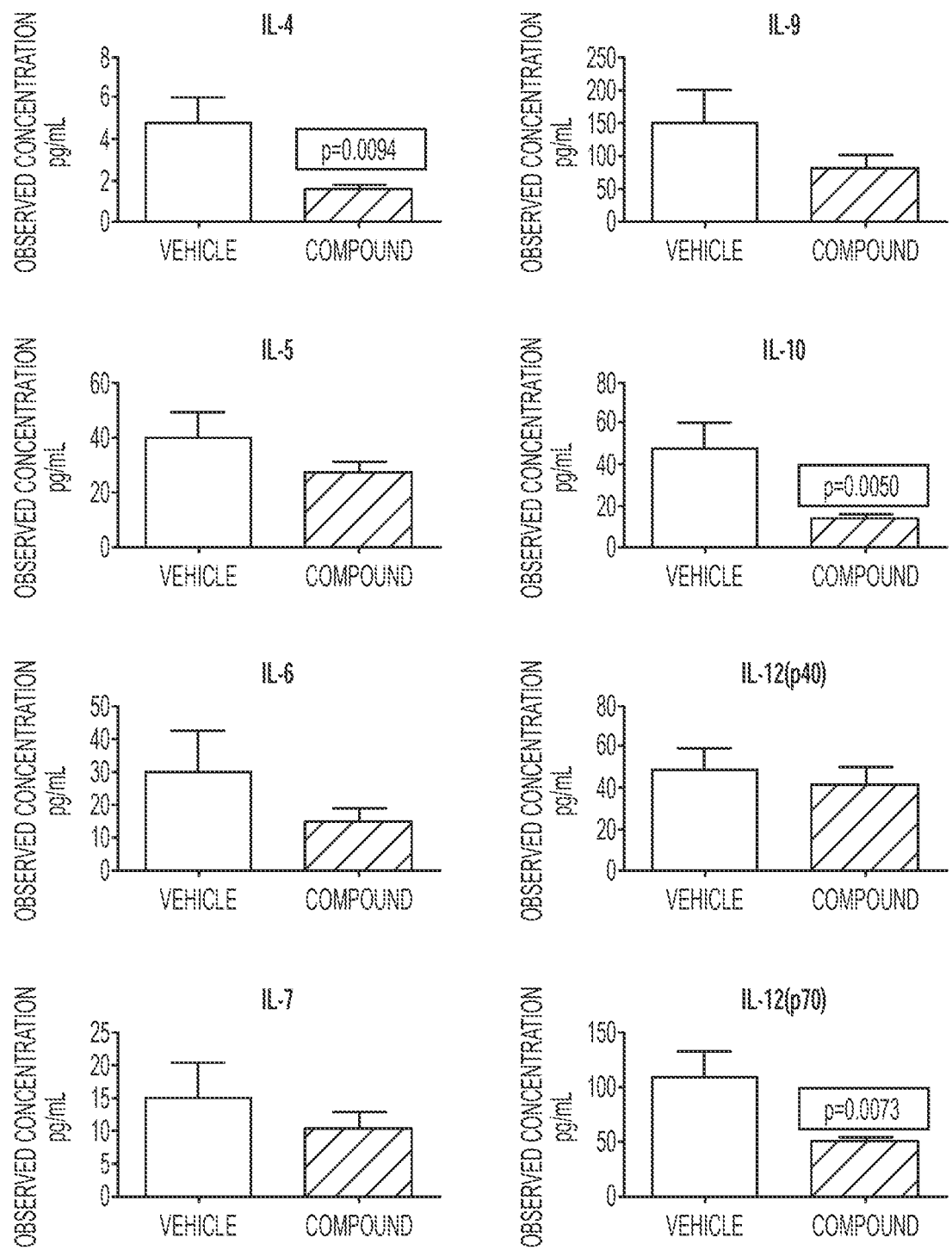

FIG. 17 summarizes plasma cytokine levels (pg/ml) in PSAPP mice treated daily for 100 days with vehicle or compound 5 (10 µg/kg). Compound or vehicle was administered intraperitoneally (i.p.). Concentration of plasma cytokine levels are measured in pg/ml, as represented on the y-axis. For each cytokine examined, plasma levels of vehicle treated or compound treated animals are shown, as represented on the x-axis. Data for the following cytokines are presented: IL-4, IL-9, IL-5, IL-10, IL-6, IL-12, and IL-7. For IL-12, levels of just the p40 subunit (p40), as well as levels of the heterodimeric cytokine (p70) are assayed.

Figure 18:
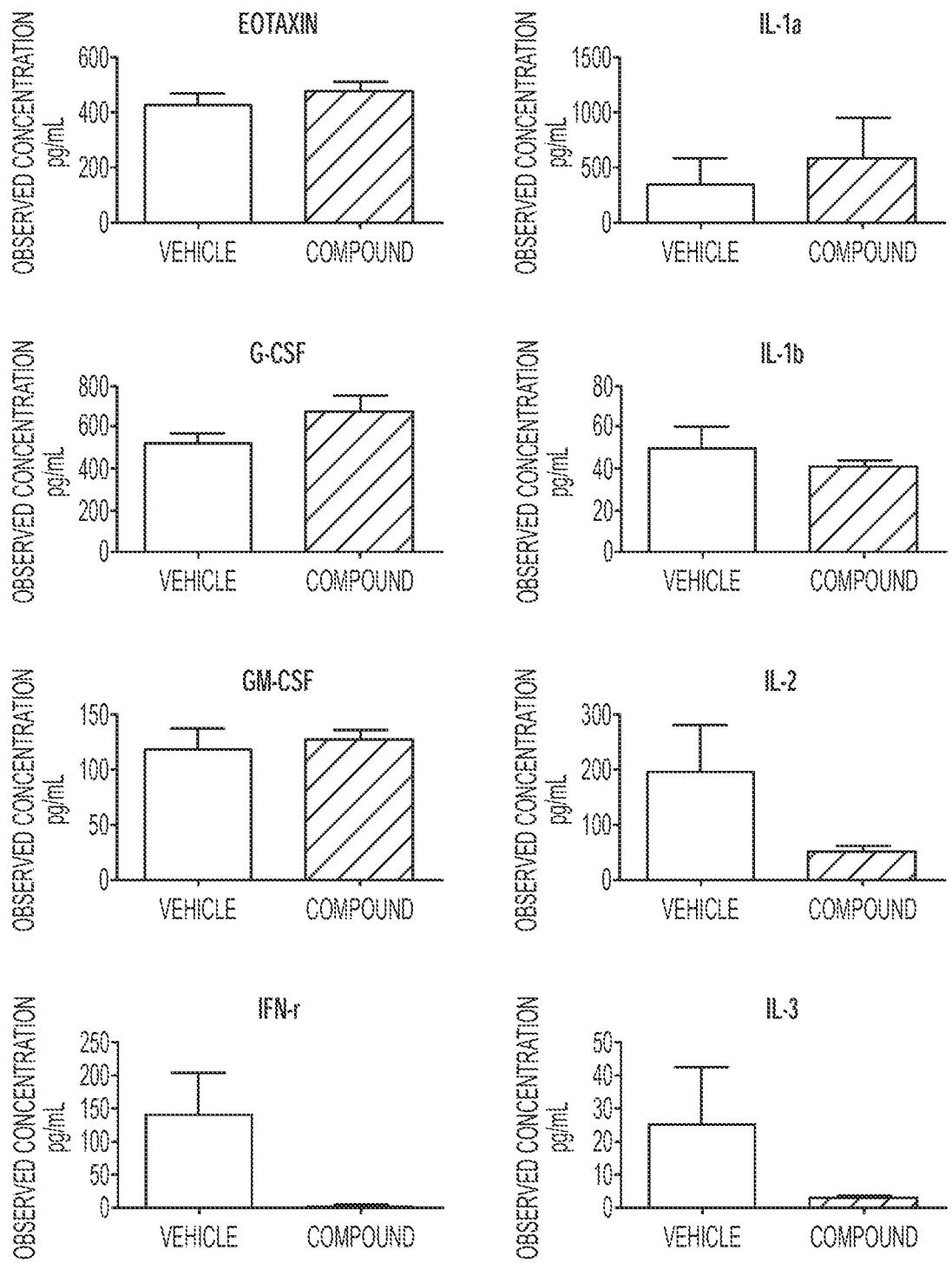

FIG. 18 summarizes plasma cytokine levels (pg/ml) in PSAPP mice treated for 100 days with vehicle or compound 5 (10 µg/kg). Compound or vehicle was administered intraperitoneally (i.p.). Concentration of plasma cytokine levels are measured in pg/ml, as represented on the y-axis. For each cytokine examined, plasma levels of vehicle treated or compound treated animals are shown, as represented on the x-axis. Data for the following cytokines are presented: eotaxin, IL-1α, G-CSF, IL-1β, GM-CSF, IL-2, IFN-r, IL-3.

Figure 19:
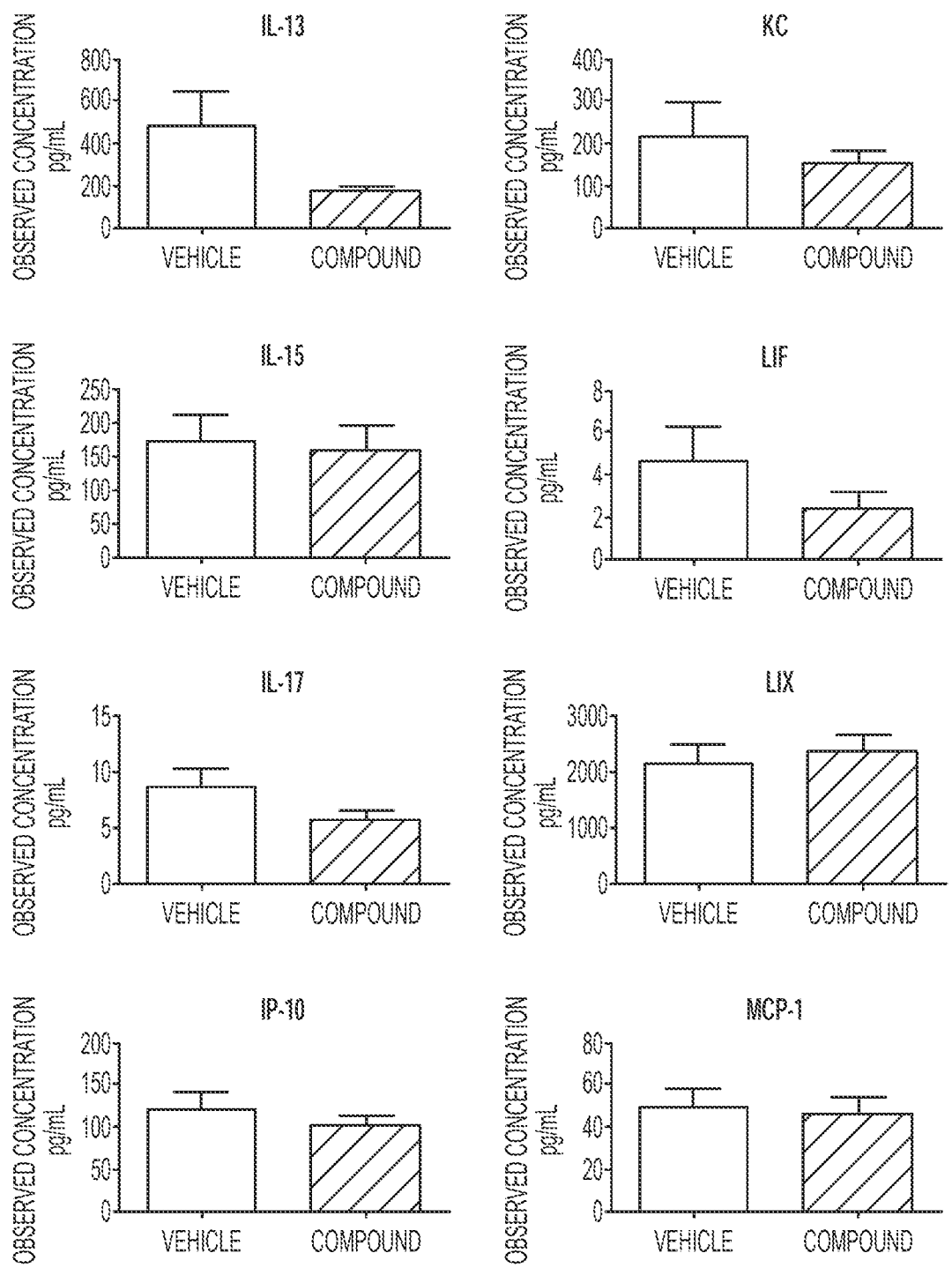

FIG. 19 summarizes plasma cytokine levels (pg/ml) in PSAPP mice treated for 100 days with vehicle or compound 5 (10 µg/kg). Compound or vehicle was administered intraperitoneally (i.p.). Concentration of plasma cytokine levels are measured in pg/ml, as represented on the y-axis. For each cytokine examined, plasma levels of vehicle treated or compound treated animals are shown, as represented on the x-axis. Data for the following cytokines are presented: IL-13, KC, IL-15, LIF, IL-17, LIX, IP-10, and MCP-1.

Figure 20:
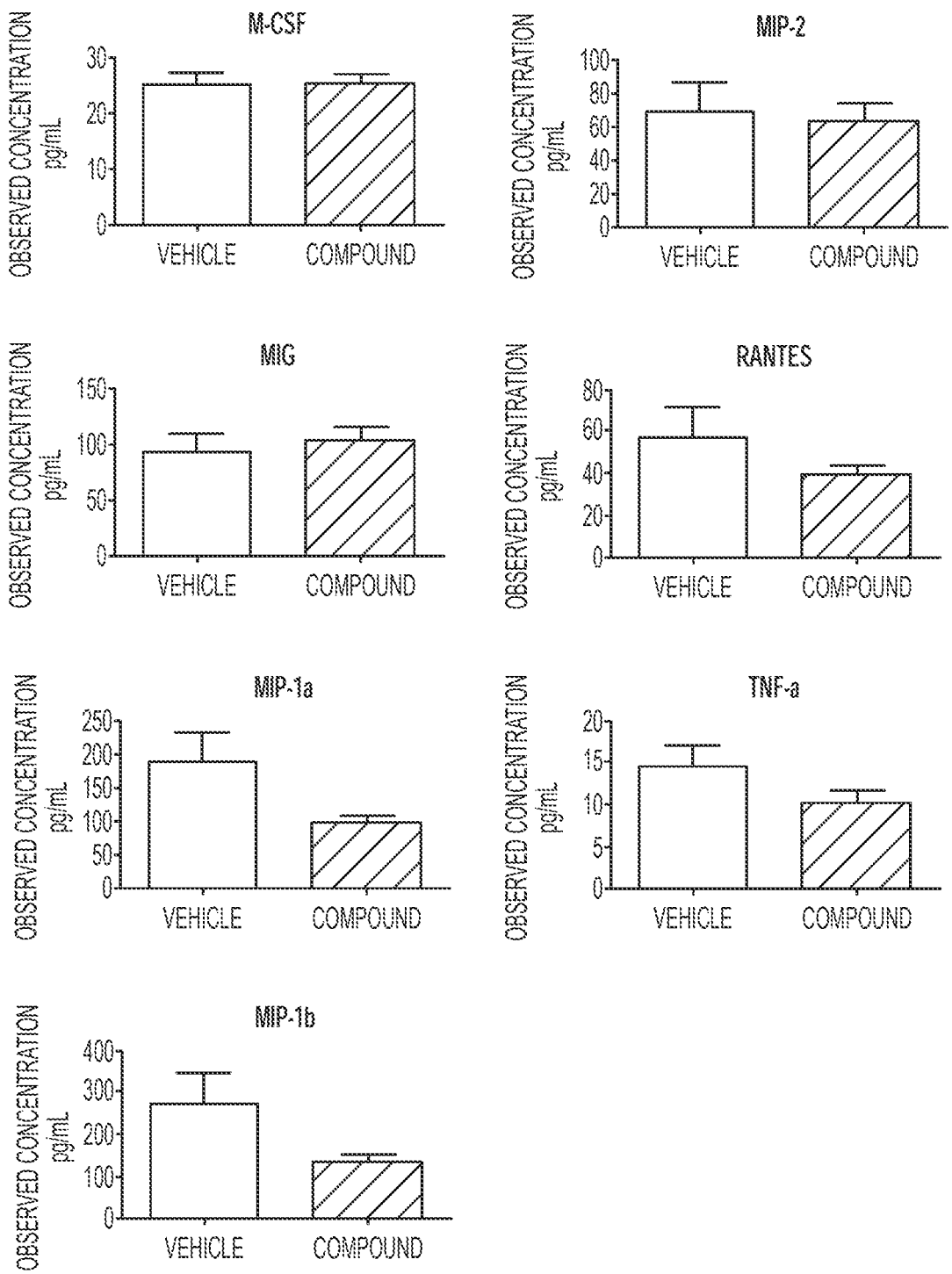

FIG. 20 summarizes plasma cytokine levels (pg/ml) in PSAPP mice treated for 100 days with vehicle or compound 5 (10 µg/kg). Compound or vehicle was administered intraperitoneally (i.p.). Concentration of plasma cytokine levels are measured in pg/ml, as represented on the y-axis. For each cytokine examined, plasma levels of vehicle treated or compound treated animals are shown, as represented on the x-axis. Data for the following cytokines are presented: M-CSF, MIP2, MIG, RANTES, MIP-1a, and MIP-1b, and TNFα.

Figure 21:
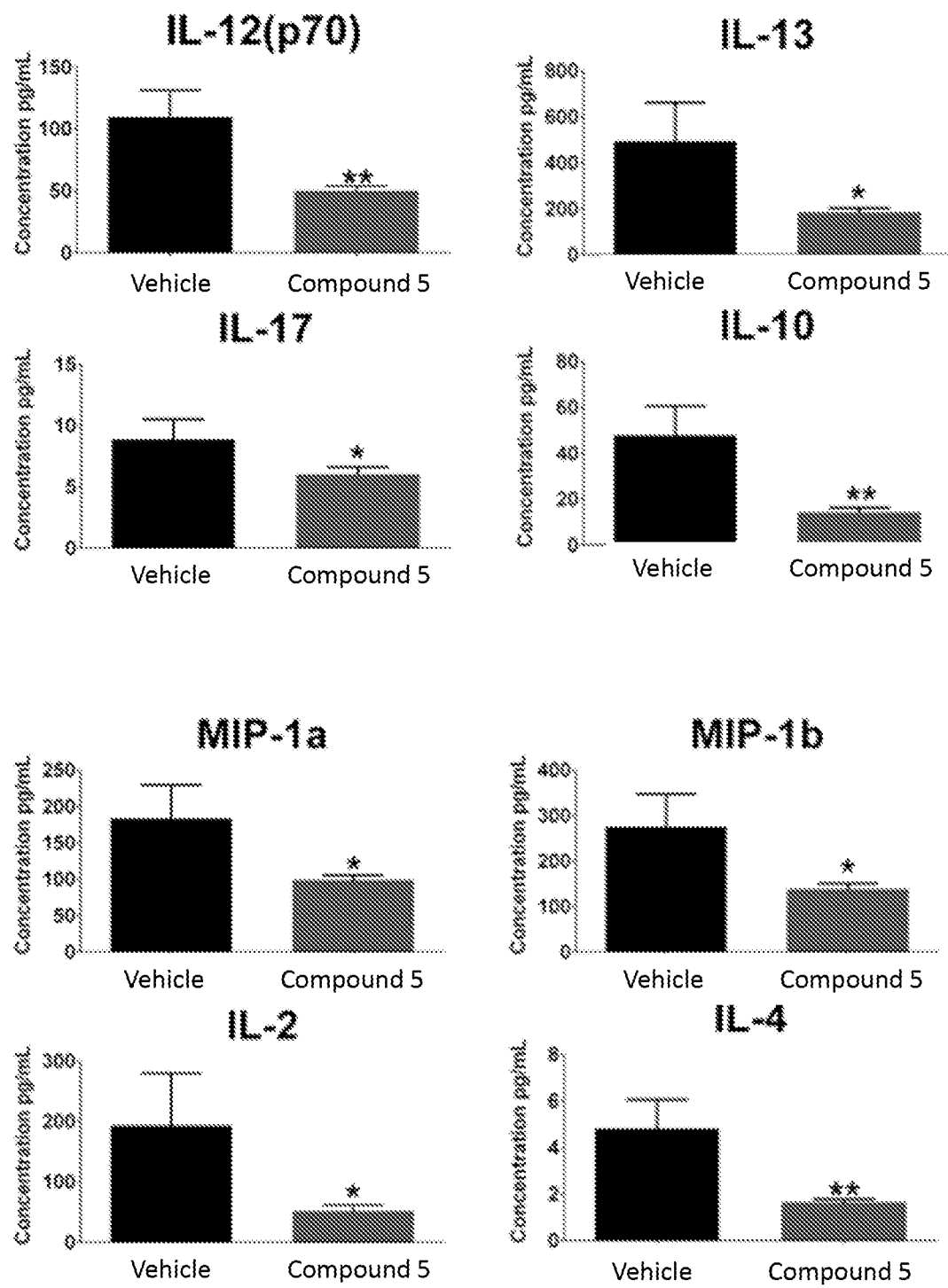

FIG. 21 summarizes plasma cytokine levels (pg/ml) in PSAPP mice treated for 100 days with vehicle or compound 5 (10 µg/kg), with treatment beginning at approximately 3 months of age. Compound or vehicle was administered intraperitoneally (i.p). Concentration of plasma cytokine levels are measured in pg/ml, as represented on the y-axis. For each cytokine examined, plasma levels of vehicle treated or compound treated animals are shown, as represented on the x-axis. Data for the following cytokines are presented: IL-12, IL-13, IL-17, IL-10, MIP-1a, MIP-1b, IL-2, and IL-4. * denotes $p<0.05$; ** denotes $p<0.01$.

Figure 22:
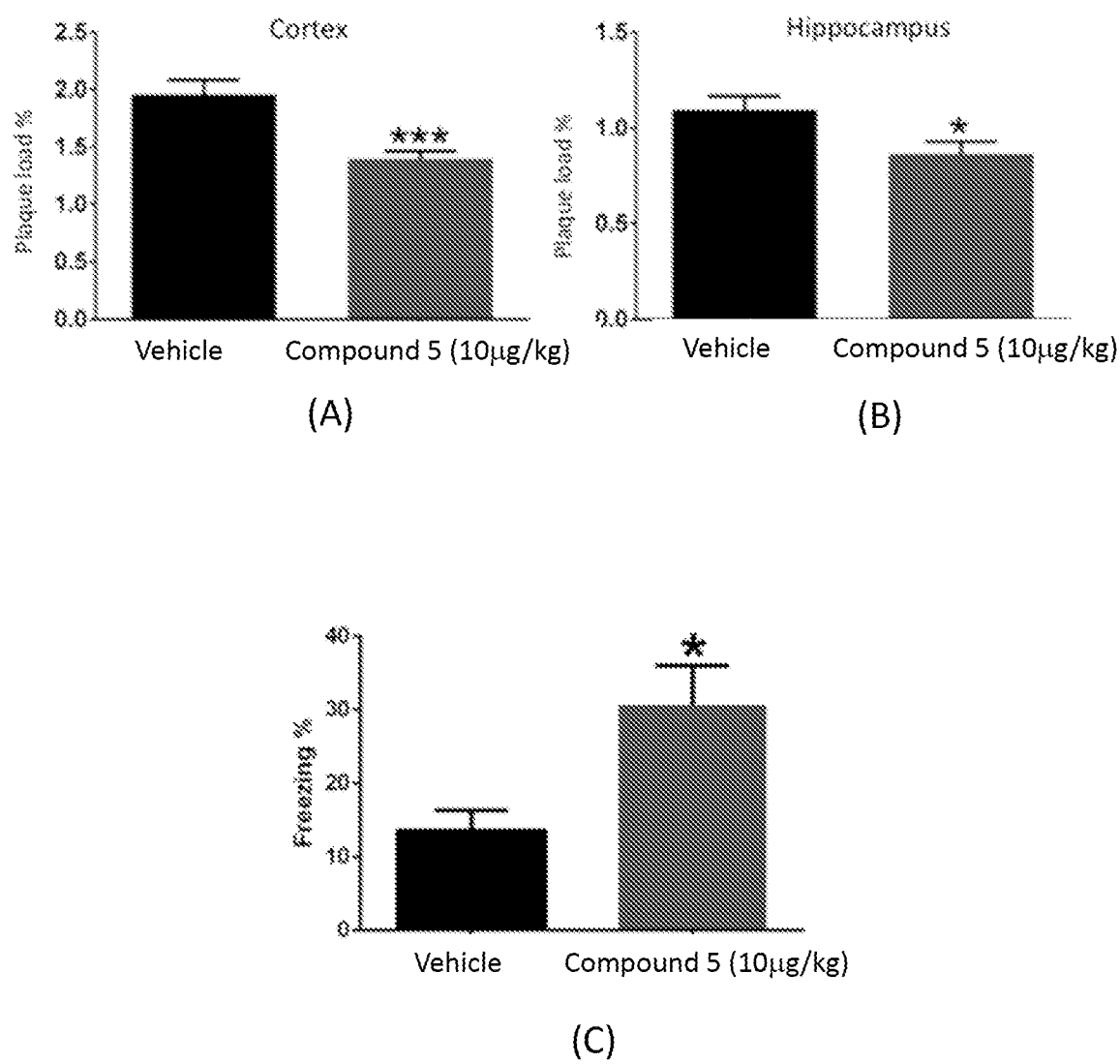

FIG. 22 summarizes additional data obtained as part of the same study as in FIG. 21 in which PSAPP mice were treated for 100 days with vehicle or compound 5, with treatment beginning at approximately 3 months of age. Plaque load was evaluated in the cortex (FIG. 22A) or hippocampus (FIG. 22B). The mice were also evaluated in a fear conditioning test of memory (FIG. 22C). In FIG. 22A, *** denotes $p<0.01$. In FIGS. 22B and 22C, * denotes $p<0.02$.

Figure 23:
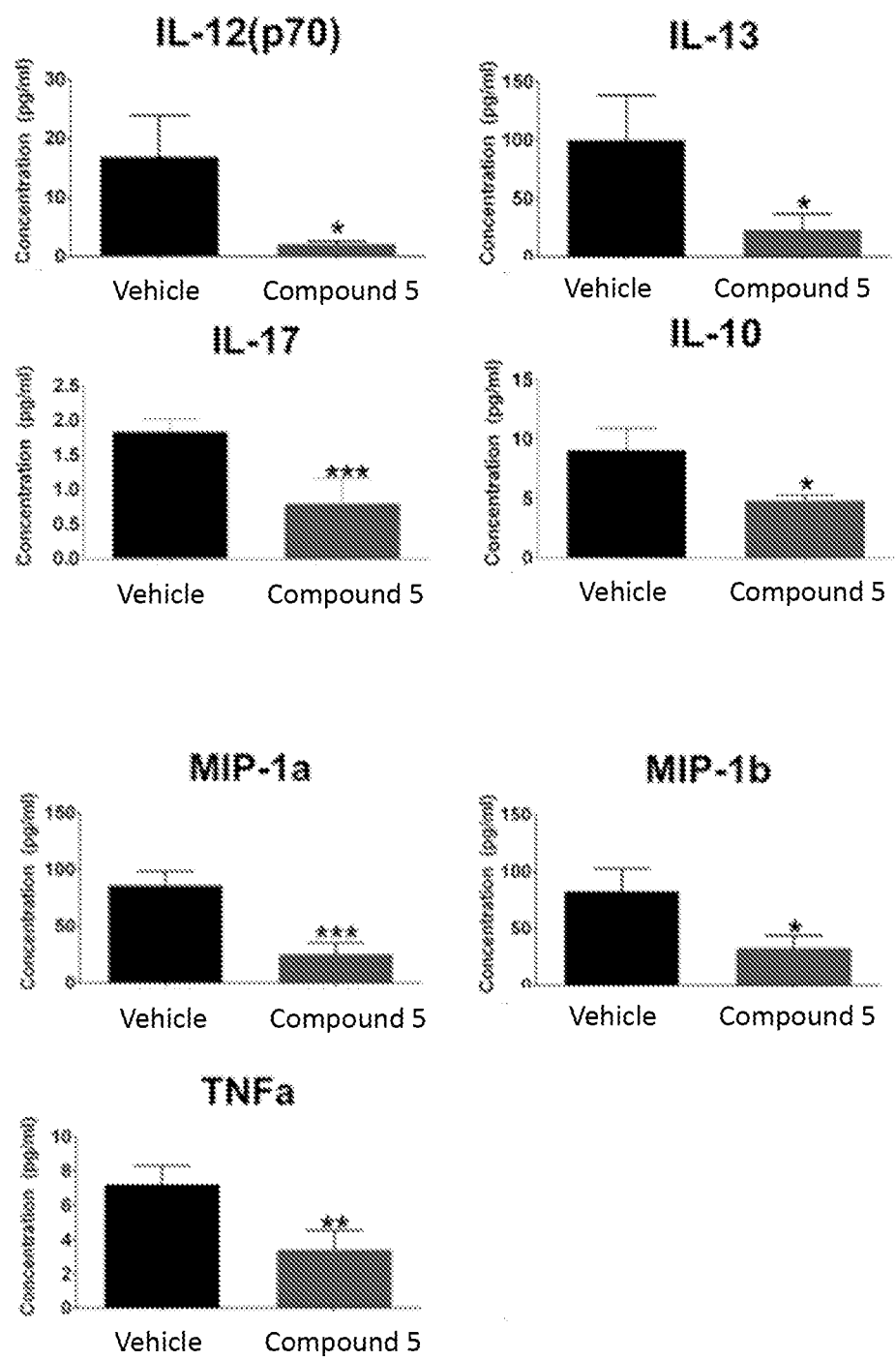

FIG. 23 summarizes plasma cytokine levels (pg/ml) in PSAPP mice treated for 7 days with vehicle or compound 5 (10 µg/kg), with treatment beginning at approximately 6 months of age after onset of symptoms in these PSAPP mice. Compound or vehicle was administered intraperitoneally (i.p). Concentration of plasma cytokine levels are measured in pg/ml, as represented on the y-axis. For each cytokine examined, plasma levels of vehicle treated or compound treated animals are shown, as represented on the x-axis. Data for the following cytokines are presented: IL-12, IL-13, IL-17, IL-10, MIP-1a, and TNFalpha. * denotes $p<0.05$;  denotes $p<0.005$; * denotes $p<0.0005$.

Figure 24:
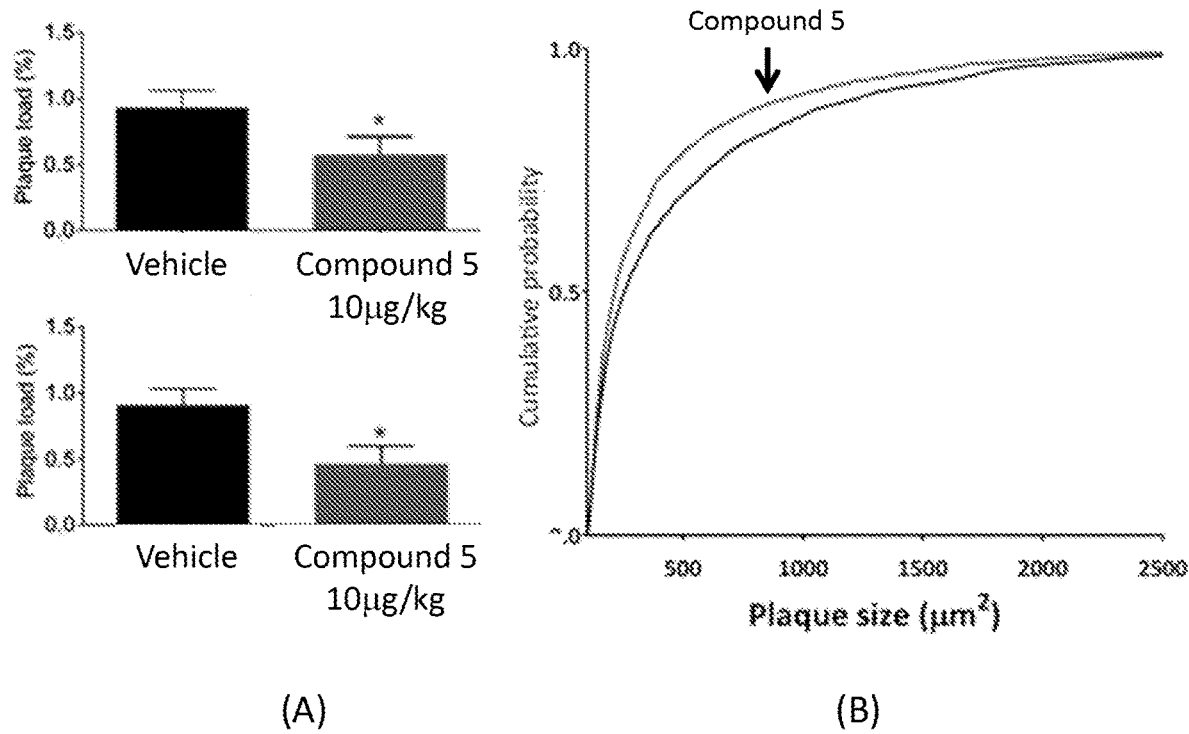

FIG. 24 summarizes additional data obtained as part of the same study as in FIG. 23 in which PSAPP mice were treated for 7 days with vehicle or compound 5 (10 µg/kg), with treatment beginning at approximately 6 months of age after onset of symptoms in these PSAPP mice. Plaque load was evaluated in the cortex (FIG. 24A, top panel) and hippocampus (FIG. 24A, bottom panel). In addition to plaque load, plaque size was evaluated (FIG. 24B). * denotes $p<0.05$.

Figure 25:
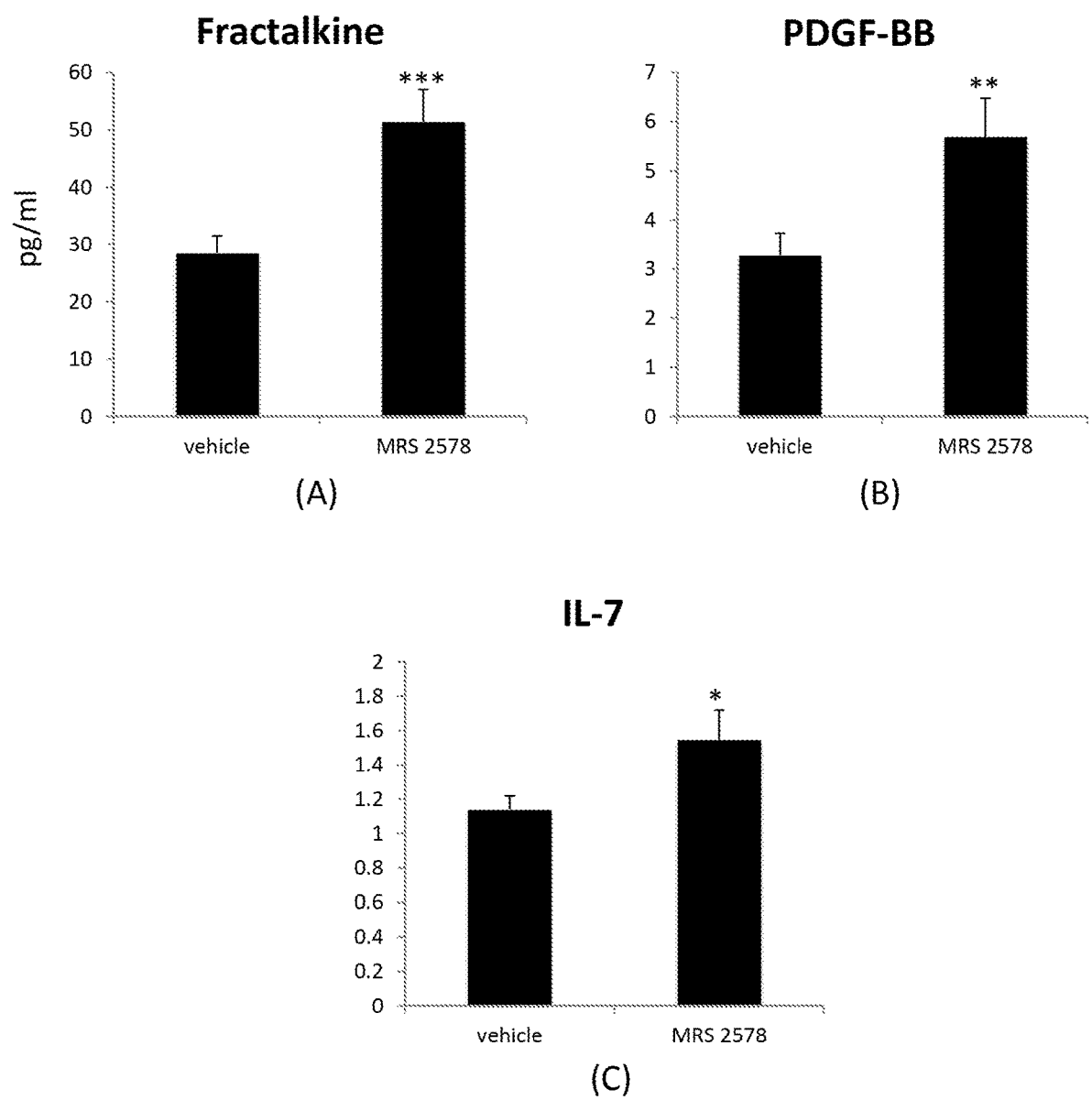

FIG. 25 summarize data evaluating cytokine release from human THP-1 cells treated in vitro with vehicle or the $P_2Y_6$ antagonist MRS 2578 (CAS No. 711019-86-2). Concentration of cytokine secreted into the culture media is measured in pg/ml, as represented on the y-axis. For each cytokine examined, levels of cytokine released into the culture media following treatment with vehicle or MRS 2578, as represented on the x-axis, are shown. Results for the following cytokines are depicted: fractalkine (FIG. 25A), PDGF-BB (FIG. 25B), and IL-7 (FIG. 25C). Treatment with MRS 2578 increased release of each of these three cytokines from human THP-1 cells, relative to treatment with vehicle control. Increased release is assayed by measuring concentration of the cytokine in the cell culture supernatant following treatment. * denotes $p<0.05$;  denotes $p<0.02$; * denotes $p<0.002$.

Figure 26:
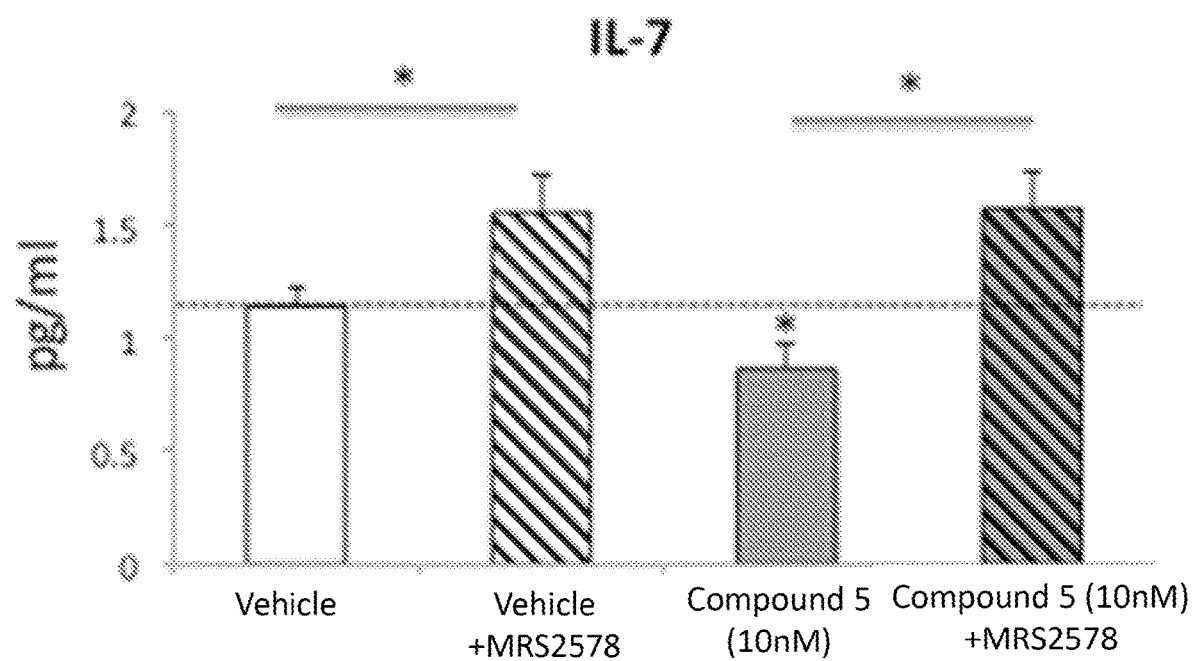

FIG. 26 summarizes data evaluating concentration of cytokine (IL-7) released from human THP-1 cells treated in vitro with vehicle, compound 5, the $P_2Y_6$ antagonist MRS 2578, or both compound 5 and MRS 2578. Concentration of cytokine secreted into the culture media is measured in pg/ml, as represented on the y-axis. Treatment with MRS 2578 increased release of IL-7 from human THP-1 cells. Treatment with compound 5 decreased release of IL-7 from human THP-1 cells, and this effect was abrogated by co-treatment with MRS 2578. * denotes $p<0.05$.

DETAILED DESCRIPTION OF THE INVENTION

A. Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents that are known with respect to structure, and those that are not known with respect to structure. The $P_2Y_6$ receptor-modulating activity (such as direct or indirect agonist activity) of such agents may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. Beneficial or desired clinical results include, but are not limited to, alleviation, amelioration, or slowing the progression, of one or more symptoms associated with a neuronal disorder, including neurodegeneration and traumatic brain injury, as well as pain. In certain embodiments, treatment may be prophylactic. Exemplary beneficial clinical results are described herein.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Appropriate methods of administering a substance, a compound or an agent to a subject will also depend, for example, on the age of the subject, whether the subject is active or inactive at the time of administering, whether the subject is cognitively impaired at the time of administering, the extent of the impairment, and the chemical and biological properties of the compound or agent (e.g. solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of cognitive impairment or other symptoms of the condition being treated, such as neurodegeneration (such as Alzheimer's disease), pain and traumatic brain injury, the therapeutics or combination of therapeutics selected for administration, and the mode of administration. The skilled worker can readily determine the effective amount for a given situation by routine experimentation.

"Ligand" as used herein refers to any molecule that is capable of specifically binding to another molecule, such as the $P_2Y_6$ receptor. The term "ligand" includes both agonists and antagonists. "Agonist" means an agent which, when interacting, either directly or indirectly, with a biologically active molecule (e.g. an enzyme or a receptor) causes an increase in the biological activity thereof "Antagonist" means an agent which, when interacting, either directly or indirectly, with a biologically active molecule(s) (e.g. an enzyme or a receptor) causes a decrease in the biological activity thereof. In certain embodiments, the compounds of the present disclosure modulate $P_2Y_6$ receptor activity, either directly or indirectly. In certain embodiments, the compounds agonize $P_2Y_6$ receptor activity, for example, directly, for example, by direct interaction with the $P_2Y_6$ receptor, or indirectly, for example, via a metabolite that interacts with the $P_2Y_6$ receptor. In certain embodiments, the compounds of the disclosure (such as compounds of formulae I (including compounds of formula I-A and formula I-B) and II and pharmaceutically acceptable salts and prodrugs thereof, as well as the individual compounds disclosed herein) are used, directly or indirectly, as $P_2Y_6$ receptor agonists or $P_2Y_6$ receptor-modulating compounds, and may be used in any of the in vitro and/or in vivo methods disclosed herein. In certain embodiments, compounds disclosed herein are themselves $P_2Y_6$ receptor-modulating compounds, and the disclosure encompasses these compounds as well as their salts and/or prodrugs as agonists of the disclosure. Other compounds, salts, and prodrugs described herein are not active themselves, but are converted in vivo to compounds that are active $P_2Y_6$ receptor-modulating compounds. The disclosure contemplates that all such compounds, salts, or prodrugs of the disclosure, whether active themselves or are converted into active compounds in vivo, may be used to treat any of conditions described herein.

The term "aliphatic" as used herein means a straight chained or branched alkyl, alkenyl or alkynyl. It is understood that alkenyl or alkynyl embodiments need at least two carbon atoms in the aliphatic chain. Aliphatic groups typically contains from 1 (or 2) to 12 carbons, such as from 1 (or 2) to 4 carbons.

The term "aryl" as used herein means a monocyclic or bicyclic carbocyclic aromatic ring system. Phenyl is an example of a monocyclic aromatic ring system. Bicyclic aromatic ring systems include systems wherein both rings are aromatic, e.g., naphthyl, and systems wherein only one of the two rings is aromatic, e.g., tetralin.

The term "heterocyclic" as used herein means a monocyclic or bicyclic non-aromatic ring system having 1 to 3 heteroatom or heteroatom groups in each ring selected from O, N, NH, S, SO, or $SO_2$ in a chemically stable arrangement. In a bicyclic non-aromatic ring system embodiment of "heterocyclyl", one or both rings may contain said heteroatom or heteroatom groups. In another heterocyclic ring system embodiment, a non-aromatic heterocyclic ring may optionally be fused to an aromatic carbocycle.

Examples of heterocyclic rings include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydroimidazol-2-one.

The term "heteroaryl" as used herein means a monocyclic or bicyclic aromatic ring system having 1 to 3 heteroatom or heteroatom groups in each ring selected from O, N, NH or S in a chemically stable arrangement. In such a bicyclic aromatic ring system embodiment of "heteroaryl" both rings may be aromatic; and one or both rings may contain said heteroatom or heteroatom groups.

Examples of heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "cycloalkyl or cycloalkenyl" refers to a monocyclic or fused or bridged bicyclic carbocyclic ring system that is not aromatic. Cycloalkenyl rings have one or more units of unsaturation. Exemplary cycloalkyl or cycloalkenyl groups include cyclopropyl, cyclobutyl, cyclopentyl, cyclohexyl, cyclohexenyl, cycloheptyl, cycloheptenyl, norbornyl, adamantyl and decalinyl.

As used herein, the carbon atom designations may have the indicated integer and any intervening integer. For example, the number of carbon atoms in a (C1-C4)-alkyl group is 1, 2, 3, or 4. It should be understood that these designation refer to the total number of atoms in the appropriate group. For example, in a (C3-C10)-heterocyclyl the total number of carbon atoms and heteroatoms is 3 (as in aziridine), 4, 5, 6 (as in morpholine), 7, 8, 9, or 10.

"Pharmaceutically acceptable salt" or "salt" is used herein to refer to an agent or a compound according to the disclosure that is a therapeutically active, non-toxic base and acid salt form of the compounds. The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like. See, e.g., WO 01/062726.

Compounds containing acidic protons may be converted into their therapeutically active, non-toxic base addition salt form, e. g. metal or amine salts, by treatment with appropriate organic and inorganic bases. Appropriate base salt forms include, for example, ammonium salts, alkali and earth alkaline metal salts, e. g., lithium, sodium, potassium, magnesium, calcium salts and the like, salts with organic bases, e. g. N-methyl-D-glucamine, hydrabamine salts, and salts with amino acids such as, for example, arginine, lysine and the like. Conversely, said salt forms can be converted into the free forms by treatment with an appropriate base or acid. Compounds and their salts can be in the form of a solvate, which is included within the scope of the present disclosure. Such solvates include for example hydrates, alcoholates and the like. See, e.g., WO 01/062726.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure also relates to all stereoisomeric forms such as enantiomeric and diastereoisomeric forms of the compounds or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers. Multiple substituents on a piperidinyl or the azepanyl ring can also stand in either cis or trans relationship to each other with respect to the plane of the piperidinyl or the azepanyl ring. Some of the compounds may also exist in tautomeric forms. Such forms, although not explicitly indicated in the formulae described herein, are intended to be included within the scope of the present disclosure. With respect to the methods and compositions of the present disclosure, reference to a compound or compounds is intended to encompass that compound in each of its possible isomeric forms and mixtures thereof unless the particular isomeric form is referred to specifically. See, e.g., WO 01/062726.

"Prodrug" or "pharmaceutically acceptable prodrug" refers to a compound that is metabolized, for example hydrolyzed or oxidized, in the host after administration to form the compound of the present disclosure (e.g., compounds of formula I or II). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of formula I or II, which are agonists or modulators of the $P_2Y_6$ receptor.

The disclosure further provides pharmaceutical compositions comprising one or more compounds of the disclosure together with a pharmaceutically acceptable carrier or excipient. Compounds or pharmaceutical compositions of the disclosure may be used in vitro or in vivo.

B. Uridine Nucleoside Derivatives and Compositions

The present disclosure provides a compound of formula I:

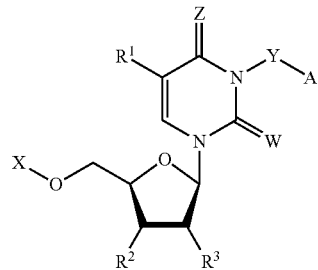

I or a prodrug or salt thereof, wherein:

A is a 3- to 10-membered aromatic or non-aromatic ring having up to 5 heteroatoms independently selected from N, O, S, SO, or $SO_2$, wherein the aromatic or non-aromatic ring is independently and optionally substituted with one or more $R^7$;

X is selected from:
—H, —C(O)$R^5$, —C(O)O$R^5$, and —P(O)(O$R^5$)$_2$, preferably X is —H, —C(O)$R^5$, or —C(O)O$R^5$;

Y is a bond or a (C1-C5)-aliphatic group independently and optionally substituted with one or more $R^4$;

Z and W are each independently selected from =O, =S, =N($R^5$), and =NO$R^5$;

$R^1$ is selected from:
—H, halogen, —O$R^5$, —CN, —CF$_3$, —OCF$_3$ and a (C1-C6)-aliphatic group optionally substituted with one or more $R^7$;

$R^2$ and $R^3$ are each independently selected from —O$R^5$, —S$R^5$, —N$R^5R^6$, —OC(O)$R^5$, —OC(O)N$R^5R^6$, and —OC(O)O$R^5$; preferably, $R^2$ and $R^3$ are each independently selected from —O$R^5$, —S$R^5$, —N$R^5R^6$ and —OC(O)$R^5$;

each occurrence of $R^4$ is independently selected from:
halogen, —O$R^5$, —NO$_2$, —CN, —CF$_3$, —OCF$_3$, —$R^5$, 1,2-methylenedioxy, 1,2-ethylenedioxy, —N($R^5$)$_2$, —S$R^5$, —SO$R^5$, —SO$_2R^5$, —SO$_2$N($R^5$)$_2$, —SO$_3R^5$, —C(O)$R^5$, —C(O)C(O)$R^5$, —C(O)CH$_2$C(O)$R^5$, —C(S)$R^5$, —C(S)O$R^5$, —C(O)O$R^5$, —C(O)C(O)O$R^5$, —C(O)C(O)N($R^5$)$_2$, —OC(O)$R^5$, —C(O)N($R^5$)$_2$, —OC(O)N($R^5$)$_2$, —C(S)N($R^5$)$_2$, —(CH$_2$)$_{0-2}$NHC(O)$R^5$, —N($R^5$)N($R^5$)COR$^5$, —N($R^5$)N($R^5$)C(O)O$R^5$, —N($R^5$)N($R^5$)CON($R^5$)$_2$, —N($R^5$)SO$_2R^5$, —N($R^5$)SO$_2$N($R^5$)$_2$, —N($R^5$)C(O)O$R^5$, —N($R^5$)C(O)$R^5$, —N($R^5$)C(S)$R^5$, —N($R^5$)C(O)N($R^5$)$_2$, —N($R^5$)C(S)N($R^5$)$_2$, —N(COR$^5$)COR$^5$, —N(OR$^5$)$R^5$, —C(=NH)N($R^5$)$_2$, —C(O)N(OR$^5$)$R^5$, —C(=NOR$^5$)$R^5$, —OP(O)(O$R^5$)$_2$, —P(O)($R^5$)$_2$, —P(O)(O$R^5$)$_2$, or —P(O)(H)(O$R^5$);

each occurrence of $R^5$ is independently selected from:
H—,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, and
(C5-C10)-heteroaryl-(C1-C12)-aliphatic-;
wherein two $R^5$ groups bound to the same atom optionally form a 3- to 10-membered aromatic or non-aromatic ring having up to 3 heteroatoms independently selected from N, O, S, SO, or $SO_2$, wherein said ring is optionally fused to a (C6-C10)aryl, (C5-C10)hetero aryl, (C3-C10)cyclo alkyl, or a (C3-C10)heterocyclyl; and wherein each $R^5$ group is independently and optionally substituted with one or more $R^7$;

$R^6$ is selected from:
—$R^5$, —C(O)$R^5$, —C(O)O$R^5$, —C(O)N($R^5$)$_2$ and —S(O)$_2R^5$;

each occurrence of $R^7$ is independently selected from:
halogen, —O$R^8$, —NO$_2$, —CN, —CF$_3$, —OCF$_3$, —$R^8$, oxo, thioxo, 1,2-methylenedioxy, 1,2-ethylenedioxy, —N($R^8$)$_2$, —S$R^8$, —SO$R^8$, —SO$_2R^8$, —SO$_2$N($R^8$)$_2$, —SO$_3R^8$, —C(O)$R^8$, —C(O)C(O)$R^8$, —C(O)CH$_2$C(O)$R^8$, —C(S)$R^8$, —C(S)O$R^8$, —C(O)O$R^8$, —C(O)C(O)O$R^8$, —C(O)C(O)N($R^8$)$_2$, —OC(O)$R^8$, —C(O)N($R^8$)$_2$, —OC(O)N($R^8$)$_2$, —C(S)N($R^8$)$_2$, —(CH$_2$)$_{0-2}$NHC(O)$R^8$, —N($R^8$)N($R^8$)COR$^8$, —N($R^8$)N($R^8$)C(O)OR$^8$, —N($R^8$)N($R^8$)CON($R^8$)$_2$, —N($R^8$)SO$_2R^8$, —N($R^8$)SO$_2$N($R^8$)$_2$, —N($R^8$)C(O)O$R^8$, —N($R^8$)C(O)$R^8$, —N($R^8$)C(S)$R^8$, —N($R^8$)C(O)N($R^8$)$_2$, —N($R^8$)C (S)N(R⁸)₂, —N(COR⁸)COR⁸, —N(OR⁸)R⁸, —C(=NH)N(R⁸)₂, —C(O)N(OR⁸)R⁸, —C(=NOR⁸)R⁸, —OP(O)(OR⁸)₂, —P(O)(R⁸)₂, —P(O)(OR⁸)₂, or —P(O)(H)(OR⁸);

each occurrence of R⁸ is independently selected from:
H— and (C1-C6)-aliphatic-.

In some embodiments of compound of formula I, each occurrence of R⁴ is independently selected from:
halogen, —OR⁵, —NO₂, —CN, —CF₃, —OCF₃, —R⁵, —N(R⁵)₂, —SR⁵, —SOR⁵, —SO₂R⁵, —SO₂N(R⁵)₂, —SO₃R⁵, —C(O)R⁵, —C(O)C(O)R⁵, —C(O)CH₂C(O)R⁵, —C(S)R⁵, —C(S)OR⁵, —C(O)OR⁵, —C(O)C(O)OR⁵, —C(O)C(O)N(R⁵)₂, —OC(O)R⁵, —C(O)N(R⁵)₂, —OC(O)N(R⁵)₂, —C(S)N(R⁵)₂, —(CH₂)₀₋₂NHC(O)R⁵, —N(R⁵)N(R⁵)COR⁵, —N(R⁵)N(R⁵)C(O)OR⁵, —N(R⁵)N(R⁵)CON(R⁵)₂, —N(R⁵)SO₂R⁵, —N(R⁵)SO₂N(R⁵)₂, —N(R⁵)C(O)OR⁵, —N(R⁵)C(O)R⁵, —N(R⁵)C(S)R⁵, —N(R⁵)C(O)N(R⁵)₂, —N(R⁵)C(S)N(R⁵)₂, —N(COR⁵)COR⁵, —N(OR⁵)R⁵, —C(=NH)N(R⁵)₂, —C(O)N(OR⁵)R⁵, —C(=NOR⁵)R⁵, —OP(P)(OR⁵)₂, —P(O)(R⁵)₂, —P(O)(OR⁵)₂, or —P(O)(H)(OR⁵).

In certain embodiments, each occurrence of R⁷ is independently selected from halogen, —OR⁸, —NO₂, —CN, —CF₃, —OCF₃, —R⁸, thioxo, 1,2-methylenedioxy, 1,2-ethylenedioxy, —N(R⁸)₂, —SR⁸, —SOR⁸, —SO₂R⁸, —SO₂N(R⁸)₂, —SO₃R⁸, —C(O)R⁸, —C(O)C(O)R⁸, —C(O)CH₂C(O)R⁸, —C(S)R⁸, —C(S)OR⁸, —C(O)OR⁸, —C(O)C(O)OR⁸, —C(O)C(O)N(R⁸)₂, —OC(O)R⁸, —C(O)N(R⁸)₂, —OC(O)N(R⁸)₂, —C(S)N(R⁸)₂, —(CH₂)₀₋₂NHC(O)R⁸, —N(R⁸)N(R⁸)COR⁸, —N(R⁸)N(R⁸)C(O)OR⁸, —N(R⁸)N(R⁸)CON(R⁸)₂, —N(R⁸)SO₂R⁸, —N(R⁸)SO₂N(R⁸)₂, —N(R⁸)C(O)OR⁸, —N(R⁸)C(O)R⁸, —N(R⁸)C(S)R⁸, —N(R⁸)C(O)N(R⁸)₂, —N(R⁸)C(S)N(R⁸)₂, —N(COR⁸)COR⁸, —N(OR⁸)R⁸, —C(=NH)N(R⁸)₂, —C(O)N(OR⁸)R⁸, —C(=NOR⁸)R⁸, —OP(O)(OR⁸)₂, —P(O)(R⁸)₂, —P(O)(OR⁸)₂, or —P(O)(H)(OR⁸);

each occurrence of R⁸ is independently selected from H— and (C1-C6)-aliphatic-.

In some embodiments, each occurrence of R⁷ is independently selected from —OR⁸, —NO₂, —CN, —CF₃, —OCF₃, —R⁸, thioxo, 1,2-methylenedioxy, 1,2-ethylenedioxy, —N(R⁸)₂, —SR⁸, —SOR⁸, —SO₂R⁸, —SO₂N(R⁸)₂, —SO₃R⁸, —C(O)R⁸, —C(O)C(O)R⁸, —C(O)CH₂C(O)R⁸, —C(S)R⁸, —C(S)OR⁸, —C(O)OR⁸, —C(O)C(O)OR⁸, —C(O)C(O)N(R⁸)₂, —OC(O)R⁸, —C(O)N(R⁸)₂, —OC(O)N(R⁸)₂, —C(S)N(R⁸)₂, —(CH₂)₀₋₂NHC(O)R⁸, —N(R⁸)N(R⁸)COR⁸, —N(R⁸)N(R⁸)C(O)OR⁸, —N(R⁸)N(R⁸)CON(R⁸)₂, —N(R⁸)SO₂R⁸, —N(R⁸)SO₂N(R⁸)₂, —N(R⁸)C(O)OR⁸, —N(R⁸)C(O)R⁸, —N(R⁸)C(S)R⁸, —N(R⁸)C(O)N(R⁸)₂, —N(R⁸)C(S)N(R⁸)₂, —N(COR⁸)COR⁸, —N(OR⁸)R⁸, —C(=NH)N(R⁸)₂, —C(O)N(OR⁸)R⁸, —C(=NOR⁸)R⁸, —OP(O)(OR⁸)₂, —P(O)(R⁸)₂, —P(O)(OR⁸)₂, or —P(O)(H)(OR⁸);

each occurrence of R⁸ is independently selected from H— and (C1-C6)-aliphatic-.

According to certain embodiments, the present disclosure provides a compound of formula I, where Y is a C1-aliphatic group optionally substituted with one or more R⁴. For example, Y is —CH₂—.

In some embodiments, when Y is a C1-aliphatic group optionally substituted with lower alkyl (e.g., C1-C7 alkyl), A is not: (i) unsubstituted phenyl; or
(ii) phenyl substituted with halo (e.g., F— and Cl—) or lower alkyl (e.g., C1-C7 alkyl).

In some embodiments, when Y is a C1-aliphatic group optionally substituted with lower alkyl (e.g., C1-C7 alkyl), A is not:
(i) unsubstituted phenyl;
(ii) phenyl substituted with halo (e.g., F— and Cl—) or lower alkyl (e.g., C1-C7 alkyl); or (iii)
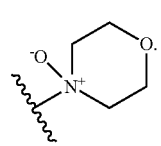

In some embodiments, when Y is a C1-aliphatic group optionally substituted with lower alkyl (e.g., C1-C7 alkyl), A is not:
(i) unsubstituted phenyl;
(ii) phenyl substituted with halo (e.g., F— and Cl—) or lower alkyl (e.g., C1-C7 alkyl);

(iii)
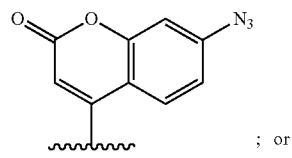
; or (iv)
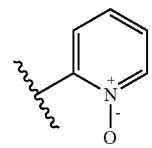

In some embodiments, when Y is a C1-aliphatic group optionally substituted with lower alkyl (e.g., C1-C7 alkyl), A is not:
(i) unsubstituted phenyl; (ii) phenyl substituted with halo (e.g., F— and Cl—) or lower alkyl (e.g., C1-C7 alkyl), (iii)
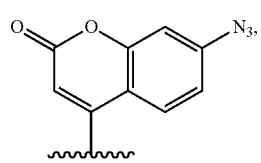

(iv)
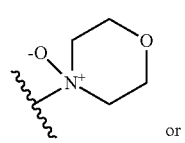
or (v)
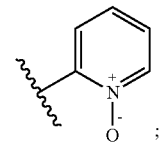
;

and when Y is

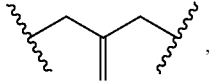
,

A is not

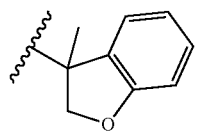

According to certain embodiments, the present disclosure provides a compound of formula I, I-A or I-B, as described herein, where Y is a C1-aliphatic or C1-alkylene group optionally substituted with one or more $R^4$. For example, Y is —CH$_2$—. In some embodiments, when Y is a C1-aliphatic or C1-alkylene group (e.g., —CH$_2$—) optionally substituted with lower alkyl (e.g., C1-C7 alkyl), A is not:
(i) unsubstituted phenyl;
(ii) phenyl substituted with halo (e.g., F— and Cl—) or lower alkyl (e.g., C1-C7 alkyl).

In some embodiments, the provisos or exceptions outlined above for formula I are embodiments of formula I-A or I-B. In other words, in certain embodiments, the disclosure provides a compound of formula I-A or I-B, subject to any one or more of the negative provisos set forth above for formula I.

With respect to formula I, I-A, I-B, or II, it is understood that, as context requires, the term "ring" when used for variable A may be used to refer to "ring system".

In some embodiments of a compound of formula I, Y is a bond or a (C2-C5)-aliphatic group independently and optionally substituted with one or more $R^4$. In some embodiments, Y is a C2-aliphatic group optionally substituted with one or more $R^4$. In some embodiments, Y is —CH$_2$—C($R^4$)$_2$—, such as —CH$_2$—CH$_2$—. In other embodiments, Y is —CH$_2$—C($R^4$)$_2$—, where each $R^4$ is independently selected from halogen. In some embodiments, Y is —CH$_2$—C($R^4$)$_2$—, where both occurrences of $R^4$ are —F. In another embodiment, Y is —CH$_2$—C($R^4$)$_2$—, where each occurrence of $R^4$ is independently a (C1-C3)-aliphatic group. In yet another embodiment, Y is —CH$_2$—C($R^4$)$_2$—, where both occurrences of $R^4$ are —CH$_3$.

In some embodiments, the salt is a pharmaceutically acceptable salt of a compound of formula I, such as a sodium salt. In some embodiments, the salt is a pharmaceutically acceptable salt of a compound of formula I-A or I-B, such as a sodium salt.

In certain embodiments of compound of formula I, A is a (C5-C10)-aromatic ring having up to 5 heteroatoms independently selected from N, O and S, wherein the aromatic ring is independently and optionally substituted with one or more $R^7$. In some embodiments, A is an optionally substituted 5- or 6-membered aromatic ring having up to 2 heteroatoms selected from N, O and S. In some embodiments, A is an optionally substituted bi-cyclic aromatic ring having up to 4 heteroatoms selected from N, O and S.

In some embodiments, A is a bi-cyclic heteroaryl, such as a bicyclic heteroaryl containing at least N (e.g., containing at least one heteroatom which is N, such as containing one to three heteroatoms or containing up to four heteroatoms, wherein at least one heteroatom is N). In some embodiments, A is an optionally substituted bi-cyclic aromatic ring (e.g., an aromatic ring system) containing at least one N. In some embodiments, A contains at least one N, and when A is substituted, $R^7$ is not an oxo substituent. In some embodiments, A is an optionally substituted heteroaryl. In some embodiments, A is an optionally substituted monocylic heteroaryl. In some embodiments, A contains one to three heteroatoms selected from N, O or S. In some embodiments, A contains at least one N. In some embodiments, A is an optionally substituted bicyclic heteroaryl, such as a bi-cyclic heteroaryl containing at least one N (e.g., containing at least one heteroatom which is N, such as containing one to three heteroatoms or containing up to four heteroatoms, wherein at least one heteroatom is N).

In some embodiments, A may be an optionally substituted 5- or 6-membered aromatic group selected from:

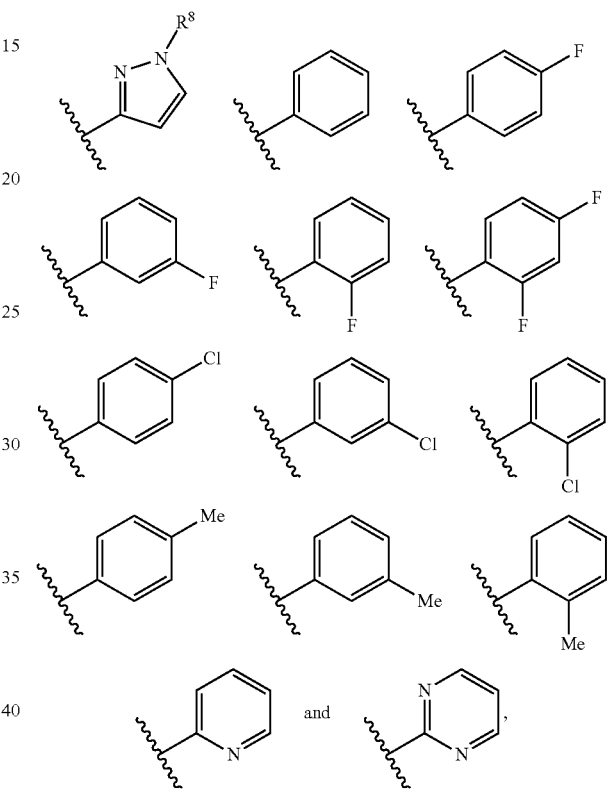

wherein A is optionally further substituted with one or more $R^7$. In some of these embodiments, Y is a bond or a (C2-C5)-aliphatic group independently and optionally substituted with one or more $R^4$. In some of these embodiments, Y is a C2-aliphatic group independently and optionally substituted with one or more $R^4$. In certain embodiments, A is not phenyl.

In some embodiments of formula I, A is an optionally substituted 9- or 10-membered bicyclic aromatic ring having up to 4 heteroatoms selected from N, O and S. In some embodiments, A is an optionally substituted bicyclic aromatic ring containing two fused 6-membered aromatic rings, wherein the optionally substituted bicyclic aromatic ring may contain up to 4 nitrogen atoms. In some embodiments, A is an optionally substituted bicyclic aromatic ring containing one 6-membered aromatic ring fused to one 5-membered aromatic ring, wherein the optionally substituted bicyclic aromatic ring may contain up to 4 heteroatoms selected from N, O and S. These are examples of ring systems. For example, A may be a bicyclic aromatic group (e.g., bicyclic heteroaryl) selected from:

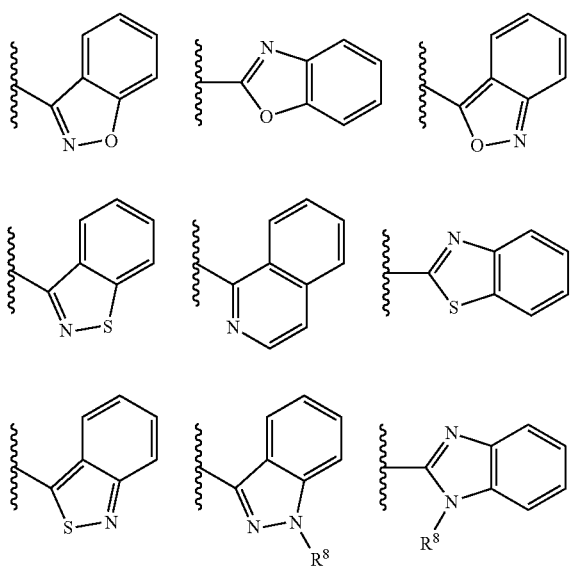

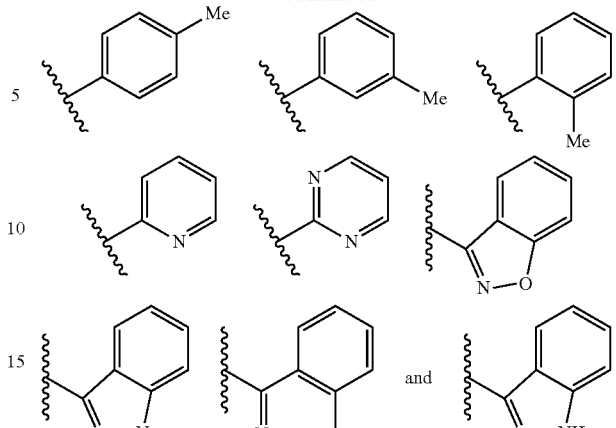

wherein A is optionally further substituted with one or more R[7]. In some of these embodiments, Y is a bond or a (C2-C5)-aliphatic group independently and optionally substituted with one or more independently selected R[4]. In some of these embodiments, Y is a C2-aliphatic group independently and optionally substituted with one or more independently selected R[4].

In certain embodiments, A is a bicyclic aromatic ring (e.g., bicyclic heteroaryl) selected from:

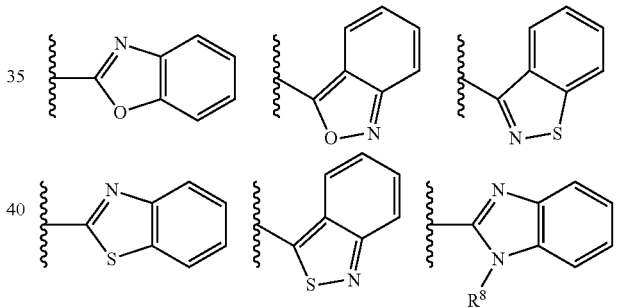

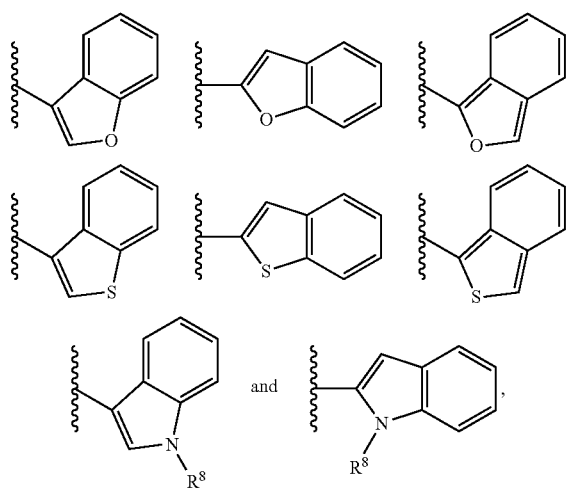

wherein A is optionally further substituted with one or more R[7]. In some embodiments, A is an aromatic group selected from:

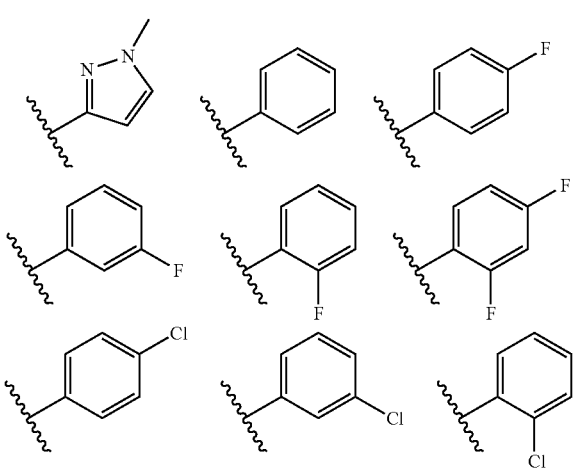

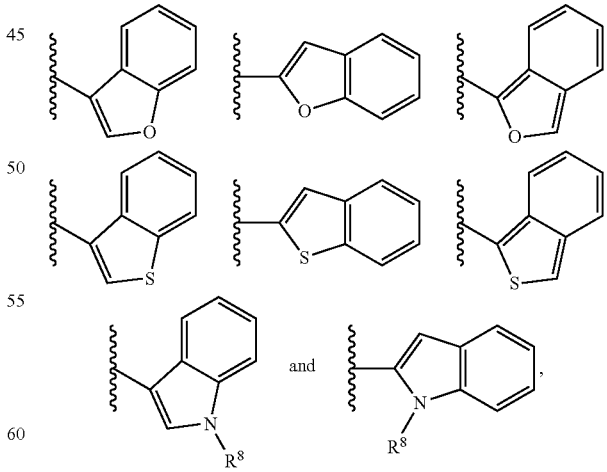

wherein A is optionally further substituted with one or more R[7]. In certain embodiment, A is a bicyclic aromatic group (e.g., a ring system) (e.g., bicyclic heteroaryl) selected from:

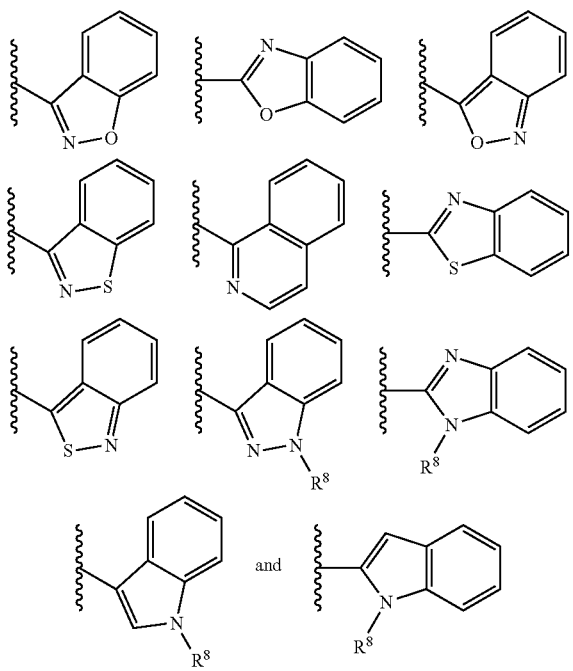

wherein A is optionally further substituted with one or more R[7].

In certain embodiments, A is selected from:

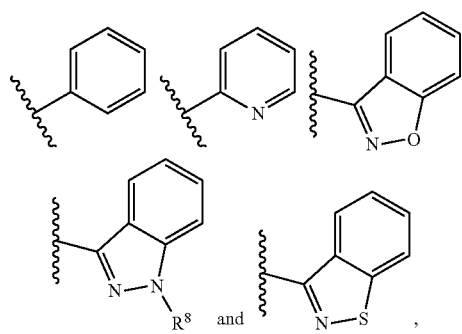

wherein A is optionally further substituted with one or more R[7].

In certain embodiments, A is selected from:

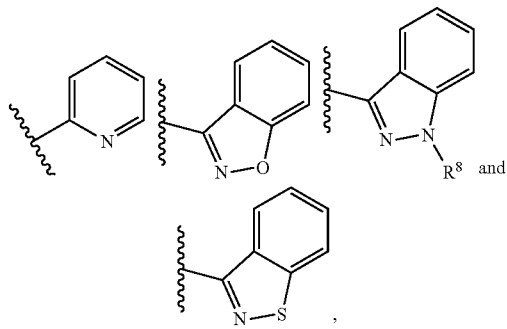

wherein A is optionally further substituted with one or more R[7].

In certain embodiments, A is selected from:

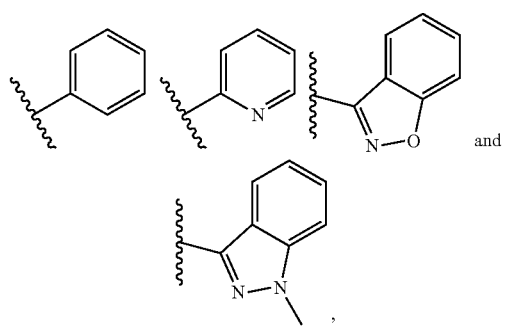

wherein A is optionally further substituted with one or more R[7].

In some embodiments, A is selected from:

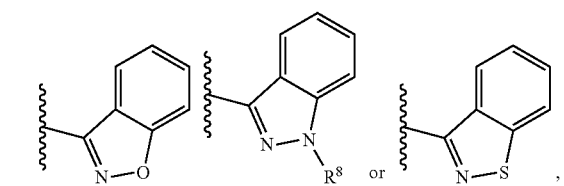

optionally further substituted with one or more R[7].

In some embodiments, A is

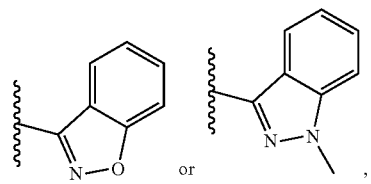

optionally further substituted with one or more R[7].

In certain embodiments, A is

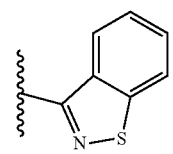

optionally further substituted with one or more R[7]. In certain embodiments, A is

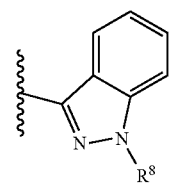

optionally further substituted with one or more R[7], wherein R[8] is not methyl.

In another embodiment, A is

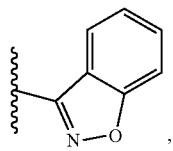

optionally substituted with one or more $R^7$. In some of the above embodiments of A, each occurrence of $R^7$ is independently selected from halogen, —$CF_3$, —$OCF_3$, —C1-C4 aliphatic (e.g., —C1-C4 alkyl), and —O(C1-C4 aliphatic) (e.g., —O(C1-C4 alkyl)).

In certain embodiments, the present disclosure provides compounds of formula I, where X is —H, —C(O)$R^5$, or —C(O)O$R^5$. In some embodiments, X is —H. In other embodiments, X is a prodrug moiety that is cleaved under physiological conditions to provide a compound wherein X is H. In some embodiments, X is —P(O)(O$R^5$)$_2$. In some embodiments, X is a prodrug moiety that is cleaved under physiological conditions to provide a compound wherein X is —P(O)(O$R^5$)$_2$, such as $PO_3H_2$, or a salt thereof.

In some embodiments, the present disclosure also provides compounds of formula I, where $R^1$ is —H, bromine, iodine, methyl, ethyl or —$CF_3$. In some embodiments, $R^1$ is —H.

According to certain embodiments, the present disclosure provides a compound of formula I, where Z is =O or =S. In some embodiments, Z is =O.

In some embodiments, the compound of the present disclosure has a W that is =O or =S. In some embodiments, W is =O.

In some embodiments, the present disclosure provides a compound of formula I, where $R^2$ and $R^3$ are each independently —O$R^5$. In some embodiments, $R^2$ is —OH. In another embodiment, $R^3$ is —OH.

The disclosure also includes various combinations of A, X, Y, Z, W, $R^1$, $R^2$ and $R^3$ as described above. These combinations can in turn be combined with any or all of the values of the other variables described above. For example, in some embodiments, Y is a C1- or C2-aliphatic group optionally substituted with one or more $R^4$ and X is —H, —C(O)$R^5$, or —C(O)O$R^5{}_2$. In another embodiment, Y is a C1- or C2-aliphatic group optionally substituted with one or more $R^4$; X is —H, —C(O)$R^5$, or —C(O)O$R^5$; and Z is =O. In another embodiment, Y is a C1- or C2-aliphatic group optionally substituted with one or more $R^4$; X is —H, —C(O)$R^5$, or —C(O)O$R^5{}_2$; Z is =O; and W is =O. In yet another embodiment, Y is a C1- or C2-aliphatic group optionally substituted with one or more $R^4$; X is —H, —C(O)$R^5$, or —C(O)O$R^5$; Z is =O; W is =O; and $R^1$ is selected from —H, bromine, iodine, methyl, ethyl, and —$CF_3$, for example, $R^1$ is —H. In a further embodiment, Y is a C1- or C2-aliphatic group optionally substituted with one or more $R^4$; X is —H, —C(O)$R^5$, or —C(O)O$R^5$; Z is =O; W is =O; and $R^1$ is selected from —H, bromine, iodine, methyl, ethyl, and —$CF_3$; and A is selected from the following groups:

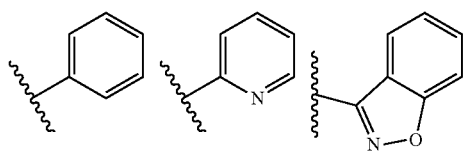

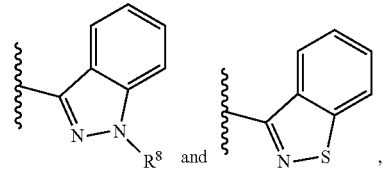

wherein A is optionally further substituted with one or more $R^7$, for example, A is optionally substituted

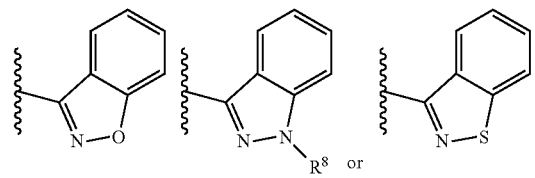

In a further embodiment, Y is a C1- or C2-aliphatic group optionally substituted with one or more $R^4$; X is —H, —C(O)$R^5$, or —C(O)O$R^5$—; Z is =O; W is =O; and $R^1$ is selected from —H, bromine, iodine, methyl, ethyl, and —$CF_3$; A is selected from the following group:

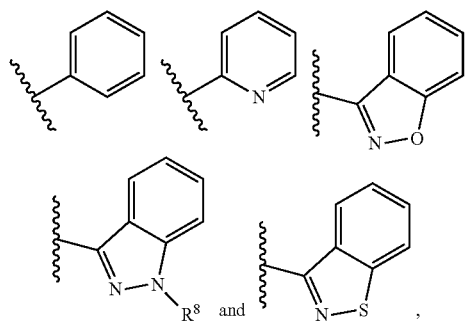

wherein A is optionally further substituted with one or more $R^7$; and $R^2$ and $R^3$ are each independently —O$R^5$, for example, $R^2$ and $R^3$ are each independently —OH. In some of the above embodiments, A is

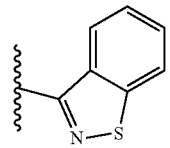

optionally further substituted with one or more $R^7$. In some of the above embodiments, A is

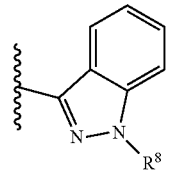

optionally further substituted with one or more $R^7$, wherein $R^8$ is not methyl. In another embodiment, Y is a C1- or C2-aliphatic group optionally substituted with one or more $R^4$; X is —H, —C(O)$R^5$, or —C(O)O$R^5$; Z is =O; W is =O; and R¹ is selected from —H, bromine, iodine, methyl, ethyl, and —CF₃; and A is selected from the following groups:

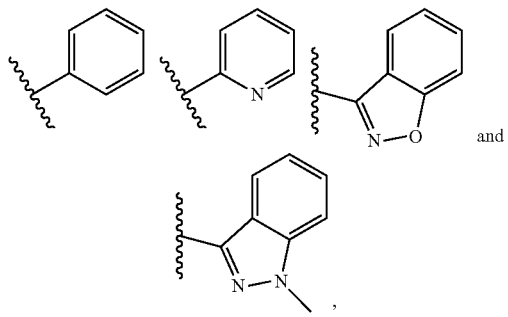

wherein A is optionally further substituted with one or more R⁷, for example, A is optionally substituted

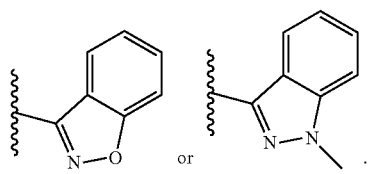

In a further embodiment, Y is a C1- or C2-aliphatic group optionally substituted with one or more R⁴; X is —H, —C(O)R⁵, or —C(O)OR⁵; Z is =O; W is =O; and R¹ is selected from —H, bromine, iodine, methyl, ethyl, and —CF₃; A is selected from the following groups:

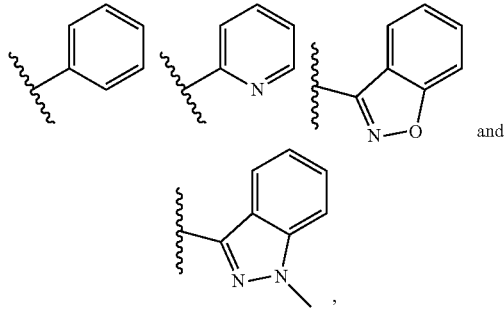

wherein A is optionally further substituted with one or more R⁷;
and R² and R³ are each independently —OR⁵, for example, R² and R³ are each independently —OH. In some of the above embodiments, when Y is a C1-aliphatic group optionally substituted with lower alkyl (e.g., C1-C7 alkyl), A is not:
(i) unsubstituted phenyl;
(ii) phenyl substituted with halo (e.g., F— and Cl—) or lower alkyl (e.g., C1-C7 alkyl);

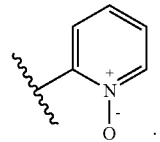

(iii)

In some embodiments, when Y is a C1-aliphatic group optionally substituted with lower alkyl (e.g., C1-C7 alkyl), A is not:
(i) unsubstituted phenyl; (ii) phenyl substituted with halo (e.g., F— and Cl—) or lower alkyl (e.g., C1-C7 alkyl),

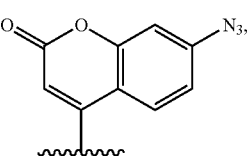

(iii)

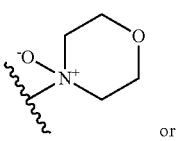

(iv)

or

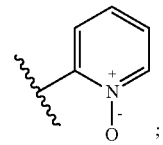

(v)

and
when Y is

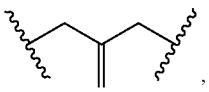

A is not

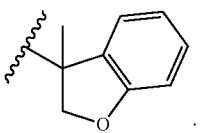

In some of the above embodiments, Y is a C2-aliphatic group independently and optionally substituted with one or more independently selected R⁴. In some of the above embodiments, each occurrence of R⁷ is independently selected from halogen, —CF₃, —OCF₃, —C1-C4 aliphatic (e.g., —C1-C4 alkyl), and —O(C1-C4 aliphatic) (e.g., —O(C1-C4 alkyl)).

The present disclosure also provides a compound of formula I-A:

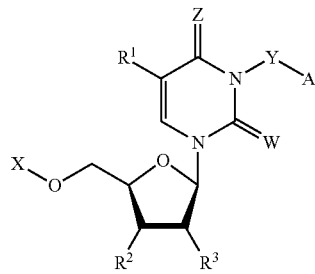

or a salt thereof, wherein:
A is a 3- to 10-membered aromatic or non-aromatic ring having up to 5 heteroatoms independently selected from N, O, S, SO, or $SO_2$, wherein the aromatic or non-aromatic ring is independently and optionally substituted with one or more $R^7$;
X is selected from:
—H, —C(O)$R^5$, —C(O)O$R^5$, and —P(O)(O$R^5$)$_2$, preferably X is —H, —C(O)$R^5$, or —C(O)O$R^5$;
Y is a bond or a (C1-C5)-aliphatic group independently and optionally substituted with one or more $R^4$;
Z and W are each independently selected from =O, =S, =N($R^5$), and =NO$R^5$;
$R^1$ is selected from:
—H, halogen, —O$R^5$, —CN, —CF$_3$, —OCF$_3$ and a (C1-C6)-aliphatic group optionally substituted with one or more $R^7$;
$R^2$ and $R^3$ are each independently selected from —O$R^5$, —S$R^5$, —N$R^5R^6$, —OC(O)$R^5$, —OC(O)N$R^5R^6$, and —OC(O)O$R^5$; preferably, $R^2$ and $R^3$ are each independently selected from —O$R^5$, —S$R^5$, —N$R^5R^6$ and —OC(O)$R^5$;
each occurrence of $R^4$ is independently selected from:
halogen, —O$R^5$, —NO$_2$, —CN, —CF$_3$, —OCF$_3$, —$R^5$, 1,2-methylenedioxy, 1,2-ethylenedioxy, —N($R^5$)$_2$, —S$R^5$, —SO$R^5$, —SO$_2R^5$, —SO$_2$N($R^5$)$_2$, —SO$_3R^5$, —C(O)$R^5$, —C(O)C(O)$R^5$, —C(O)CH$_2$C(O)$R^5$, —C(S)$R^5$, —C(S)O$R^5$, —C(O)O$R^5$, —C(O)C(O)O$R^5$, —C(O)C(O)N($R^5$)$_2$, —OC(O)$R^5$, —C(O)N($R^5$)$_2$, —OC(O)N($R^5$)$_2$, —C(S)N($R^5$)$_2$, —(CH$_2$)$_{0-2}$NHC(O)$R^5$, —N($R^5$)N($R^5$)COR$^5$, —N($R^5$)N($R^5$)C(O)O$R^5$, —N($R^5$)N($R^5$)CON($R^5$)$_2$, —N($R^5$)SO$_2R^5$, —N($R^5$)SO$_2$N($R^5$)$_2$, —N($R^5$)C(O)O$R^5$, —N($R^5$)C(O)$R^5$, —N($R^5$)C(S)$R^5$, —N($R^5$)C(O)N($R^5$)$_2$, —N($R^5$)C(S)N($R^5$)$_2$, —N(COR$^5$)COR$^5$, —N(OR$^5$)$R^5$, —C(=NH)N($R^5$)$_2$, —C(O)N(OR$^5$)$R^5$, —C(=NOR$^5$)$R^5$, —OP(O)(O$R^5$)$_2$, —P(O)($R^5$)$_2$, —P(O)(O$R^5$)$_2$, or —P(O)(H)(O$R^5$);
each occurrence of $R^5$ is independently selected from:
H—,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, and
(C5-C10)-heteroaryl-(C1-C12)-aliphatic-;
wherein two $R^5$ groups bound to the same atom optionally form a 3- to 10-membered aromatic or non-aromatic ring having up to 3 heteroatoms independently selected from N, O, S, SO, or SO$_2$, wherein said ring is optionally fused to a (C6-C10)aryl, (C5-C10)heteroaryl, (C3-C10)cycloalkyl, or a (C3-C10)heterocyclyl; and wherein each $R^5$ group is independently and optionally substituted with one or more $R^7$;
$R^6$ is selected from:
—$R^5$, —C(O)$R^5$, —C(O)O$R^5$, —C(O)N($R^5$)$_2$ and —S(O)$_2R^5$;
each occurrence of $R^7$ is independently selected from:
halogen, —O$R^8$, —NO$_2$, —CN, —CF$_3$, —OCF$_3$, —$R^8$, oxo, thioxo, 1,2-methylenedioxy, 1,2-ethylenedioxy, —N($R^8$)$_2$, —S$R^8$, —SOR$^8$, —SO$_2R^8$, —SO$_2$N($R^8$)$_2$, —SO$_3R^8$, —C(O)$R^8$, —C(O)C(O)$R^8$, —C(O)CH$_2$C(O)$R^8$, —C(S)$R^8$, —C(S)O$R^8$, —C(O)O$R^8$, —C(O)C(O)O$R^8$, —C(O)C(O)N($R^8$)$_2$, —OC(O)$R^8$, —C(O)N($R^8$)$_2$, —OC(O)N($R^8$)$_2$, —C(S)N($R^8$)$_2$, —(CH$_2$)$_{0-2}$NHC(O)$R^8$, —N($R^8$)N($R^8$)COR$^8$, —N($R^8$)N($R^8$)C(O)OR$^8$, —N($R^8$)N($R^8$)CON($R^8$)$_2$, —N($R^8$)SO$_2R^8$, —N($R^8$)SO$_2$N($R^8$)$_2$, —N($R^8$)C(O)O$R^8$, —N($R^8$)C(O)$R^8$, —N($R^8$)C(S)$R^8$, —N($R^8$)C(O)N($R^8$)$_2$, —N($R^8$)C(S)N($R^8$)$_2$, —N(COR$^8$)COR$^8$, —N(OR$^8$)$R^8$, —C(=NH)N($R^8$)$_2$, —C(O)N(OR$^8$)$R^8$, —C(=NOR$^8$)$R^8$, —OP(O)(O$R^8$)$_2$, —P(O)($R^8$)$_2$, —P(O)(O$R^8$)$_2$, or —P(O)(H)(O$R^8$);
each occurrence of $R^8$ is independently selected from:
H— and (C1-C6)-aliphatic-;
provided that A is not

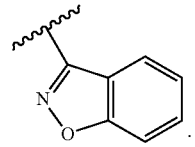

In certain embodiments, the present disclosure provides compounds of formula I-A where the definition of one or more of variables A, X, Y, Z, W, and $R^1$-$R^8$ is as defined by embodiments described above for Formula I, including any of the combinations thereof, as well as the provisos provided for Formula I.

According to certain embodiments, the present disclosure provides a compound of formula I-A, where Y is a C1-aliphatic group optionally substituted with one or more $R^4$. For example, Y is —CH$_2$—. In some embodiments, when Y is a C1-aliphatic group optionally substituted with lower alkyl (e.g., C1-C7 alkyl), A is not:
(i) unsubstituted phenyl; or
(ii) phenyl substituted with halo (e.g., F— and Cl—) or lower alkyl (e.g., C1-C7 alkyl).

The present disclosure also provides a compound of formula I-B:

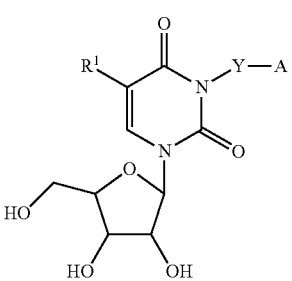

I-B or a salt thereof, wherein:

A is selected from:
- a phenyl group;
- a naphthalene group;
- a 5- to 10-membered heteroaryl group having up to 5 heteroatoms independently selected from N, O, and S; and
- a 3- to 10-membered non-aromatic ring having up to 5 heteroatoms independently selected from N, O, and S;
- wherein A is optionally further substituted with 1, 2, or 3 substituents independently selected from the group consisting of halogen, hydroxyl, (C1-C6)-alkyl, and (C1-C6)-alkoxyl;

Y is a (C1-C6)-alkylene optionally substituted with halogen; and

R$^1$ is —H, halogen, or a (C1-C6)-aliphatic group optionally substituted with one or more halogen.

In certain embodiments, A is a 5- to 10-membered heteroaryl group having up to 3 heteroatoms independently selected from N, O, and S. In certain other embodiments, A is not

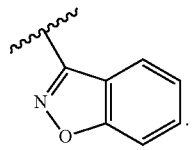

In certain other embodiments, R$^1$ is hydrogen or methyl. In certain other embodiments, the present disclosure provides compounds of formula I-B, wherein Y is (C1-C5)-alkylene optionally substituted with halogen.

According to certain embodiments, the present disclosure provides a compound of formula I-B, where Y is a C1-alkylene group (for example, Y is —CH$_2$—), which is optionally substituted with one or more R$^4$. In some embodiments, when Y is a C1-alkylene group optionally substituted with lower alkyl (e.g., C1-C7 alkyl), A is not:
(i) unsubstituted phenyl; or
(ii) phenyl substituted with halo (e.g., F— and Cl—) or lower alkyl (e.g., C1-C7 alkyl).

In certain embodiments, when Y is a C1-aliphatic group optionally substituted with lower alkyl, A is not:
(i) unsubstituted phenyl;
(ii) phenyl substituted with halo or lower alkyl; or (iii)

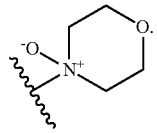

In certain embodiments, when Y is a C1-aliphatic group optionally substituted with lower alkyl, A is not:
(i) unsubstituted phenyl;
(ii) phenyl substituted with halo or lower alkyl;

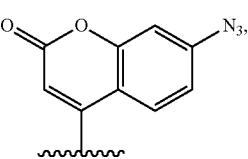

(iii)

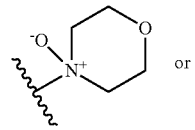

(iv)

or

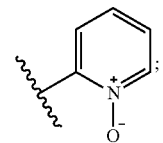

(v)

and
when Y is

A is not

In some embodiments of formula I-A and I-B, A is an optionally substituted 9- or 10-membered bicyclic aromatic ring having up to 4 heteroatoms selected from N, O and S. In some embodiments, A is an optionally substituted bicyclic aromatic ring containing two fused 6-membered aromatic rings, wherein the optionally substituted bicyclic aromatic ring may contain up to 4 nitrogen atoms. In some embodiments, A is an optionally substituted bicyclic aromatic ring containing one 6-membered aromatic ring fused to one 5-membered aromatic ring, wherein the optionally substituted bicyclic aromatic ring may contain up to 4 heteroatoms selected from N, O and S. In certain embodiments, A is

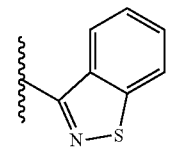

optionally further substituted with one or more R$^7$. In certain embodiments, A is

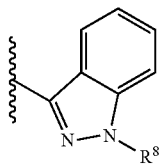

optionally further substituted with one or more R⁷. In certain other embodiments, A is

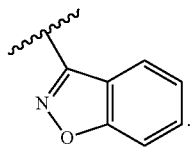

In certain other embodiments, A is not

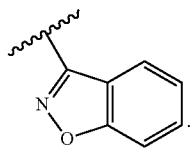

In some embodiments, A contains at least one N, and when A is substituted, R⁷ is not an oxo substituent. In some embodiments, A is an optionally substituted heteroaryl. In some embodiments, A is an optionally substituted monocylic heteroaryl. In some embodiments, A contains one to three heteroatoms selected from N, O or S. In some embodiments, A contains at least one N. In some embodiments, A is an optionally substituted bicyclic heteroaryl. In some embodiments, A contains at least one N.

The present disclosure also provides a compound of formula II:

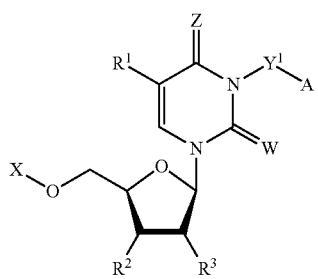

II or a prodrug or salt thereof, wherein:
A is selected from:
  a phenyl group;
  a naphthalene group;
  a 5- to 10-membered heteroaryl group having up to 5 heteroatoms independently selected from N, O and S; and
  a 3- to 10-membered non-aromatic ring having up to 5 heteroatoms independently selected from N, O, S, SO, or SO₂;
  wherein A is optionally further substituted with one or more R⁷;

X is selected from:
  —H, —C(O)R⁵, —C(O)OR⁵, and —P(O)(OR⁵)₂, preferably X is —H, —C(O)R⁵, or —C(O)OR⁵;
Y¹ is a (C1-C5)-aliphatic group substituted with at least one oxo and further independently and optionally substituted with one or more R⁴;
Z and W are each independently selected from =O, =S, =N(R⁵), and =NOR⁵;
R¹ is selected from:
  —H, halogen, —OR⁵, —CN, —CF₃, —OCF₃ and a (C1-C6)-aliphatic-group optionally substituted with one or more R⁴;
R² and R³ are each independently selected from —OR⁵, —SR⁵, —NR⁵R⁶, —OC(O)R⁵, —OC(O)NR⁵R⁶, and —OC(O)OR⁵; preferably, R² and R³ are each independently selected from —OR⁵, —SR⁵, —NR⁵R⁶ and —OC(O)R⁵;
each occurrence of R⁴ is independently selected from:
  halogen, —OR⁵, —NO₂, —CN, —CF₃, —OCF₃, —R⁵, oxo, thioxo, 1,2-methylenedioxy, 1,2-ethylenedioxy, —N(R⁵)₂, —SR⁵, —SOR⁵, —SO₂R⁵, —SO₂N(R⁵)₂, —SO₃R⁵, —C(O)R⁵, —C(O)C(O)R⁵, —C(O)CH₂C(O)R⁵, —C(S)R⁵, —C(S)OR⁵, —C(O)OR⁵, —C(O)C(O)OR⁵, —C(O)C(O)N(R⁵)₂, —OC(O)R⁵, —C(O)N(R⁵)₂, —OC(O)N(R⁵)₂, —C(S)N(R⁵)₂, —(CH₂)₀₋₂NHC(O)R⁵, —N(R⁵)N(R⁵)COR⁵, —N(R⁵)N(R⁵)C(O)OR⁵, —N(R⁵)N(R⁵)CON(R⁵)₂, —N(R⁵)SO₂R⁵, —N(R⁵)SO₂N(R⁵)₂, —N(R⁵)C(O)OR⁵, —N(R⁵)C(O)R⁵, —N(R⁵)C(S)R⁵, —N(R⁵)C(O)N(R⁵)₂, —N(R⁵)C(S)N(R⁵)₂, —N(COR⁵)COR⁵, —N(OR⁵)R⁵, —C(=NH)N(R⁵)₂, —C(O)N(OR⁵)R⁵, —C(=NOR⁵)R⁵, —OP(O)(OR⁵)₂, —P(O)(R⁵)₂, —P(O)(OR⁵)₂, or —P(O)(H)(OR⁵);
each occurrence of R⁵ is independently selected from:
  H—,
  (C1-C12)-aliphatic-,
  (C3-C10)-cycloalkyl- or -cycloalkenyl-,
  [(C3-C10)-cycloalkyl or -cycloalkenyl]-(C1-C12)-aliphatic-,
  (C6-C10)-aryl-,
  (C6-C10)-aryl-(C1-C12)aliphatic-,
  (C3-C10)-heterocyclyl-,
  (C6-C10)-heterocyclyl-(C1-C12)aliphatic-,
  (C5-C10)-heteroaryl-, and
  (C5-C10)-heteroaryl-(C1-C12)-aliphatic-;
  wherein two R⁵ groups bound to the same atom optionally form a 3- to 10-membered aromatic or non-aromatic ring having up to 3 heteroatoms independently selected from N, O, S, SO, or SO₂, wherein said ring is optionally fused to a (C6-C10)aryl, (C5-C10)heteroaryl, (C3-C10)cycloalkyl, or a (C3-C10)heterocyclyl; and wherein each R⁵ group is independently and optionally substituted with one or more R⁷;
R⁶ is selected from:
  —R⁵, —C(O)R⁵, —C(O)OR⁵, —C(O)N(R⁵)₂ and —S(O)₂R⁵;
each occurrence of R⁷ is independently selected from:
  halogen, —OR⁸, —NO₂, —CN, —CF₃, —OCF₃, —R⁸, oxo, thioxo, 1,2-methylenedioxy, 1,2-ethylenedioxy, —N(R⁸)₂, —SR⁸, —SOR⁸, —SO₂R⁸, —SO₂N(R⁸)₂, —SO₃R⁸, —C(O)R⁸, —C(O)C(O)R⁸, —C(O)CH₂C(O)R⁸, —C(S)R⁸, —C(S)OR⁸, —C(O)OR⁸, —C(O)C(O)OR⁸, —C(O)C(O)N(R⁸)₂, —OC(O)R⁸, —C(O)N(R⁸)₂, —OC(O)N(R⁸)₂, —C(S)N(R⁸)₂, —(CH₂)₀₋₂NHC(O)R⁸, —N(R⁸)N(R⁸)COR⁸, —N(R⁸)N(R⁸)C(O)OR⁸, —N(R⁸)N(R⁸)CON(R⁸)₂, —N(R⁸)SO₂R⁸, —N(R⁸)SO₂N(R⁸)₂, —N(R⁸)C(O)OR⁸, —N(R⁸)C(O)

R⁸, —N(R⁸)C(S)R⁸, —N(R⁸)C(O)N(R⁸)₂, —N(R⁸)C(S)N(R⁸)₂, —N(COR⁸)COR⁸, —N(OR⁸)R⁸, —C(=NH)N(R⁸)₂, —C(O)N(OR⁸)R⁸, —C(=NOR⁸)R⁸, —OP(O)(OR⁸)₂, —P(O)(R⁸)₂, —P(O)(OR⁸)₂, or —P(O)(H)(OR⁸);

each occurrence of R⁸ is independently selected from:
H— and (C1-C6)-aliphatic-.

In some embodiments of compound of formula II, each occurrence of R⁴ is independently selected from:
halogen, —OR⁵, —NO₂, —CN, —CF₃, —OCF₃, —R⁵, oxo, thioxo, —N(R⁵)₂, —SR⁵, —SOR⁵, —SO₂R⁵, —SO₂N(R⁵)₂, —SO₃R⁵, —C(O)R⁵, —C(O)C(O)R⁵, —C(O)CH₂C(O)R⁵, —C(S)R⁵, —C(S)OR⁵, —C(O)OR⁵, —C(O)C(O)OR⁵, —C(O)C(O)N(R⁵)₂, —OC(O)R⁵, —C(O)N(R⁵)₂, —OC(O)N(R⁵)₂, —C(S)N(R⁵)₂, —(CH₂)₀₋₂NHC(O)R⁵, —N(R⁵)N(R⁵)COR⁵, —N(R⁵)N(R⁵)C(O)OR⁵, —N(R⁵)N(R⁵)CON(R⁵)₂, —N(R⁵)SO₂R⁵, —N(R⁵)SO₂N(R⁵)₂, —N(R⁵)C(O)OR⁵, —N(R⁵)C(O)R⁵, —N(R⁵)C(S)R⁵, —N(R⁵)C(O)N(R⁵)₂, —N(R⁵)C(S)N(R⁵)₂, —N(COR⁵)COR⁵, —N(OR⁵)R⁵, —C(=NH)N(R⁵)₂, —C(O)N(OR⁵)R⁵, —C(=NOR⁵)R⁵, —OP(O)(OR⁵)₂, —P(O)(R⁵)₂, —P(O)(OR⁵)₂, or —P(O)(H)(OR⁵).

In some embodiments, R⁷ is independently selected from halogen, —OR⁸, —NO₂, —CN, —CF₃, —OCF₃, —R⁸, thioxo, 1,2-methylenedioxy, 1,2-ethylenedioxy, —N(R⁸)₂, —SR⁸, —SOR⁸, —SO₂R⁸, —SO₂N(R⁸)₂, —SO₃R⁸, —C(O)R⁸, —C(O)C(O)R⁸, —C(O)CH₂C(O)R⁸, —C(S)R⁸, —C(S)OR⁸, —C(O)OR⁸, —C(O)C(O)OR⁸, —C(O)C(O)N(R⁸)₂, —OC(O)R⁸, —C(O)N(R⁸)₂, —OC(O)N(R⁸)₂, —C(S)N(R⁸)₂, —(CH₂)₀₋₂NHC(O)R⁸, —N(R⁸)N(R⁸)COR⁸, —N(R⁸)N(R⁸)C(O)OR⁸, —N(R⁸)N(R⁸)CON(R⁸)₂, —N(R⁸)SO₂R⁸, —N(R⁸)SO₂N(R⁸)₂, —N(R⁸)C(O)OR⁸, —N(R⁸)C(O)R⁸, —N(R⁸)C(S)R⁸, —N(R⁸)C(O)N(R⁸)₂, —N(R⁸)C(S)N(R⁸)₂, —N(COR⁸)COR⁸, —N(OR⁸)R⁸, —C(=NH)N(R⁸)₂, —C(O)N(OR⁸)R⁸, —C(=NOR⁸)R⁸, —OP(O)(OR⁸)₂, —P(O)(R⁸)₂, —P(O)(OR⁸)₂, or —P(O)(H)(OR⁸);

each occurrence of R⁸ is independently selected from H— and (C1-C6)-aliphatic-.

In some embodiments, R⁷ is independently selected from —OR⁸, —NO₂, —CN, —CF₃, —OCF₃, —R⁸, thioxo, 1,2-methylenedioxy, 1,2-ethylenedioxy, —N(R⁸)₂, —SR⁸, —SOR⁸, —SO₂R⁸, —SO₂N(R⁸)₂, —SO₃R⁸, —C(O)R⁸, —C(O)C(O)R⁸, —C(O)CH₂C(O)R⁸, —C(S)R⁸, —C(S)OR⁸, —C(O)OR⁸, —C(O)C(O)OR⁸, —C(O)C(O)N(R⁸)₂, —OC(O)R⁸, —C(O)N(R⁸)₂, —OC(O)N(R⁸)₂, —C(S)N(R⁸)₂, —(CH₂)₀₋₂NHC(O)R⁸, —N(R⁸)N(R⁸)COR⁸, —N(R⁸)N(R⁸)C(O)OR⁸, —N(R⁸)N(R⁸)CON(R⁸)₂, —N(R⁸)SO₂R⁸, —N(R⁸)SO₂N(R⁸)₂, —N(R⁸)C(O)OR⁸, —N(R⁸)C(O)R⁸, —N(R⁸)C(S)R⁸, —N(R⁸)C(O)N(R⁸)₂, —N(R⁸)C(S)N(R⁸)₂, —N(COR⁸)COR⁸, —N(OR⁸)R⁸, —C(=NH)N(R⁸)₂, —C(O)N(OR⁸)R⁸, —C(=NOR⁸)R⁸, —OP(O)(OR⁸)₂, —P(O)(R⁸)₂, —P(O)(OR⁸)₂, or —P(O)(H)(OR⁸);

each occurrence of R⁸ is independently selected from H— and (C1-C6)-aliphatic-.

According to certain embodiments, the present disclosure also provides a compound of formula II, where Y¹ is a C1-aliphatic group substituted with oxo. In some embodiments, Y¹ is a C2-aliphatic group substituted with at least one oxo and optionally further substituted with one or more R⁴. In another embodiment, Y¹ is —C(O)—C(R⁴)₂— or —C(R⁴)₂—C(O)—, for example, —C(O)—CH₂— or —CH₂—C(O)—. In a further embodiment, Y¹ is —C(O)—C(R⁴)₂— or —C(R⁴)₂—C(O)—, where each R⁴ is independently selected from halogen. For example, Y¹ is —C(O)—C(R⁴)₂— or —C(R⁴)₂—C(O)—, where both occurrences of R⁴ in are —F. In yet another embodiment, Y¹ is —C(O)—C(R⁴)₂— or —C(R⁴)₂—C(O)—, where each R⁴ is independently a (C1-C3)-aliphatic group. For example, Y¹ is —C(O)—C(R⁴)₂— or —C(R⁴)₂—C(O)—, where both occurrences of R⁴ are —CH₃. In some of the above embodiments, when Y¹ is a —CH₂—C(O)—, wherein the carbonyl group of Y¹ is connected directly to A, A is not:

(i) unsubstituted phenyl; or (ii) phenyl substituted with halo (e.g., F— and Cl—) or lower alkyl (e.g., C1-C7 alkyl);

In some embodiments, the salt is a pharmaceutically acceptable salt of a compound of formula II, such as a sodium salt.

In certain embodiments of compound of formula II, A is a phenyl group; a naphthalene group; or a 5- to 10-membered heteroaryl group having up to 5 heteroatoms independently selected from N, O and S, wherein A is optionally substituted with one or more R⁷. For example, A is selected from the following groups:

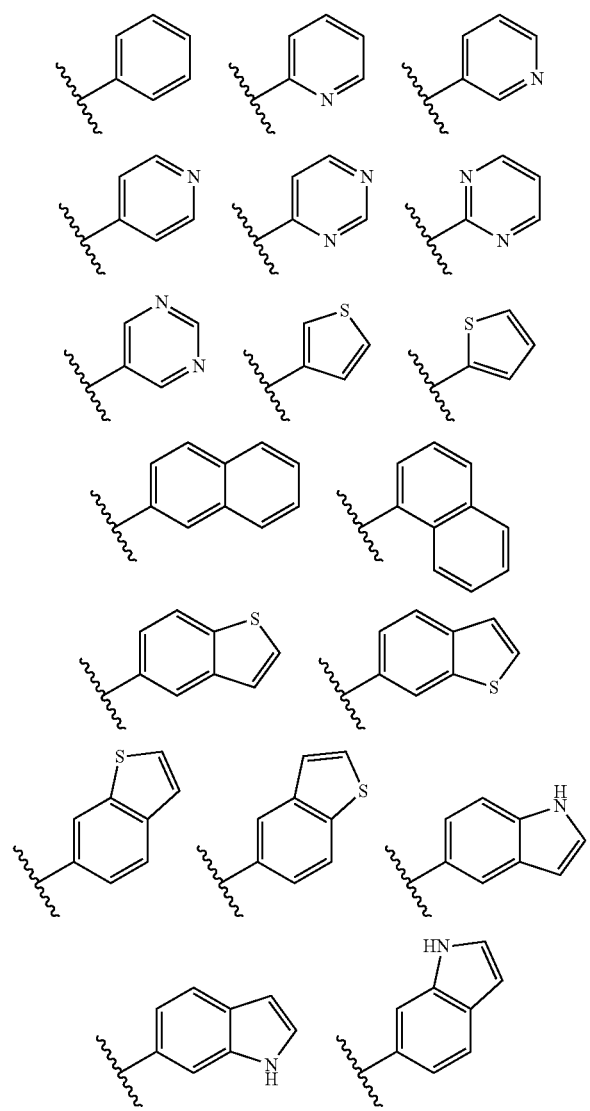

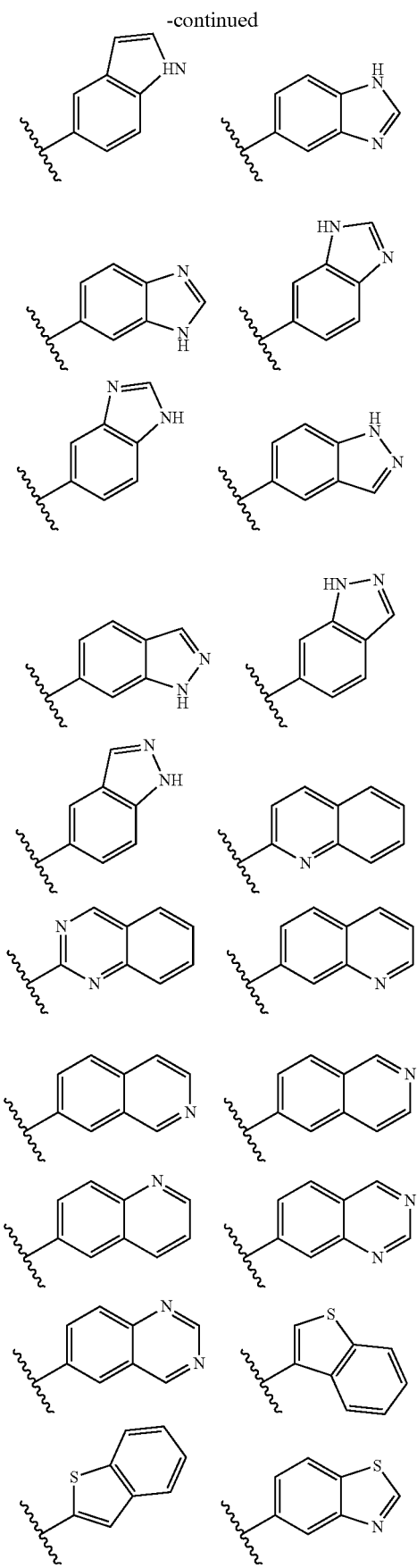
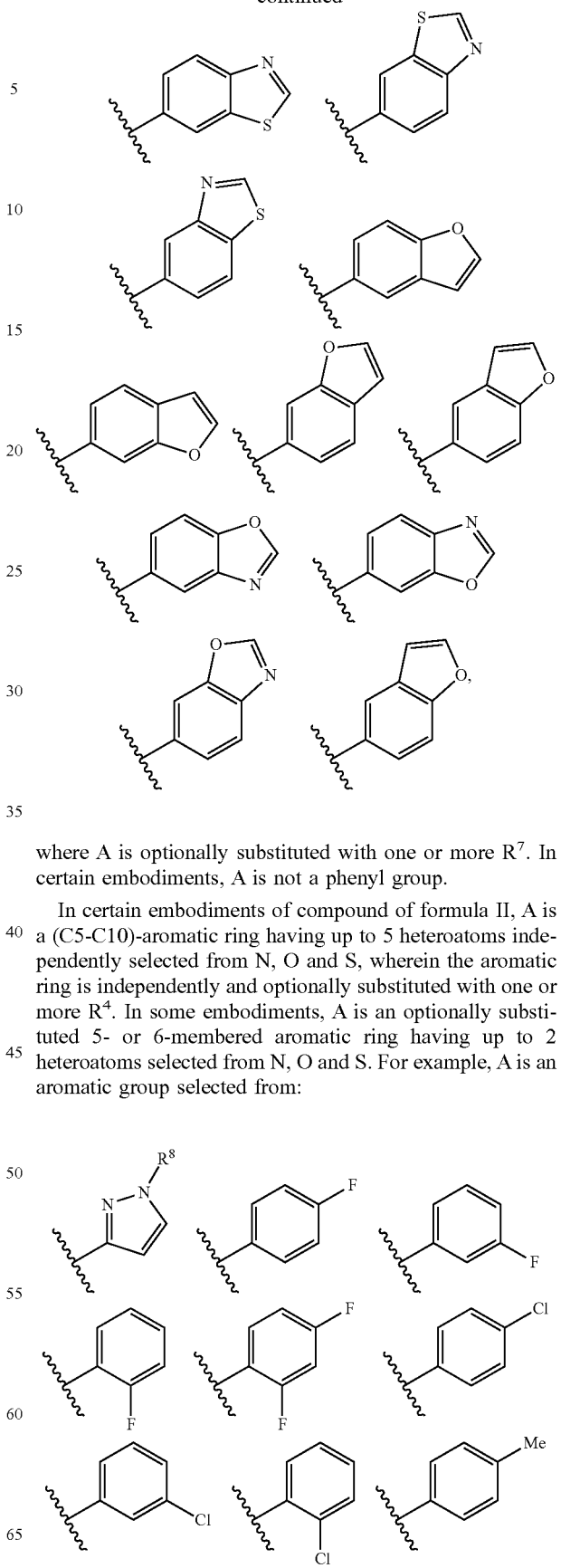

where A is optionally substituted with one or more $R^7$. In certain embodiments, A is not a phenyl group.

In certain embodiments of compound of formula II, A is a (C5-C10)-aromatic ring having up to 5 heteroatoms independently selected from N, O and S, wherein the aromatic ring is independently and optionally substituted with one or more $R^4$. In some embodiments, A is an optionally substituted 5- or 6-membered aromatic ring having up to 2 heteroatoms selected from N, O and S. For example, A is an aromatic group selected from:

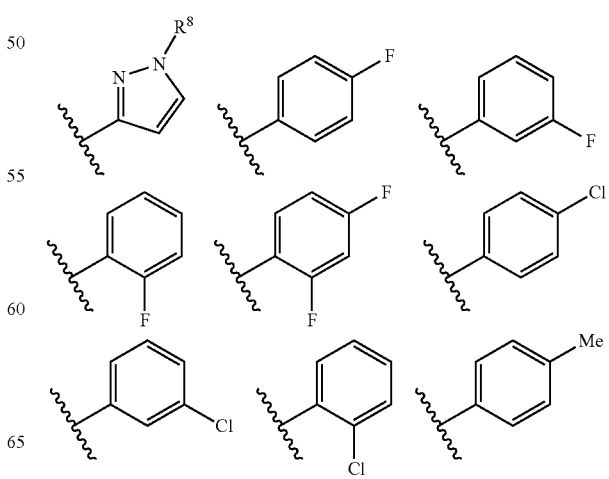

-continued

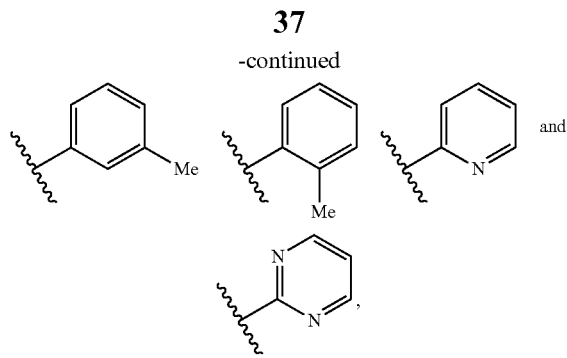

wherein A is optionally further substituted with one or more R⁷. In some of these embodiments, $Y^1$ is a C1-aliphatic or a C3-C5-aliphatic group substituted with at least one oxo and further independently and optionally substituted with one or more independently selected $R^4$;

In some embodiments of formula II, A is an optionally substituted 9- or 10-membered bicyclic aromatic ring having up to 4 heteroatoms selected from N, O and S. In some embodiments, A is an optionally substituted bicyclic aromatic ring containing two fused 6-membered aromatic rings, wherein the optionally substituted bicyclic aromatic ring may contain up to 4 nitrogen atoms. In some embodiments, A is an optionally substituted bicyclic aromatic ring containing one 6-membered aromatic ring fused to one 5-membered aromatic ring, wherein the optionally substituted bicyclic aromatic ring may contain up to 4 heteroatoms selected from N, O and S. For example, A may be a bicyclic aromatic group selected from:

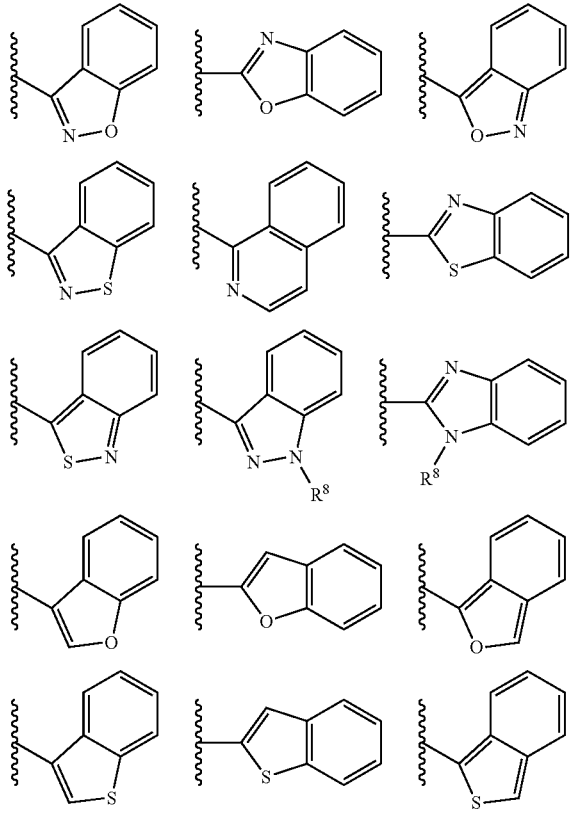

-continued

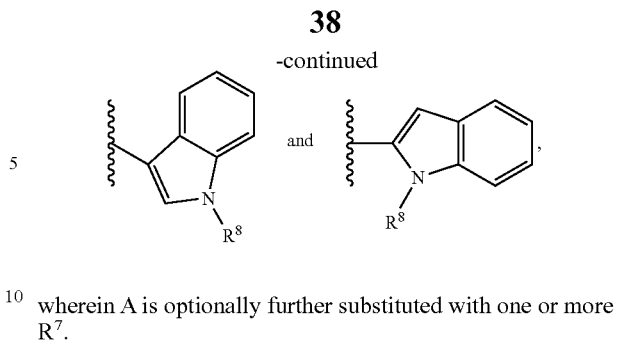

wherein A is optionally further substituted with one or more $R^7$.

In some embodiments of compound of formula II, A is selected from the following groups:

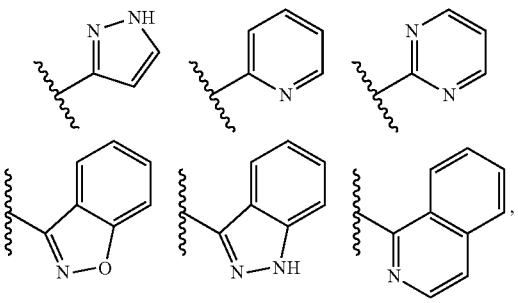

where A is optionally substituted with one or more $R^7$.

In such embodiments, A is one of the following groups:

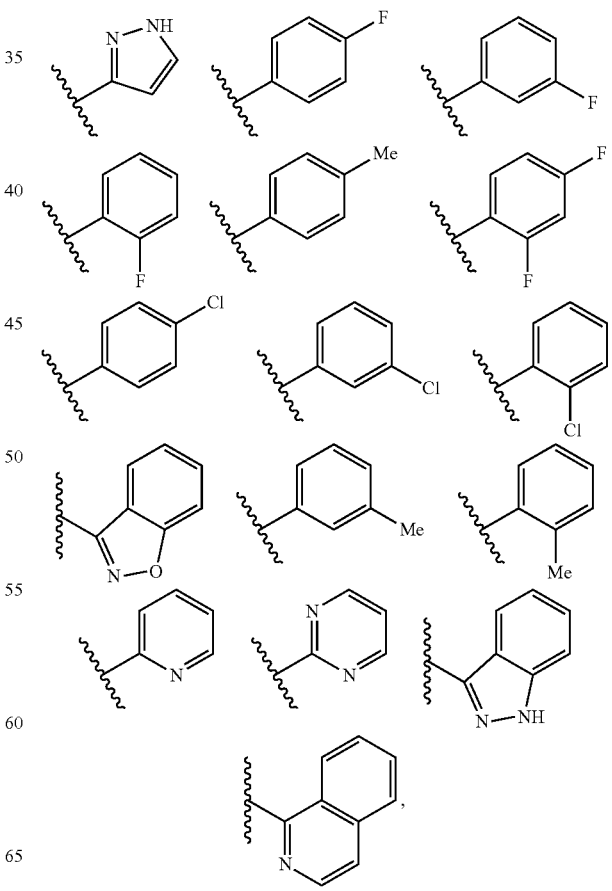

where A is optionally further substituted with one or more R⁷. In some of these embodiments, $Y^1$ is a C1-aliphatic or a C3-C5-aliphatic group substituted with at least one oxo and further independently and optionally substituted with one or more independently selected $R^4$;

In some embodiments, A is a bicyclic aromatic group selected from:

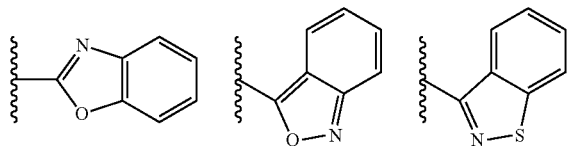
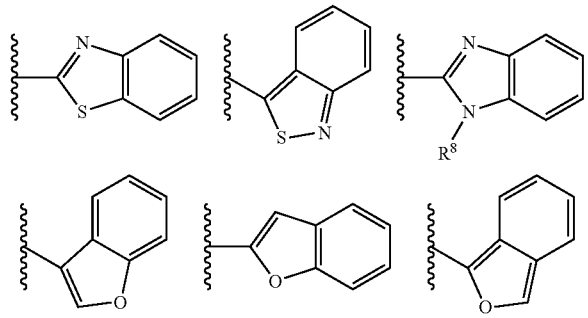
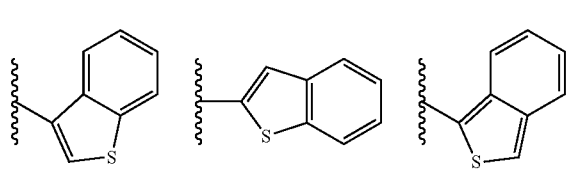
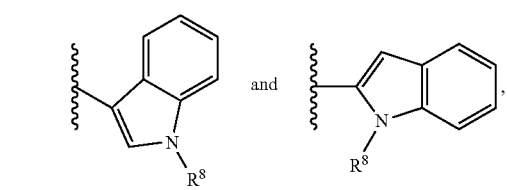
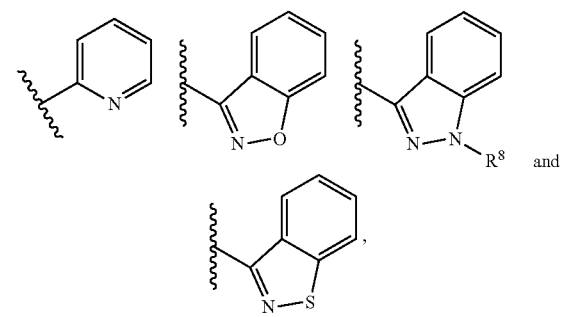

wherein A is optionally further substituted with one or more R⁷.

In some embodiments, A is selected from:

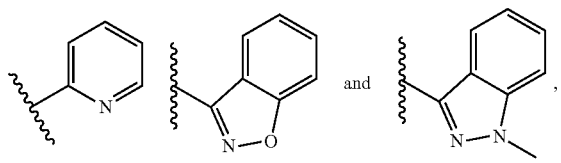

where A is optionally further substituted with one or more R⁷.

In some embodiments, A is selected from:

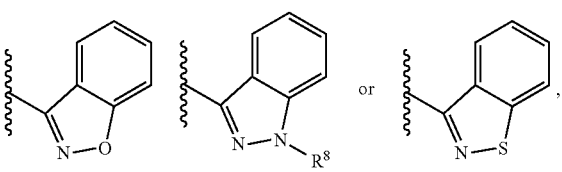

where A is optionally further substituted with one or more R⁷.

In some embodiments, A is

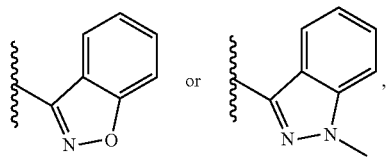

where A is optionally further substituted with one or more R⁷.

In some embodiments, A is

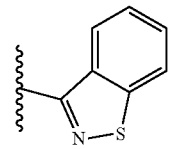

optionally further substituted with one or more R⁷. In some embodiments, A is

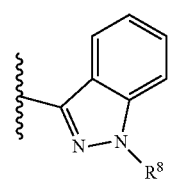

optionally further substituted with one or more R⁷, wherein R⁸ is not methyl.

In a further embodiment, A is

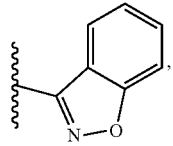

optionally substituted with one or more $R^7$. In some of the above embodiments of A, each occurrence of $R^4$ is independently selected from halogen, —$CF_3$, —$OCF_3$, —C1-C4 aliphatic (e.g., —C1-C4 alkyl), and —O(C1-C4 aliphatic) (e.g., —O(C1-C4 alkyl)).

In some embodiments, $Y^1$ is a C2-aliphatic group substituted with at least one oxo and optionally further substituted with one or more $R^4$, and A is selected from:

a phenyl group;

a naphthalene group; and a 6-membered monocyclic or a 9- to 10-membered bicyclic heteroaryl group having up to 5 heteroatoms independently selected from N, O and S, wherein the bicyclic heteroaryl group has a 6-membered aryl or heteroaryl ring that is directly connected to Y';

wherein A is optionally further substituted with one or more $R^7$. In some such embodiments, $Y^1$ is a C2-aliphatic group substituted with one oxo, and A is selected from:

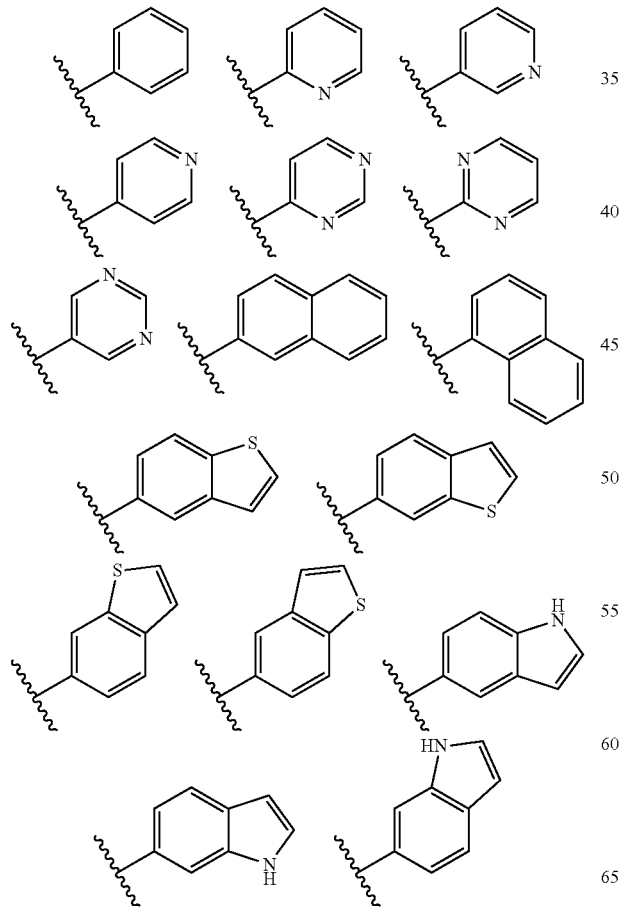

-continued

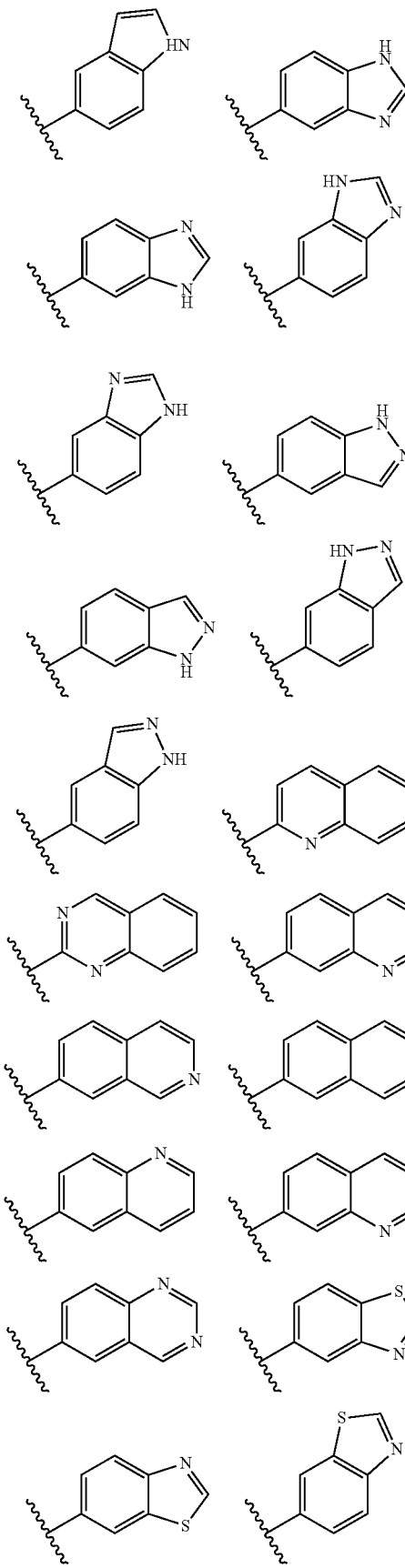

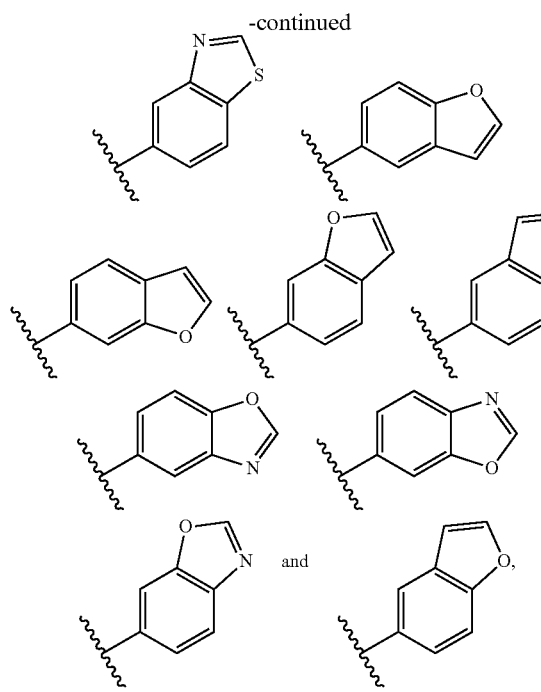

wherein A is optionally further substituted with one or more R⁷. In some of the above embodiments, when Y¹ is a —CH₂—C(O)—, wherein the carbonyl group of Y¹ is connected directly to A, A is not:

(i) unsubstituted phenyl; or
(ii) phenyl substituted with halo (e.g., F— and Cl—) or lower alkyl (e.g., C1-C7 alkyl)

According to certain embodiments, the present disclosure provides a compound of formula II, where X is —H, —C(O)R⁵, or —C(O)OR⁵. In some embodiments, X is —H. In other embodiments, X is a prodrug moiety that is cleaved under physiological conditions to provide a compound wherein X is H. In some embodiments, X is —P(O)(OR⁵)₂. In some embodiments, X is a prodrug moiety that is cleaved under physiological conditions to provide a compound wherein X is —P(O)(OR⁵)₂, such as PO₃H₂, or a salt thereof.

In some embodiments of the compound of formula II, R¹ is —H, bromine, iodine, methyl, ethyl or —CF₃. In some embodiments, R¹ is —H.

According to certain embodiments, the present disclosure also provides a compound of formula II, where Z is =O or =S. In some embodiments, Z is =O.

In some embodiments of the compound of formula II, W is =O or =S. In some embodiments, W is =O.

In some embodiments of compound of formula II, R² and R³ are each independently —OR⁵. In some embodiments, R² is —OH. In another embodiment, R³ is —OH.

The disclosure also includes various combinations of A, X, Y¹, Z, W, R¹, R² and R³ as described above. These combinations can in turn be combined with any or all of the values of the other variables described above. For example, in some embodiments, Y¹ is a C1-aliphatic group substituted with an oxo or a C2-aliphatic group substituted with at least one oxo and optionally further substituted with one or more R⁴ and X is —H, —C(O)R⁵, or —C(O)OR⁵. In another embodiment, Y¹ is a C1-aliphatic group substituted with an oxo or a C2-aliphatic group substituted with at least one oxo and optionally further substituted with one or more R⁴; X is —H, —C(O)R⁵, or —C(O)OR⁵; and Z is =O. In another embodiment, Y¹ is a C1-aliphatic group substituted with an oxo or a C2-aliphatic group substituted with at least one oxo and optionally further substituted with one or more R⁴; X is —H, —C(O)R⁵, or —C(O)OR⁵; Z is =O; and W is =O. In yet another embodiment, Y¹ is a C1-aliphatic group substituted with an oxo or a C2-aliphatic group substituted with at least one oxo and optionally further substituted with one or more R⁴; X is —H, —C(O)R⁵, or —C(O)OR⁵; Z is =O; W is =O; and R¹ is selected from —H, bromine, iodine, methyl, ethyl, and —CF₃, for example, R¹ is —H. In a further embodiment, Y¹ is a C1-aliphatic group substituted with an oxo or a C2-aliphatic group substituted with at least one oxo and optionally further substituted with one or more R⁴; X is —H, —C(O)R⁵, or —C(O)OR⁵; Z is =O; W is =O; and R¹ is selected from —H, bromine, iodine, methyl, ethyl, and —CF₃; and A is selected from the following groups:

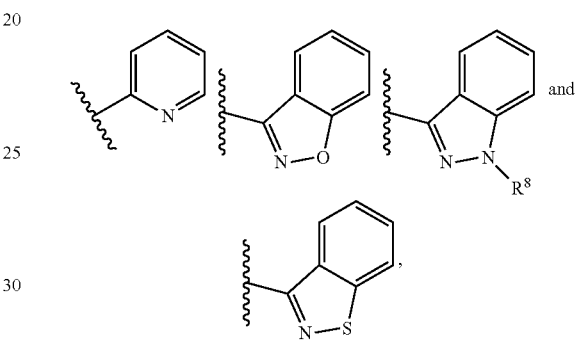

wherein A is optionally further substituted with one or more R⁷, for example, A is optionally further substituted

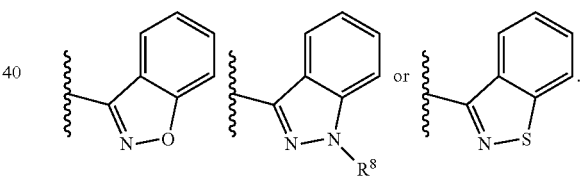

In yet a further embodiment, Y¹ is a C1-aliphatic group substituted with an oxo or a C2-aliphatic group substituted with at least one oxo and optionally further substituted with one or more R⁴; X is —H, —C(O)R⁵, or —C(O)OR⁵; Z is =O; W is =O; and R¹ is selected from —H, bromine, iodine, methyl, ethyl, and —CF₃; A is selected from the following group:

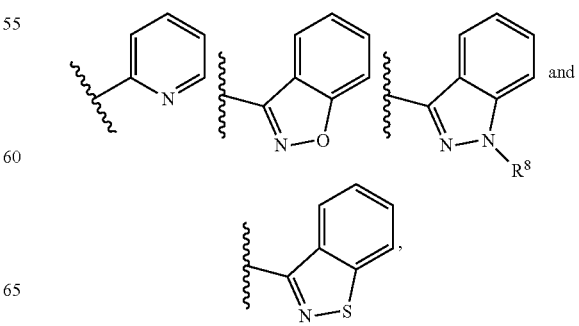

wherein A is optionally further substituted with one or more R⁷;

and R² and R³ are each independently —OR⁵, for example, R² and R³ are each independently —OH. In some of the above embodiments, A is

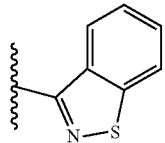

optionally further substituted with one or more R⁴. In some of the above embodiments, A is

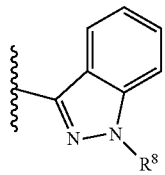

optionally further substituted with one or more R⁴, wherein R⁸ is not methyl. In a further embodiment, Y¹ is a C1-aliphatic group substituted with an oxo or a C2-aliphatic group substituted with at least one oxo and optionally further substituted with one or more R⁴; X is —H, —C(O)R⁵, or —C(O)OR⁵; Z is =O; W is =O; and R¹ is selected from —H, bromine, iodine, methyl, ethyl, and —CF₃; and A is selected from the following groups:

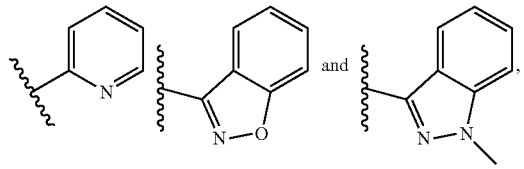

wherein A is optionally further substituted with one or more R⁷, for example, A is optionally further substituted

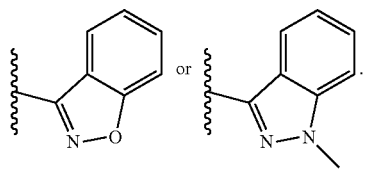

In yet a further embodiment, Y¹ is a C1-aliphatic group substituted with an oxo or a C2-aliphatic group substituted with at least one oxo and optionally further substituted with one or more R⁴; X is —H, —C(O)R⁵, or —C(O)OR⁵; Z is =O; W is =O; and R¹ is selected from —H, bromine, iodine, methyl, ethyl, and —CF₃; A is selected from the following group:

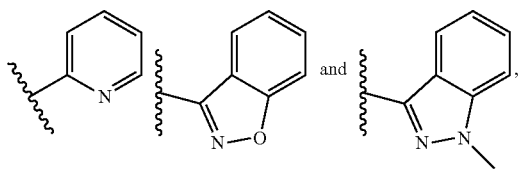

wherein A is optionally further substituted with one or more R⁷;

and R² and R³ are each independently —OR⁵, for example, R² and R³ are each independently —OH. In some of the above embodiments, each occurrence of R⁷ is independently selected from halogen, —CF₃, —OCF₃, —C1-C4 aliphatic (e.g., —C1-C4 alkyl), and —O(C1-C4 aliphatic) (e.g., —O(C1-C4 alkyl)). In some of the above embodiments, when Y¹ is a —CH₂—C(O)—, wherein the carbonyl group of Y¹ is connected directly to A, A is not:

(i) unsubstituted phenyl; or (ii) phenyl substituted with halo (e.g., F— and Cl—) or lower alkyl (e.g., C1-C7 alkyl)

Examples of particular compounds of the present disclosure include:

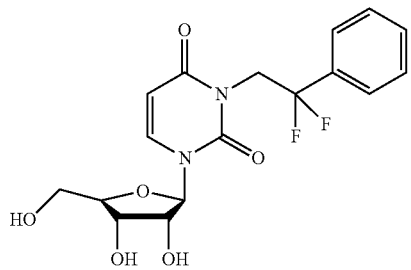

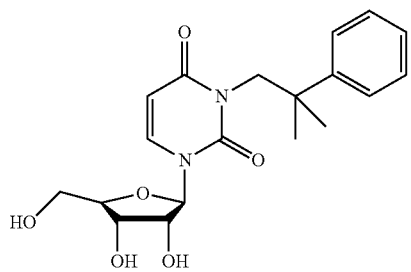

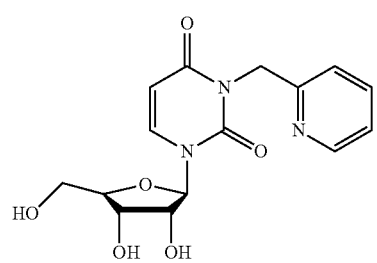

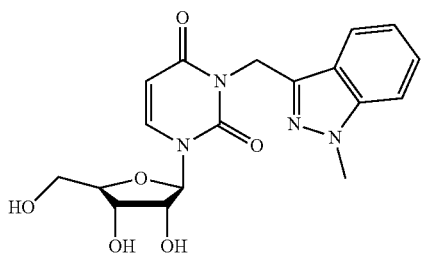
4
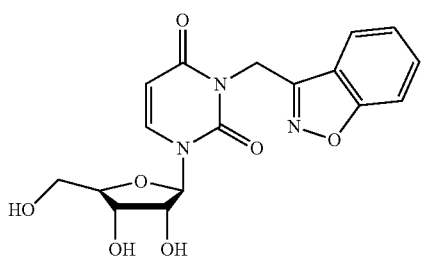
5
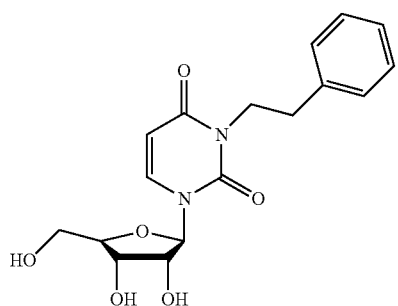
6
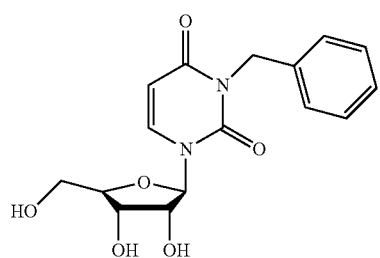
7
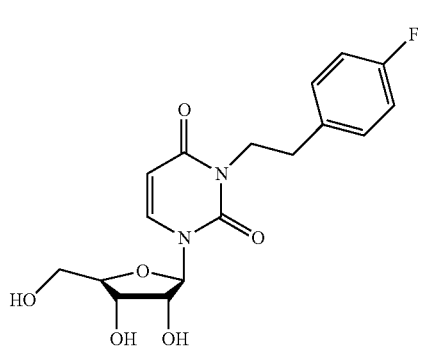
8
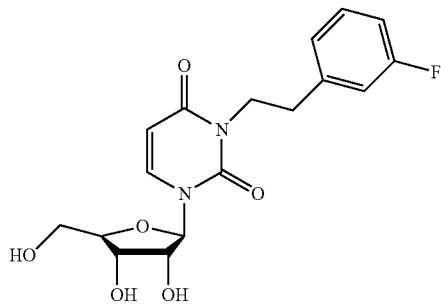
9
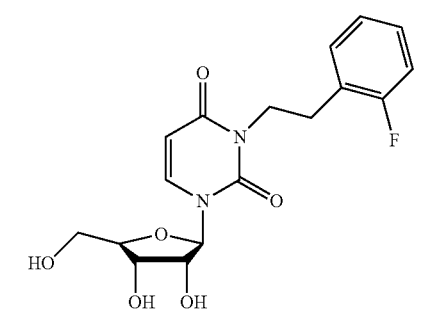
10
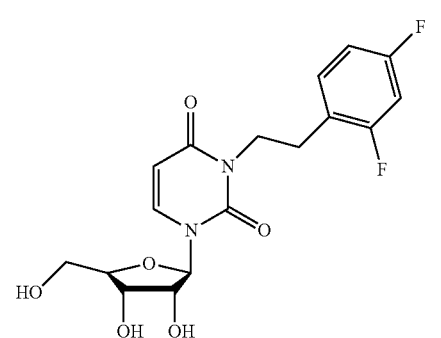
11
12
13

14
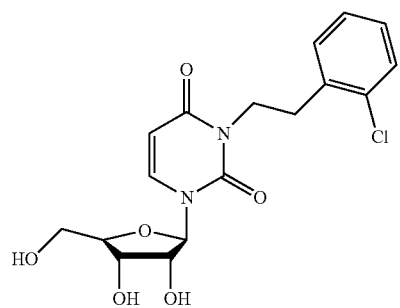
15
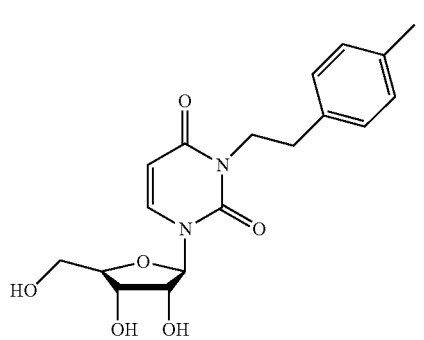
16
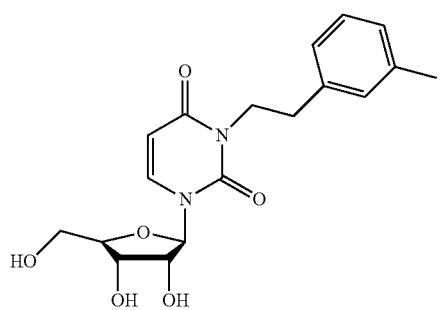
17
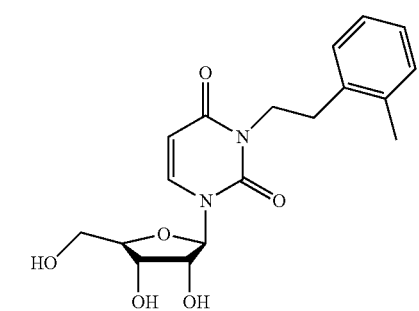
18
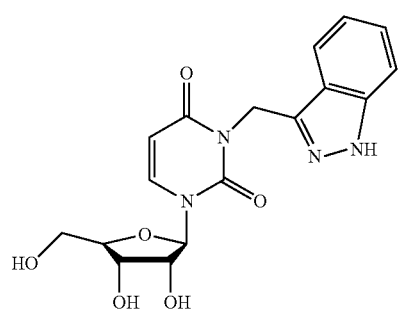
19
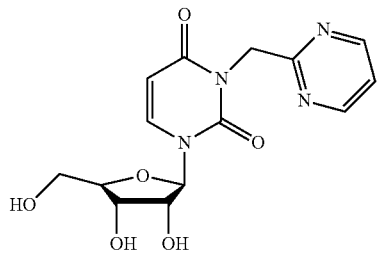
20
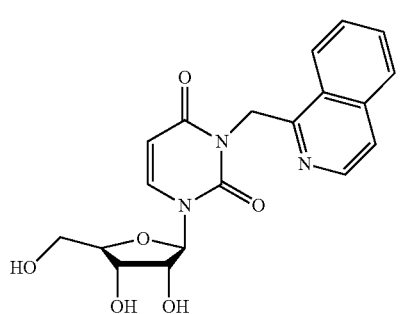
21
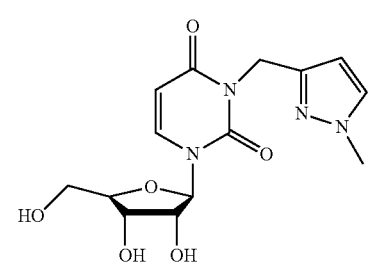
22
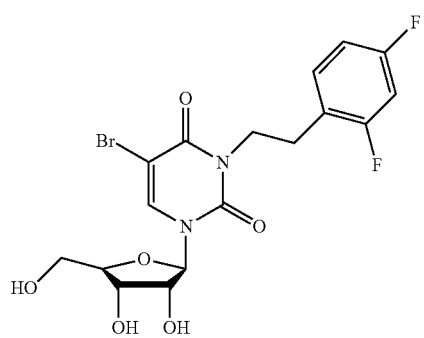
23
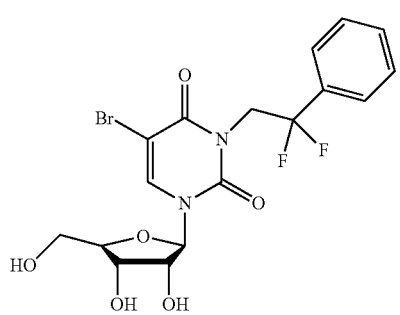

24
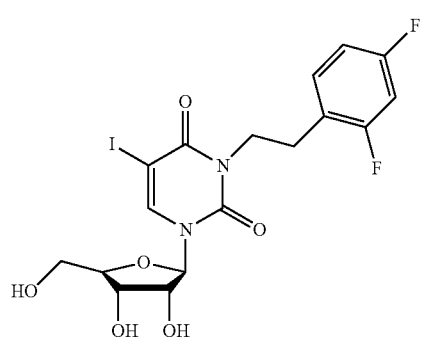
25
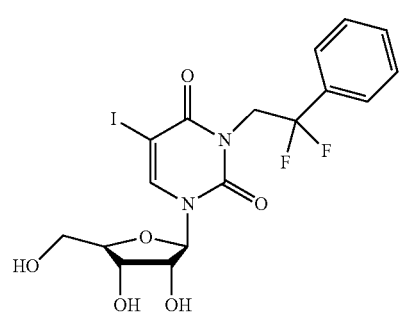
26
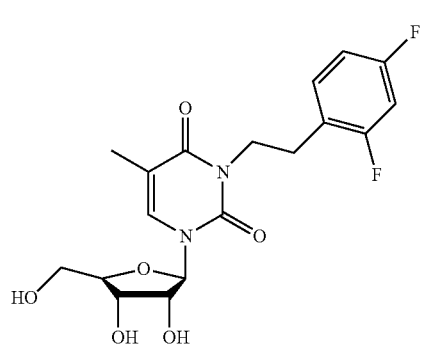
27
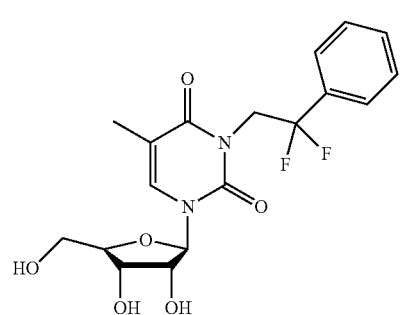
28
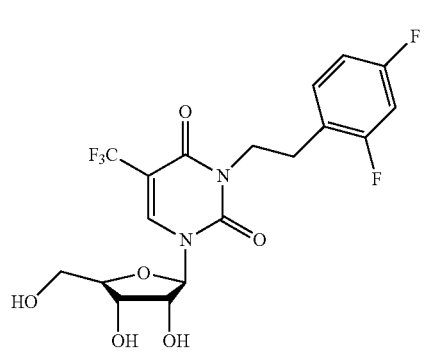
29
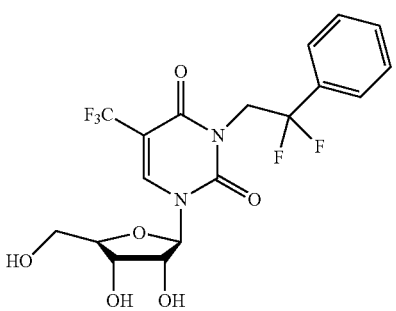
30
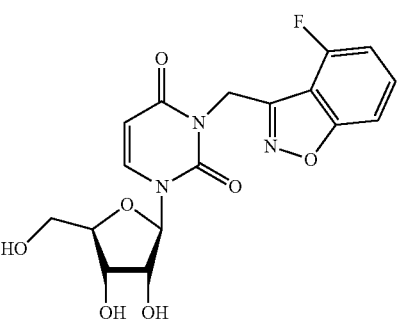
31
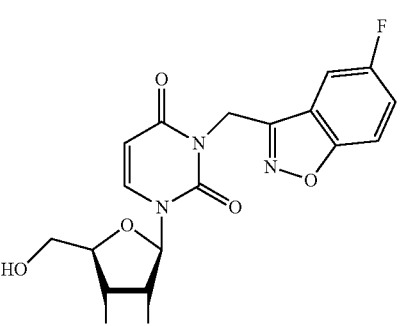
32
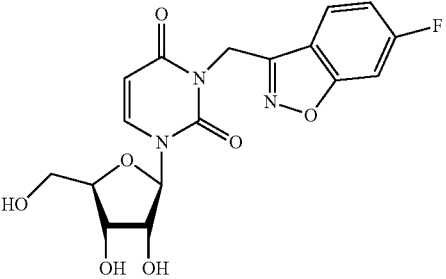
33
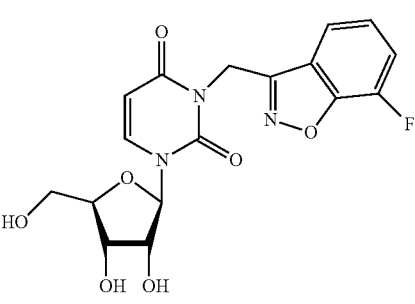

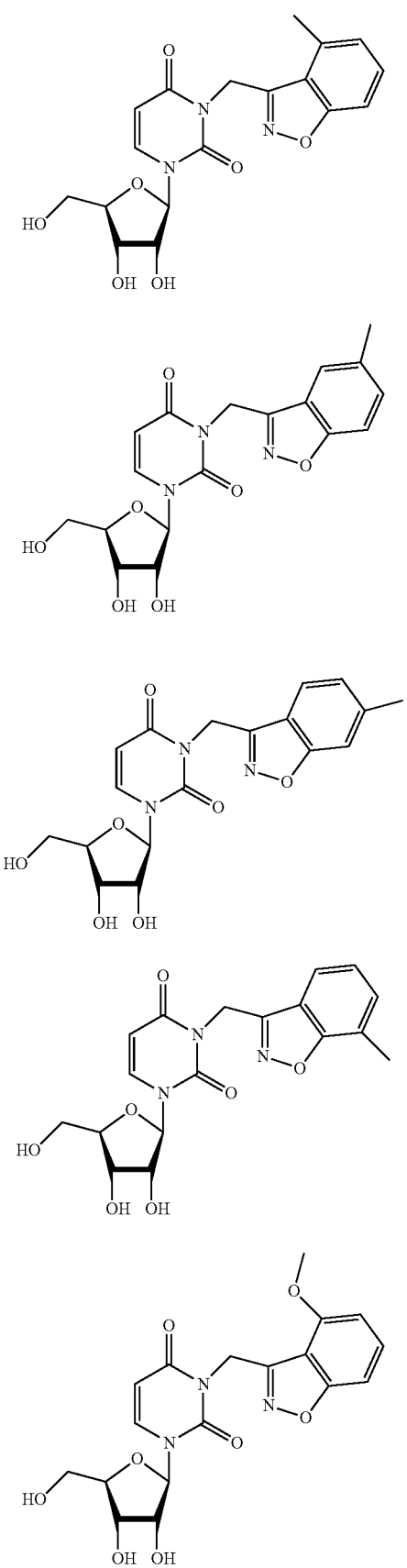

44
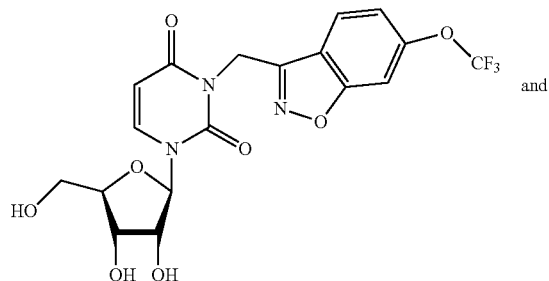
45
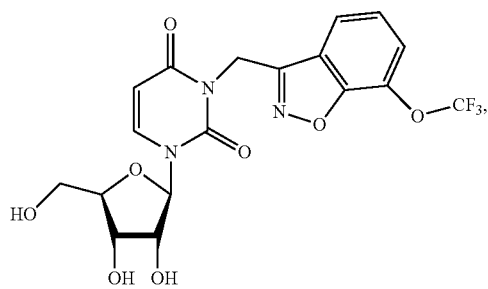
or pharmaceutically acceptable salts thereof. In certain embodiments, the pharmaceutically acceptable salt is a sodium salt.
Examples of particular compounds of the present disclosure include:
1
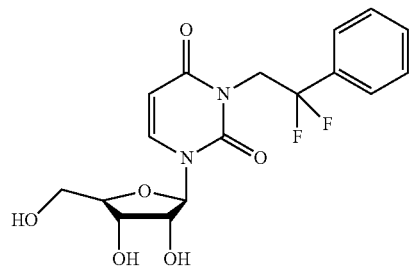
2
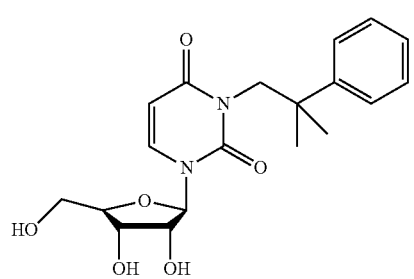
3
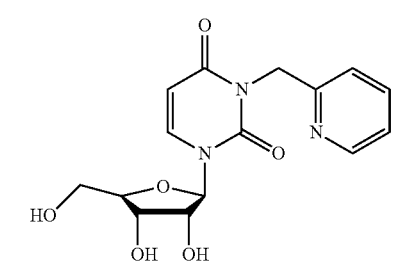
4
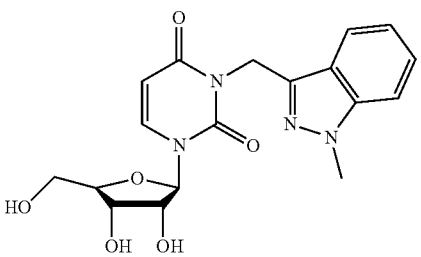
5
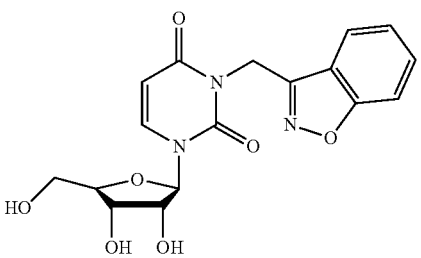
6
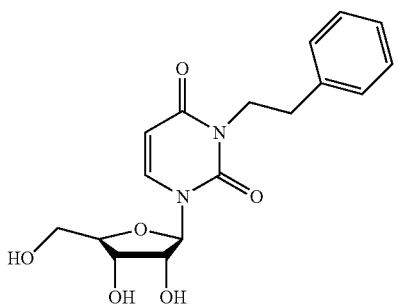
7
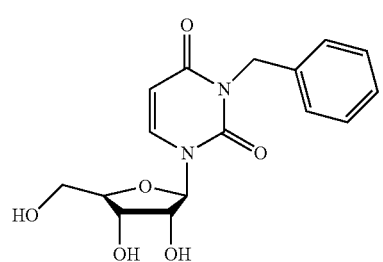
8
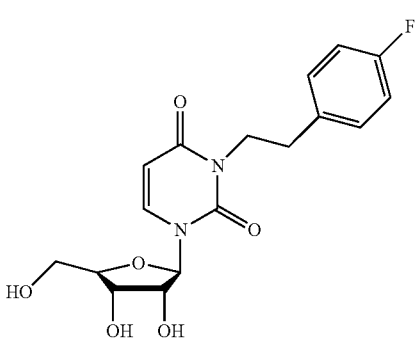

9
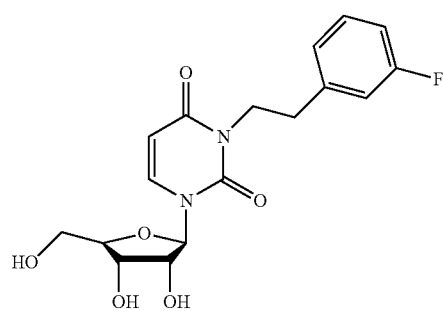
10
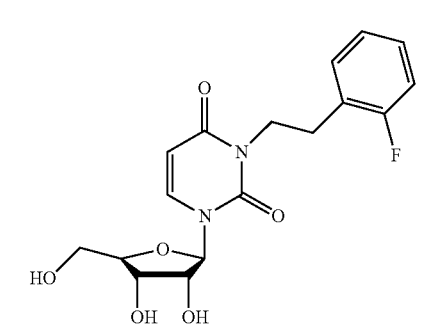
11
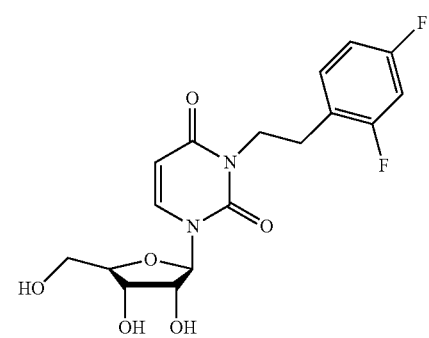
12
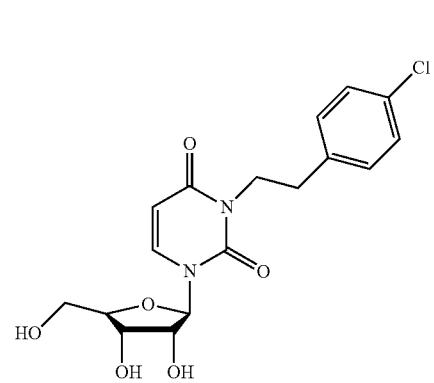
13
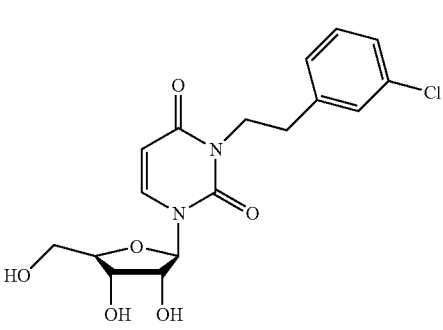
14
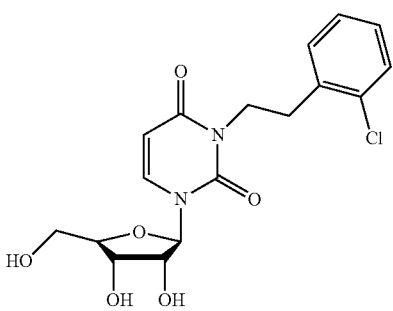
15
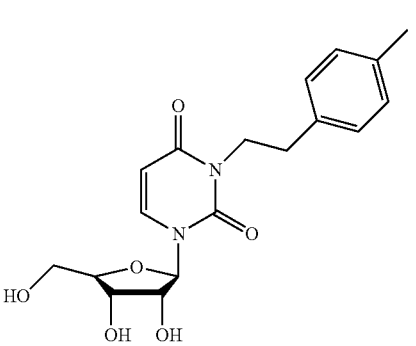
16
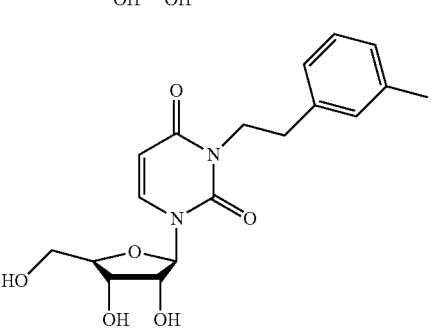
17
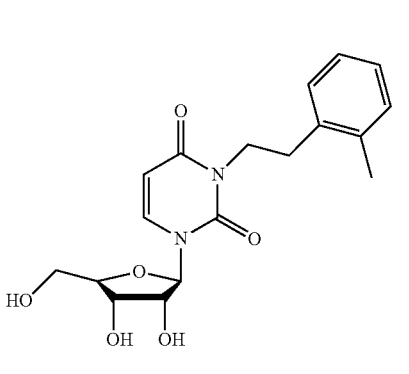
18
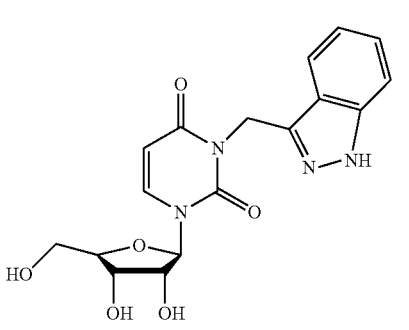

19
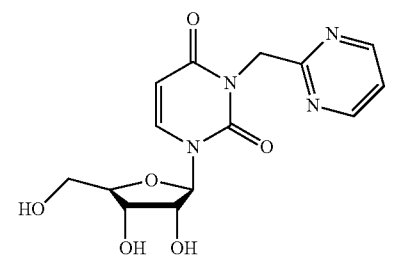
20
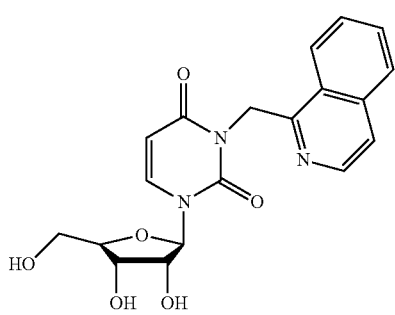
21
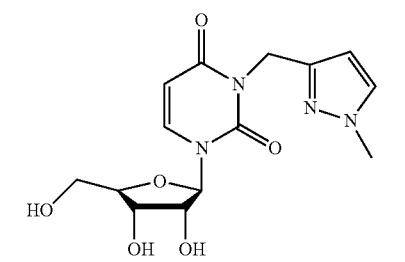
22
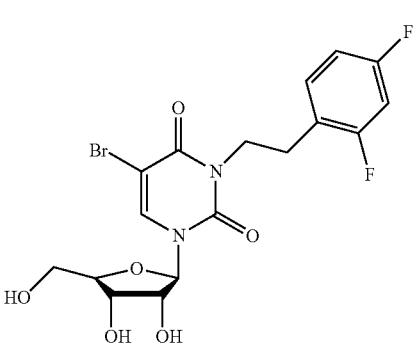
23
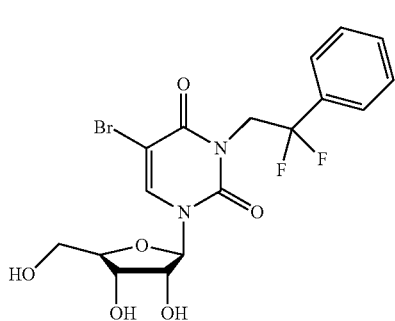
24
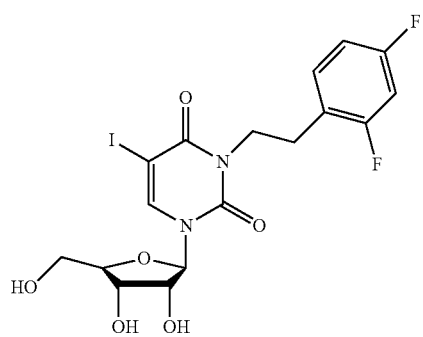
25
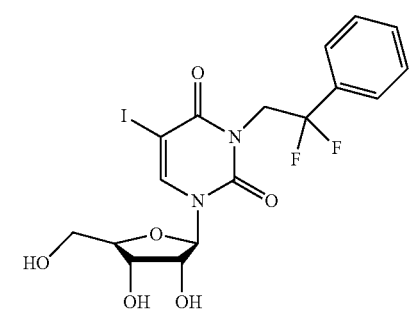
26
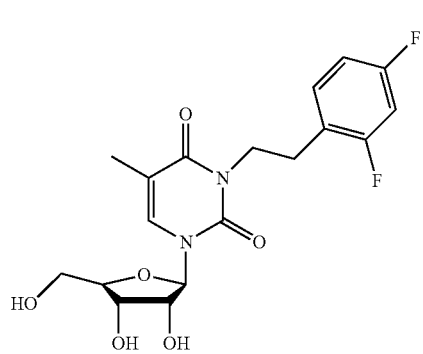
27
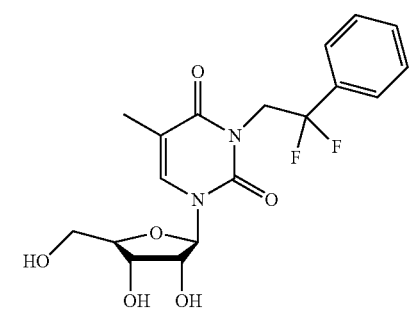
28
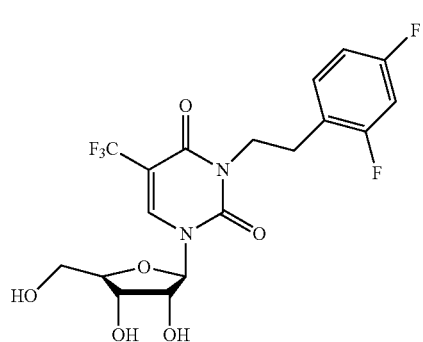

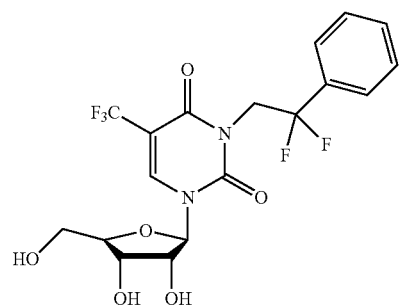
29
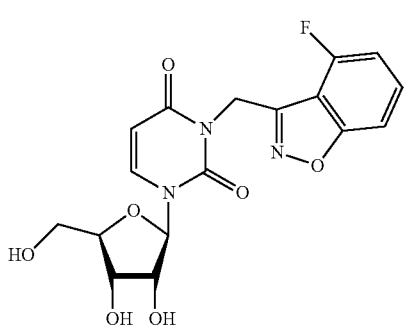
30
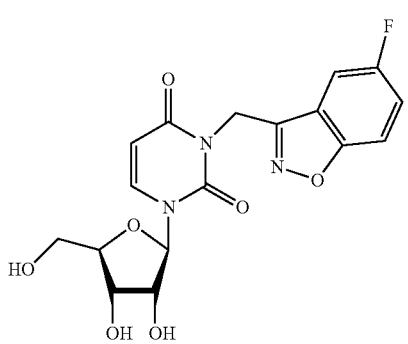
31
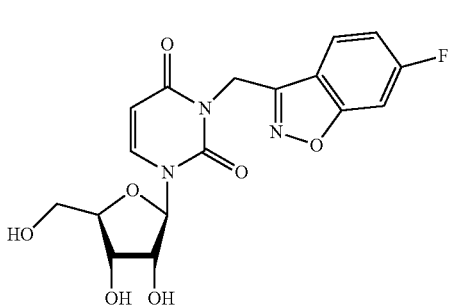
32
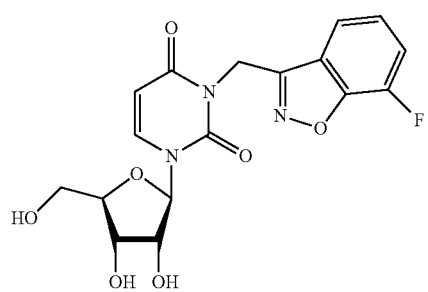
33
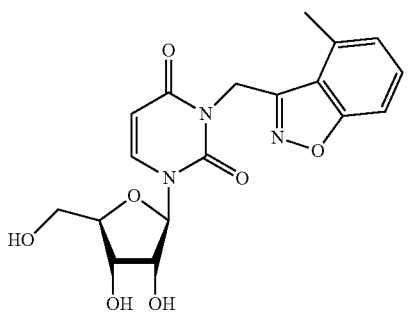
34
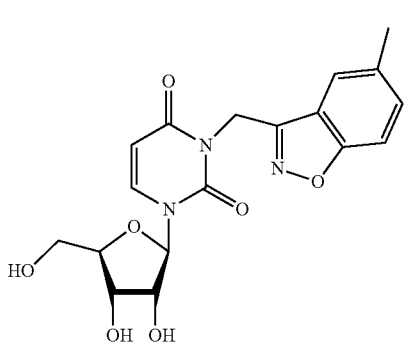
35
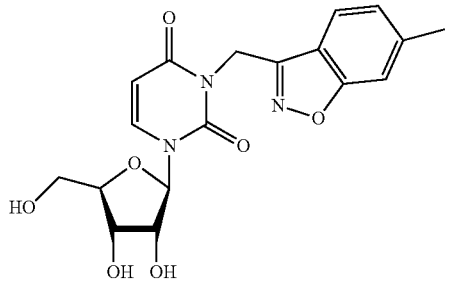
36
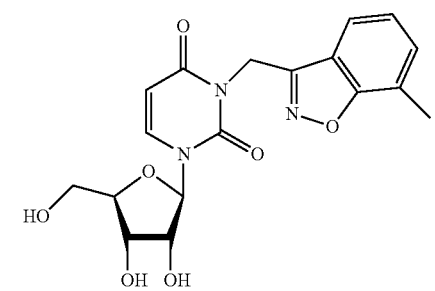
37
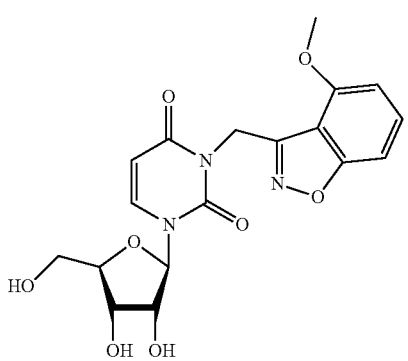
38

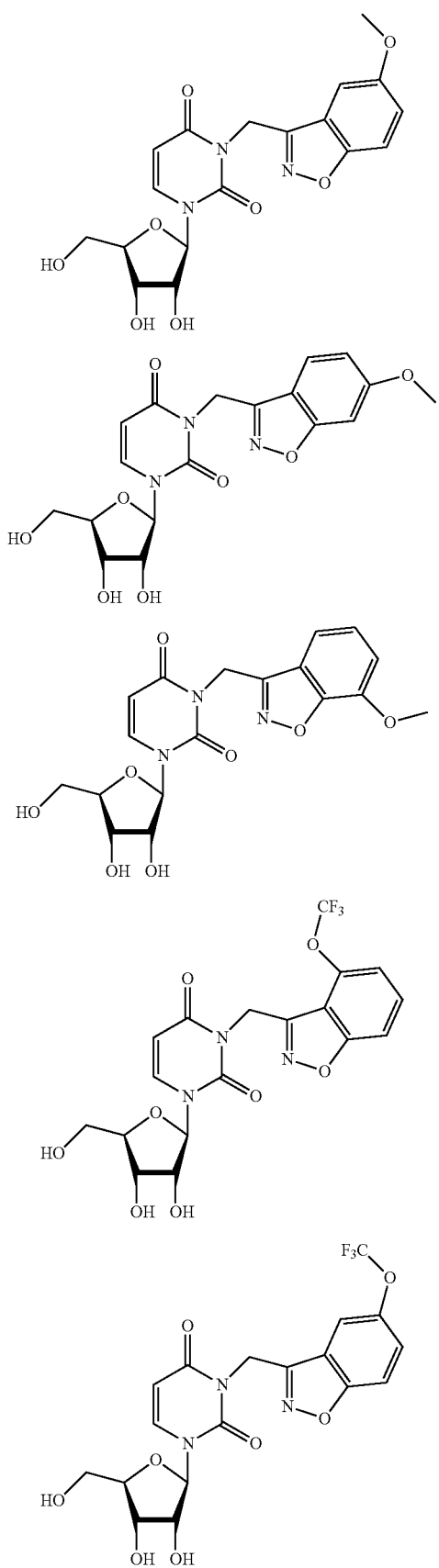

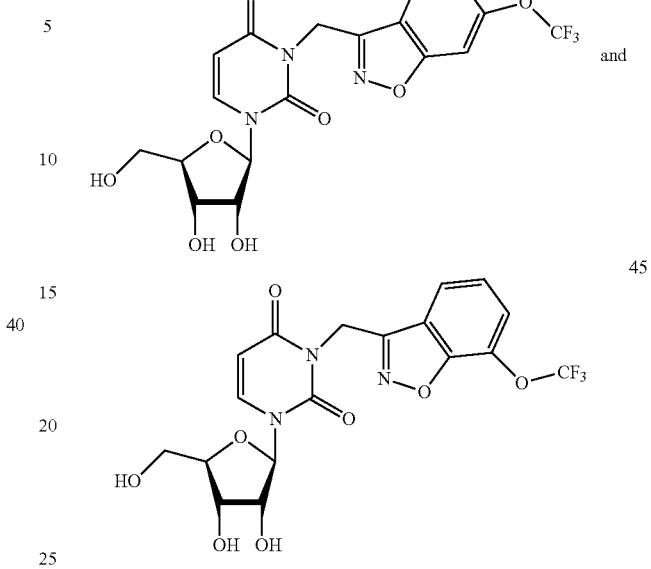

or pharmaceutically acceptable salts thereof. In certain embodiments, the pharmaceutically acceptable salt is a sodium salt.

In another embodiment, the present disclosure provides a pharmaceutical composition comprising a pharmaceutically acceptable carrier and a compound of formula I (including formula I-A and formula I-B) or formula II or pharmaceutically acceptable salt form thereof. In yet other embodiments, the present disclosure provides a pharmaceutical composition comprising a pharmaceutically acceptable carrier and any one of compounds 1-45 or a pharmaceutically acceptable salt form thereof. In certain embodiments, the present disclosure provides a pharmaceutical composition comprising a pharmaceutically acceptable carrier and the following compound or a pharmaceutically acceptable salt form thereof:

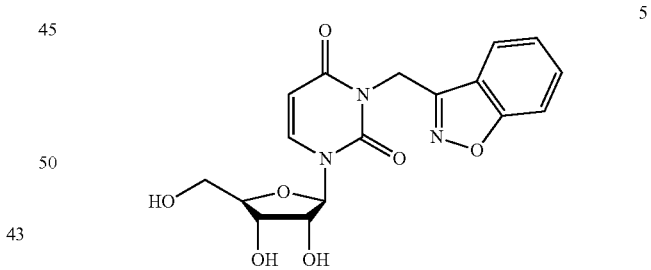

In another embodiment, the present disclosure provides a compound described herein in isolated form, i.e., an isolated compound. Exemplary embodiments are an isolated compound of formula I (including formula I-A and formula I-B), an isolated compound of formula II, or any of compounds 1-45 in isolated form. The term "isolated" refers to material that is removed from its original environment (e.g., the natural environment if it is naturally occurring or a synthetic mixture if the material is synthesized in vitro or ex vivo). The isolated compound is desirably substantially pure, such as having a purity of at least about 80%, 85%, 90%, 95%, or 99% by weight.

It is understood that the compounds of the invention (e.g., compounds 1-45) including pharmaceutically acceptable salts thereof and pharmaceutical compositions comprising at least one of the compounds of the invention (e.g., compounds 1-45), can be used in each of the methods described hereinbelow.

C. General Synthetic Methodology

The compounds of this disclosure may be prepared in general by methods known to those skilled in the art. Scheme 1 below illustrates a general synthetic route to the compounds of the present disclosure. Other equivalent schemes, which will be readily apparent to the ordinary skilled organic chemist, may alternatively be used to synthesize various portions of the molecules as illustrated by the general scheme below.

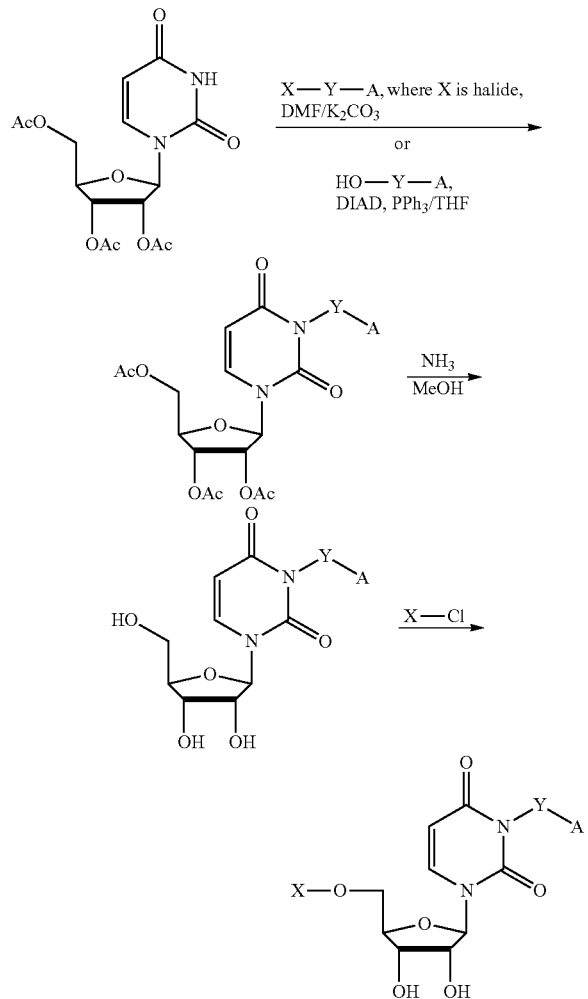

In another embodiment, the present disclosure provides a pharmaceutical composition comprising a pharmaceutically acceptable carrier and a compound described herein, such as a compound of formula I or II.

The disclosure contemplates that any one or more of the foregoing aspects and embodiments (including compounds of all of the preceding formulae as well as their salts and prodrugs) can be combined with each other and/or with any of the embodiments or features provided below.

D. Exemplary Uses

1. Neuronal Diseases/Disorders

In certain aspects, the compounds and compositions as described herein can be used to treat patients suffering from $P_2Y_6$ receptor-related conditions or conditions that can be ameliorated by agonizing $P_2Y_6$ receptor activity, such as neurodegenerative diseases, and traumatic or mechanical injury to the central nervous system (CNS), spinal cord or peripheral nervous system (PNS). Any of the compounds and compositions, including pharmaceutical compositions, of the disclosure can be used in vitro or in vivo, including in any one or more of the in vivo or in vitro methods described herein. For example, any of the compounds and compositions of the disclosure can be used in vitro or in vivo, for example to modulate $P_2Y_6$ receptor activity and/or to treat any one or more of the diseases or conditions described herein. Moreover, any of the compounds and compositions of the disclosure can be used in vitro or in vivo, for example to modulate $P_2Y_6$ receptor activity and/or to inhibit release and/or reduce elevated levels of pro-inflammatory cytokines and/or to decrease levels of pro-inflammatory cytokines, such as in plasma or secreted from cells. The disclosure contemplates that any of the compounds of the disclosure, including salts thereof, may be used in any of the in vitro or in vivo methods described herein, such as to treat any one or more of the diseases or conditions described herein. Similarly any of the compounds of the disclosure may be used in vitro, such as to modulate $P_2Y_6$ receptor activity. Moreover, any of the compounds of the disclosure may be formulated as a pharmaceutical composition comprising a compound and one or more acceptable carriers and/or excipients. Compositions, such as pharmaceutical compositions, may be used in any of the in vitro or in vivo methods described herein, such has to treat any one or more of the diseases or conditions described herein.

Accordingly, the disclosure contemplates methods of treating (decreasing the frequency or severity of or otherwise alleviating one or more symptoms of the condition) a subject in need thereof (e.g., a subject having any of the conditions described herein, including any of the neurodegenerative or neuronal conditions described herein) by administering a compound of the disclosure. Many of these, as well as other conditions described herein, are characterized by a level of cognitive impairment and/or some decrease or loss of cognitive function. Cognitive function and cognitive impairment are used as understood in the art. For example, cognitive function generally refers to the mental processes by which one becomes aware of, perceives, or comprehends ideas. Cognitive function involves all aspects of perception, thinking, learning, reasoning, memory, awareness, and capacity for judgment. Cognitive impairment generally refers to conditions or symptoms involving problems with thought processes. This may manifest itself in one or more symptoms indicating a decrease in cognitive function, such as impairment or decrease of higher reasoning skills, forgetfulness, impairments to memory, learning disabilities, concentration difficulties, decreased intelligence, and other reductions in mental functions.

Neurodegenerative disease typically involves reductions in the mass and volume of the human brain, which may be due to the atrophy and/or death of brain cells, which are far more profound than those in a healthy person that are attributable to aging.

Neurodegenerative diseases can evolve gradually, after a long period of normal brain function, due to progressive degeneration (e.g., nerve cell dysfunction and death) of specific brain regions. Alternatively, neurodegenerative diseases can have a quick onset, such as those associated with trauma or toxins. The actual onset of brain degeneration may precede clinical expression by many years. Examples of neurodegenerative diseases include, but are not limited to, Alzheimer's disease (AD), Parkinson's disease (PD), Huntington's disease (HD), amyotrophic lateral sclerosis (ALS; Lou Gehrig's disease), diffuse Lewy body disease, choreaacanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia. $P_2Y_6$ receptor-modulating compounds of the present disclosure can be used to treat these disorders and others as described below.

AD is a CNS disorder that results in memory loss, unusual behavior, personality changes, and a decline in thinking abilities. These losses are related to the death of specific types of brain cells and the breakdown of connections and their supporting network (e.g. glial cells) between them. The earliest symptoms include loss of recent memory, faulty judgment, and changes in personality. Without being bound by theory, these changes in the brain and symptoms associated with cognitive impairment, including memory and learning impairment, are caused, in whole or in part, by accumulation of beta amyloid and the resulting deposition of amyloid plaques. PD is a CNS disorder that results in uncontrolled body movements, rigidity, tremor, and dyskinesia, and is associated with the death of brain cells in an area of the brain that produces dopamine. ALS (motor neuron disease) is a CNS disorder that attacks the motor neurons, components of the CNS that connect the brain to the skeletal muscles.

HD is another neurodegenerative disease that causes uncontrolled movements, loss of intellectual faculties, and emotional disturbance. Tay-Sachs disease and Sandhoff disease are glycolipid storage diseases where GM2 ganglioside and related glycolipids substrates for β-hexosaminidase accumulate in the nervous system and trigger acute neurodegeneration.

It is well-known that apoptosis plays a role in AIDS pathogenesis in the immune system. However, HIV-1 also induces neurological disease, which can be treated with $P_2Y_6$ receptor-modulating compounds of the disclosure.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats. $P_2Y_6$ receptor-modulating compounds as described herein, may be useful for treating or preventing neuronal loss due to these prion diseases.

In another embodiment, the compounds as described herein may be used to treat or prevent any disease or disorder involving axonopathy. Distal axonopathy is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. Those with distal axonopathies usually present with symmetrical glove-stocking sensorimotor disturbances. Deep tendon reflexes and autonomic nervous system (ANS) functions are also lost or diminished in affected areas.

Diabetic neuropathies are neuropathic disorders that are associated with diabetes mellitus. Relatively common conditions which may be associated with diabetic neuropathy include third nerve palsy; mononeuropathy; mononeuritis multiplex; diabetic amyotrophy; a painful polyneuropathy; autonomic neuropathy; and thoracoabdominal neuropathy.

Peripheral neuropathy is the medical term for damage to nerves of the peripheral nervous system, which may be caused either by diseases of the nerve or from the side-effects of systemic illness. Major causes of peripheral neuropathy include seizures, nutritional deficiencies, and HIV, though diabetes is the most likely cause.

In an exemplary embodiment, a $P_2Y_6$ receptor-modulating compound as described herein may be used to treat or prevent multiple sclerosis (MS), including relapsing MS and monosymptomatic MS, and other demyelinating conditions, such as, for example, chronic inflammatory demyelinating polyneuropathy (CIDP), or symptoms associated therewith.

In yet another embodiment, compounds of the present disclosure may be used to treat trauma to the nerves, including, trauma due to disease, injury (including surgical intervention), or environmental trauma (e.g., neurotoxins, alcoholism, etc.). In certain embodiments, compounds of the present disclosure may be used to treat traumatic brain injury, such as to improve cognitive function in a subject suffering from a traumatic brain injury. Without being bound by theory, there is often an increase in beta amyloid observed following traumatic brain injuries. The present disclosure provides methods suitable for enhancing clearance of beta amyloid or otherwise reducing beta amyloid and/or plaque burden in a subject.

Compounds of the present disclosure may also be useful to prevent, treat, and alleviate symptoms of various PNS disorders. The term "peripheral neuropathy" encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

PNS diseases treatable with $P_2Y_6$ receptor-modulating compounds as described herein, include: diabetes, leprosy, Charcot-Marie-Tooth disease, Guillain-Barré syndrome and Brachial Plexus Neuropathies (diseases of the cervical and first thoracic roots, nerve trunks, cords, and peripheral nerve components of the brachial plexus).

In another embodiment, compounds of the present disclosure may be used to treat or prevent a polyglutamine disease. Exemplary polyglutamine diseases include Spinobulbar muscular atrophy (Kennedy disease), Huntington's Disease (HD), Dentatorubral-pallidoluysian atrophy (Haw River syndrome), Spinocerebellar ataxia type 1, Spinocerebellar ataxia type 2, Spinocerebellar ataxia type 3 (Machado-Joseph disease), Spinocerebellar ataxia type 6, Spinocerebellar ataxia type 7, and Spinocerebellar ataxia type 17.

In certain embodiments, the disclosure provides a method to treat a central nervous system cell to prevent damage in response to a decrease in blood flow to the cell. Typically the severity of damage that may be prevented will depend in large part on the degree of reduction in blood flow to the cell and the duration of the reduction. In some embodiments, apoptotic or necrotic cell death may be prevented. In still a further embodiment, ischemic-mediated damage, such as cytoxic edema or central nervous system tissue anoxemia, may be prevented. In each embodiment, the central nervous system cell may be a spinal cell or a brain cell.

Another aspect encompasses administrating a compound as described herein to a subject to treat a central nervous system ischemic condition. A number of central nervous system ischemic conditions may be treated by the compounds described herein.

In some embodiments, the ischemic condition is a stroke that results in any type of ischemic central nervous system damage, such as apoptotic or necrotic cell death, cytoxic edema or central nervous system tissue anoxia. The stroke may impact any area of the brain or be caused by any etiology commonly known to result in the occurrence of a stroke. In one alternative of this embodiment, the stroke is a brain stem stroke. In another alternative of this embodiment, the stroke is a cerebellar stroke. In still another embodiment, the stroke is an embolic stroke. In yet another alternative, the stroke may be a hemorrhagic stroke. In a further embodiment, the stroke is a thrombotic stroke.

In yet another aspect, compounds of the disclosure may be administered to reduce infarct size of the ischemic core following a central nervous system ischemic condition. Moreover, compounds of the present disclosure may also be beneficially administered to reduce the size of the ischemic penumbra or transitional zone following a central nervous system ischemic condition.

In some embodiments, a combination drug regimen may include drugs or compounds for the treatment or prevention of neurodegenerative disorders or secondary conditions associated with these conditions. Thus, a combination drug regimen may include one or more compounds as described herein and one or more anti-neurodegeneration agents.

In a particular embodiment, the disclosure provides methods for doing one or more of decreasing plaque burden, improving cognitive function, decreasing or delaying cognitive impairment, or improving hippocampal long term potentiation by administering to a subject in need thereof a compound of the disclosure. These methods may also be used for one or more of enhancing beta amyloid clearance, increasing synaptic plasticity, or improving or restoring memory. The foregoing are exemplary of beneficial results that would help alleviate (e.g., treat) one or more symptoms of conditions associated with cognitive impairment. Exemplary conditions include AD, traumatic brain injury, and Down Syndrome, as well as other neurological and neurodegenerative diseases. Moreover, the disclosure contemplates the alleviation of symptoms in conditions and scenarios associated with milder forms of cognitive impairment, such as age-related dementia, mild cognitive impairment, and even to improve memory and cognitive function that typically declines, even in relatively healthy individuals, as part of the normal aging process. Exemplary such agonists are described herein, and the disclosure contemplates that any such compounds can be used in the treatment of any of the conditions described herein. Regardless of whether one of the agonists described herein are used or whether another agonist is used, the disclosure contemplates that the agonist may be formulated in a pharmaceutically acceptable carrier and administered by any suitable route of administration. These methods are of particular use when the subject in need thereof has Alzheimer's disease. It is understood by those of skill in the art that definitive diagnosis of Alzheimer's disease is difficult and may require postmortem examination. Thus, in this context and in the context of the present disclosure, having Alzheimer's disease is used to refer to subjects who have been diagnosed with Alzheimer's disease or who are suspected by a physician of having Alzheimer's disease. However, these methods are also of particular use when the subject in need thereof has any other condition associated with cognitive impairment, for example, a condition in which the impairment is accompanied with an increase in beta amyloid, a decrease in the rate of beta amyloid clearance, and/or an increase in amyloid plaque deposition.

Cognitive function and cognitive impairment may be readily evaluated using tests well known in the art. Performance in these tests can be compared over time to determine whether a treated subject is improving or whether further decline has stopped or slowed, relative to the previous rate of decline of that patient or compared to an average rate of decline. Exemplary tests used in animal studies are provided in, for example, Animal Models of Cognitive Impairment, Levin E D, Buccafusco J J, editors. Boca Raton (Fla.): CRC Press; 2006. Tests of cognitive function, including memory and learning for evaluating human patients are well known in the art and regularly used to evaluate and monitor subjects having or suspected of having cognitive disorders such as AD. Even in healthy individuals, these and other standard tests of cognitive function can be readily used to evaluate beneficial affects over time.

Compounds of the disclosure are also useful in the treatment of Parkinson's disease. For example, compounds of the disclosure can be used to improve the motor impairments symptomatic of Parkinson's disease. Moreover, compounds of the disclosure are useful for treating the memory impairment symptomatic of Parkinson's disease. Without being bound by theory, impairment of microglial phagocytosis is thought to be a mechanism of action underlying accumulation of alpha synuclein and the formation of Lewy bodies (and resulting neurodegeneration) in Parkinson's disease. Compounds of the disclosure may be used to increase clearance or otherwise decrease extracellular alpha-synuclein, to decrease intracellular accumulation of alpha-synuclein, and/or to decrease or prevent the formation of Lewy bodies in a subject in need thereof. In certain embodiments, compounds of the disclosure enhance phagocytosis, such as microglial phagocytosis.

Compounds of the disclosure, including salts and prodrugs, may be tested in animal models of Parkinson's disease. Exemplary models include mice that over express α-synuclein, express human mutant forms of α-synuclein, mice that express LRKK2 mutations, as well as mice treated with MTTP. Additional information regarding these animal models is readily available from Jackson Laboratories (see also the website research.jax.org/grs/parkinsons.html), as well as in numerous publications disclosing the use of these validated models.

2. Down Syndrome

Compounds of the present disclosure may also be useful to prevent, treat, and alleviate symptoms of Down Syndrome (DS). Down Syndrome (DS) is a genetic condition characterized by trisomy of chromosome 21. DS is named after Dr. John Langdon Down, an English physician who first described the characteristics of DS in 1866. It was not until 1959 that Jerome Leieune and Patricia Jacobs independently first determined the cause to be trisomy of the 21st chromosome.

In recent years, it has become evident that there is relationship between Alzheimer's Disease (AD) and DS. Specifically, the production of excessive beta amyloid plaques and amyloid angiopathy occurs in both DS and Alzheimer's Disease (AD) (Delabar et al. (1987) "Beta amyloid gene triplication in Alzheimer's disease and karyo-typically normal Down Syndrome. Science 235: 1390-1392). Without being bound by theory, given that both AD and Down Syndrome are characterized by both beta amyloid plaques and cognitive impairment, methods and compositions that decrease plaque burden and/or enhance beta amyloid clearance are useful for treating AD and Down Syndrome (e.g., providing a beneficial effect and/or decreasing one or more symptoms of AD or Down Syndrome). Exemplary beneficial effects include, but are not limited to, improving cognitive function, decreasing cognitive impairment, decreasing plaque burden, enhancing beta amyloid clearance, improving memory, and the like.

3. Pain

In certain aspects, the compounds as described herein can be used to treat patients having pain. Pain is a complex physiological process that involves a number of sensory and neural mechanisms. Compounds to be used according to the present disclosure are suitable for administration to a subject for treatment (including prevention and/or alleviation) of chronic and/or acute pain, in particular non-inflammatory musculoskeletal pain such as back pain, fibromyalgia and myofascial pain, more particularly for reduction of the associated muscular hyperalgesia or muscular allodynia. Nonlimiting examples of types of pain that can be treated by the compounds, compositions and methods of the present disclosure include chronic conditions such as musculoskeletal pain, including fibromyalgia, myofascial pain, back pain, pain during menstruation, pain during osteoarthritis, pain during rheumatoid arthritis, pain during gastrointestinal inflammation, pain during inflammation of the heart muscle, pain during multiple sclerosis, pain during neuritis, pain during AIDS, pain during chemotherapy, tumor pain, headache, CPS (chronic pain syndrome), central pain, neuropathic pain such as trigeminal neuralgia, shingles, stamp pain, phantom limb pain, temporomandibular joint disorder, nerve injury, migraine, post-herpetic neuralgia, neuropathic pain encountered as a consequence of injuries, amputation infections, metabolic disorders or degenerative diseases of the nervous system, neuropathic pain associated with diabetes, pseudesthesia, hypothyroidism, uremia, vitamin deficiency or alcoholism; and acute pain such as pain after injuries, postoperative pain, pain during acute gout or pain during operations, such as jaw surgery.

Acute pain is typically a physiological signal indicating a potential or actual injury. Chronic pain can be somatogenic (organic) or psychogenic. Chronic pain is frequently accompanied or followed by vegetative signs, such as, for example, lassitude or sleep disturbance. Acute pain may be treated with compounds as described herein.

Somatogenic pain may be of nociceptive, inflammatory or neuropathic origin. Nociceptive pain is related to activation of somatic or visceral pain-sensitive nerve fibers, typically by physical or chemical injury to tissues. Inflammatory pain results from inflammation, for example an inflammatory response of living tissues to any stimulus including injury, infection or irritation. Neuropathic pain results from dysfunction in the nervous system. Neuropathic pain is believed to be sustained by aberrant somatosensory mechanisms in the peripheral nervous system, the central nervous system (CNS), or both. According to one aspect of the disclosure, somatogenic pain may be treated by compounds as described herein.

Non-inflammatory musculoskeletal pain is a particular form of chronic pain that is generally not traced to a specific structural or inflammatory cause and that generally does not appear to be induced by tissue damage and macrophage infiltration (resulting in edema) as occurs in a classical immune system response. Although non-inflammatory musculoskeletal pain is believed to result from peripheral and/or central sensitization, the cause is not presently fully understood. It is often associated with physical or mental stress, lack of adequate or restful sleep, or exposure to cold or damp. Non-inflammatory musculoskeletal pain is also believed to be associated with or precipitated by systemic disorders such as viral or other infections. Examples of non-inflammatory musculoskeletal pain include neck and shoulder pain and spasms, low back pain, and achy chest or thigh muscles, which may be treated by a compound of the present disclosure. Non-inflammatory musculoskeletal pain may be generalized or localized.

According to a further aspect of the disclosure, a compound as described herein may be administered to a subject to treat fibromyalgia syndrome (FMS) and myofascial pain syndrome (MPS). FMS and MPS are medical conditions characterized by fibromyalgia and myofascial pain respectively, which are two types of non-inflammatory musculoskeletal pain. FMS is a complex syndrome associated with significant impairment of quality of life and can result in substantial financial costs. Fibromyalgia is a systemic process that typically causes tender points (local tender areas in normal-appearing tissues) in particular areas of the body and is frequently associated with a poor sleep pattern and/or stressful environment. Diagnosis of fibromyalgia is typically based on a history of widespread pain (e.g., bilateral, upper and lower body, and/or spinal pain), and presence of excessive tenderness on applying pressure to a number of (sometimes more precisely defined as at least 11 out of 18) specific muscle-tender sites. FMS is typically a chronic syndrome that causes pain and stiffness throughout the tissues that support and move the bones and joints. Myofascial pain syndrome (MPS) is a chronic non-degenerative, non-inflammatory musculoskeletal condition often associated with spasm or pain in the masticatory muscles. Distinct areas within muscles or their delicate connective tissue coverings (fascia) become abnormally thickened or tight. When the myofascial tissues tighten and lose their elasticity, the ability of neurotransmitters to send and receive messages between the brain and body is disrupted. Specific discrete areas of muscle may be tender when firm fingertip pressure is applied; these areas are called tender or trigger points. Symptoms of MPS include muscle stiffness and aching and sharp shooting pains or tingling and numbness in areas distant from a trigger point. The discomfort may cause sleep disturbance, fatigue and depression. Most commonly trigger points are in the jaw (temporomandibular) region, neck, back or buttocks. Myofascial pain differs from fibromyalgia: MPS and FMS are two separate entities, each having its own pathology, but sharing the muscle as a common pathway of pain. Myofascial pain is typically a more localized or regional (along the muscle and surrounding fascia tissues) pain process that is often associated with trigger point tenderness. Myofascial pain can be treated by a variety of methods (sometimes in combination) including stretching, ultrasound, ice sprays with stretching, exercises, and injections of anesthetic.

A further non-inflammatory musculoskeletal pain condition is back pain, notably low back pain, which may also be treated with a compound of the present disclosure. This condition may also be treating by administering a compound of the present disclosure to a subject in need thereof. Back pain is a common musculoskeletal symptom that may be either acute or chronic. It may be caused by a variety of diseases and disorders that affect the lumbar spine. Low back pain is often accompanied by sciatica, which is pain that involves the sciatic nerve and is felt in the lower back, the buttocks, and the backs of the thighs.

4. Glaucoma and Intraocular Pressure

In another aspect, the disclosure provides for methods of treating glaucoma in a subject in need thereof. Compounds of the disclosure, such as any of the compounds described herein, may be used to treat glaucoma. For example, compounds of the disclosure may be used to decrease intraocular pressure (IOP), such as the elevated intraocular pressure observed in most cases of glaucoma. Also provided are methods for treating ocular hypertension in a subject in need thereof. Without being bound by theory, compounds of the disclosure may be used to reduce IOP, thereby treating ocular hypertension. For any of the foregoing, the disclosure contemplates administering an effective amount of a $P_2Y_6$ receptor agonist, such as any of the agonists described herein, to a subject in need thereof to decrease intraocular pressure, such as elevated intraocular pressure and/or to treat glaucoma (e.g., improve, or stop or slow the progression of one or more symptoms of the condition).

Glaucoma refers to a group of eye conditions that lead to damage to the optic nerve. This nerve carries visual information from the eye to the brain. In most cases, damage to the optic nerve is due to increased pressure in the eye, also known as intraocular pressure (IOP). Over time, the elevated intraocular pressure and optic nerve damage leads to visual field loss, and may result in blindness. Ocular hypertension is intraocular pressure higher than normal in the absence of optic nerve damage or visual field loss. Currently, ophthalmologists generally define normal intraocular pressure as from 10 mmHg and 21 mmHg, and intraocular pressure above 21 mmHg is considered ocular hypertension or elevated intraocular pressure. Ocular hypertension is considered a significant risk factor for developing glaucoma, and thus, patients with ocular hypertension should be closely monitored for glaucoma.

Glaucoma is the second-most common cause of blindness in the United States. The nerve damage involves loss of retinal ganglion cells in a characteristic pattern. The many different subtypes of glaucoma can all be considered to be a type of optic neuropathy. Raised intraocular pressure (above 21 mmHg or 2.8 kPa) is the most important and only modifiable risk factor for glaucoma. However, some patients may have high eye pressure for years and never develop damage, while others can develop nerve damage at a relatively low pressure. Untreated glaucoma can lead to permanent damage of the optic nerve and resultant visual field loss, which over time can progress to blindness.

The two main types of glaucoma, each of which are marked by elevated intraocular pressure, are open-angle and angle-closure. Open-angle and angle-closure glaucoma also include the following variants: (i) secondary glaucoma; (ii) pigmentary glaucoma; (iii) pseudoexfoliative glaucoma; (iv) traumatic glaucoma; (v) neovascular glaucoma; and (vi) irido corneal endothelial syndrome (ICE).

Open-angle glaucoma, the most common form of glaucoma, accounts for at least 90% of all glaucoma cases. Open-angle glaucoma is also called primary or chronic glaucoma and generally has the following characteristics: (i) caused by the slow clogging of the drainage canals, resulting in increased eye pressure; (ii) has a wide and open angle between the iris and cornea; and (iii) develops slowly and is a lifelong condition. Angle-closure glaucoma, a less common form of glaucoma, is also called acute glaucoma or narrow-angle glaucoma. Unlike open-angle glaucoma, angle-closure glaucoma is a result of the angle between the iris and cornea closing, and angle-closure glaucoma generally has the following characteristics: (i) caused by blocked drainage canals, resulting in a sudden rise in intraocular pressure; (ii) has a closed or narrow angle between the iris and cornea; (iii) develops very quickly; and (iv) demands immediate medical attention.

The disclosure contemplates methods of treating open-angle and/or angle-closure glaucoma, including methods of treating variants of open-angle and/or angle-closure glaucoma. In certain embodiments, administration of a compound of the disclosure to a patient having open-angle and/or angle-closure glaucoma decreases intraocular pressure, thereby treating the glaucoma in the patient. In certain embodiments, reducing intraocular pressure slows or stops further damage to the optic nerve (e.g., prevents occurrence of further damage to the optic nerve). In certain embodiments, reducing intraocular pressure slows or stops further loss of or damage to vision or the visual field. Moreover, the disclosure contemplates methods of treating optic neuropathy in a patient in need thereof by administering an effective amount of a compound of the disclosure.

In addition to open-angle and angle-closure glaucoma, an additional rare type of glaucoma is congenital glaucoma. In certain embodiments, the disclosure contemplates methods of treating congenital glaucoma in a subject in need thereof. This type of glaucoma occurs in babies when there is incorrect or incomplete development of the eye's drainage canals during the prenatal period.

A fourth type of glaucoma is referred to as secondary glaucoma. Secondary glaucoma occurs as a consequence of trauma, systemic disease, or as a side-effect of certain drugs (e.g., corticosteroids). In certain embodiments, the disclosure contemplates methods of treating secondary glaucoma in a subject in need thereof. Systemic diseases that may lead to or exacerbate glaucoma include hypertension and diabetes.

Additionally, although most glaucoma is characterized by elevated intraocular pressure which leads to damage of the optic nerve, there are cases of glaucoma referred to as low-tension or normal-pressure glaucoma. In these cases, the optic nerve is damaged despite the fact that eye pressure is not very high. In certain embodiments, the disclosure contemplates methods of treating low-tension or normal pressure glaucoma. In certain embodiments, glaucoma treated using the methods of the disclosure is characterized by elevated intraocular pressure and/or ocular hypertension (e.g., the glaucoma is not low-tension or normal pressure glaucoma).

In addition to elevated intraocular pressure, which results in damage to the optic nerve, the various types of glaucoma are characterized by particular symptoms. The disclosure contemplates that administration of the compounds of this disclosure may be used to alleviate one or more symptoms of glaucoma, including to alleviate one or more symptoms of any of the particular types of glaucoma described herein.

In open-angle glaucoma, there are actually few overt symptoms. Patients have elevated intraocular pressure or, at least, periods of elevated intraocular pressure. However, the intraocular pressure slowly damages the optic nerve, and thus, vision loss is slow and not typically accompanied by pain. In fact, noticeable vision loss, which typically manifests as slow loss of peripheral vision leading to tunnel vision, is a symptom of relatively advanced and severe disease. Ultimately, open-angle glaucoma can lead to blindness.

In angle-closure glaucoma, patients do experience one or more of the following symptoms, and these symptoms may come and go or steadily become worse. Exemplary symptoms include sudden, severe pain (typically in only one eye), decreased or cloudy vision (also known as "steamy" vision), nausea, vomiting, rainbow-like halos around lights, red eye, and the sensation that the eye is swollen.

In congenital glaucoma, the symptoms are usually noticed when the child is a few months old. Exemplary symptoms include one or more of the following: cloudiness of the front of the eye, enlargement of one or both eyes, red eye, sensitivity to light, and excessive tearing.

There are currently several tests that are used to measure intraocular pressure, to detect elevated intraocular pressure and to diagnose glaucoma. In certain embodiments, one or more of these tests are used to diagnose glaucoma and/or intraocular hypertension prior to initiation of treatment with a compound of the disclosure. Exemplary tests that can be used, alone or in combination, include tonometry, gonioscopy, optic nerve imaging, slit lamp examination, examination of the retina, visual acuity measurements, and visual field measurements. These tests can also be used to monitor a patient after initiation of treatment. For example, these tests can be used to determine whether treatment has slowed or stopped the progress of the disease, has decreased elevated intraocular pressure (e.g., restored normal intraocular pressure), and whether the patient's vision has improved or ceased further deterioration.

In addition, the disclosure provides methods of decreasing elevated intraocular pressure in a subject in need thereof. Suitable subjects include, as discussed in detail above, subjects having glaucoma (any of the forms of glaucoma described herein) or subjects with ocular hypertension. Decreasing intraocular pressure, such as elevated intraocular pressure in these subjects (e.g., such as by administering an effective amount of a compound of the disclosure, including any of the compounds described herein), such as human patients, helps ameliorate one or more symptoms of the condition, helps slow or stop damage to the optic nerve and to vision, and may even permit improvement in the patient's condition—particularly in cases where significant damage has not yet occurred. Given that elevated intraocular pressure in ocular hypertension is a major risk factor for developing glaucoma, decreasing elevated IOP in such patients may help decrease the patient's risk of developing glaucoma.

Compounds of the disclosure, including salts and prodrugs, may be tested in animal models of glaucoma and ocular hypertension. Exemplary models are known in the art and, for example, described in Bouhenni et al., Journal of Biomedicine and Biotechnology, Volumne 2012, Article ID 692609, 11 pages, doi: 10.1155/2012/692609.

Agonists of the disclosure may be administered using any suitable route of administration described herein, including oral, intravenous, or local administration to the eye (e.g., eye drops, injection into the eye, or implantation of a drug eluting device).

In other embodiments, the disclosure provides methods of decreasing intraocular pressure (e.g., decreasing elevated intraocular pressure) in a subject in need thereof, wherein the subject in need thereof has a condition other than or in addition to glaucoma. Exemplary conditions caused or exacerbated by elevated IOP which may be treated include: Reese-Ellsworth syndrome, hydrophthalmos, and ophthalmic zoster.

5. Inflammatory Conditions

In another aspect, the compounds, salts and/or prodrugs thereof, and compositions as described herein can be used to treat patients suffering from $P_2Y_6$ receptor-related conditions or conditions that can be ameliorated by modulating, for example, agonizing $P_2Y_6$ receptor activity, such as an inflammatory condition. Accordingly, the disclosure provides methods of treating an inflammatory condition in a subject in need thereof. Compounds of the disclosure, such as any of the compounds or salts or prodrugs described herein, may be used to treat an inflammatory condition. As used herein, an inflammatory condition is a disease or condition characterized, in whole or in part, by inflammation or an inflammatory response in the patient. Typically, one or more of the symptoms of the inflammatory disease or condition is caused or exacerbated by an inappropriate, misregulated, or overactive inflammatory response. Inflammatory diseases or conditions may be chronic or acute. In certain embodiments, the inflammatory disease or condition is an autoimmune disorder. In certain embodiments, compounds of the disclosure are used to decrease inflammation, to decrease expression of one or more inflammatory cytokines, and/or to decrease an overactive inflammatory response in a subject having an inflammatory condition. Thus, the disclosure provides a method of decreasing inflammation, a method of decreasing expression of one or more inflammatory cytokines, and/or a method of decreasing an overactive inflammatory response in a subject in need thereof.

Inflammatory conditions treatable using the compounds of the disclosure may be characterized, for example, based on the primary tissue affected, the mechanism of action underlying the condition, or the portion of the immune system that is misregulated or overactive. Examples of inflammatory conditions, as well categories of diseases and conditions are provided herein. The disclosure contemplates methods of treating (e.g., such as by decreasing inflammation, decreasing expression of one or more inflammatory cytokines, and/or decreasing an overactive inflammatory response) inflammatory conditions, generally, as well as methods of treating any of the categories of conditions or any of the specific conditions described herein.

In certain embodiments, examples of inflammatory conditions that may be treated include inflammation of the lungs, joints, connective tissue, eyes, nose, bowel, kidney, liver, skin, central nervous system, vascular system, heart, or adipose tissue. In certain embodiments, inflammatory conditions which may be treated include inflammation due to the infiltration of leukocytes or other immune effector cells into affected tissue. In certain embodiments, inflammatory conditions which may be treated include inflammation mediated by IgE antibodies. Other relevant examples of inflammatory conditions which may be treated by the present disclosure include inflammation caused by infectious agents, including but not limited to viruses, bacteria, fungi, and parasites. In certain embodiments, the inflammatory condition that is treated is an allergic reaction. In certain embodiments, the inflammatory condition is an autoimmune disease. The disclosure contemplates that some inflammatory conditions involve inflammation in multiple tissues. Moreover, the disclosure contemplates that some inflammatory conditions may fall into multiple categories. For example, a condition may be described and categorized as an autoimmune condition and/or it may also be described and categorized based on the primary tissue(s) affected (e.g., an inflammatory skin or joint condition). In certain embodiments, an inflammatory condition treatable according to the methods described herein falls into more than one category of condition.

Inflammatory lung conditions include asthma, adult respiratory distress syndrome, bronchitis, pulmonary inflammation, pulmonary fibrosis, and cystic fibrosis (which may additionally or alternatively involve the gastro-intestinal tract or other tissue(s)). In certain embodiments, the pulmonary inflammation is allergen induced pulmonary inflammation. In certain embodiments, the disclosure provides methods of treating an inflammatory lung condition in a patient in need thereof (e.g., a patient having an inflammatory lung condition) by administering an effective amount a compound, salt, or prodrug of the disclosure. In certain embodiments, treating an inflammatory lung condition comprises decreasing inflammation in the lung in the patient, decreasing misregulation of inflammatory cytokines in the patient, and/or decreasing one or more symptoms of the inflammatory lung condition in the subject. By way of example, symptoms of the inflammatory lung condition that may be improved, locally or systemically, by decreasing inflammation or the inflammatory response include, but are not limited to: oxygen saturation (patients have improved oxygen saturation following treatment), ease of breathing (patients experience greater ease when breathing and a decrease in labored breather), reliance on external oxygen (patient reliance on external oxygen supplementation is decreased), and reliance on inhalers or nebulizers (patient reliance on other drugs is decreased). Improvement in a patient (e.g., decrease in symptoms) may be measured directly by assessing inflammation or scarring in the lung or by evaluating cytokine expression in lung fluids. Improvement can also be assessed by evaluating improvement in patient activity levels, walking distance and speed, and decreased reliance on oxygen supplementation.

Inflammatory joint conditions include rheumatoid arthritis, rheumatoid spondylitis, juvenile rheumatoid arthritis, osteoarthritis, gouty arthritis and other arthritic conditions. In certain embodiments, the inflammatory joint condition is rheumatoid arthritis or psoriatic arthritis. In certain embodiments, the disclosure provides methods of treating an inflammatory joint condition in a patient in need thereof, such as treating any of the foregoing conditions, by administering an effective amount of a compound, salt and/or prodrug of the disclosure. In certain embodiments, treating an inflammatory joint condition comprises decreasing inflammation in the joints in the patient, decreasing circulating levels of one or more cytokines, for example, IL-4, IL-10 and/or IL-12, in plasma of the patient, decreasing misregulation of inflammatory cytokines in the patient, and/or decreasing one or more symptoms of the inflammatory joint condition in the subject. By way of example, symptoms of the inflammatory joint condition that may be improved by decreasing inflammation or the inflammatory response, locally and/or systemically, include, but are not limited to: swelling in one or more joints, tenderness and/or pain in one or more joints, decreased mobility and/or use of one or more joints, impaired ability to perform daily tasks (e.g., ability to perform daily tasks including self care tasks is improved), and reliance on walking assistance (patient reliance on a walker, cane, or wheel chair is decreased). Improvement in patients (e.g., decrease in symptoms) may be measured directly by assessing inflammation in the joints or by evaluating cytokine expression in joint fluid. Improvement can also be assessed by evaluating improvement in patient activity levels and quality of life measures, walking distance and speed, range of motion, mobility, and decreased reliance on mobility aids. In certain embodiments, the inflammatory joint condition is also an autoimmune condition, and the disclosure contemplates treating such condition.

Inflammatory eye conditions include uveitis (including iritis), conjunctivitis, scleritis, and keratoconjunctivitis sicca. In certain embodiments, the disclosure contemplates treating an inflammatory eye condition in a patient in need thereof, including by administering a compound, salt and/or prodrug of the disclosure systemically or locally to the eye, such as via eye drops.

Inflammatory bowel conditions include Crohn's disease, ulcerative colitis, inflammatory bowel disease, inflammatory bowel syndrome, and distal proctitis. In certain embodiments, the disclosure provides methods of treating an inflammatory bowel condition in a patient in need thereof by administering an effective amount a compound, salt and/or prodrug of the disclosure. In certain embodiments, treating an inflammatory bowel condition comprises decreasing inflammation in the gastro-intestinal tract in the patient, decreasing misregulation of inflammatory cytokines in the patient, decreasing the circulating levels of one or more cytokines, for example, IL-4, IL-10 and/or IL-12, in plasma of the patient, and/or decreasing one or more symptoms of the inflammatory bowel condition in the subject. By way of example, symptoms of the inflammatory bowel condition that may be improved by decreasing inflammation or the inflammatory response, locally and/or systemically, include, but are not limited to: diarrhea, constipation, blotting, pain, flatulence, blood in stool, weight loss (treating stabilizes weight and/or prevents further weight loss; treatment helps promote improved nutrition and weight gain, where needed), malabsorption, and malnutrition. Improvement in patients (e.g., decrease in symptoms) may be measured directly by assessing inflammation in the gastrointestinal tract or by evaluating cytokine expression or levels of cytokines in plasma in patients. Improvement can also be assessed by evaluating improvement in any of the foregoing symptoms, evaluating patient self-reporting of quality of life and symptom reduction, evaluating patient weight and nutrition status. In certain embodiments, the inflammatory bowel condition being treated is also an autoimmune condition, such as ulcerative colitis.

Inflammatory skin conditions include conditions associated with cell proliferation, such as psoriasis, eczema, and dermatitis (e. g., eczematous dermatitides, topic and seborrheic dermatitis, allergic or irritant contact dermatitis, eczema craquelee, photoallergic dermatitis, phototoxicdermatitis, phytophotodermatitis, radiation dermatitis, and stasis dermatitis). Other inflammatory skin conditions include, but are not limited to, ulcers and erosions resulting from trauma, burns, bullous disorders, or ischemia of the skin or mucous membranes, several forms of ichthyoses, epidermolysis bullosae, hypertrophic scars, keloids, cutaneous changes of intrinsic aging, photo aging, frictional blistering caused by mechanical shearing of the skin and cutaneous atrophy resulting from the topical use of corticosteroids. Additional inflammatory skin conditions include inflammation of mucous membranes, such as cheilitis, nasal irritation, mucositis and vulvovaginitis. Other inflammatory skin conditions include acne, rosacea, boils, carbuncles, pemphigus, cellulitis, Grover's disease, hidradenitis suppurativa, and lichen planus. In certain embodiments, the disclosure provides methods of treating an inflammatory skin condition in a patient in need thereof by administering an effective amount a compound, salt and/or prodrug of the disclosure. In certain embodiments, treating an inflammatory skin condition comprises decreasing skin inflammation in the patient, decreasing misregulation of inflammatory cytokines in the patient, decreasing the circulating levels of one or more cytokines, for example, IL-4, IL-10 and/or IL-12, in plasma of the patient, and/or decreasing one or more symptoms of the inflammatory skin condition in the subject. By way of example, symptoms of the inflammatory skin condition that may be improved by decreasing inflammation or the inflammatory response, locally and/or systemically, include, but are not limited to: skin swelling, redness, itching, flaking, blistering, bleeding, sensitivity to touch, and sensitivity to light or sun. Improvement in patients (e.g., decrease in symptoms) may be measured directly by assessing inflammation or by evaluating cytokine expression in patients. Improvement can also be assessed by evaluating improvement in any of the foregoing symptoms, or by evaluating patient self-reporting of quality of life and symptom reduction. In certain embodiments, the inflammatory skin condition is also an autoimmune condition, such as psoriasis. The disclosure provides methods of treating an inflammatory skin condition.

Inflammatory conditions of the endocrine system include, but are not limited to, autoimmune thyroiditis (Hashimoto's disease), Type I diabetes, inflammation in liver and adipose tissue associated with Type II diabetes, and acute and chronic inflammation of the adrenal cortex. Inflammatory conditions of the cardiovascular system include, but are not limited to, coronary infarct damage, peripheral vascular disease, myocarditis, vasculitis, revascularization of stenosis, atherosclerosis, and vascular disease associated with Type II diabetes. In certain embodiments, the disclosure provides methods of treating an inflammatory endocrine condition or cardiovascular condition in a patient in need thereof by administering an effective amount a compound, salt and/or prodrug of the disclosure. In certain embodiments, treating an inflammatory endocrine condition or cardiovascular condition comprises decreasing inflammation in the patient, decreasing misregulation of inflammatory cytokines in the patient, decreasing circulating levels of one or more cytokines, for example, IL-4, IL-10 and/or IL-12, in plasma of the patient, and/or decreasing one or more symptoms of the inflammatory endocrine condition or the inflammatory cardiovascular condition in the subject. As noted above, endocrine disorders impact a diverse array of organs, and thus, the symptoms of the disorders vary depending on the tissue affected. By way of example, symptoms of the inflammatory cardiovascular condition that may be improved by decreasing inflammation or the inflammatory response, locally and/or systemically, include, but are not limited to: chest pain, irregular heart rhythm, angina, shortness of breath, dizziness, decreased activity level, and fatigue. Improvement in patients (e.g., decrease in symptoms) may be measured directly by assessing inflammation or by evaluating cytokine expression in patients. Improvement can also be assessed by evaluating improvement in any of the foregoing symptoms, evaluating patient self-reporting of quality of life and symptom reduction, and evaluating improvement in activity levels.

Inflammatory conditions of the kidney include, but are not limited to, glomerulonephritis, interstitial nephritis, lupus nephritis, nephritis secondary to Wegener's disease, acute renal failure secondary to acute nephritis, Goodpasture's syndrome, post-obstructive syndrome and tubular ischemia. In certain embodiments, the disclosure provides methods of treating an inflammatory kidney condition in a patient in need thereof by administering an effective amount a compound of the disclosure. In certain embodiments, treating an inflammatory kidney condition comprises decreasing inflammation in the kidney in the patient, decreasing misregulation of inflammatory cytokines in the patient, decreasing circulating levels of one or more cytokines, for example, IL-4, IL-10 and/or IL-12, in plasma of the patient, and/or decreasing one or more symptoms of the inflammatory kidney condition in the subject. By way of example, symptoms of the inflammatory kidney condition that may be improved by decreasing inflammation or the inflammatory response, locally and/or systemically, include, but are not limited to: increased or decreased frequency of urination, difficulty urinating, abnormal levels of protein in urine, misregulation of salt levels, blood in urine, kidney failure, and reliance on dialysis (treatment is used to decrease or eliminate reliance on dialysis). Improvement in patients (e.g., decrease in symptoms) may be measured directly by assessing inflammation or by evaluating cytokine expression in patients. Improvement can also be assessed by evaluating improvement in any of the foregoing symptoms, evaluating patient self-reporting of quality of life and symptom reduction, or evaluating decreased reliance on dialysis (or increasing the period of time between diagnosis and onset of the time when the patient requires dialysis). Improvement can also be assessed by an increase in the period of time between diagnosis and progressing to end stage renal disease (ESRD) and/or delay or elimination of the need for a kidney transplant. In certain embodiments, the inflammatory condition of the kidney is an autoimmune condition, and the disclosure provides for methods of treating such a condition.

Inflammatory conditions of the liver include, but are not limited to, hepatitis (arising from viral infection, autoimmune responses, drug treatments, toxins, environmental agents, or as a secondary consequence of a primary disorder), obesity, biliary atresia, primary biliary cirrhosis and primary sclerosing cholangitis. Inflammatory diseases of the adipose tissues include, but are not limited to, obesity. In certain embodiments, the disclosure provides methods of treating an inflammatory liver condition in a patient in need thereof by administering an effective amount a compound of the disclosure. In certain embodiments, treating an inflammatory liver condition comprises decreasing inflammation in the liver in the patient, decreasing misregulation of inflammatory cytokines in the patient, decreasing circulating levels of one or more cytokines, for example, IL-4, IL-10 and/or IL-12, in plasma of the patient, and/or decreasing one or more symptoms of the inflammatory liver condition in the subject. By way of example, symptoms of the inflammatory liver condition that may be improved by decreasing inflammation or the inflammatory response, locally and/or systemically, include, but are not limited to: jaundice, abdominal swelling, dark urine, pale stool, bloody stool, fatigue, nausea, and loss of appetite. Improvement in patients (e.g., decrease in symptoms) may be measured directly by assessing inflammation or by evaluating cytokine expression in patients. Improvement can also be assessed by evaluating improvement in any of the foregoing symptoms, evaluating patient self-reporting of quality of life and symptom reduction. Improvement can also be assessed by a delay or elimination of the need for a liver transplant.

Inflammatory conditions of the central nervous system include, but are not limited to, multiple sclerosis and neurodegenerative diseases such as Alzheimer's disease, Parkinson's disease or dementia associated with HIV infection. In certain embodiments, the disclosure provides methods of treating an inflammatory condition in a subject in need thereof, with the proviso that the subject does not have and/or is not being treated for Alzheimer's disease or Parkinson's disease. In certain embodiments, the disclosure provides methods of treating an inflammatory condition in a subject in need thereof, with the proviso that the subject does not have and/or is not being treated for an inflammatory condition of the central nervous system and/or a neuronal or neurodegenerative condition characterized by an inflammatory component. In certain embodiments, the inflammatory condition to be treated by the methods of the disclosure is not an inflammatory condition of the central nervous system. In certain embodiments, the inflammatory condition to be treated by the methods of the disclosure is not an inflammatory condition of the peripheral nervous system.

In certain embodiments, the inflammatory condition is an autoimmune disease. Exemplary autoimmune diseases include, but are not limited to, rheumatoid arthritis, psoriasis (including plaque psoriasis), psoriatic arthritis, ankylosing spondylitis, ulcerative colitis, multiple sclerosis, lupus, alopecia, autoimmune pancreatitis, Celiac disease, Behcet's disease, Cushing syndrome, and Grave's disease. In certain embodiments, the disclosure provides methods of treating an autoimmune disease in a patient in need thereof by administering an effective amount a compound, salt and/or prodrug of the disclosure.

In certain embodiments, the inflammatory condition is a rheumatoid disorder. Exemplary rheumatoid disorders include, but are not limited to, rheumatoid arthritis, juvenile arthritis, bursitis, spondylitis, gout, scleroderma, Still's disease, and vasculitis. We note that certain categories of conditions overlap. For example, rheumatoid arthritis is an inflammatory rheumatoid disorder, an inflammatory joint disorder, and an autoimmune disorder. In certain embodiments, the disclosure provides methods of treating a rheumatoid disorder in a patient in need thereof by administering an effective amount a compound, salt or prodrug of the disclosure.

Other inflammatory conditions include periodontal disease, tissue necrosis in chronic inflammation, endotoxin shock, smooth muscle proliferation disorders, tissue damage following ischemia reperfusion injury, and tissue rejection following transplant surgery.

In certain embodiments, the compounds and/or compositions of the disclosure are not for use in the treatment of Alzheimer's disease or Parkinson's disease. In certain embodiments, the compounds and/or compositions of the disclosure are not for use in the treatment of a patient who has been diagnosed with or is suspected of having Alzheimer's disease or Parkinson's disease. In certain embodiments, the compounds and/or compositions of the disclosure are not for use in the treatment of a neural or neurodegenerative disease or disorder. In certain embodiments, the compounds and/or compositions of the disclosure are not for use in the treatment of inflammatory pain. In certain embodiments, the compounds and/or compositions of the disclosure are not for use in the treatment of pain. In certain embodiments of any of the foregoing, the term "are not for use in the treatment of" means that a compound is not being used to treat the condition and/or is not being used with the purpose of treating the condition. In other words, in certain embodiments, the inflammatory condition being treated is not Alzheimer's disease or is not Parkinson's disease, or is not a neurodegenerative disease (in other words, is a non-neurodegenerative, inflammatory condition). Similarly, in certain embodiments, the subject in need of treatment for an inflammatory condition, including any of the inflammatory disorders set forth herein, is not a subject diagnosed with or suspected of having Alzheimer's disease and/or Parkinson's disease. In certain embodiments, the subject in need of treatment for an inflammatory condition, including any of the inflammatory disorders set forth herein, is not a subject being treated for a neurological condition or a neurodegenerative condition.

The present disclosure further provides a method of treating or preventing inflammation associated with post-surgical wound healing in a patient.

It should be noted that the inflammatory conditions and categories of conditions cited above are meant to be exemplary rather than exhaustive. Those skilled in the art would recognize that additional inflammatory diseases (e.g., systemic or local immune imbalance or dysfunction due to an injury, infection, insult, inherited disorder, or an environmental intoxicant or perturbant to the subject's physiology) may be treated by the methods of the current disclosure.

Inflammatory conditions can be categorized by the primary tissue affected. Illustrative examples of inflammatory conditions so categorized are provided above. The disclosure contemplates treating any such categories of inflammatory conditions by administering an effective amount of a compound, salt and/or prodrug of the disclosure to a patient in need thereof. Moreover, inflammatory conditions can be further categorized based on the mechanism of action underlying the condition. For example, inflammatory conditions may be categorized as autoimmune, as chronic versus acute, based on the portion of the immune system that is hyperactivated or upregulated in the condition, or based on the cytokines or category of cytokines misregulated in the condition. In certain embodiments, the inflammatory condition is an allergic reaction or other inflammatory response mediated by IgE antibodies. In certain embodiments, the inflammatory condition is mediated by misregulation of inflammatory cytokines, such as interleukins (ILs) or tumor necrosis factor alpha (TNF).

Inflammatory conditions suitable for treatment with a compound, salt or prodrug of the disclosure may also be categorized based on the one or more cytokines that are elevated in patients (for example, in a tissue or body fluid (e.g., blood, serum or plasma) of the patient) having the conditions and/or that mediate, in whole or in part, the symptoms of the condition. In certain embodiments, inflammatory conditions suitable for treatment are conditions characterized, in whole or in part, by elevated levels (e.g., elevated levels in plasma and/or in a tissue in which symptoms are present) of one or more of the following cytokines IL-4, IL-10, and/or IL-12. It should be noted that additional cytokines may also be elevated. However, in certain embodiments, the inflammatory condition is characterized by elevated concentrations, such as elevated in plasma concentrations, of at least IL-4, IL-10, and/or IL-12. Exemplary conditions that may, in certain embodiments, be characterized by elevated levels of IL-4, IL-10 and/or IL-12 include, but are not limited to, rheumatoid arthritis, psoriasis (including plaque psoriasis), psoriatic arthritis, atherosclerosis, Crohn's disease, irritable bowel syndrome, ulcerative colitis, multiple sclerosis, joint autoimmune inflammation, and immune-mediated inflammatory disorders. The disclosure contemplates methods in which a subject in need of treatment for any of the foregoing conditions or any condition characterized by elevated levels of IL-4, IL-10, and/or IL-12 may be treated by administering an effective amount of a compound of the disclosure (e.g., a compound, salt or prodrug). In certain embodiments, the condition being treated is not Alzheimer's disease and/or the subject in need thereof does not have and/or is not being treated for and/or has not been diagnosed with and/or is not suspected of having Alzheimer's disease. In certain embodiments, the condition being treated is not Parkinson's disease and/or the subject in need thereof is not being treated for and/or has not been diagnosed with and/or is not suspected of having Parkinson's disease. In certain embodiments, the condition is characterized by elevated levels of, at least, IL-12, and the disclosure provides methods for reducing levels of IL-12, such as in the plasma, of patients having any of the foregoing conditions or another condition mediated, in whole or in part, by IL-12 misregulation. Throughout the disclosure, a reference to an increased (elevated) level or concentration of one or more cytokines, for example, IL-12, in a subject (for example, in a tissue or body fluid sample of the subject) with a particular condition, for example, an inflammatory condition, refers to an increased (elevated) level or concentration of the cytokine in a subject with the condition relative to a subject without the condition.

In certain embodiments, a compound, salt, or prodrug of the disclosure is administered to decrease levels of one or more cytokines in a subject in need thereof (e.g., a subject with an inflammatory condition). In certain embodiments, levels of cytokine are decreased in the plasma of the treated subject. Exemplary cytokines that may be decreased, such as decreased in a subject in need thereof, include, but are not limited to, IL-15, IL-1b, IL-2, IL-7, IL-9, IL-10, IL-17, MIG, and MIP1a. Further exemplary cytokines that may be decreased, such as decreased in the plasma of treated subjects, include, but are not limited to, IL-3, IL-4, IL-10, IL-12, IFN-r, IL-5, IL-6, IL-13, and MIP1b. In certain embodiments, at least one, at least two, at least three, at least four, at least five, at least six, at least seven, at least eight, at least nine cytokines are decreased following treatment. In certain embodiments, at least IL-4, IL-10, and/or IL-12 are reduced in treated subjects, such as in plasma of treated subjects. In other words, in certain embodiments, the disclosure provides a method for reducing the level of one or more of IL-4, IL-10, and/or IL-12 in a subject in need thereof, such as reducing cytokine levels in plasma of the subject. In certain embodiments, at least IL-4, IL-10, and IL-12 are reduced in treated subjects, and the disclosure provides a method for reducing levels of IL-4, IL-10, and IL-12 in a subject in need thereof. In certain embodiments, at least IL-12 is reduced in treated subjects. In any of the foregoing, the disclosure contemplates that one or more (e.g., 1, 2, 3, 4, 5, 6, 7, 8, 9, 10, or more than 10) additional cytokines may also be reduced following treatment. The disclosure contemplates that, in certain embodiments, administering a compound, salt, or prodrug of the disclosure may result in a statistically significant decrease in levels of a particular cytokine or of one or more cytokines in plasma in the subject, relative to the levels prior to one or more treatments. However, the disclosure also contemplates that the levels of such cytokines or of other cytokines, though reduced following one or more treatments, may be reduced to a lesser degree (e.g., the average level may decrease even if the total change is not statistically significant). As is common with the administration of compounds, the intended affect (e.g., reduction in plasma levels of certain cytokines) may require multiple treatments over some period of time. Thus, the disclosure contemplates that a reduction in cytokine levels in plasma, or any other affect, may be observable after a single treatment or after multiple treatments.

Without being bound by theory, the reduction in circulating cytokines in the plasma may be mediated by actions on macrophages and monocytes, thereby indicating applicability of treatment with a compound, salt, or prodrug of the disclosure to numerous inflammatory conditions. In certain embodiments, the inflammatory condition is mediated, in whole or in part, by elevated interleukins.

Without being bound by theory, generally suppressing the immune system may result in unwanted side effects. Thus, in certain embodiments, administering a compound, salt or prodrug of the disclosure to a patient to treat an inflammatory condition reduces levels of one or more cytokines, but does not generally decrease levels of all cytokines Thus, in certain embodiments, administering a compound, salt or prodrug of the disclosure does not cause general immunosuppression. For example, in certain embodiments, although the levels of one or more cytokines are decreased, the levels of one or more of the following are unchanged, substantially unchanged, or even slightly increased following administration of a compound, salt or prodrug of the disclosure: M-CSF, GM-CSF, G-CSF, MCP-1, IP-10, MIG, eotaxin, MIP-2, or LIX. In certain embodiments, administering a compound, salt or prodrug of the disclosure to a subject does not result in a statistically significant increase in the risk of opportunistic infections versus that for subjects having the same condition but not so treated. In certain embodiments, administering a compound, salt or prodrug of the disclosure to a subject does not result in neutropenia.

In certain embodiments, the condition being treated comprises rheumatoid arthritis. In certain embodiments, the patient has elevated levels of IL-12, such as elevated levels in plasma and/or in synovial tissue. Rheumatoid arthritis is an autoimmune disease and is a chronic, systemic inflammatory disorder. Rheumatoid arthritis primarily affects the joints, particularly the synovial joints, but it may also affect many other tissues and organs including the lungs, pericardium, and sclera. The condition can be disabling and painful, and patients whose disease is not adequately managed may have significant loss of mobility and substantial impairments in daily functioning. Numerous animal models of rheumatoid arthritis exist and may be used, for example, to optimize treatment regimens. These models include the collagen-induced arthritis model, the collagen-antibody-induced arthritis model, the zymosan-induced arthritis model, and the methylated BSA model. In addition, genetically manipulated transgenic mouse lines exist and provide suitable models. For a review of numerous models see Asquith et al., 2009, *European Journal of Immunology* 39(8): 2040-4.

In certain embodiments, the condition being treated comprises psoriasis, such as plaque. In certain embodiments, the condition being treated comprises psoriatic arthritis. There are five types of psoriasis: plaque, guttate, inverse, pustular, and erythrodermic. The most common form, plaque psoriasis, is commonly seen as red and white hues of scaly patches appearing on the epidermis. In certain embodiments, the condition being treated herein is plaque psoriasis. Psoriasis can also cause inflammation of the joints, which is known as psoriatic arthritis. Approximately 10-30% of patients with psoriasis also have psoriatic arthritis. In certain embodiments, the disclosure provides methods for treating psoriatic arthritis. In certain embodiments the patient in need of treatment for psoriasis, such as plaque psoriasis, or for psoriatic arthritis has elevated levels of IL-12. Animal models of psoriasis are available and may be used, for example, to optimize treatment regimens. See, for example, Conrad, 2006, *Current Rheumatology Report* 8(5): 342-347.

In certain embodiments, the condition being treated comprises atherosclerosis. Atherosclerosis is a condition in which an artery wall thickens as a result of the accumulation of fatty materials such as cholesterol and triglyceride. It affects arterial blood vessels and involves a chronic inflammatory response, such as in the walls of arteries. Animal models are available and may be used, for example, to optimize treatment regimens. See, for example, Getz, 2012, *Arterioscler Thromb Vasc Biol.* 32(5): 1104-15.

In certain embodiments, the condition being treated is inflammatory bowel disease, such as Crohn's disease or ulcerative colitis. Crohn's disease is a type of inflammatory bowel disease that may affect any part of the gastrointestinal tract (e.g., mouth to anus), leading to diverse GI symptoms. Approximately 50% of cases affect both ileum and the large intestines. The primary symptoms include abdominal pain, diarrhea, vomitting, and/or weight loss. In addition, patients may experience symptoms and complications in other tissues and organs, such as anemia, skin rash, arthritis, inflammation of the eye, and fatigue. In some cases, uncontrolled disease may lead to obstruction, fistula, or abscess. Ulcerative colitis affects the colon and is characterized by ulcers or open sores. The main symptom of active disease includes constant diarrhea mixed with blood and/or mucus. The frequency and severity of the diarrhea varies with the severity of the disease, and the GI-tract bleeding may lead to anemia. Like with Crohn's disease, non-GI symptoms may also be present. Severe ulcerative colitis can lead to perforation and may be fatal. Numerous animal models to, for example, study inflammatory bowel disease and/or optimize treatment are available. See, for example, Mizoguchi, 2012, *Prog Mol Biol Trans' Sci.* 105: 263-320.

In certain embodiments, the condition being treated comprises irritable bowel syndrome. Irritable bowel syndrome generally involves a sensitization of the nerves responsible for peristalsis. As a result, the muscles controlled by these nerves spasm in response to mild stimuli, such as certain foods or stress. Symptoms include pain, diarrhea, and/or constipation.

In certain embodiments, the condition being treated, such as the inflammatory condition being treated, is endometriosis. For example, a subject, specifically a female subject, having or suspected of having endometriosis is treated with a compound, salt or prodrug of the disclosure. Endometriosis is a gynecological condition in which cells from the lining of the uterus (endometrium) appear and flourish outside the uterine cavity, most commonly on the membrane which lines the abdominal cavity, the peritoneum. Symptoms of endometriosis are pain, particularly pelvic pain, and infertility. The pain often is worse with the menstrual cycle. Endometriosis is typically seen during the reproductive years, and has been estimated to occur in roughly 6-10% of women. Current treatments are primarily pain management, hormone treatment, and surgery.

In addition to infertility, the other primary symptom of endometriosis is recurring pelvic pain. The pain can range from mild to severe cramping or stabbing pain that occurs on both sides of the pelvis, in the lower back and rectal area, and even down the legs. The amount of pain a woman feels correlates poorly with the extent or stage (1 through 4) of endometriosis, with some women having little or no pain despite having extensive endometriosis or endometriosis with scarring, while other women may have severe pain even though they have only a few small areas of endometriosis. Thus, pain is a poor indicator of the extent of the condition. Symptoms of the pain include: dysmenorrhea (painful cramps during menses); chronic pelvic pain; dyspareunia (painful intercourse); and dysuria (frequent and sometimes painful urination).

Endometriosis lesions may bleed and swell. This can trigger both an inflammatory response and pain. However, the pathophysiology of the condition is multifactorial and aspects of that pathophysiology broadly include underlying predisposing factors, inflammation, metabolic changes, formation of ectopic endometrium, and generation of pain. Adhesions may form, thereby causing both pain and additional complications such as organ dislocation. Recently, it has been shown that there are elevated levels of IL-10, IL-12(p70), MIP1a, MIP1b, and TNFα in the supernatant of peritoneal macrophages from subjects with endometriosis. Additionally, subjects having endometriosis have been reported to have elevated IL-10 serum levels. These findings underscore the inflammatory component to endometriosis.

In certain embodiments, a compound, salt or prodrug of the disclosure is used to treat endometriosis, such as to reduce inflammation associated with endometriosis. In certain embodiments, a compound, salt or prodrug of the disclosure is used to decrease elevated IL-10, IL-12(p70), MIP1a, MIP1b, and/or TNFα levels in subjects having endometriosis, such as to reduce concentration of pro-inflammatory cytokines in the peritoneal cavity and/or in the plasma, such as in circulating plasma.

In certain embodiments, the disclosure provides a method of decreasing concentration of a pro-inflammatory cytokine (e.g., decreasing elevated concentrations; decreasing elevated levels), such as decreasing levels in the plasma, by administering a compound, salt or prodrug of the disclosure. In certain embodiments, the pro-inflammatory cytokine is selected from one or more of: IL-4, IL-12(p70), MIPa, MIPb, TNFα, IL-7, IL-13, IL-17, or IL-10. In certain embodiments, the method is performed in vitro or in vivo. In certain embodiments, the method is performed in a subject (e.g., a human or non-human animal) having an inflammatory condition or an immune mediated disorder, such as any one or more of the diseases and conditions described herein.

In certain embodiments, a compound, salt, and prodrug of the disclosure is administered topically, for example, to decrease inflammation in an inflammatory skin disorder. In certain embodiments, a compound, salt, and/or prodrug of the disclosure is administered locally, for example, injected into the space around an inflamed joint in a subject with rheumatoid arthritis. In certain embodiments, a compound, salt, and prodrug of the disclosure is administered systemically, such as orally or intravenously. These are merely exemplary. The appropriate route of administration may be selected based on the particular indication being treated and the patient's condition, and numerous exemplary routes of administration are described herein and known in the art. In certain embodiments, a compound, salt or prodrug of the disclosure is administered orally (e.g., is orally bioavailable).

In certain embodiments, any of the methods described herein comprise providing a composition (e.g., a pharmaceutical composition) comprising a compound or salt of the disclosure or providing a compound of the disclosure, which composition is formulated with an acceptable carrier and/or excipient, and delivering or otherwise administering to a subject or patient in need thereof that composition or compound. In certain embodiments, the composition is for oral delivery to a subject or patient, and administering to a subject or patient in need thereof comprises orally administering that composition to the subject or patient.

The disclosure contemplates methods of treating any one or more of the foregoing diseases or conditions (including categories of diseases or conditions) using a compound, salt or prodrug of the disclosure. Similarly, the disclosure contemplates methods of treating any one or more of the foregoing diseases or conditions (including categories of diseases or conditions) using a composition, such as a pharmaceutical composition of the disclosure (e.g., a pharmaceutical composition comprising a compound, salt or prodrug of the disclosure). The disclosure contemplates methods of treating any one or more of the foregoing diseases or conditions (e.g., treating a subject or patient in need of treatment for any one or more of the foregoing diseases of conditions) using any of the compounds or compositions (e.g., pharmaceutical compositions) of the disclosure. In certain embodiments, the disclosure contemplates methods of treating a subject or patient in need of treatment for any one or more of the foregoing diseases and conditions (e.g., a patient having or suspected of having a particular disease or condition), which subject or patient does not have and/or has not been diagnosed with and/or is not suspected of having another one or more of the foregoing diseases and conditions.

E. Compositions and Modes of Administration

It will be appreciated that compounds and agents used in the compositions and methods of the present disclosure preferably should readily penetrate the blood-brain barrier when peripherally administered. Compounds which cannot penetrate the blood-brain barrier, however, can still be effectively administered directly into the central nervous system, e.g., by an intraventricular route.

In some embodiments of this disclosure, the compound of the present disclosure is formulated with a pharmaceutically acceptable carrier. In other embodiments, no carrier is used. For example, the compound as described herein can be administered alone or as a component of a pharmaceutical formulation (therapeutic composition; pharmaceutical composition). The compound may be formulated for administration in any convenient way for use in human medicine. Any compound of the disclosure or salt or prodrug thereof can be provided as a composition, such as a pharmaceutical composition, such as a composition having any of the features described herein. Any such compound of the disclosure or composition of the disclosure may be used in any of the in vitro or in vivo methods described herein.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some embodiments, the therapeutic methods of the disclosure include administering the composition of a compound topically, systemically, or locally. For example, therapeutic compositions of compounds of the disclosure may be formulated for administration by, for example, injection (e.g., intravenously, subcutaneously, or intramuscularly), inhalation or insufflation (either through the mouth or the nose) or oral, buccal, sublingual, transdermal, nasal, or parenteral administration. The compositions of compounds described herein may be formulated as part of an implant or device, or formulated for slow or extended release. When administered parenterally, the therapeutic composition of compounds for use in this disclosure is preferably in a pyrogen-free, physiologically acceptable form. Techniques and formulations generally may be found in Remington's Pharmaceutical Sciences, Meade Publishing Co., Easton, Pa.

In certain embodiments, pharmaceutical compositions suitable for parenteral administration may comprise the compound of the present disclosure in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

A composition comprising a compound of the present disclosure may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In certain embodiments of the disclosure, compositions comprising a compound of the present disclosure can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like, each containing a predetermined amount of the compound of the present disclosure as an active ingredient. In some embodiments, compounds of the present invention have good oral availability, e.g., oral availability of at least about 50%, at least about 60%, or even at least about 70%.

In solid dosage forms for oral administration (capsules, tablets, pills, dragees, powders, granules, and the like), one or more compositions comprising the compound of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the compound of the present disclosure, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

A person of ordinary skill in the art, such as a physician, is readily able to determine the required amount of the compound of the present disclosure to treat the subject using the compositions and methods of this disclosure. It is understood that the dosage regimen will be determined for an individual, taking into consideration, for example, various factors that modify the action of a compound of the present disclosure, the severity or stage of the disease, route of administration, and characteristics unique to the individual, such as age, weight, size, and extent of cognitive impairment.

It is well-known in the art that normalization to body surface area is an appropriate method for extrapolating doses between species. To calculate the human equivalent dose (HED) from a dosage used in the treatment of age-dependent cognitive impairment in rats, the formula HED (mg/kg)=rat dose (mg/kg)×0.16 may be employed (see Estimating the Safe Starting Dose in Clinical Trials for Therapeutics in Adult Healthy Volunteers, December 2002, Center for Biologics Evaluation and Research). For example, using that formula, a dosage of 10 mg/kg in rats is equivalent to 1.6 mg/kg in humans. This conversion is based on a more general formula HED=animal dose in mg/kg×(animal weight in kg/human weight in kg)$^{0.33}$ Similarly, to calculate the HED can be calculated from a dosage used in the treatment in mouse, the formula HED (mg/kg)=mouse dose (mg/kg)×0.08 may be employed (see Estimating the Safe Starting Dose in Clinical Trials for Therapeutics in Adult Healthy Volunteers, December 2002, Center for Biologics Evaluation and Research).

In certain embodiments of the disclosure, the dose of the compound or composition of the present disclosure is between 0.00001 and 100 mg/kg/day (which, given a typical human subject of 70 kg, is between 0.0007 and 7000 mg/day). Desired duration of administration of the compound described herein can be determined by routine experimentation by one skilled in the art. For example, the compound of the present disclosure may be administered for a period of 1-4 weeks, 1-3 months, 3-6 months, 6-12 months, 1-2 years, or more, up to the lifetime of the patient. For example, daily administration of the compounds over this period is contemplated.

In addition to compound of the present disclosure, the compositions and methods of this disclosure can also include other therapeutically useful agents. These other therapeutically useful agents may be administered in a single formulation, simultaneously or sequentially with the compound of the present disclosure according to the methods of the disclosure.

It will be understood by one of ordinary skill in the art that the compositions and methods described herein may be adapted and modified as is appropriate for the application being addressed and that the compositions and methods described herein may be employed in other suitable applications, and that such other additions and modifications will not depart from the scope hereof. For example, the compounds of the disclosure are also useful as agents for agonizing $P_2Y_6$ receptor activity, and can be used in vitro or in vivo to study normal and abnormal $P_2Y_6$ receptor function. In certain embodiments, the compounds of the disclosure are used, directly or indirectly, to agonize $P_2Y_6$ receptor activity, and may be used in any of the in vitro and/or in vivo methods disclosed herein. In certain embodiments, compounds disclosed herein are themselves $P_2Y_6$ receptor-modulating compounds, and the disclosure encompasses these compounds as well as their salts and/or prodrugs as agonists of the disclosure. Other compounds, salts, and prodrugs described herein are not active themselves, but are converted in vivo to compounds that are active $P_2Y_6$ receptor-modulating compounds. The disclosure contemplates that all such compounds, salts, or prodrugs of the disclosure, whether active themselves or are converted into active compounds in vivo, may be used to treat any of conditions described herein.

This disclosure will be better understood from the Experimental Details which follow. However, one skilled in the art will readily appreciate that the specific methods and results discussed are merely illustrative of the disclosure as described more fully in the embodiments which follow thereafter.

EXAMPLES

Example 1

Preparation of Compound 6

Scheme 2 below provides a general synthetic route for the preparation of compound 6.

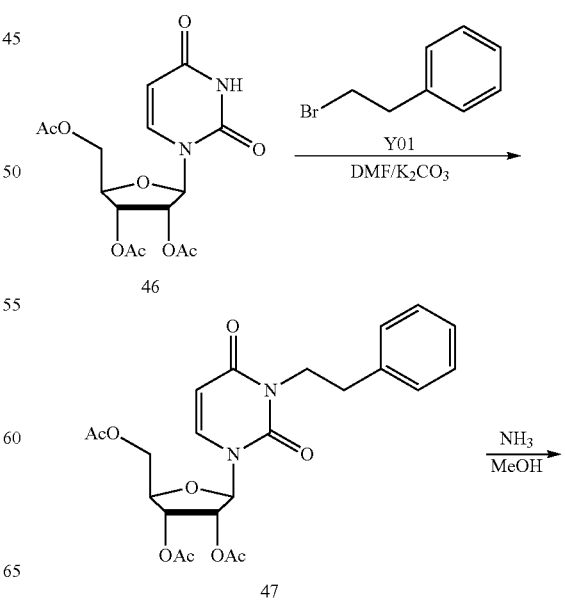

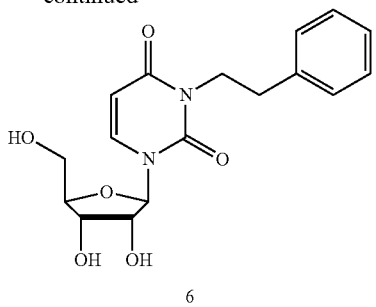

6

Step 1: Synthesis of Compound 47

To a solution of compound 46 (3.0 g, 8.11 mmol) in DMF (90 mL) was added Y01 (3.0 g, 16.22 mmol) and $K_2CO_3$ (4.47 g, 16.22 mmol), the resulting mixture was stirred at 70° C. for 1 h. After cooling down, the mixture was diluted with 250 mL water, extracted with ethyl acetate (EA) (250 mL×3), the organic layer was dried over anhydrous $Na_2SO_4$, concentrated to give a crude product. The crude product was purified on column (eluted with PE/EA=3:1) to give 3.61 g 47 as a colorless oil, yield: 94%. $^1$H NMR (300 MHz, $CDCl_3$) δ 7.36 (d, J=8.1 Hz, 1H), 7.32-7.27 (m, 4H), 7.25-7.18 (m, 1H), 5.98 (d, J=4.0 Hz, 1H), 5.81 (d, J=8.1 Hz, 1H), 5.34 (d, J=2.4 Hz, 2H), 4.35 (s, 3H), 4.13 (m, 2H), 3.01-2.84 (m, 2H), 2.14 (dd, J=12.1, 4.2 Hz, 9H), 1.26 (t, J=7.1 Hz, 1H).

Step 2: Synthesis of Compound 6

3.61 g 47 was dissolved in 150 mL 5N $NH_3$/methanol then stirred at room temperature for 12 hrs. After the reaction was finished, methanol was removed under vacuum to give the crude product. The crude product was recrystallized from EA to give 1.94 g 6 as a white solid, yield: 73%. $^1$H NMR (300 MHz, DMSO) δ 7.95 (d, J=8.1 Hz, 1H), 7.37-7.11 (m, 5H), 5.77 (m, 2H), 5.42 (d, J=5.4 Hz, 1H), 5.12 (m, 1H), 4.06-3.88 (m, 4H), 3.84 (m, 1H), 3.64 (m, 1H), 3.53 (m, 1H), 2.80 (t, J=9.0 Hz, 2H).

Example 2

Preparation of Compound 3

Scheme 3 below provides a general synthetic route for the preparation of compound 3.

Scheme 3

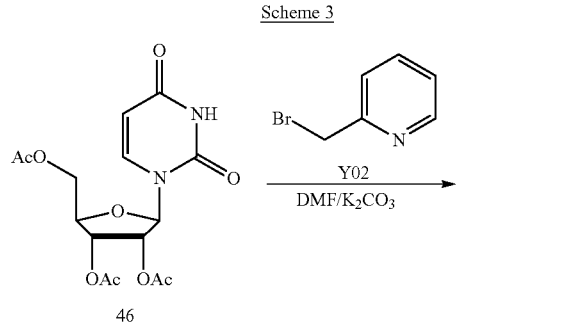

46

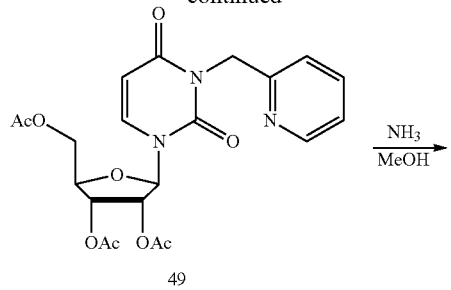

49

3

Step 1: Synthesis of Compound 49

Compound 49 was prepared from compound 46 according to the same procedure as described in step 1 of Example 1. 2.98 g compound 49 was obtained from 3.0 g compound 46, yield: 79.7%. $^1$H NMR (300 MHz, $CDCl_3$) δ 8.47 (d, J=4.7 Hz, 1H), 7.58 (m, 1H), 7.43 (d, J=8.2 Hz, 1H), 7.19-7.07 (m, 2H), 6.01 (d, J=4.8 Hz, 1H), 5.85 (d, J=8.2 Hz, 1H), 5.36-5.26 (m, 2H), 5.20 (s, 2H), 4.31 (s, 3H), 2.05 (t, J=10.5 Hz, 9H).

Step 2: Synthesis of Compound 50

Compound 3 was prepared from compound 49 according to the same procedure as described in step 2 of Example 1. 1.79 g compound 3 was obtained from 2.98 g compound 49, yield: 82.7%. $^1$H NMR (300 MHz, DMSO) δ 8.42 (d, J=3.5 Hz, 1H), 8.03 (d, J=8.1 Hz, 1H), 7.76-7.67 (m, 1H), 7.26-7.18 (m, 2H), 5.81 (dd, J=14.9, 6.5 Hz, 2H), 5.44 (d, J=5.7 Hz, 1H), 5.23-5.01 (m, 4H), 4.03 (m, 1H), 3.96 (m, 1H), 3.84 (m, 1H), 3.70-3.59 (m, 1H), 3.53 (m, 1H).

Example 3

Preparation of Compound 4

Scheme 4 below provides a general synthetic route for the preparation of compound 4.

Scheme 4

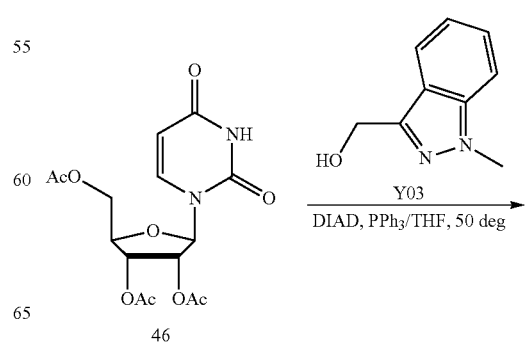

46

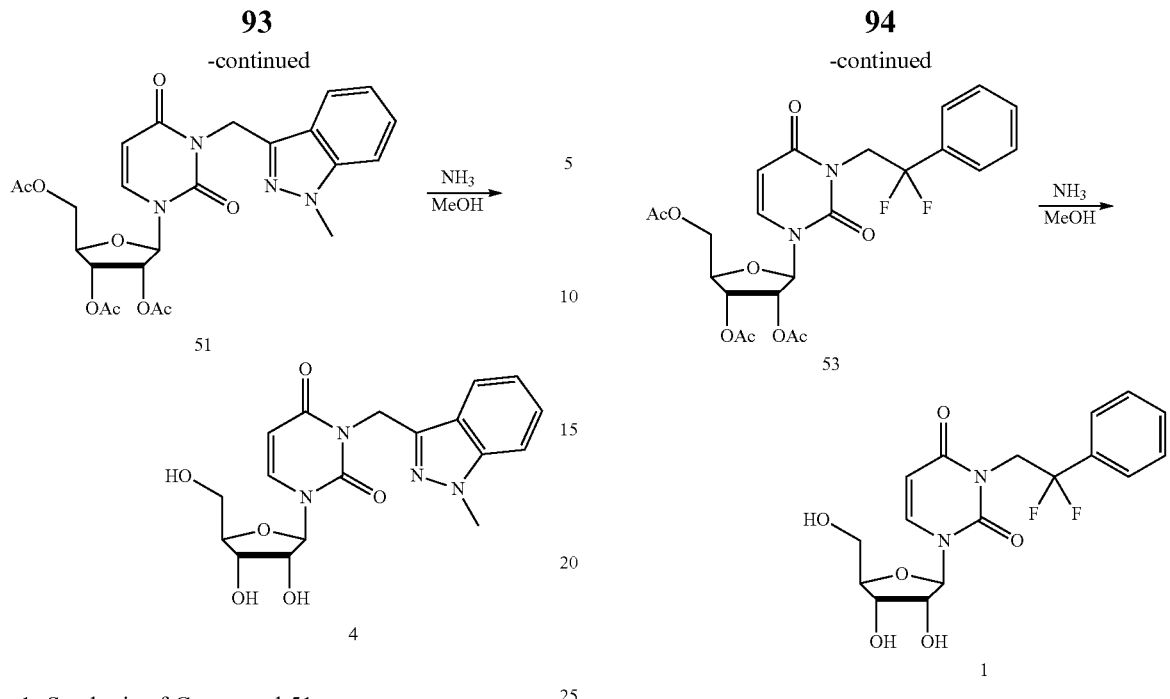

Step 1: Synthesis of Compound 51

To a solution of compound 46 (1.061 g, 1.87 mmol), Y03 (930 mg, 5.73 mmol) and PPh$_3$ (1.501 g, 5.73 mmol) in 25 mL THF was added dropwise a solution of DIAD (1.159 g, 5.73 mmol) in 5 mL THF over 30 min, the resulting mixture was stirred at 50° C. for 3 h. After the reaction was finished, THF was removed to give the crude product. The crude product was purified on column (eluted with EA) to give 1.37 g compound 51 as an oil, yield: 88.8%.

Step 2: Synthesis of Compound 4

Compound 4 was prepared from compound 51 according to the same procedure as described in step 2 of Example 1. 0.8 g compound 4 was obtained from 1.37 g compound 51, yield: 77.4%. $^1$H NMR (300 MHz, DMSO) δ 7.99 (d, J=8.1 Hz, 1H), 7.73 (d, J=8.2 Hz, 1H), 7.55 (d, J=8.5 Hz, 1H), 7.36 (t, J=7.7 Hz, 1H), 7.09 (t, J=7.5 Hz, 1H), 5.87-5.76 (m, 2H), 5.38 (d, J=5.7 Hz, 1H), 5.30 (d, J=4.0 Hz, 2H), 5.12-5.06 (m, 1H), 4.01 (t, J=5.2 Hz, 1H), 3.94 (s, 4H), 3.84 (d, J=3.6 Hz, 1H), 3.68-3.46 (m, 2H).

Example 4

Preparation of Compound 1

Scheme 5 below provides a general synthetic route for the preparation of compound 1.

Step 1: Synthesis of Compound 53

Compound 53 was prepared from compound 46 according to the same procedure as described in step 1 of Example 1. A crude product of compound 53 was obtained from 1.14 g compound 46. The crude product was used in the next step directly without further purification.

Step 2: Synthesis of Compound 1

Compound 1 was prepared from compound 53 according to the same procedure as described in step 2 of Example 1. 700 mg compound 1 was obtained from the 1.14 g compound 53, yield: 59.2%. $^1$H NMR (300 MHz, DMSO) δ 7.99 (d, J=9.0 Hz, 1H), 7.46-7.52 (m, 5H), 5.72-5.82 (m, 2H), 5.07-5.10 (m, 1H), 4.45-4.55 (m, 2H), 3.92-4.00 (m, 2H), 3.86 (s, 1H), 3.54-3.64 (m, 2H), 3.30-3.32 (m, 1H).

Example 5

Preparation of Compound 5

Scheme 5 below provides a general synthetic route for the preparation of compound 5.

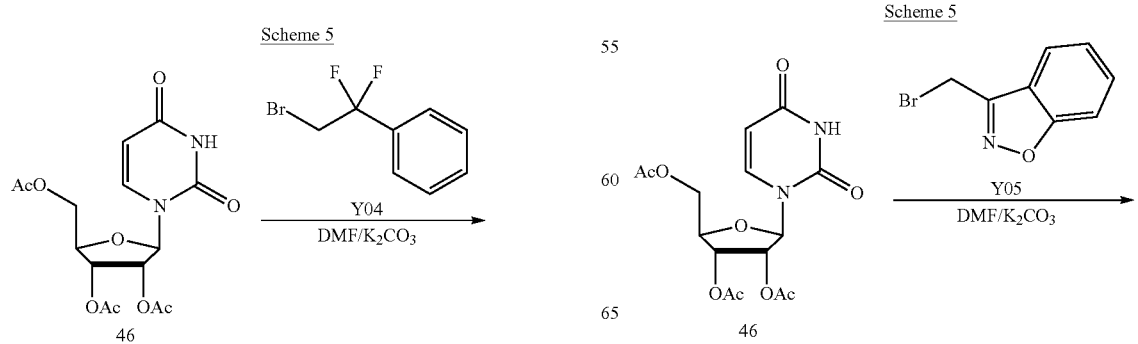

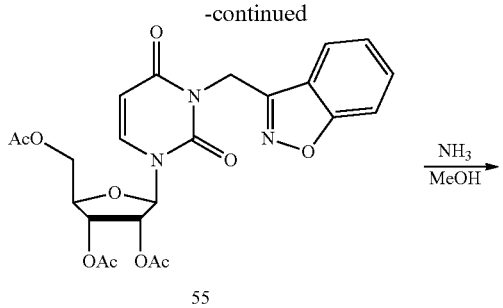

Step 1: Synthesis of Compound 55

Compound 55 was prepared from compound 46 according to the same procedure as described in step 1 of Example 1. 4.2 g compound 55 was obtained from 3.0 g compound 46, yield: 100%. $^1$H NMR (300 MHz, CDCl$_3$) δ 7.79 (d, J=8.0 Hz, 1H), 7.53 (dd, J=3.7, 1.6 Hz, 2H), 7.45 (d, J=8.2 Hz, 1H), 7.30 (m, 1H), 6.04 (d, J=4.7 Hz, 1H), 5.89 (d, J=8.2 Hz, 1H), 5.50 (d, J=1.7 Hz, 2H), 5.33 (m, 2H), 4.34 (d, J=4.3 Hz, 3H), 2.10 (d, J=6.6 Hz, 6H), 2.04 (s, 3H).

Step 2: Synthesis of Compound 5

Compound 5 was prepared from compound 55 according to the same procedure as described in step 2 of Example 1. 2.36 g compound 5 was obtained from 4.2 g compound 55, yield: 75.6%. $^1$H NMR (300 MHz, DMSO) δ 8.06 (d, J=8.2 Hz, 2H), 7.86 (d, J=8.0 Hz, 2H), 7.76–7.61 (m, 4H), 7.39 (t, J=7.4 Hz, 2H), 5.89 (d, J=7.9 Hz, 2H), 5.80 (m, 2H), 5.38-5.42 (m, 3H), 5.16 (m, 1H), 3.85-4.04 (m, 2H), 3.50-3.66 (m, 2H).

Compounds 32-37 were prepared according to similar synthetic procedures as those used for preparing compound 5 (see Scheme 5 above). The characterization of these sodium salts are summarized in Table 1 below.

TABLE 1

Characterization of compounds 32-37:

| Compound | Characterization |
|---|---|
| 32 | Yield: 97% as a solid<br>TLC information:<br>(DCM/MeOH = 10/1)<br>Material: R$_f$ = 0.5<br>Product: R$_f$ = 0.2<br>$^1$H NMR(400 MHz, MeOD): δ 8.15 (1H, d, J = 8 Hz), 7.93-7.89 (1H, m), 7.43 (1H, d, J = 8.8 Hz), 7.30-7.26 (1H, m), 7.23-7.18 (1H, m), 5.94 (1H, d, J = 4.0 Hz), 5.87 (1H, d, J = 8 Hz), 5.51 (2H, s), 4.19-4.17 (1H, m), 3.88 (1H, d, J = 8.8 Hz), 3.78-3.75 (1H, m), 3.33-3.15 (1H, m). |
| 33 | Yield: 64% as a solid<br>TLC information:<br>(DCM/MeOH = 10/1)<br>Material: R$_f$ = 0.5<br>Product: R$_f$ = 0.2<br>$^1$H NMR (400 MHz, MeOD): δ 8.15 (1H, d, J = 8 Hz), 7.69 (1H, d, J = 8 Hz), 7.45-7.37 (2H, m), 5.94 (1H, d, J = 4.0 Hz), 5.86 (1H, d, J = 8 Hz), 5.54 (2H, s), 4.20-4.17 (1H, m), 4.03 (1H, d, J = 4 Hz), 3.86-3.77 (1H, m), 3.33-3.15 (1H, m). |

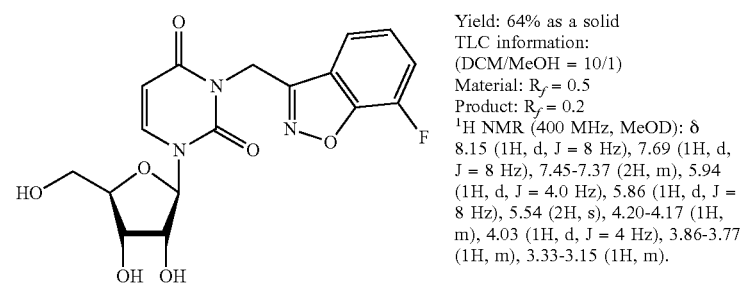

TABLE 1-continued

Characterization of compounds 32-37:

| Compound | Characterization |
|---|---|
| 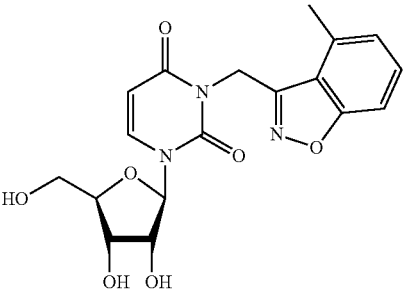<br>34 | Yield: 93% as solid<br>TLC information:<br>(DCM/MeOH = 10/1)<br>Material: $R_f$ = 0.5<br>Product: $R_f$ = 0.2 |
| 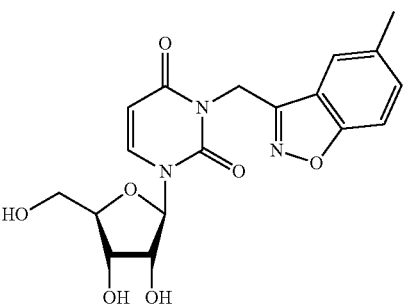<br>35 | Yield: 75% as a solid<br>TLC information:<br>(DCM/MeOH = 10/1)<br>Material: $R_f$ = 0.5<br>Product: $R_f$ = 0.2<br>$^1$H NMR (400 MHz, MeOD): δ 8.15 (1H, d, J = 8 Hz), 7.64 (1H, s), 7.52-7.46 (2H, m), 5.95 (1H, d, J = 4.0 Hz), 5.87 (1H, d, J = 8 Hz), 5.50 (2H, s), 4.20-4.17 (1H, m), 4.04 (1H, d, J = 4 Hz), 3.86-3.77 (1H, m), 3.33-3.15 (1H, m). |
| 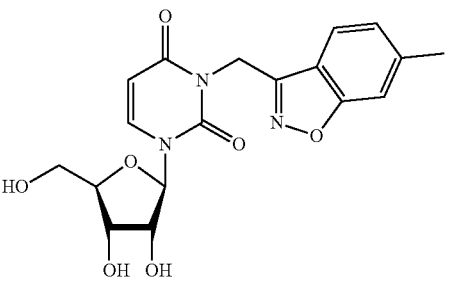<br>36 | Yield: 83% as a solid<br>TLC information:<br>(DCM/MeOH = 10/1)<br>Material: $R_f$ = 0.5<br>Product: $R_f$ = 0.2<br>$^1$H NMR (400 MHz, MeOD): δ 8.15 (1H, d, J = 8 Hz), 7.72 (1H, d, J = 8 Hz), 7.43 (1H, s), 7.21 (1H, d, J = 8.0 Hz), 5.95 (1H, d, J = 4.0 Hz), 5.87 (1H, d, J = 8.0 Hz), 5.49 (2H, s), 4.19-4.17 (2H, m), 4.04 (1H, d, J = 4.0 Hz), 3.87-3.77 (1H, m), 3.36-3.33 (1H, m), 2.53 (3H, s). |
| 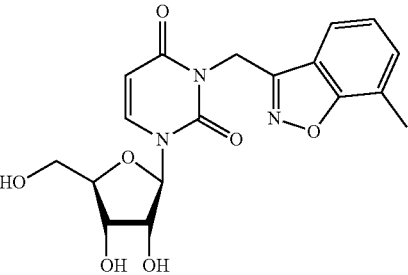<br>37 | Yield: 74% as a solid<br>TLC information:<br>(DCM/MeOH = 10/1)<br>Material: $R_f$ = 0.5<br>Product: $R_f$ = 0.2<br>$^1$H NMR (400 MHz, MeOD): δ 8.15 (1H, d, J = 8 Hz), 7.66 (1H, d, J = 8 Hz), 7.43 (1H, d, J = 7.2 Hz), 7.30-7.26 (1H, m), 5.94 (1H, d, J = 4.0 Hz), 5.87 (1H, d, J = 8.0 Hz), 5.52 (2H, s), 4.20-4.16 (2H, m), 4.04 (1H, s), 3.87-3.85 (1H, m), 3.78-3.75 (1H, m), 2.55 (3H, s). |

Example 6

Materials and Methods for In Vitro and In Vivo Studies

Activation of $P_2Y_6$ Receptor

Synthetic ligands were tested for activation of $P_2Y_6$ receptor by measuring receptor induced $Ca^{2+}$ changes with the fluorescent $Ca^{2+}$ indicator fluo-4. 1321N1 human astrocytoma cell lines either expressing $P_2Y_2$, $P_2Y_4$ or $P_2Y_6$ receptors were plated into 24-well plates. Two days after plating, fluorometric measurements were made and responses of cells to a serial dilution of ligands were determined. $P_2Y_6$ receptor mediated $Ca^{2+}$ fluorescent change was determined by normalized accumulation of fluorescent change of 3 timepoints after ligand administration subtracted by value from ACSF control. Changes in fluorescent intensity were plotted corresponding to ligand concention in GraphPad. Dose-response curve and $EC_{50}$ for each ligand was estimated using nonlinear curve fit and Sigmoidal dose-response analysis. The sodium salt of the diphosphate derivative of compound 5 exhibited an $EC_{50}$ of 12 nM. The sodium salt of the diphosphate derivative of compound 5 was demonstrated to selectively activate $P_2Y_6$ receptors by comparing its $Ca^{2+}$ mobilizing effects in three 1321N1 human astrocytoma cell lines expressing $P_2Y_2$, $P_2Y_4$ or $P_2Y_6$ receptors. The sodium salt of the diphosphate derivative of compound 5 was only effective at elevating $Ca^{2+}$ levels when applied to cells expressing $P_2Y_6$ receptors and not effective in $P_2Y_2$, or $P_2Y_4$ receptor expressing cells. The ability of the sodium salt of the diphosphate derivative of compound 5 to elevate $Ca^{2+}$ signals in $P_2Y_6$ receptor expressing cells was attenuated by addition of the $P_2Y_6$ antagonist MRS2578.

PSAPP Mice

Heterozygous mutant (K670N/M671L) APP (50% C57B6, 50% SJL) transgenic mice were crossed with heterozygous mutant (A246E) PS-1 (50% C57B6, 50% SJL) transgenic mice to generate heterozygous PSAPP transgenic mice (also referred to as PS-1/APP or PSAPP+/+ mice), which refers to animals heterozygous for the PS-1 A246E transgene and the APP K670N/M671L transgene. Non-transgenic control animals were littermates (also referred to as PSAPP_-/- mice) generated in the breeding for PSAPP transgenic animals. Mouse genotype was determined by Polymerase Chain Reaction (PCR). Both male and female mice of 6-7 months old were used for the experiments below. All animal experiments were performed in accordance with the Tufts Animal Care and Use Committee and with national regulations and policies.

Two-Photon In Vivo Imaging Study

In this study, PSAPP mice were anesthetized using isoflurane and a thin-skull preparation was used to minimize the surface damage. Amyloid plaques were visualized with methoxyX04 labeling and blood plasma was labeled with Rhodamine dextran to facilitate re-localization of the same imaging area. Stack images were obtained using a two-photon system (Prairie Technologies) with excitation at 850 nm. The emission was detected by external photomultiplier tubes (525/70; DLCP 575; 607/45 nm).

Stereotaxic Injection

Animals were anesthetized and immobilized in a stereotaxic frame. For each injection, 1 µl of 10 mM UDP or other suitable compounds in artificial cerebrospinal fluid (ACSF) as the vehicle were injected intraventricularly using the following coordinates: AP 0.2 mm, ML 1 mm, and DV 2.2 mm.

Histology and Immunohistochemistry

Mice were perfused transcardially with 4% paraformaldehyde and 40 µm Coronal sections were collected. Sections were sequentially incubated in 0.3% $H_2O_2$ for 10 minutes, blocking solution for 2 hrs, blocking solution containing the primary antibody (rabbit anti-beta1-42; rabbit anti-beta1-40, from Chemicon International and rat anti-CD45) for 48 hours at 4° C., and blocking solution containing biotinylated antibody or fluorescently-labeled antibody for 2 hours at room temperature. Sections were visualized in a bright field microscope or a confocal microscope, and the optical density was obtained using MetaMorph software.

Fear Conditioning Test

On day one, animals were trained in a fear conditioning apparatus for a total of 7 minutes with a two-pairing paradigm of cue and mild foot shock (a 30-s acoustic-conditioned stimulus, 80 dB; a 2-s shock stimulus, 0.5 mA). To evaluate contextual fear learning, the animals were returned to the training context 24 hours post-training, and freezing behavior was scored for 5 minutes. Freezing behavior was monitored by MotorMonitor (Hamilton Kinder) and scored every 5 seconds.

Electrophysiology and Long-Term Potentiation (LTP) Recording

Hippocampal slices (350 µm thick) were prepared from 6-month-old PSAPP mice. Baseline responses were obtained every 10 seconds and Input-output (I/O) curves, paired-pulse modification and LTP were successively measured. The stimulation intensity was set to a level that gives a value of 30% of the maximum obtained. LTP were induced by high frequency stimulation (HFS, 100 pulses at 100 Hz, four times) or by theta-burst stimulation (TBS, 10 bursts at 5 Hz, repeated 10 times in 15 s intervals).

Example 7

Dose-Dependent Activation of $P_2Y_6$ Receptor

Synthetic ligands were tested for activation of $P_2Y_6$ receptor by measuring receptor induced $Ca^{2+}$ changes with the fluorescent $Ca^{2+}$ indicator fluo-4, and results are shown in FIG. 10(A)-(K). 1321N1 human astrocytoma cell lines either expressing $P_2Y_2$, $P_2Y_4$ or $P_2Y_6$ receptors were plated into 24-well plates. Two days after plating, fluorometric measurements were made and responses of cells to a serial dilution of ligands were determined. $P_2Y_6$ receptor mediated $Ca^{2+}$ fluorescent change was determined by normalized accumulation of fluorescent change of 3 timepoints after ligand administration subtracted by value from ACSF control. Changes in fluorescent intensity were plotted corresponding to ligand concentration in GraphPad. Dose-response curve and $EC_{50}$ for each ligand was estimated using nonlinear curve fit and Sigmoidal dose-response analysis. The sodium salt of the diphosphate derivative of compound 5 exhibited an $EC_{50}$ of 12 nM. The sodium salt of the diphosphate derivative of compound 5 was demonstrated to selectively activate $P_2Y_6$ receptors by comparing its $Ca^{2+}$ mobilizing effects in three 1321N1 human astrocytoma cell lines expressing $P_2Y_2$, $P_2Y_4$ or $P_2Y_6$ receptors. The sodium salt of the diphosphate derivative of compound 5 was only effective at elevating $Ca^{2+}$ levels when applied to cells expressing $P_2Y_6$ receptors and not effective in $P_2Y_2$, or $P_2Y_4$ receptor expressing cells. The ability of the sodium salt of the diphosphate derivative of compound 5 to elevate $Ca^{2+}$ signals in $P_2Y_6$ receptor expressing cells was attenuated by addition of the $P_2Y_6$ receptor antagonist MRS2578. These experiments demonstrated that the diphosphate derivative of compound 5 is a $P_2Y_6$ receptor agonist.

Example 8

Acute UDP Administration Reduced Plaque Burden in PSAPP Mice

To evaluate the effect of UDP on plaque burden, two-photon microscopy was used to assess the amyloid plaques in the barrel cortex in living PSAPP mice. Amyloid plaques were stained by systemically administered methoxy-X04. One day prior to imaging, PSAPP mice were injected with methoxyX04 to label the amyloid plaques. On the imaging day, to facilitate the re-location of the same imaging area, blood plasma was labeled with Rhodamine dextran. Images were obtained from the same start- and end-point to ensure the same image volume.

The results were shown in a maximum intensity projection of a fluorescent stack containing 45 planes. Representative images of methoxyX04 labeled amyloid plaques and angiopathy on days 1 are shown in FIG. 1(A)-(C). Immediately after imaging, animals were injected with ACSF or UDP intracerebroventricularly (i.c.v.) and allowed to recover. On day 4, animals were subjected to a second period of imaging of the same regions studied on day 1 and the results are shown in FIG. 1(D)-(F). The similar pattern of angiopathy (shown by open arrows) indicated the same imaging area.

Overall, decreased plaque occupied-area was observed on day 4 following administration of UDP. In the images with higher magnification (FIGS. 1(C) and (F)), the same dense core plaques (as shown by arrows) could be identified based on its morphology and location relative to the blood vessel. It was observed that the dense core plaques had more intense methoxyX04 labeling, but with decreased plaque size (as shown by arrows), when compared to the size of the same plaques on day 1. This suggested that acute UDP treatment reduced plaques size in live animals. This effect was further evaluated by quantifying the number of plaques, plaque load, and size of cross-section of individual plaques. See FIG. 2(A)-(E). Quantitative analysis showed that acute UDP treatment led to a 12.6% reduction in the number of plaques (P<0.01) and a 17.2% reduction in plaque load (P<0.01) in barrel cortex as assessed by two-photon microscopy. Individual identified plaques that were detected on the second imaging session showed an 18.2% reduction (P<0.01) in cross-sectional area following UDP treatment.

After repeated imaging, brains were fixed and subjected to postmortem immunohistochemistry with amyloid beta specific antibodies β1-40 and β1-42 to evaluate the plaque load (area occupied by immunostaining of plaque) in cortex and hippocampus. See FIG. 3(A)-(D). UDP treatment resulted in a 60% (p<0.05) and 62% (p<0.01) decrease in plaque load in the cortex and hippocampus, respectively, as assessed by staining with the β1-40 antibody. Quantification of staining with β1-42 antibody showed a 48% (P<0.01) and 47% (P<0.05) decrease in plaque load in the cortex and hippocampus, respectively. See FIG. 4(A)-(F). Both in vivo imaging and post hoc staining showed decrease in plaque burden in brains of PSAPP mice, consistent with reduced plaque load in the tested animals following acute administration of UDP (e.g., a $P_2Y_6$ receptor agonist).

Example 9

Activation of $P_2Y_6$ Receptors Reduced Plaque Burden in PSAPP Mice 3-phenacyl-UDP (also referred to as PSB0474) is a potent and selective $P_2Y_6$ receptor agonist (EC50=70 nM, >500-fold selective). In this study, $P_2Y_6$ receptor was activated in vivo using 3-phenacyl-UDP (PSB0474). The effect of this activation may have on plaque burden was also evaluated.

PSB0474 was systemically administered to PSAPP mice via intraperitoneal injection for 2, 4 and 6 consecutive days. In one group, prior to evaluation and following to administration for 6 consecutive days, treatment was suspended for two weeks (6+2 weeks group). Brains were then fixed and plaque load was evaluated by immunostaining with the amyloid beta specific antibodies: β1-40 and β1-42. Representative images of plaque load in cortex and hippocampus from animals that received injections of PSB0474 according to the foregoing injection schedules are shown in FIG. 5(A)-(D). Quantitative data showed that administration of PSB0474 for 4 and 6 consecutive days significantly decreased immunoreactivity of β1-40 in both cortex and hippocampus (FIGS. 6(A) and 6(B)). Whereas, when administration of PSB0474 was stopped for 2 weeks following six consecutive days of treatment (denoted as the 6+2 weeks group), β1-40 staining rebounded; although to a level lower than observed in mice treated with saline as a vehicle control. FIGS. 6A and 6B depict the reduction in plaque load (%) the cortex and hippocampus, respectively, in PSAPP mice after treatment with 3-phenacyl-UDP for 2, 4, or 6 consecutive days, as assayed by staining with the β1-40 antibody. FIGS. 6C-6F depict data obtained following administration of different dosages of PSB0474. It is important to note that a 1000× increase in dose of PSB0474 did not cause detrimental effects to the animal, suggesting that there is a wide therapeutic window for $P_2Y_6$ receptor agonists. However, with the higher dose of 1 mg/kg we did observe smaller effects on the efficacy endpoint presumably because the enhanced receptor occupancy led to some desensitization/internalization of the $P_2Y_6$ receptor. This result indicates that activation of $P_2Y_6$ receptor significantly attenuated plaque load in both the cortex and hippocampus in PSAPP mice.

Example 10

Acute UDP Administration Improved Cognitive Function and Hippocampal LTP in PSAPP Mice Amyloid beta peptide has been reported to be toxic to synaptic transmission, and accumulation of amyloid protein is associated with cognitive impairment both in animal models of AD and in AD patients. Additionally, accumulation of amyloid protein is observed in other conditions associated with cognitive impairment, such as in Down Syndrome. Therefore, we further investigated in PSAPP mice whether the observed reduction in plaque burden would also lead to reversal in cognitive and memory deficits typically observed in AD patients, such as impaired cognition, impaired memory, and deficits in long-term potentiation (LTP).

In this study, the fear conditioning associative learning paradigm was used as a rapid cognition assay for PSAPP mice. This study allowed us to probe cognitive function with a single training day followed in 24 hours by tests for contextual and cued fear learning. Contextual fear learning is dependent upon a brain area that has been implicated as a locus for cognitive decline in AD: the hippocampus. Two pairings of CS-US for fear conditioning were followed 24 hours later by testing for contextual and cued fear learning. Previous studies have reported that PSAPP animals appear to have a selective hippocampus-dependent impairment in associative learning following two pairings of conditioned stimuli for fear conditioning.

In this study, it was found that PSAPP mice treated with ACSF showed low freezing behavior during 5 minute-testing time (FIG. 7(A)), which is similar to the level reported in previous study (Dineley, et al. 2002). After UDP treatment, PSAPP mice exhibited increased freezing behavior during the first 4 minutes but not during the last minute. Analysis of total freezing percentage (FIGS. 7(B) and 7(C)) showed that PSAPP mice treated with acute UDP exhibited significantly higher freezing behavior (49%±5%) compared to an animal treated with ACSF (18%±3%). This data suggested that acute UDP treatment rescued the deficit in contextual fear learning in PSAPP mice.

In the fear conditioning test mice exhibit a freezing behavior if they have a memory of the application of the aversive shock that was delivered 24 hours earlier. When placed in the appropriate environment the mice "freeze" and do not explore their environment as they anticipate the delivery of an additional shock. Thus the greater percent time that they exhibit freezing indicates a greater memory of their previous experience and thus improved memory. This represents a decrease in the cognitive impairment observed in the untreated mice.

Accumulated evidence has shown that amyloid peptides naturally secreted or isolated from Alzheimer's brains impair synaptic plasticity, especially hippocampal long-term potentiation (Walsh et al., 2002). Therefore, we further performed LTP recordings in PASPP mice and investigated whether $P_2Y_6$ receptor-mediated plaque clearance affects synaptic plasticity. In this study, LTP was successfully induced in CA1 area of the hippocampus in aged PSAPP mice with high-frequency stimulation (HFS, 100 pulses at 100 Hz, four times in 20 s intervals). First, it was observed that LTP at the schaffer collateral synapse within the CA1 region was depressed in PSAPP mice, as compared with littermates (FIG. 8(A)). This result confirmed previous reports about synaptic toxicity of Abeta. Acute UDP treatment reversed this LTP deficit in PSAPP mice, and the LTP significantly increased compared with mice injected with ACSF (FIG. 8(B)). Analysis of the last 15 min potentiation showed a significant increase in field excitatory postsynaptic potential (fEPSP) in PSAPP mice treated with UDP, which is comparable to the level in PSAPP littermates (FIG. 8(C)). These data supports the conclusion that activation of $P_2Y_6$ receptor rescues the LTP deficiency in PSAPP mice, which is consistent with improvement in cognition mediated by $P_2Y_6$ receptor.

Example 11

Activation of $P_2Y_6$ Receptor with Chronic Injection of PSB0474 Improved Cognitive Function of PSAPP Mice Similar to acute UDP treatment, chronic injection of the $P_2Y_6$ receptor agonist 3-phenacyl-UDP (PSB0474) increased total freezing percentage in context test in PSAPP mice (FIG. 9(A)-(C)). In this study, PSB0474 was administered at two different doses, both of which showed beneficial effect in improving cognitive function in the PSAPP mice.

Example 12

Activation of $P_2Y_6$ Receptor with the Diphosphate Derivative of Compound 5 Improved Cognitive Function of PSAPP Mice and Reduced Plaque Burden in PSAPP Mice In this study, the diphosphate derivative of compound 5 was injected intraperitoneally into 6 to 7-month-old PSAPP and WT mice daily at two different doses, i.e., 1 µg/kg or 1 mg/kg of the diphosphate derivative of compound 5 (in 1% DMSO/PBS) for 7 consecutive days. Consistent with the results observed following acute UDP or PSB0474 treatment, treatment with the diphosphate derivative of compound 5 increased total freezing percentage in the context test in PSAPP mice (FIG. 11). FIG. 11 shows freezing behavior (freezing %) of PASPP mice in fear conditioning studies after treatment with vehicle control or the diphosphate derivative of compound 5. FIG. 11 depicts the results of experiments using the contextual fear conditioning test with PSAPP mice treated with vehicle control (black bar at center of graph). These mice showed significantly decreased freezing percentage compared to the age-matched wildtype animals (white bar); indicative of the memory deficits and cognitive impairment in PSAPP mice. Administration of the diphosphate derivative of compound 5 prior to testing significantly improved the freezing behavior (hatched bar at right of graph) compared to the control treatment. In fact, this behavior which is indicative of cognitive function and memory was restored to a level equivalent to that observed in wildtype animals. This result is consistent with the conclusion that the diphosphate derivative of compound 5 improved cognitive function (decreased cognitive deficits) in these mice, such as by improving memory and/or learning.

Treatment with the diphosphate derivative of compound 5 was also found to reduce the plaque burden in cortex and hippocampus of PSAPP mice (FIG. 12 (A)-(C)). FIG. 12 shows plaque load in the cortex (Cx) and hippocampus (Hp) of the PSAPP mice after treatment with the diphosphate derivative of compound 5 or vehicle control, as assayed using the amyloid beta specific antibody β1-42. FIG. 12A depicts the substantial decrease in A13 plaque load (%) in the cortex following treatment with the diphosphate derivative of compound 5, in comparison to the vehicle control. FIG. 12 B depicts the substantial decrease in Aβ plaque load (%) in the hippocampus following treatment with the diphosphate derivative of compound 5, in comparison to the vehicle control. FIG. 12C shows postmortem immunohistochemistry analysis of the plaque load in cortex and hippocampus of PSAPP mice after treatment with the diphosphate derivative of compound 5 or vehicle control. Amyloid beta specific antibody β1-42 was used in the analysis.

To generate these graphs showing plaque load, mice were euthanized, brain sections cut and antibodies directed against Aβ 42 were used to disclose Aβ plaques. Images were acquired digitally and an algorithm was applied to threshold the image so that plaques were isolated from the background. The algorithm then calculated the percent area of the field of view occupied by the plaques.

Example 13

Nucleoside Compound 5 Reduces Plaque Burden in PS1/APP Mice

In this study, the effect of systemic administration of nucleoside compound 5 on reducing plaque burden in PS1/APP mice was examined.

Animal groups:

| Animal Group | Compound | Dose | I.P. Injection time frame |
|---|---|---|---|
| 1) PS1/APP+/+ (26 weeks, n = 7) | Group A | 10 µg/kg compound 5 | Once per day for 7 days |
| 2) PS1/APP+/+ (26 weeks, n = 8) | Group B | vehicle | Once per day for 7 days |

Brain samples were collected for Abeta analysis with immunostaining Brains samples were collected after transcardial perfusion with phosphate buffer and 4% paraformaldehyde. Floating brain sections (40 micron) were collected using a microtome. Immunostaining for Aβ40 and Aβ42 were performed according to previously established protocol. Images with DAB staining were collected with brightfield microscopy and analyzed with ImageJ Macro. All data analysis and statistics were performed in GraphPad Prism 6.0.

The results are shown on FIGS. 13(A) and 13(B), where it can be seen that i.p. treatment with the nucleoside significantly reduced Aβ40 and Aβ42 plaque burden as well as the size distribution of remaining plaques after seven days of treatment. All studies were performed blind to treatment condition.

In addition to testing in rodent models, as described above, compounds of the present disclosure may be tested in canine models for human neurodegenerative diseases, such as dogs with canine counterpart of Alzheimer's disease. Further, ADME (Absorption, Distribution, Metabolism and Excretion) and Toxicity (ADMET) Studies for safety, tolerability, and pharmacokinetic (PK) profiles of the compounds of the present disclosure are conducted in rodents and a second species (such as dogs). For example, an aged beagle model is available from InterVivo (see, the website on the world wide web intervivo.com/aged-dog/ad). Other models have been reported in the literature, such as by Insua et al., Neurobiol Aging, 2010, 31(4): 625-635 (epub 2008 Jun. 24, doi: 10.1016/j.neurobiolaging.2008.05.014).

Example 14

Oral Bioavailability of Compound 5

The mean value of oral bioavailability of the nucleoside compound 5 is 72.2%. In human whole blood compound 5 has a half-life of 982 minutes.

Example 15

Administration of the Diphosphate Derivative of Compound 5 Decreased Levels of Circulating Cytokines in the Plasma of PSAPP Mice Inflammatory cytokines were assessed in mouse plasma of both wild type and PS1/APP mice (Alzheimer's mouse model) and the impact of intraperitoneal delivery of the diphosphate derivative of compound 5 on circulating cytokines was assessed. Seven daily intraperitoneal injections of 1 μg/kg of the diphosphate derivative of compound 5 were delivered to mice. 24 hours following the final injection, plasma was collected. Wildtype, age matched littermates and PSAPP mice (>6 months of age) were treated either with vehicle (phosphate buffered saline) or vehicle containing compound. Compared to wildtype mice, PSAPP mice exhibited greater levels of several cytokines (where cytokine levels were measured in pg/ml. In particular IL-9, IL-15 and MIG were elevated compared to WT vehicle controls. Treatment with compound reduced the levels of several cytokines in PSAPP mice including Il-1β, IL-2, IL-7, IL-9, IL-10, IL-15, MIG and MIP1α. Additionally, treatment reduced the levels of certain cytokines in wildtype animals (e.g. IL-2 and IL-10) supporting the conclusion that agonizing $P_2Y_6$ receptor activity, directly or indirectly, affects inflammatory cytokines more generally (e.g., not specifically in Alzheimers models). See FIG. 14.

Examples 16

Administration of Compound 5 to Pre-Symptomatic PSAPP Mice Reduced Amyloid β Accumulation and Reduced Impairment In this study, treatment of PSAPP mice commenced when the mice were pre-symptomatic. Specifically, treatment was initiated when the mice were approximately 3 months old. PSAPP mice were treated for 100 days with daily, intraperitoneal injections of 10 μg/kg of compound 5 or vehicle. Following treatment, mice were assessed in a fear conditioning task for memory formation. Subsequently, plaque burden in the mice was also evaluated. The data provided in Examples 16 and 17 is for 19 vehicle treated mice and 22 compound treated mice. The data provided for the vehicle-treated group is the average across those mice, and error bars depict the standard error (SEM). Similarly, the data provided for the compound-treated group is the average across those mice, and the error bars depict the SEM.

Treatment with compound 5 prevented impairments in contextual fear memory. In other words, treatment decreased loss of memory that otherwise develops and is observed in PSAPP mice. Memory is assessed by the percent time that mice "freeze" 24 hours after a fear inducing electric shock. The greater the freezing the greater the memory of the prior shock. As depicted in FIG. 15, the compound 5 treated mice show a statistically significant increase in this freezing time, as compared to vehicle treated mice.

In addition, mice treated with compound 5 had reduced plaque burden. This reflects a reduction in amyloid β accumulation in the compound 5 treated mice versus the vehicle treated mice. See FIG. 16. In FIGS. 15 and 16, compound 5 is indicated along the x-axis as "compound".

Example 17

Administration of Compound 5 Decreased Levels of Cytokines in the Plasma of PSAPP Mice As part of the study described in Example 16, the levels of numerous cytokines in plasma of mice treated with vehicle or compound 5 were also evaluated. As described in Example 16, treatment was initiated when the mice were approximately 3 months old. PSAPP mice were treated for 100 days with daily injections of 10 μg/kg of compound 5 or vehicle. Following treatment and the fear conditioning task experiment, plasma was taken for multiplex cytokine analysis of circulating cytokine levels in vehicle-treated versus compound-treated PSAPP mice. Cytokine levels are assayed using a multi-plex system where beads are labelled with capture antibody specific for each analyte tested. Each bead set is coupled to a specific capture antibody and is distinguishable from beads coupled to a different capture antibody. Thus, the levels of each analyte can be evaluated and distinguished. These results are summarized in FIGS. 17-20, and levels of each analyte are shown in pg/ml. In FIGS. 17-20, compound 5 is indicated along the x-axis as "compound".

Briefly, following treatment for 100 days with compound 5, a statistically significant reduction, in plasma levels of IL-4, IL-10, and IL-12 (also referred to as IL-12(p70)) was observed, in comparison to vehicle control treated mice. See FIG. 17. For IL-12, the reduction observed represents an actual reduction in the functional IL-12, heterodimeric cytokine, and not just a reduction in the p40 subunit common to multiple cytokines Specifically, the data examining the p40 subunit alone (depicted as IL-12(p40); using a capture antibody that measures the p40 subunit) does not reflect a change following treatment with compound 5 while the IL-12(p70) data shows a statistically significant reduction following treatment with compound 5 (see FIG. 17). Regardless of the mechanism of action by which IL-12 is reduced, these results indicate that it is not merely via a mechanism generic to all cytokines that share the p40 subunit. Throughout the application, we refer to a reduction in IL-12 cytokine levels interchangeably by reference to either "IL-12" or "IL-12(p70)".

In addition, the average plasma levels of numerous other cytokines, such as IFN-r, IL-1β, IL-2, IL-3, IL-5, IL-6, IL-7, IL-9, IL-13, IL-17, LIF, MIP-1α, and MIP-1β, were also reduced. However, administration of the compound did not result in overall immunosuppression, as the levels of several cytokines were not changed in treated mice. For example, no or substantially no change in the levels of M-CSF, MIP-2, Eotaxin, GM-CSF, G-CSF, LIX, MCP-1, IL-1α and IP-10 was observed.

Example 18

Administration of Compound 5 Reduced Amyloid β, Prevented Memory Deficit and Reduced Levels of Pro-Inflammatory Cytokines in PSAPP Mice In this study, treatment of PSAPP mice commenced when the mice were pre-symptomatic. Specifically, treatment was initiated when the mice were approximately 3 months old. PSAPP mice were treated for 100 days with daily, intraperitoneal injections of 10 μg/kg of compound 5 or vehicle. Following treatment, mice were assessed for the following: concentration of circulating pro-inflammatory cytokines; amyloid beta load (e.g., plaque burden); and memory in a fear conditioning task for memory formation. The data provided in Example 18 is for 18 vehicle treated mice and 20 compound treated mice. The data provided for the vehicle-treated group is the average across those mice, and error bars depict the standard error (SEM). Similarly, the data provided for the compound-treated group is the average across those mice, and the error bars depict the SEM. Mice were first evaluated in the fear conditioning task experiment. Subsequently, plasma was taken for multiplex cytokine analysis of circulating levels of cytokine in the plasma. Finally, plaque burden was assessed in the cortex and hippocampus of the mice.

As depicted in FIG. 21, following treatment for 100 days with compound 5, a statistically significant reduction in plasma levels of the following cytokines was observed: IL-12 (also referred to as IL-12(p70)), IL-13, IL-17, IL-10, IL-4, MIP-1a, MIP-1b, and IL-2. See FIG. 21. For IL-12, the reduction observed represents an actual reduction in functional IL-12, heterodimeric cytokine, and not just a reduction in the p40 subunit common to multiple cytokines, as explained above. For each cytokine examined, plasma levels (e.g., plasma concentration) are measured in pg/ml and the observed levels in compound 5 treated mice are compared to those observed in vehicle control treated mice.

As depicted in FIG. 22(C), treatment with compound 5 prevented impairments in contextual fear memory. In other words, treatment decreased loss of memory that otherwise develops and is observed in PSAPP mice. Memory is assessed by the percent time that mice "freeze" 24 hours after a fear inducing electric shock. The greater the freezing the greater the memory of the prior shock. As depicted in FIG. 22(C), the compound 5 treated mice show a statistically significant increase in this freezing time, as compared to vehicle treated mice.

In addition, mice treated with compound 5 had reduced plaque burden. This reflects a reduction in amyloid β accumulation in the compound 5 treated mice versus the vehicle treated mice (See FIGS. 22(A) and 22(B)). Amyloid beta accumulation was decreased in both the cortex and the hippocampus of compound 5 treated mice. See FIGS. 22(A) and 22(B), respectively. In FIG. 21, the asterisks correspond to the following p values: * p<0.05;  p<0.01. In FIG. 22, the asterisks correspond to the following p values: for 22A, * p<0.01; for 22B and C, * p<0.02.

Example 19

Seven Day Treatment with Compound 5 Reversed Amyloid β Accumulation and Reduced Levels of Pro-Inflammatory Cytokines in PSAPP Mice In this study, treatment of PSAPP mice commenced after the mice were already symptomatic. Specifically, treatment was initiated when the mice were approximately 6 months old. PSAPP mice were treated for 7 days with daily, intraperitoneal injections of 10 μg/kg of compound 5 or vehicle. Following treatment, mice were assessed for the following: concentration of circulating pro-inflammatory cytokines; amyloid beta load (e.g., plaque burden); and plaque size. The data provided in Example 19 is for 7 vehicle treated mice and 7 compound treated mice. The data provided for the vehicle-treated group is the average across those mice, and error bars depict the standard error (SEM). Similarly, the data provided for the compound-treated group is the average across those mice, and the error bars depict the SEM. Plasma was taken for multiplex cytokine analysis of circulating levels of cytokine in the plasma. Subsequently, plaque burden was assessed in the cortex (using Aβ40) and hippocampus (using Aβ42) of the mice, and plaque size was also assessed.

As depicted in FIG. 23, following treatment for 7 days with compound 5, a statistically significant reduction in plasma levels of the following cytokines was observed: IL-12 (also referred to as IL-12(p70)), IL-13, IL-17, IL-10, MIP-1a, MIP-1b, and TNFα. See FIG. 23. For each cytokine examined, plasma levels (e.g., plasma concentration) were measured in pg/ml and the observed levels in compound 5 treated mice were compared to those observed in vehicle control treated mice.

As depicted in FIGS. 24(A) and 24(B), mice treated with compound 5 had reduced plaque burden. This reflects a reduction in amyloid β accumulation in the compound 5 treated mice versus the vehicle treated mice (See FIG. 24(A)). Amyloid beta accumulation was decreased in both the cortex (upper panel of FIG. 24(A)) and the hippocampus (lower panel of FIG. 24(A)) of compound 5 treated mice. In addition, a decrease in plaque size was observed in compound 5 treated mice (See FIG. 24(B)). In FIG. 23, the asterisks correspond to the following p values: * p<0.05;  p<0.005; * p<0.0005. In FIG. 24, the asterisks correspond to the following p values: * p<0.05.

Example 20

$P_2Y_6$ Modulating Compounds Mediate Cytokine Release in Human THP-1 Cells

THP-1 cells, a human cell line derived from monocytes, were treated in vitro with vehicle, the $P_2Y_6$ receptor antagonist MRS 2578, or compound 5, singly or in combination. THP-1 cells were seeded in 24 well plates at a density of $4 \times 10^5$ cells/well in culture medium for 24 hours. Thereafter, vehicle, compound 5, or MRS 2578 (singly or in combination) were added to the cultures for 24 hours. Subsequently the culture medium was aspirated and subjected to multiplex cytokine analysis. Data are presented as means+/−sem. See FIGS. 25 and 26. MRS 2578 has a molecular weight of about 472 and is also described using CAS number 711019-86-2.

As summarized in FIG. 25, treatment of human THP-1 cells with the $P_2Y_6$ receptor antagonist MRS 2578 increased the release of certain cytokines from the cells, as measured by an increase in the observed concentration of particular cytokines in the culture medium, consistent with an anti-inflammatory effect endogenously exerted by this receptor. Numerous cytokines were evaluated, and data for fractalkine, PDGF-BB, and IL-7 are shown in FIG. 25. Observed concentration of these cytokines in the culture medium, following treatment, is indicated along the y-axis in pg/ml. In FIG. 25, the asterisks correspond to the following p values: * p<0.05;  p<0.02; * p<0.002.

Moreover, our studies in human THP-1 cells showed that the effects of modulating $P_2Y_6$ receptor activity were reciprocal. Specifically, treating cells in culture with compound 5 (10 nM) reduced the release of cytokines. This is consistent with the inhibitory affects on plasma cytokine concentration observed following administration of compound 5 to mice. This inhibitory affect was blocked by co-incubating the cells in both compound 5 and the $P_2Y_6$ receptor antagonist MRS 2578. FIG. 26 summarizes the results of an experiment in which IL-7 release from human THP-1 cells was examined.

Interestingly, the concentration of compound 5 used in this experiment, 10 nM, is in good agreement with the effective dose of compound 5 (10 ug/kg) that gives a Cmax of 13 nM.

FIG. 26 summarizes data evaluating concentration of cytokine (IL-7) released from human THP-1 cells treated in vitro with vehicle, compound 5, the $P_2Y_6$ antagonist MRS 2578, or both compound 5 and MRS 2578. Concentration of cytokine secreted into the culture media is measured in pg/ml, as represented on the y-axis. Treatment with MRS 2578 increased release of IL-7 from human THP-1 cells. Treatment with compound 5 decreased release of IL-7 from human THP-1 cells, and this effect was abrogated by co-treatment with MRS 2578. In FIG. 26, the asterisks correspond to the following p values: * p<0.05.

What is claimed is:

1. A method of improving cognitive function in a subject in need thereof, wherein the subject in need thereof has Alzheimer's disease, comprising administering to the subject an effective amount of a composition comprising a compound of formula I:

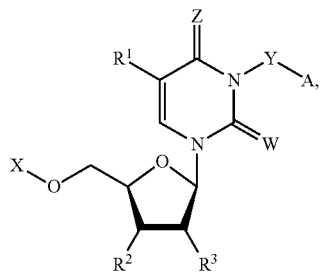

or a salt thereof, wherein:
A is a bicyclic aromatic ring having up to 4 heteroatoms selected from N, O and S, wherein the bicyclic aromatic ring is independently and optionally substituted with one or more $R^7$;
X is selected from:
—H, —C(O)$R^5$, and —C(O)O$R^5$;
Y is a bond or a (C1-C5)-aliphatic group independently and optionally substituted with one or more $R^4$;
Z and W are each independently selected from =O, =S, =N($R^5$), and =NO$R^5$;
$R^1$ is selected from:
—H, halogen, —O$R^5$, —CN, —CF$_3$, —OCF$_3$ and a (C1-C6)-aliphatic group optionally substituted with one or more $R^7$;
$R^2$ and $R^3$ are each independently selected from —O$R^5$, —S$R^5$, —N$R^5R^6$, —OC(O)$R^5$, —OC(O)N$R^5R^6$, and —OC(O)O$R^5$;
each occurrence of $R^4$ is independently selected from:
halogen, —O$R^5$, —NO$_2$, —CN, —CF$_3$, —OCF$_3$, —$R^5$, 1,2-methylenedioxy, 1,2-ethylenedioxy, —N($R^5$)$_2$, —S$R^5$, —SO$R^5$, —SO$_2$ $R^5$, —SO$_2$N($R^5$)$_2$, —SO$_3R^5$, —C(O)$R^5$, —C(O)C(O)$R^5$, —C(O)CH$_2$C(O)$R^5$, —C(S)$R^5$, —C(S)O$R^5$, —C(O)O$R^5$, —C(O)C(O)O$R^5$, —C(O)C(O)N($R^5$)$_2$, —OC(O)$R^5$, —C(O)N($R^5$)$_2$, —OC(O)N($R^5$)$_2$, —C(S)N($R^5$)$_2$, —(CH$_2$)$_{0-2}$NHC(O)$R^5$, —N($R^5$)N($R^5$)COR$^5$, —N($R^5$)N($R^5$)C(O)O$R^5$, —N($R^5$)N($R^5$)CON($R^5$)$_2$, —N($R^5$)SO$_2R^5$, —N($R^5$)SO$_2$N($R^5$)$_2$, —N($R^5$)C(O) O$R^5$, —N($R^5$)C(O)$R^5$, —N($R^5$)C(S)$R^5$, —N($R^5$)C (O)N($R^5$)$_2$, —N($R^5$)C(S)N($R^5$)$_2$, —N(COR$^5$)COR$^5$, —N(OR$^5$)$R^5$, —C(=NH)N($R^5$)$_2$, —C(O)N(O$R^5$) $R^5$, —C(=NO$R^5$)$R^5$, —OP(O)(O$R^5$)$_2$, —P(O) ($R^5$)$_2$, —P(O)(O$R^5$)$_2$, and —P(O)(H)(O$R^5$);
each occurrence of $R^5$ is independently selected from:
H—,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, and
(C5-C10)-heteroaryl-(C1-C12)-aliphatic-;
wherein two $R^5$ groups bound to the same atom optionally form a 3- to 10-membered aromatic or non-aromatic ring having up to 3 heteroatoms independently selected from N, O, S, SO, and SO$_2$, wherein said ring is optionally fused to a (C6-C10)aryl, (C5-C10)heteroaryl, (C3-C10)cycloalkyl, or a (C3-C10)heterocyclyl; and
wherein each $R^5$ group is independently and optionally substituted with one or more $R^7$;
$R^6$ is selected from:
—$R^5$, —C(O)$R^5$, —C(O)O$R^5$, —C(O)N($R^5$)$_2$ and —S(O)$_2R^5$;
each occurrence of $R^7$ is independently selected from:
halogen, —O$R^8$, —NO$_2$, —CN, —CF$_3$, —OCF$_3$, —$R^8$, oxo, thioxo, 1, 2-methylenedioxy, 1,2-ethylenedioxy, —N($R^8$)$_2$, —S$R^8$, —SO$R^8$, —SO$_2$ $R^8$, —SO$_2$N($R^8$)$_2$, —SO$_3R^8$, —C(O)$R^8$, —C(O)C(O) $R^8$, —C(O)CH$_2$C(O)$R^8$, —C(S)$R^8$, —C(S)O$R^8$, —C(O)O$R^8$, —C(O)C(O)O$R^8$, —C(O)C(O)N($R^8$)$_2$, —OC(O)$R^8$, —C(O)N($R^8$)$_2$, —OC(O)N($R^8$)$_2$, —C(S)N($R^8$)$_2$, —(CH$_2$)$_{0-2}$NHC(O)$R^8$, —N($R^8$)N ($R^8$)COR$^8$, —N($R^8$)N($R^8$)C(O)O$R^8$, —N($R^8$)N($R^8$) CON($R^8$)$_2$, —N($R^8$)SO$_2R^8$, —N($R^8$)SO$_2$N($R^8$)$_2$, —N($R^8$)C(O)O$R^8$, —N($R^8$)C(O)$R^8$, —N($R^8$)C(S) $R^8$, —N($R^8$)C(O)N($R^8$)$_2$, —N($R^8$)C(S)N($R^8$)$_2$, —N(COR$^8$)COR$^8$, —N(OR$^8$)$R^8$, —C(=NH) N($R^8$)$_2$, —C(O)N(OR$^8$)$R^8$, —C(=NOR$^8$)$R^8$, —OP (O)(OR$^8$)$_2$, —P(O)($R^8$)$_2$, —P(O)(OR$^8$)$_2$, and —P(O) (H)(OR$^8$);

each occurrence of $R^8$ is independently selected from:
H— and (C1-C6)-aliphatic-,
and an acceptable carrier, adjuvant or excipient.

2. The method of claim 1, wherein A of said compound of Formula I is selected from the group consisting of:

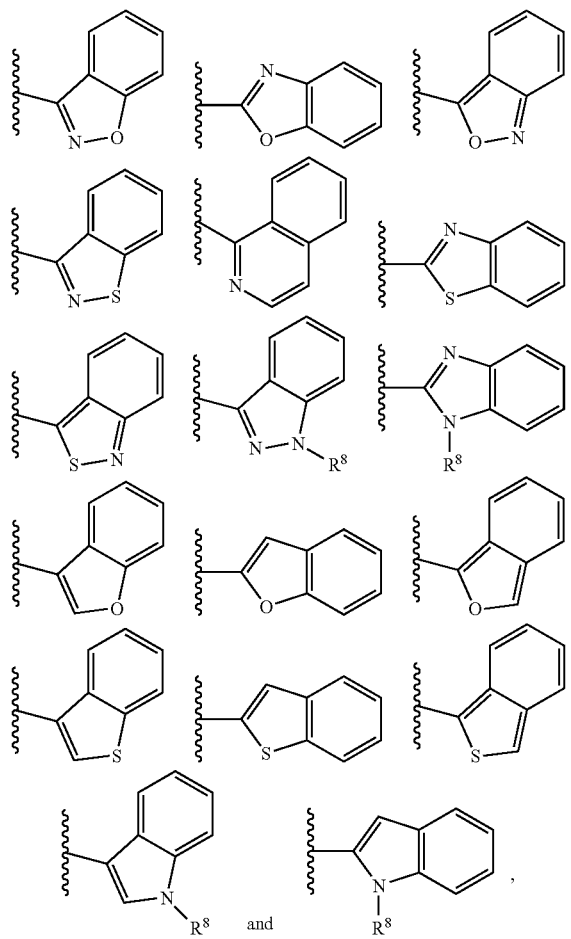

wherein A is optionally further substituted with one or more $R^7$.

3. The method of claim 1, wherein A of said compound of Formula I is

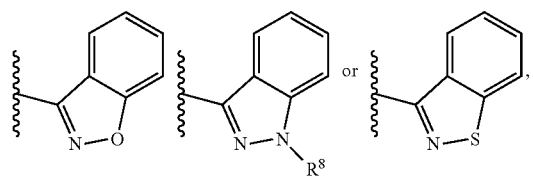

wherein A is optionally further substituted with one or more $R^7$.

4. The method of claim 1, wherein X of said compound of Formula I is —H or —C(O)$R^5$.

5. The method of claim 1, wherein $R^1$ of said compound of Formula I is H, bromine, iodine, methyl, ethyl or $CF_3$.

6. The method of claim 1, wherein $R^1$ is —H.

7. The method of claim 1, wherein Z of said compound of Formula I is =O or =S.

8. The method of claim 1, wherein Z is =O.

9. The method of claim 1, wherein W of said compound of Formula I is =O or =S.

10. The method of claim 1, wherein W is =O.

11. The method of claim 1, wherein Y of said compound of Formula I is a C1-aliphatic group optionally substituted with one or more $R^4$.

12. The method of claim 1, wherein Y is —CH$_2$—.

13. The method of claim 1, wherein $R^2$ of said compound of Formula I is —O$R^5$.

14. The method of claim 1, wherein $R^2$ is —OH.

15. The method of claim 1, wherein $R^3$ of said compound of Formula I is —O$R^5$.

16. The method of claim 1, wherein $R^3$ is —OH.

17. The method of claim 1, wherein said compound is selected from the group consisting of:

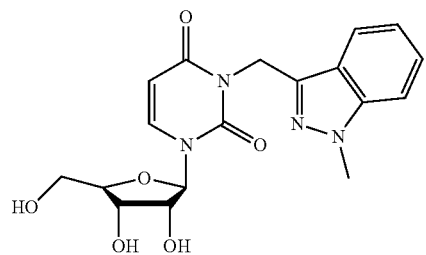

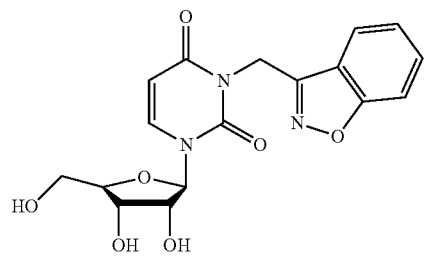

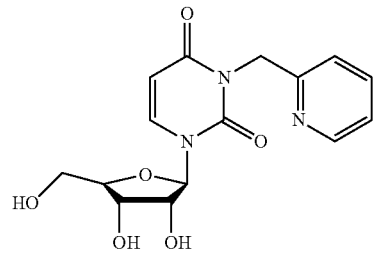

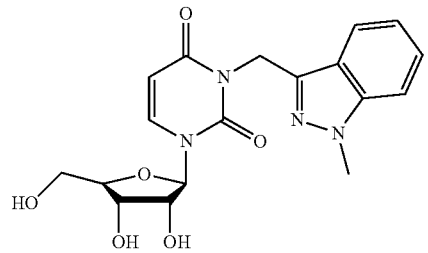

113
-continued
5
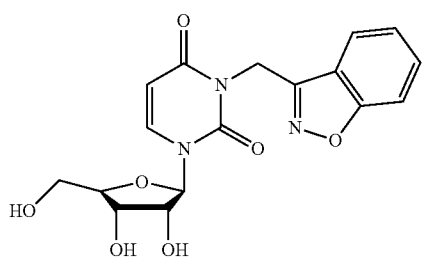
6
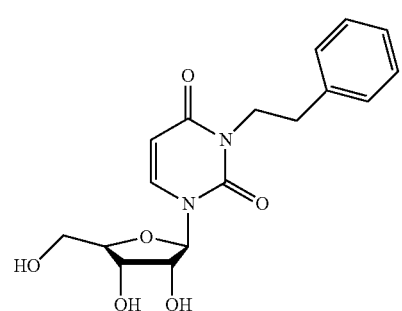
18
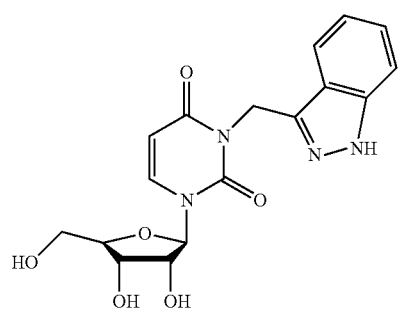
20
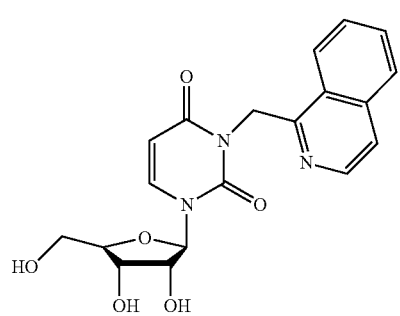
30
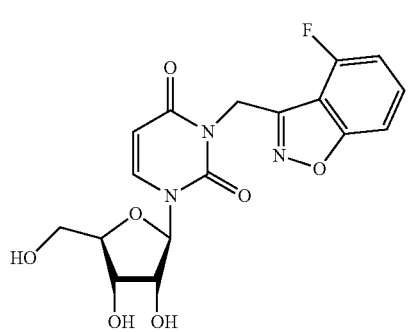
114
-continued
31
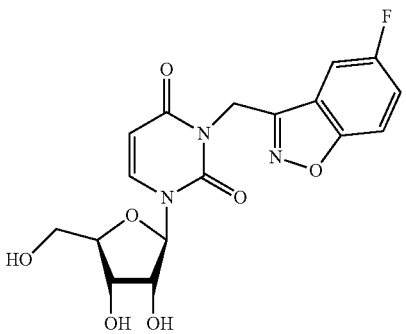
32
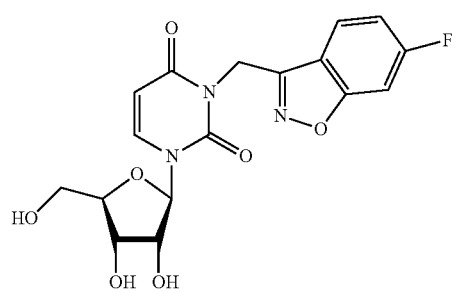
33
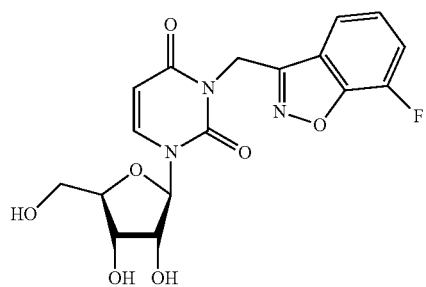
34
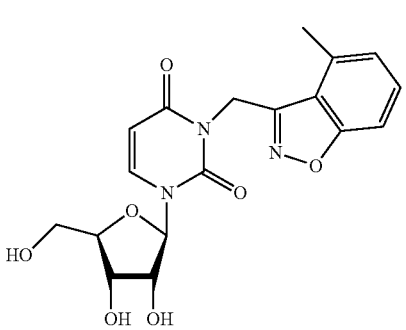
35
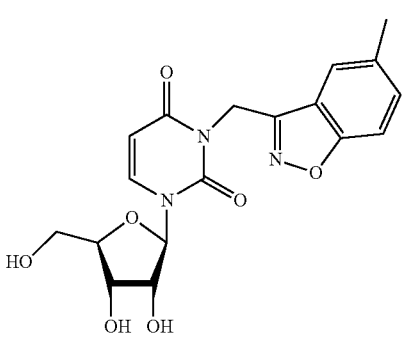

-continued
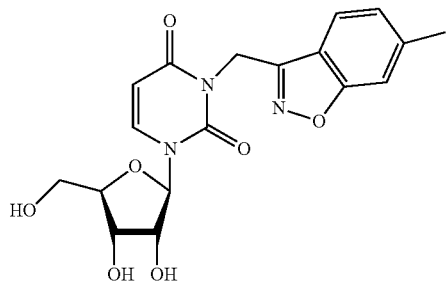
36
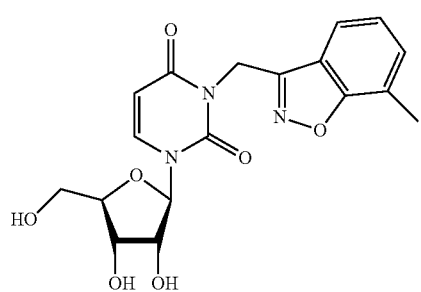
37
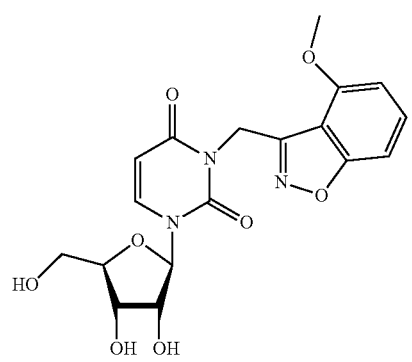
38
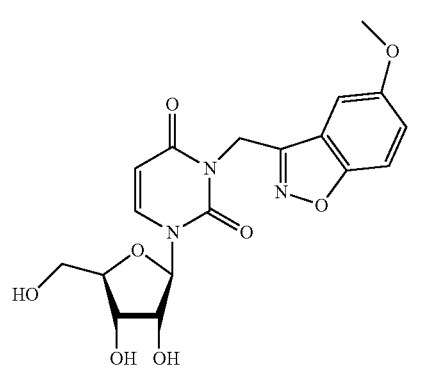
39
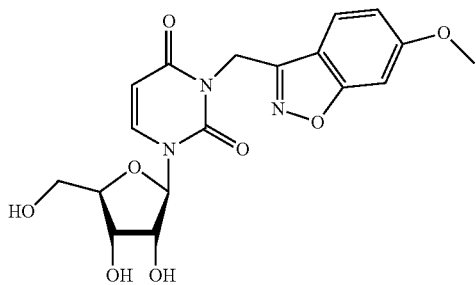
40
-continued
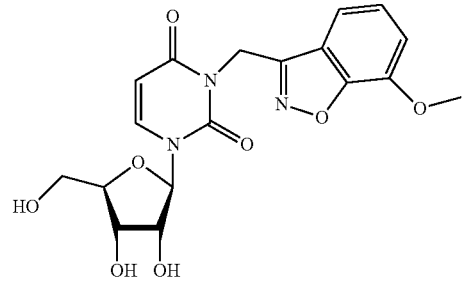
41
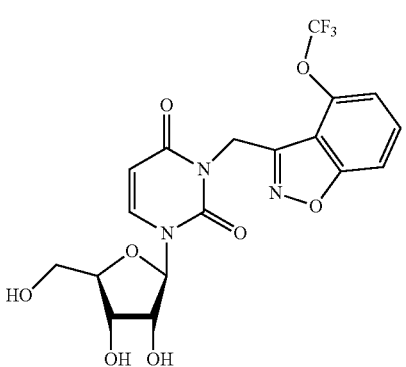
42
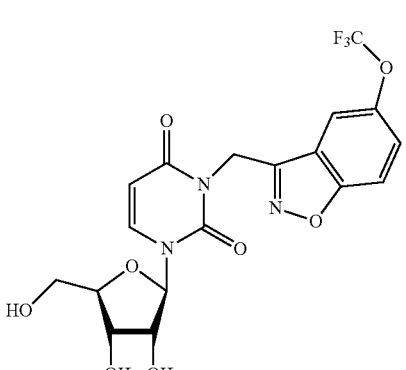
43
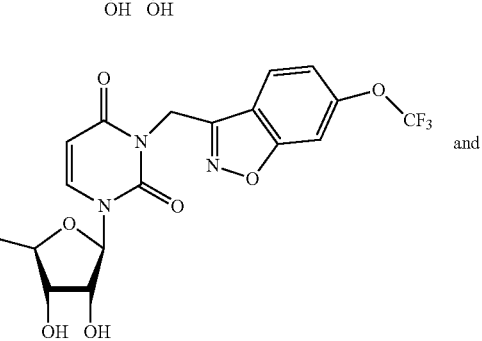
44 and
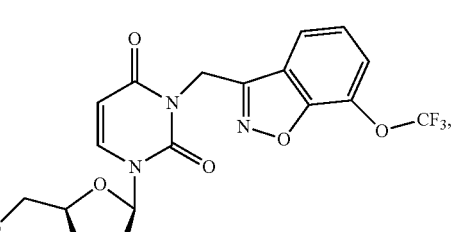
45
or a pharmaceutically acceptable salt thereof.

18. The method of claim 1, wherein the compound is:

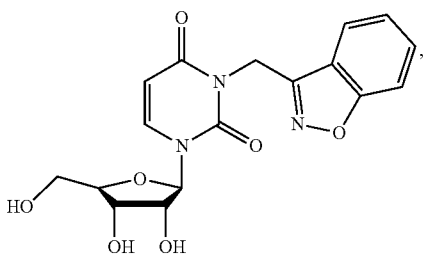

or a pharmaceutically acceptable salt thereof.

19. A method of enhancing the rate of beta amyloid clearance in a subject in need thereof, wherein the subject in need thereof has Alzheimer's disease, comprising administering an effective amount of a composition comprising a compound of formula I

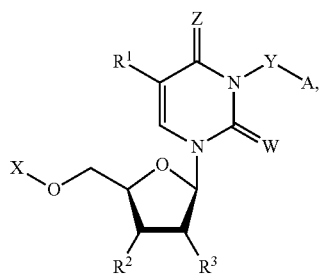

or a salt thereof, wherein:
A is a bicyclic aromatic ring having up to 4 heteroatoms selected from N, O and S, wherein the bicyclic aromatic ring is independently and optionally substituted with one or more $R^7$;
X is selected from:
—H, —C(O)$R^5$, and —C(O)O$R^5$;
Y is a bond or a (C1-C5)-aliphatic group independently and optionally substituted with one or more $R^4$;
Z and W are each independently selected from =O, =S, =N($R^5$), and =NO$R^5$;
$R^1$ is selected from:
—H, halogen, —O$R^5$, —CN, —CF$_3$, —OCF$_3$ and a (C1-C6)-aliphatic group optionally substituted with one or more $R^7$;
$R^2$ and $R^3$ are each independently selected from —O$R^5$, —S$R^5$, —N$R^5R^6$, —OC(O)$R^5$, —OC(O)N$R^5R^6$, and —OC(O)O$R^5$;
each occurrence of $R^4$ is independently selected from:
halogen, —O$R^5$, —NO$_2$, —CN, —CF$_3$, —OCF$_3$, —$R^5$, 1,2-methylenedioxy, 1,2-ethylenedioxy, —N($R^5$)$_2$, —S$R^5$, —SO$R^5$, —SO$_2$ $R^5$, —SO$_2$N($R^5$)$_2$, —SO$_3R^5$, —C(O)$R^5$, —C(O)C(O)$R^5$, —C(O)CH$_2$C(O)$R^5$, —C(S)$R^5$, —C(S)O$R^5$, —C(O)O$R^5$, —C(O)C(O)O$R^5$, —C(O)C(O)N($R^5$)$_2$, —OC(O)$R^5$, —C(O)N($R^5$)$_2$, —OC(O)N($R^5$)$_2$, —C(S)N($R^5$)$_2$, —(CH$_2$)$_{0-2}$NHC(O)$R^5$, —N($R^5$)N($R^5$)COR$^5$, —N($R^5$)N($R^5$)C(O)O$R^5$, —N($R^5$)N($R^5$)CON($R^5$)$_2$, —N($R^5$)SO$_2R^5$, —N($R^5$)SO$_2$N($R^5$)$_2$, —N($R^5$)C(O)O$R^5$, —N($R^5$)C(O)$R^5$, —N($R^5$)C(S)$R^5$, —N($R^5$)C(O)N($R^5$)$_2$, —N($R^5$)C(S)N($R^5$)$_2$, —N(COR$^5$)COR$^5$, —N(O$R^5$)$R^5$, —C(=NH)N($R^5$)$_2$, —C(O)N(O$R^5$)$R^5$, —C(=NO$R^5$)$R^5$, —OP(O)(O$R^5$)$_2$, —P(O)($R^5$)$_2$, —P(O)(O$R^5$)$_2$, and —P(O)(H)(O$R^5$);
each occurrence of $R^5$ is independently selected from:
H—,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, and
(C5-C10)-heteroaryl-(C1-C12)-aliphatic-;
wherein two $R^5$ groups bound to the same atom optionally form a 3- to 10-membered aromatic or non-aromatic ring having up to 3 heteroatoms independently selected from N, O, S, SO, and SO$_2$, wherein said ring is optionally fused to a (C6-C10)aryl, (C5-C10)heteroaryl, (C3-C10)cycloalkyl, or a (C3-C10)heterocyclyl; and
wherein each $R^5$ group is independently and optionally substituted with one or more $R^7$;
$R^6$ is selected from:
—$R^5$, —C(O)$R^5$, —C(O)O$R^5$, —C(O)N($R^5$)$_2$ and —S(O)$_2R^5$;
each occurrence of $R^7$ is independently selected from:
halogen, —O$R^8$, —NO$_2$, —CN, —CF$_3$, —OCF$_3$, —$R^8$, oxo, thioxo, 1, 2-methylenedioxy, 1,2-ethylenedioxy, —N($R^8$)$_2$, —S$R^8$, —SO$R^8$, —SO$_2$ $R^8$, —SO$_2$N($R^8$)$_2$, —SO$_3R^8$, —C(O)$R^8$, —C(O)C(O)$R^8$, —C(O)CH$_2$C(O)$R^8$, —C(S)$R^8$, —C(S)O$R^8$, —C(O)O$R^8$, —C(O)C(O)O$R^8$, —C(O)C(O)N($R^8$)$_2$, —OC(O)$R^8$, —C(O)N($R^8$)$_2$, —OC(O)N($R^8$)$_2$, —C(S)N($R^8$)$_2$, —(CH$_2$)$_{0-2}$NHC(O)$R^8$, —N($R^8$)N($R^8$)COR$^8$, —N($R^8$)N($R^8$)C(O)O$R^8$, —N($R^8$)N($R^8$)CON($R^8$)$_2$, —N($R^8$)SO$_2R^8$, —N($R^8$)SO$_2$N($R^8$)$_2$, —N($R^8$)C(O)O$R^8$, —N($R^8$)C(O)$R^8$, —N($R^8$)C(S)$R^8$, —N($R^8$)C(O)N($R^8$)$_2$, —N($R^8$)C(S)N($R^8$)$_2$, —N(COR$^8$)COR$^8$, —N(O$R^8$)$R^8$, —C(=NH)N($R^8$)$_2$, —C(O)N(O$R^8$)$R^8$, —C(=NO$R^8$)$R^8$, —OP(O)(O$R^8$)$_2$, —P(O)($R^8$)$_2$, —P(O)(O$R^8$)$_2$, and —P(O)(H)(O$R^8$);
each occurrence of $R^8$ is independently selected from:
H— and (C1-C6)-aliphatic-,
and an acceptable carrier, adjuvant or excipient.

20. The method of claim 19, wherein A of said compound of Formula I is selected from the group consisting of:

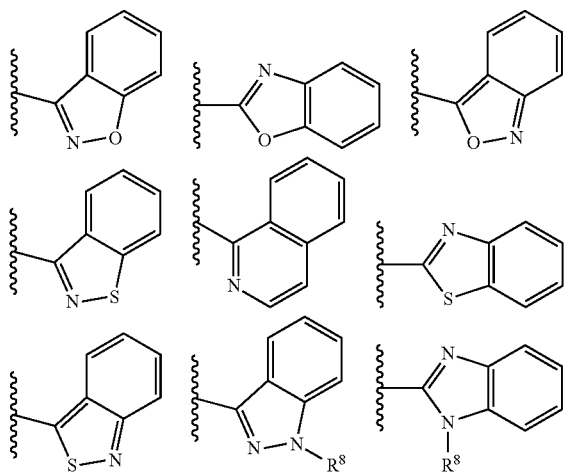

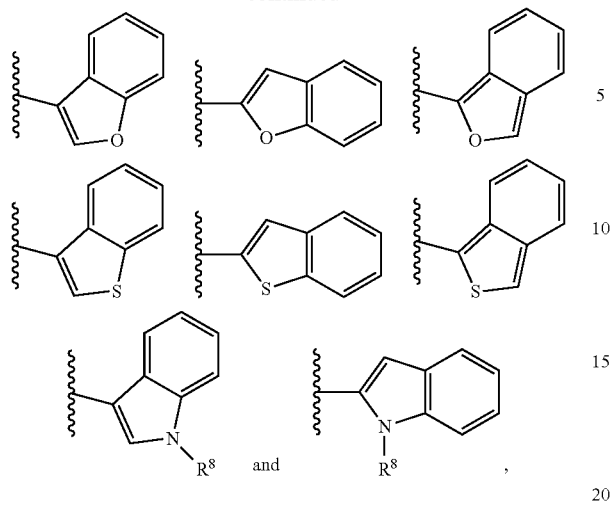

wherein A is optionally further substituted with one or more R'.

21. The method of claim 19, wherein A of said compound of Formula I is

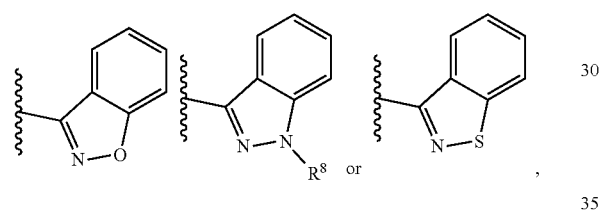

wherein A is optionally further substituted with one or more R⁷.

22. The method of claim 19, wherein X of said compound of Formula I is —H or —C(O)R⁵.

23. The method of claim 19, wherein R¹ of said compound of Formula I is —H, bromine, iodine, methyl, ethyl or —CF₃.

24. The method of claim 19, wherein R¹ is —H.

25. The method of claim 19, wherein Z of said compound of Formula I is =O or =S.

26. The method of claim 19, wherein Z is =O.

27. The method of claim 19, wherein W of said compound of Formula I is =O or =S.

28. The method of claim 19, wherein W is =O.

29. The method of claim 19, wherein Y of said compound of Formula I is a C1-aliphatic group optionally substituted with one or more R⁴.

30. The method of claim 19, wherein Y is —CH₂—.

31. The method of claim 19, wherein R² of said compound of Formula I is —OR⁵.

32. The method of claim 19, wherein R² is —OH.

33. The method of claim 19, wherein R³ of said compound of Formula I is —OR⁵.

34. The method of claim 19, wherein R³ is —OH.

35. The method of claim 19, wherein said compound is selected from the group consisting of:

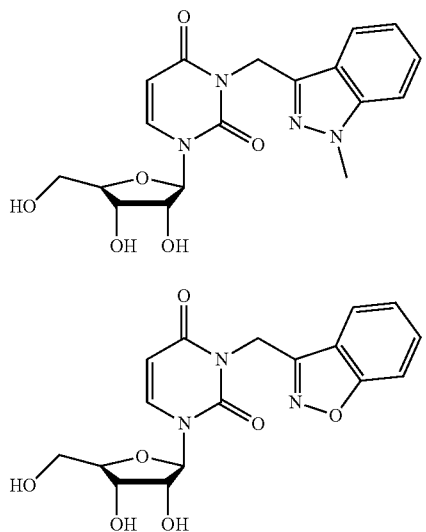

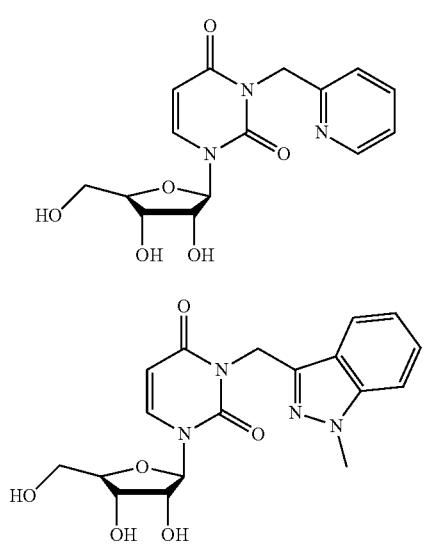

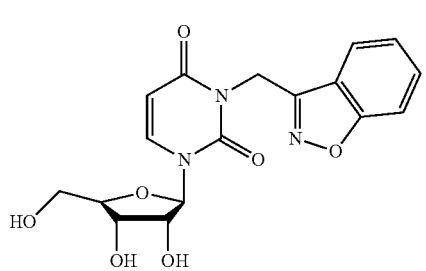

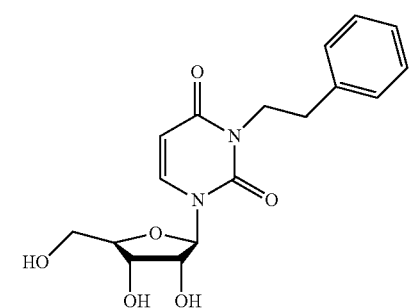

18
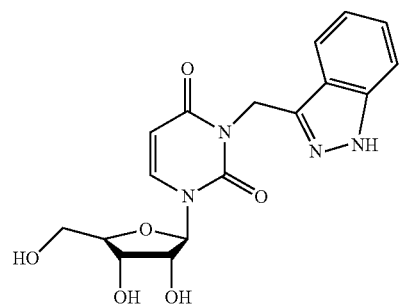
20
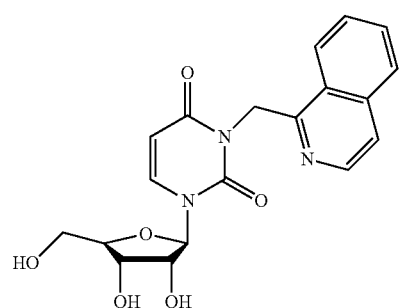
30
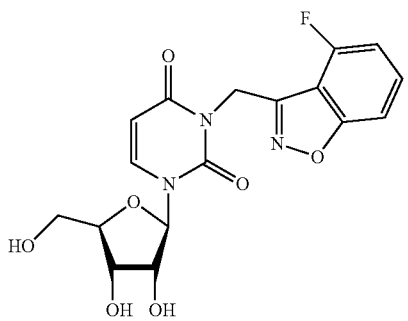
31
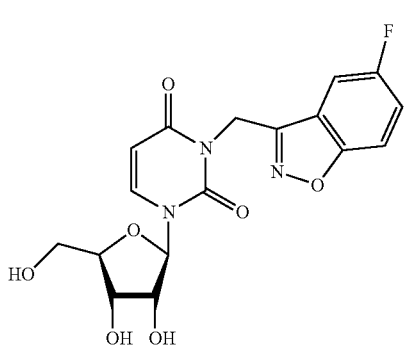
32
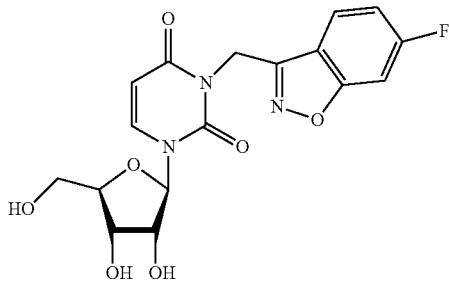
33
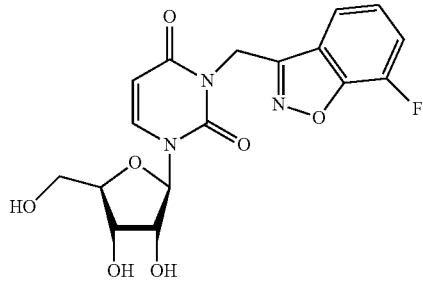
34
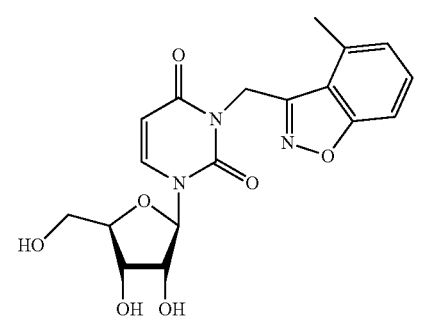
35
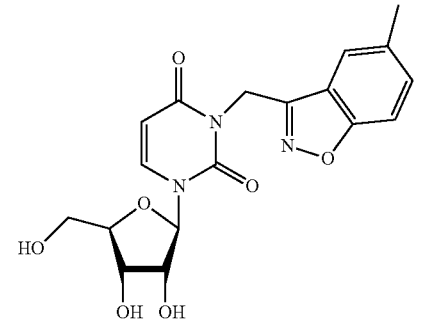
36
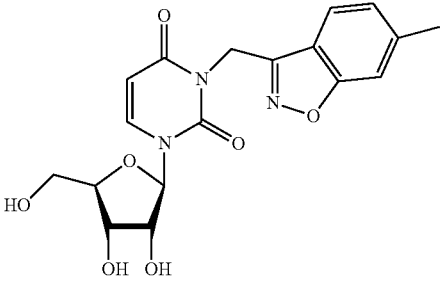
37
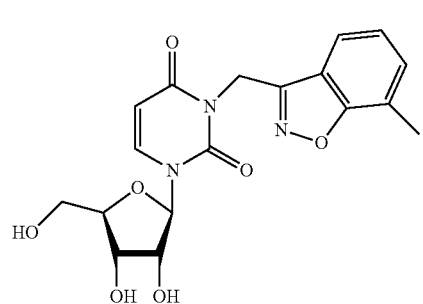

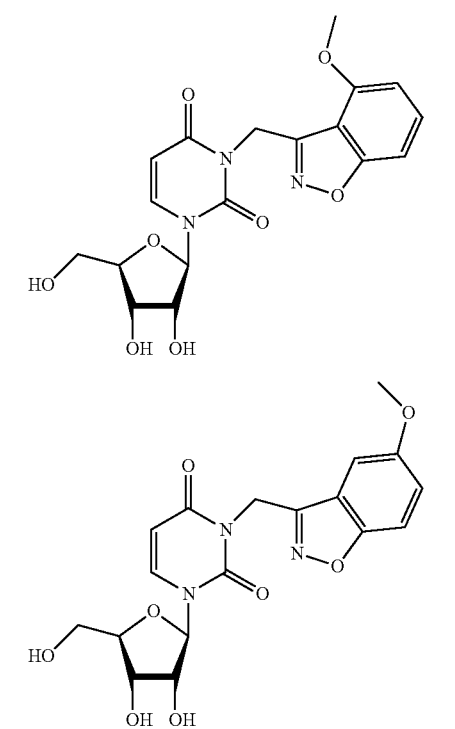
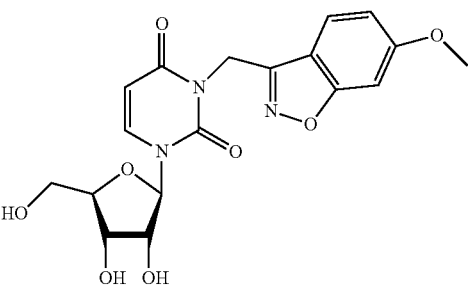
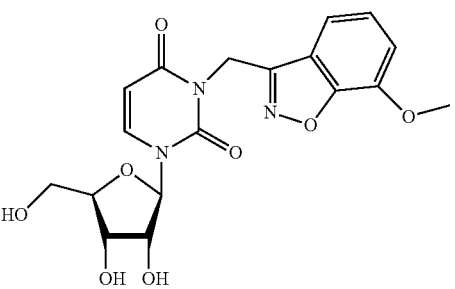
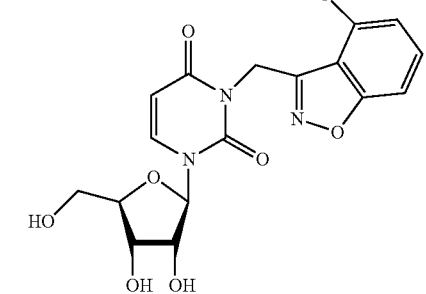
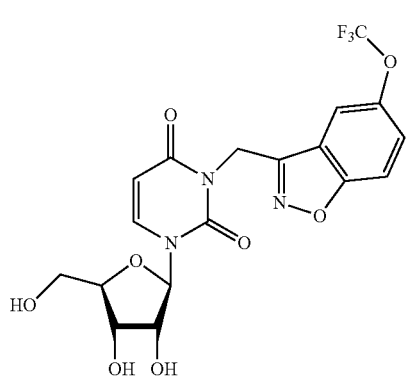
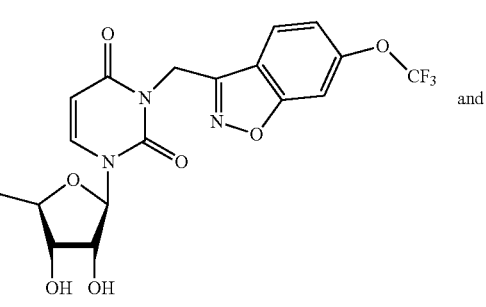
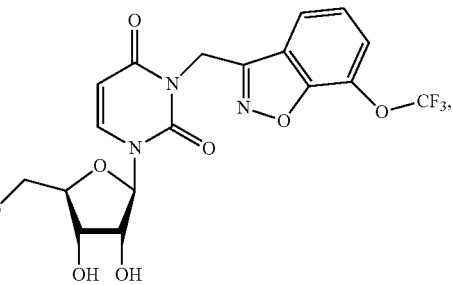 and
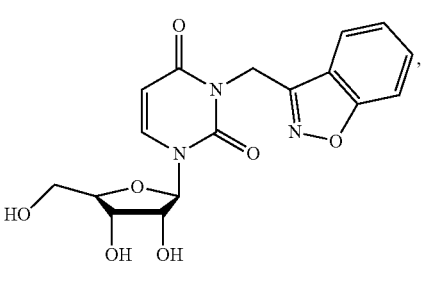
or a pharmaceutically acceptable salt thereof.
36. The method of claim 19, wherein the compound is:
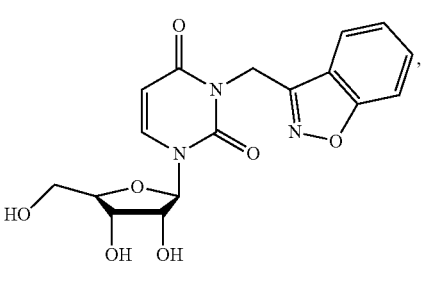,
or a pharmaceutically acceptable salt thereof.
* * * * *

UNITED STATES PATENT AND TRADEMARK OFFICE
CERTIFICATE OF CORRECTION

PATENT NO. : 10,544,183 B2
APPLICATION NO. : 14/775426
DATED : January 28, 2020
INVENTOR(S) : Philip G. Haydon and Jinbo Lee Page 1 of 2

It is certified that error appears in the above-identified patent and that said Letters Patent is hereby corrected as shown below:

In the Claims

Claim 17, Column 112, Line 20-Column 113, Line 30, the phrase "said compound is selected from the group consisting of:

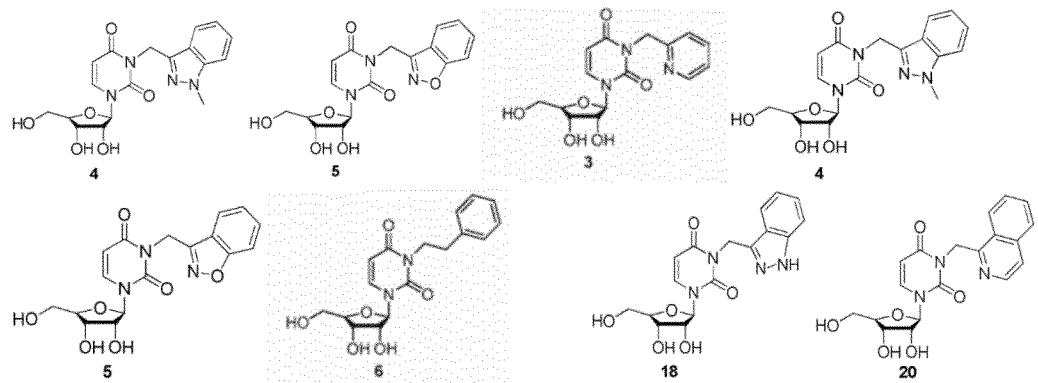

" should read "said compound is selected from the group consisting of:

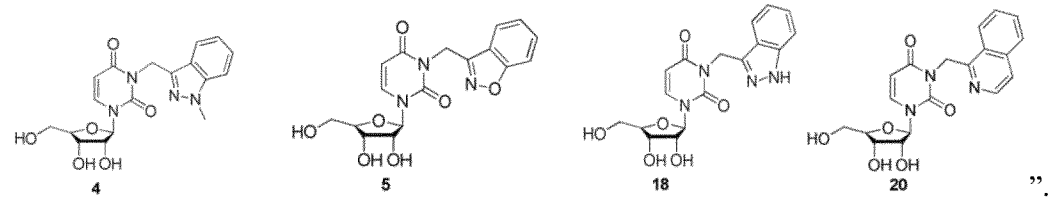

".

Claim 20, Column 119, Lines 22-23, the phrase "wherein A is optionally further substituted with one or more R'." should read "wherein A is optionally further substituted with one or more $R^7$."

Claim 35, Column 120, Line 1 to Column 121, Line 15, the phrase "said compound is selected from the group consisting of:

Signed and Sealed this
Seventh Day of September, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,544,183 B2

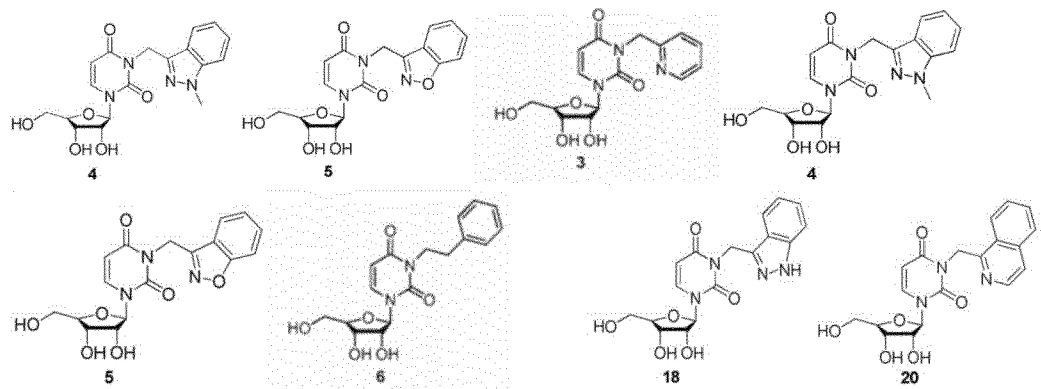

" should read

"said compound is selected from the group consisting of:

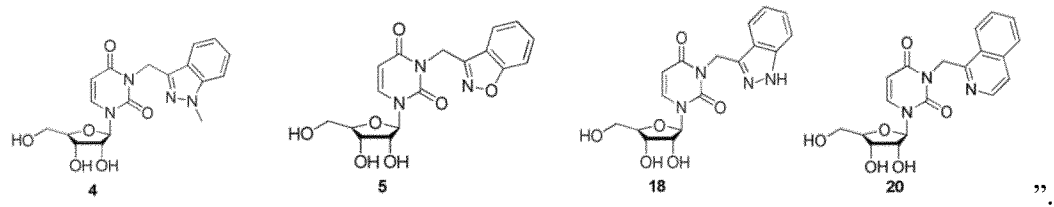

".